United States Patent
Liang et al.

(10) Patent No.: US 12,419,952 B2
(45) Date of Patent: Sep. 23, 2025

(54) SAPONIN CONJUGATE AND VACCINE OR PHARMACEUTICAL COMPOSITION COMPRISING THE SAME

(71) Applicant: Pi-Hui Liang, Taipei (TW)

(72) Inventors: Pi-Hui Liang, Taipei (TW); Yen-Hsun Lai, Taipei (TW); Chun-Kai Chang, Taipei (TW); Chee-Wai Chaw, Taipei (TW)

(73) Assignee: Pi-Hui Liang, Taipei (TW)

( * ) Notice: Subject to any disclaimer, the term of this patent is extended or adjusted under 35 U.S.C. 154(b) by 895 days.

(21) Appl. No.: 17/616,213

(22) PCT Filed: Jun. 1, 2020

(86) PCT No.: PCT/CN2020/093784
§ 371 (c)(1),
(2) Date: Dec. 3, 2021

(87) PCT Pub. No.: WO2020/244483
PCT Pub. Date: Dec. 10, 2020

(65) Prior Publication Data
US 2022/0323578 A1 Oct. 13, 2022

Related U.S. Application Data

(60) Provisional application No. 62/856,729, filed on Jun. 3, 2019.

(51) Int. Cl.
| | | |
|---|---|---|
| *A61K 39/39* | (2006.01) | |
| *A61K 31/739* | (2006.01) | |
| *A61P 31/14* | (2006.01) | |
| *A61P 31/16* | (2006.01) | |
| *A61P 35/00* | (2006.01) | |
| *C07H 15/256* | (2006.01) | |

(52) U.S. Cl.
CPC .............. *A61K 39/39* (2013.01); *A61P 31/14* (2018.01); *A61P 31/16* (2018.01); *A61P 35/00* (2018.01); *C07H 15/256* (2013.01)

(58) Field of Classification Search
CPC .......... A61K 39/39; A61K 2039/55572; A61K 2039/55577; A61K 2300/00; Y02A 50/30
See application file for complete search history.

(56) References Cited

U.S. PATENT DOCUMENTS

| | | |
|---|---|---|
| 5,977,081 A | 11/1999 | Marciani |
| 6,080,725 A | 6/2000 | Marciani |

FOREIGN PATENT DOCUMENTS

| | | |
|---|---|---|
| CN | 105111272 | 12/2015 |
| WO | 2004/092329 | 10/2004 |
| WO | 2013/142142 | 9/2013 |
| WO | 2017/106836 | 6/2017 |
| WO | 2019/183159 | 9/2019 |
| WO | 2020/190959 | 9/2020 |

OTHER PUBLICATIONS

Japanese Office Action for Japanese Patent Application No. 2021-572368 dated Mar. 7, 2024.
Wang, et al. "Synthesis of the Potent Immunostimulatory Adjuvant QS-21A", J. Am. Chem. Soc. Communications, 127, pp. 3256-3257, Published on Web Feb. 18, 2005.
Li, et al. "Gold(I)-Catalyzed Glycosylation with Glycosyl o-Alkynylbenzoates as Donors: General Scope and Application in the Synthesis of a Cyclic Triterpene Saponin", Chen. Eur. J., 2010, 16m pp. 1871-1882.
Indian Office Action for Indian Patent Application No. 202117056002 dated May 31, 2024.
Australian Office Action for Australian Patent Application No. 2020288770 dated May 26, 2023.
Kitagwa, et al. "Saponin and Sapogenal. XXI. Photochemical Cleavage of Glycoside Linkage in Triterpenoidal and Steroidal Arabinoside and Galactoside via Ultraviolet Irradiation of Their 2-Keto Derivatives", Chem. Pharm. Bull. 25(4) 800-808 (1977).
Huo, et al. "Synthesis and structure-activity relationship of oleanolic mono- or di-glycosides against Magnaporthe oryzae", Genetics and Molecular Research 15(3): gmr. 15038998.
Tian, et al. "Semisynthesis and Biological Evaluation of Oleanolic Acid 3-O-β-D-Glucuronopyranoside Derivatives for Protecting H9c2 Cardiomyoblasts against H2O2-Induced Injury", Molecules 2018, 23, 44; doi:10.3390/molecules23010044.
Extended European Search Report for European Patent Application No. 20818336.8 dated Jun. 20, 2023.
Wang, et al. "Vaccine Adjuvants Derivatized from Momordica Saponins I and II", J. Med. Chem.vol. 62(21) pp. 9976-9982 (Nov. 14, 2019).
Wang, et al. "Structural Effect on Adjuvanticity of Saponins", J. Med. Chem. vol. 63(6) pp. 3290-3297 (Feb. 26, 2020).
Australian Office Action for Australian Patent Application No. 2020288770 dated Nov. 18, 2022.
Wang, et al. "Synthesis of SQ-21-Based Immunoadjuvants", J Org Chem. 78(22): Nov. 15, 2013, pp. 11525-11534.
Liu, et al. "QS-21 structure/function studies: effect of acylation on adjuvant activity", Elsevier Vaccine 20 (2002) pp. 2808-2515.

(Continued)

*Primary Examiner* — Barry A Chestnut
(74) *Attorney, Agent, or Firm* — Amin, Turocy & Watson, LLP

(57) ABSTRACT

The present invention is directed to novel chemical compounds in which a lipophilic moiety such as a lipid, fatty acid, polyethylene glycol or terpene is covalently attached to a non-acylated or desacylated triterpene saponin via a carboxyl group present on the 3-O-glucuronic acid of the triterpene saponin. The attachment of a lipophile moiety to the 3-O-glucuronic acid of a saponin such as *Quillaja* desacylsaponin, lucyoside P, or saponin from *Gypsophila, Saponaria* and *Acanthophyllum* enhances their adjuvant effects on humoral and cell mediated immunity. Additionally, the attachment of a lipophile moiety to the 3-O-glucuronic acid residue of non- or des-acylsaponin yields a saponin analog that is easier to purify, less toxic, chemically more stable, and possesses equal or better adjuvant properties than the original saponin.

18 Claims, 10 Drawing Sheets

(56) References Cited

OTHER PUBLICATIONS

Shen, et al. "Structure-activity relationship of Triterpenes and derived Glycosides against cancer cells and mechanism of spoptosis induction", Natural Product Research, 32:6. 2017, pp. 654-661.
Mohamed, et al. "Characterization of Bioactive Phytochemical from the Leaves of Vitex trifolia", International Journal of Pharmaceutical Applications, vol. 3, Issue 4, 2012, pp. 419-428.
Zhang, et al. "Evaluation of novel saponins from Psammosilene tunicoides and their analogs as immunomodulators", Elsevier International Immunopharmacology 14 (2012) pp. 21-26.
Kim, et al. Synthetic Studies of Complex Immunostimulants from Quillaja saponaria: Synthesis of the Potent Clinical Immunoadjuvant SQ-21A, J Am Chem Soc. 128(36): Sep. 13, 2006, pp. 11906-11915.
International Search Report and Written Opinion for International Application No. PCT/CN2020/093784 mailed on Sep. 2, 2020, 8 pages.
Zhou, et al. "Three new triterpenoid saponins from the rhizomes of *Impatiens pritzellii* var. hupehensis", Journal of Asian Natural Products Research, vol. 9, No. 4, Jul. 3, 2007, pp. 379-385.
Wang, et al. "Synthesis and Evaluation of QS-21-Based Immunoadjuvants with a Terminal-Functionalized Side Chain Incorporated in the West Wing Trisaccharide", The Journal of Organic Chemistry, vol. 81, No. 20, Oct. 6, 2016, pp. 9560-9566.
Liu, et al. "QS-21 structure/function studies: effect of acylation on adjuvant activity", Vaccine, vol. 20, No. 21-22, Jun. 21, 2002, pp. 2808-2815.
Zhou, et al. "The Interleukin-18 Inhibitory Activities of Echinocystic Acid and its Saponins from *Impatiens pritzellii* var. hupehensis", Zeitschrift fur Naturforschung C, vol. 64, No. 5-6, Jun. 2, 2014, pp. 369-372.
Japanese Office Action for Japanese Patent Application No. 2021-572368 dated Aug. 8, 2024.
Zhang, et al. "Triterpenoidal saponins from Gleditsia sinensis", Phytochemistry 1999, v.52, pp. 715-722.
Zhang, et al. "Cytotoxic Oleanane-Type Saponins from Albizia inundata", J. Nat. Prod. 2011, v.74, pp. 477-482.
Romussi, et al. "Triterpensaponine aus *Anchusa officinalis* L.", Liebigs Ann. Chem. 1979, pp. 2028-2035.
Zhang, et al. "Antitumor triterpene saponins from Anemone flaccida", Chinese Chemical Letters 2008, v. 19, pp. 190-192.

SAPONIN CONJUGATE AND VACCINE OR PHARMACEUTICAL COMPOSITION COMPRISING THE SAME

FIELD OF THE INVENTION

The present invention relates to saponin conjugate, syntheses thereof, and intermediates thereto. The invention also provides pharmaceutical compositions comprising the saponin conjugate of the present invention and methods of using said saponin conjugate or compositions in the treatment of infectious diseases, cancers, and immunological disorders.

BACKGROUND OF THE INVENTION

Adjuvant has been proven for its efficacy in the current vaccine regimens. The remaining challenges nowadays are that for therapeutic vaccines, the combination of antigen and adjuvant must be effective to provide both humoral and cellular immunity in order to treat complex diseases such as HIV, malaria, tuberculosis and cancers. Providing pathogen-specific T-cell response is fundamental to develop novel therapeutic vaccines, in which adjuvant plays the role. However, few adjuvants are sufficiently potent to induce cellular immunity and non-toxic for clinical use.

Quillaja saponins (Q. saponins) are triterpene glycosides isolated form the soap bark tree Quillaja saponaria Molina in Chile. Q. saponins are strong stimulant in the production of fluid mucus in airway and cause inflammation of the digestive tract. Four major triterpenoid glucosides have been isolated and identified as QS-7, QS-17, QS-18 and QS-21 (Quillaja saponins fraction-7, 17, 18 and 21) from the Quillaja saponaria extract.[4] Their structures were characterized thereafter as shown below. These saponins all share a same triterpene backbone quillaic acid and flanked branched trisaccharide β-D-Gal-(1→2)-[β-D-Xyl-(1→3)]-β-D-GlcA on 3-O position. QS-21 contains a linear tetrasaccharide moiety β-D-Apif/Xylp-(1→3)-β-D-Xyl-(1→4)-α-L-Rha-(1→2)-β-D-Fuc on 28-O position and a fucose-linked 4-O-acyl stereochemically rich fatty acyl chain 1.

Demonstrates Structures of QS-21 and its Purified Analogues:

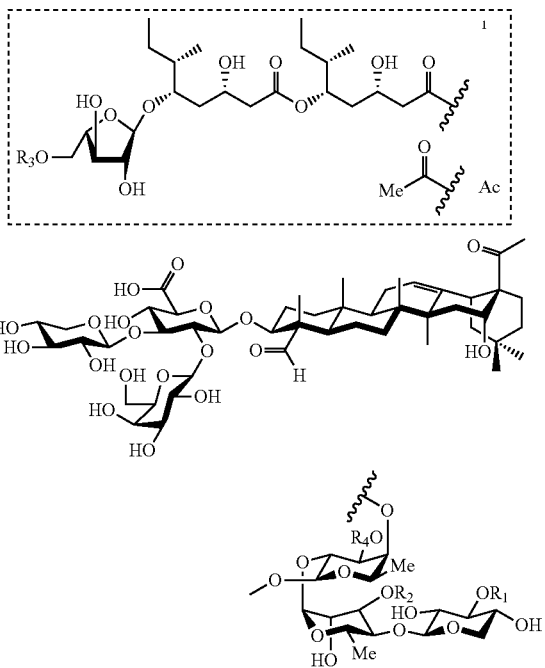

| Compound | Acyl chain | $R_1$ | $R_2$ | $R_3$ | $R_4$ |
|---|---|---|---|---|---|
| QS-7 | Ac | β-D-Apif | β-D-Glcp | N/A | α-L-Rhap |
| QS-17 | 1 | β-D-Apif | β-D-Glcp | α-L-Rhap | H |
| QS-18 | 1 | β-D-Apif | β-D-Glcp | H | H |
| QS-21$_{api}$ | 1 | β-D-Apif | H | H | H |
| QS-21$_{xyl}$ | | β-D-Xylp | | | |

Apif: apiofuranose, Xylp: xylopyranose, Glcp: glucopyranose, Rhap: rhamnopyranose The potency of QS-21 and its favorable toxicity profile in hundreds of recent and ongoing vaccine clinical trials (malaria, herpes, Alzheimer's disease, HIV-1, melanoma, breast cancer, small cell lung cancer, prostate cancer, and etc.) have established it as a promising adjuvant for immune response potentiation and dose-sparing. However, 4 major liabilities, dose limiting toxicity, poor stability, poor understanding of its molecular mechanism of action and limited availability of quality product remained to be problematic.

GPI-0100 is a semi-synthesized saponins mixture derived from soap bark extract. The crude bark extract was processed under mild basic hydrolysis and then conjugated with an aliphatic dodecyl chain via a hydrolytically stable amide bond to give GPI-0100. This modification certainly gave these molecules more tolerance at higher temperature. Furthermore, the inherent toxicity from the *Quillaja* extract was decoupled with its immunological stimulation ability. However, its adjuvant activity was dropped off. Therefore, it remains a need for adjuvants that have enhanced cellular immunity and lower toxicity. This invention developed a new generation of saponin-based adjuvants with improved efficacy in the cellular immunity, which are more suitable to combine with therapeutic vaccines then existing ones.

SUMMARY OF THE INVENTION

The present invention is directed to novel chemical compounds, referred to herein as saponin conjugates, in which In one aspect, the invention provides saponin conjugates of formula I:

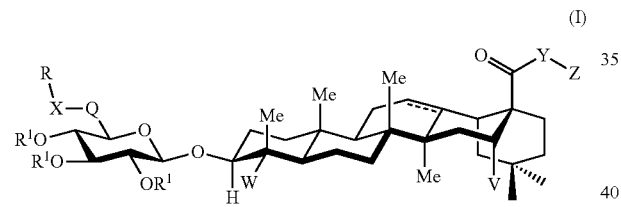

(I)

or a pharmaceutically acceptable salt thereof, wherein:
  ═ is a single or double bond;
  W is Me, —CHO,

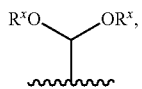

—CH$_2$OR$^1$, —C(O)R$^x$, or —CH$_2$OR$^x$;
  V is hydrogen or —OR$^1$;
  Y is CH$_2$, —O—, —S—, —NR—, or —NH—;
  Q is CH$_2$, C═O, C═N—OH, or C═N—OMe;
  X is CH$_2$, —O—, —NH—, —NH—(C═O)—, —S—, or O—(C═O)—;
  R is a cyclic or acyclic, optionally substituted moiety selected from the group consisting of acyl, aliphatic, heteroaliphatic, aryl, aryl-aliphatic, cyclo-aliphatic, heterocyclo-aliphatic, heteroaryl-aliphatic, alkyloxy-aliphatic, and aryloxy-aliphatic or optionally substituted moiety selected from the group consisting of C$_1$-C$_{18}$ aliphatic, 5-10-membered arylaliphatic, 5-10-membered heteroaryl-aliphatic having 1-4 heteroatoms independently selected from nitrogen, oxygen, or sulfur, 4-7-membered heterocyclylaliphatic having 1-2 heteroatoms independently selected from the group consisting of nitrogen, oxygen, and sulfur;
  R$^1$ is independently hydrogen, an oxygen protecting group selected from the group consisting of alkyl ethers, benzyl ethers, silyl ethers, acetals, ketals, esters, carbamates, and carbonates, or a carbohydrate having the structure of monosaccharides, such as glucose, mannose, galactose, N-acetyl glucosamine, N-acetyl galactosamine, altrose, allose, fucose, rhamnose and etc.

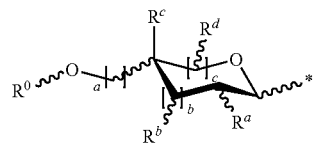

where in:
  each occurrence of a, b, and c is independently 0 or 1;
  R$^0$ is independently hydrogen or an oxygen protecting group selected from the group consisting of alkyl ethers, benzyl ethers, silyl ethers, acetals, ketals, esters, carbamates, and carbonates;
  each occurrence of R$^a$, R$^b$, R$^c$, and R$^d$ is independently hydrogen, halogen, OH, OR, OR$^x$; each occurrence of R$^x$ are independently hydrogen or an oxygen protecting group selected from the group consisting of alkyl ethers, benzyl ethers, silyl ethers, acetals, ketals, esters, carbamates, and carbonates;
  Z is hydrogen; a cyclic or acyclic, optionally substituted moiety selected from the group consisting of acyl, aliphatic, heteroaliphatic, aryl, arylalkyl, heterocyclyl, and heteroaryl; or a carbohydrate domain having the structure:

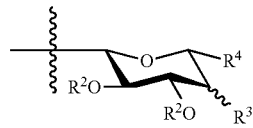

wherein:
  each occurrence of R$^2$ is H or a carbohydrate domain having the structure:

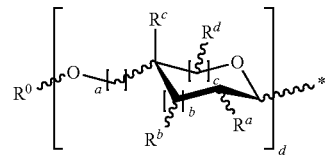

Where in:
  each occurrence of a, b, and c is independently 0, 1, or 2;
  d is an integer from 1-5, wherein each d bracketed structure may be the same or different; with the proviso that the d bracketed structure represents a furanose or pyranose moiety, and the sum of b and c is 1 or 2;
  R$^0$ is hydrogen; an oxygen protecting group selected from the group consisting of alkyl ethers, benzyl ethers, silyl ethers, acetals, ketals, esters, carbamates, and carbonates;

Each occurrence of $R^a$, $R^b$, $R^c$, and $R^d$ is independently hydrogen, halogen, OH, OR, $OR^x$, $NR_2$, NHCOR, or an optionally substituted group selected from acyl, $C_1$-$C_{10}$ aliphatic, $C_1$-$C_6$ heteroaliphatic, 6-10-membered aryl, arylaliphatic, 5-10-membered heteroaryl having 1-4 heteroatoms independently selected from nitrogen, oxygen, or sulfur; 4-7-membered heterocyclyl having 1-2 heteroatoms independently selected from the group consisting of nitrogen, oxygen, and sulfur;

$R^3$ is hydrogen, halogen, OH, $OR^x$, $R^4$ is hydrogen, halogen, $CH_2OR^x$, or an optionally substituted group selected from the group consisting of acyl, $C_1$-$C_{10}$ aliphatic;

Each occurrence of $R^x$ is independently hydrogen or an oxygen protecting group selected from the group consisting of alkyl ethers, benzyl ethers, silyl ethers, acetals, ketals, esters, carbamates, and carbonates;

The present invention encompasses the recognition that the clinical use of GPI-0100 as a mixture of adjuvant is limited due to structure complexities and is difficult to isolate in pure form. The present invention provides compounds that are analogues of GPI-0100.

According to another aspect, inventive compounds have been shown to be useful as adjuvants. Thus, in certain embodiments, vaccines are provided comprising one or more bacterial, viral, protozoal, or tumor-associated antigens, and one or more inventive compounds. In certain embodiments, one or more antigens are non-covalently associated with a pharmaceutically acceptable excipient. In some embodiments, one or more antigens are conjugated covalently to a pharmaceutically acceptable excipient.

In another aspect, the present invention provides a method of potentiating an immune response to an antigen, comprising administering to a subject a provided vaccine in an effective amount to potentiate the immune response of said subject to said antigen.

In another embodiment, the present invention provides saponin substances that induce the immune response toward humoral immunity and cellular immunity.

In another embodiment, the invention provides a method of stimulating or enhancing cytokine production in a subject, the method includes, inter alia, administering to the subject any one of the compounds of the invention, whereby immune cell secreted cytokines.

In another aspect, the present invention provides methods of vaccinating a subject, comprising administering a provided vaccine to said subject. In some embodiments, the subject is human. In some embodiments, the vaccine is administered orally. In other embodiments, the vaccine is administered intramuscularly. In other embodiments, the vaccine is administered subcutaneously. In certain embodiments, the amount of adjuvant compound administered is 10-1000 μg. In certain embodiments, the amount of adjuvant compound administered is 500-1000 μkg. In certain embodiments, the amount of adjuvant compound administered is 100-500 μg. In certain embodiments, the amount of adjuvant compound administered is 50-250 μg. In certain embodiments, the amount of adjuvant compound administered is 50-500 μg. In certain embodiments, the amount of adjuvant compound administered is 250-500 μg. The antigen to which the subject is vaccinated may be a cancer, bacterial, viral, proatozoal, or self-antigen.

In another aspect, the invention provides pharmaceutical compositions comprising compounds of the invention and pharmaceutically acceptable excipients. In certain embodiments, the pharmaceutical composition is a vaccine comprising an antigen and an inventive adjuvant.

In another aspect, the invention provides kits comprising pharmaceutical compositions of inventive compounds. In some embodiments, the kits comprise prescribing information. In some embodiments, such kits include the combination of an inventive adjuvant compound and another immunotherapeutic agent (e.g. vaccine, antibody). The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of immunotherapy. In certain embodiments, the kit includes a sufficient quantity of a pharmaceutical composition to immunize a subject against an antigen long term.

In one embodiment, the invention provides a process for the preparation f a compound presented by the structure of formula II:

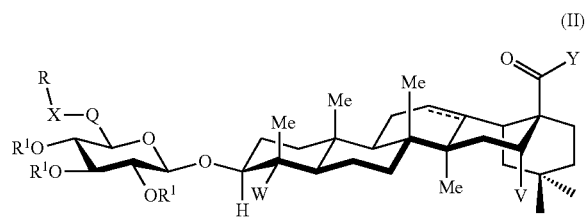

(II)

or a pharmaceutically acceptable salt thereof, wherein:

═ is a single or double bond;

W is Me, —CHO,

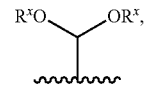

—$CH_2OR^1$, —$C(O)R^x$, or —$CH_2OR^x$;

V is hydrogen or —$OR^x$;

Y is $CH_3$, —OH, —SH, —$NHR^5$, —$NH_2$, or an oxygen protecting group selected from the group consisting of alkyl ethers, benzyl ethers, silyl ethers, acetals, ketals, esters, carbamates, and carbonates, wherein $R^5$ is selected from the group consisting of alkyl ethers, allyl ethers, benzyl ethers, silyl ethers, acetals, ketals, esters, carbamates, and carbonates;

Q is $CH_2$, C═O, C═N—OH, or C═N—OMe;

X is $CH_2$, —O—, —NH—, —NH—(C═O)—, —S—, or —O—(C═O)—;

$R^1$ is independently hydrogen, an oxygen protecting group selected from the group consisting of alkyl ethers, benzyl ethers, silyl ethers, acetals, ketals, esters, carbamates, and carbonates, or a carbohydrate having the structure of

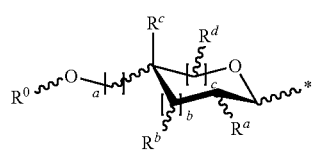

wherein:
each occurrence of a, b, and c is independently 0, or 1;
$R_0$ is independently hydrogen or an oxygen protecting group selected from the group consisting of alkyl ethers, benzyl ethers, silyl ethers, acetals, ketals, esters, carbamates, and carbonates;
each occurrence of $R_a$, $R_b$, $R_c$, and $R_d$ is independently hydrogen, halogen, OH, OR, $OR^x$; each occurrence of $R^x$ are independently hydrogen or an oxygen protecting group selected from the group consisting of alkyl ethers, benzyl ethers, silyl ethers, acetals, ketals, esters, carbamates, and carbonates; and
R is a cyclic or acyclic, optionally substituted moiety selected from the group consisting of acyl, aliphatic, heteroaliphatic, aryl, aryl-aliphatic, cyclo-aliphatic, heterocyclo-aliphatic, heteroaryl-aliphatic, aryloxy-aliphatic, and aryloxy-aliphatic or optionally substituted moiety selected from the group consisting of $C_{1-18}$ aliphatic, 5-10-membered arylaliphatic, 5-10-membered heteroaryl-aliphatic having 1-4 heteroatoms independently selected from nitrogen, oxygen, or sulfur, 4-7-membered heterocyclylaliphatic having 1-2 heteroatoms independently selected from the group consisting of nitrogen, oxygen, and sulfur.

In one embodiment of the invention, the compound of formula II may be obtained by the process including, inter alia, the step of:
reacting a compound represented by the structure of formula III.

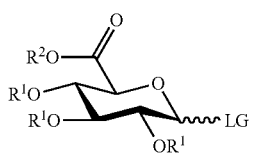

(III)

$R^1$ is independently hydrogen, an oxygen protecting group selected from the group consisting of alkyl ethers, benzyl ethers, silyl ethers, acetals, ketals, esters, carbamates, and carbonates, or a carbohydrate having the structure of

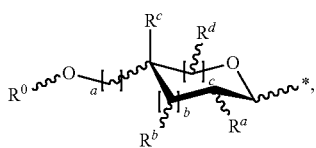

wherein:
each occurrence of a, b, and c is independently 0 or 1;
$R_0$ is independently hydrogen or an oxygen protecting group selected from the group consisting of alkyl ethers, benzyl ethers, silyl ethers, acetals, ketals, esters, carbamates, and carbonates;
each occurrence of $R_a$, $R_b$, $R_c$, and $R_d$ is independently hydrogen, halogen, OH, OR, $OR^x$; each occurrence of $R^x$ are independently hydrogen or an oxygen protecting group selected from the group consisting of alkyl ethers, benzyl ethers, silyl ethers, acetals, ketals, esters, carbamates, and carbonates;

LG is leaving group, may be, inter alia,

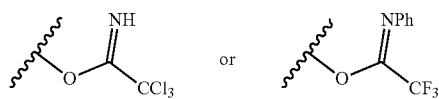

with a compound represented by the structure of formula IV

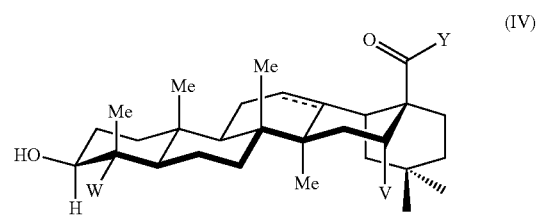

(IV)

or a pharmaceutically acceptable salt thereof, wherein:
$=\!=$ is a single or double bond;
W is Me, —CHO,

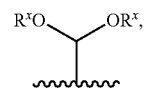

—$CH_2OR^x$, or —$C(O)R^x$;
V is hydrogen or —$OR^x$;
Y is $CH_3$, —OH, —SH, —$NHR^5$, —$NH_2$, or an oxygen protecting group selected from the group consisting of alkyl ethers, benzyl ethers, silyl ethers, acetals, ketals, esters, carbamates, and carbonates; and
$R^2$, $R^x$, or $R^5$ are independently hydrogen or an oxygen protecting group selected from the group consisting of alkyl ethers, allyl ethers, benzyl ethers, silyl ethers, acetals, ketals, esters, carbamates, and carbonates.

In one embodiment of the invention, one kind of the compound of formula I may be obtained by the process including, inter alia, the step of:
reacting formula II with formula V:

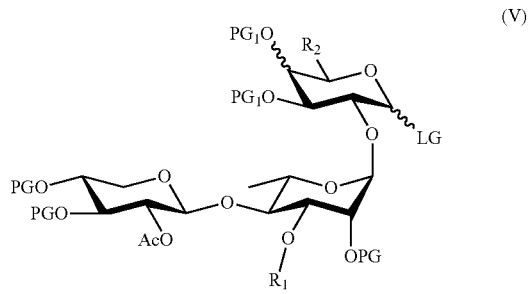

(V)

or a pharmaceutically acceptable salt thereof, wherein:
PG and $PG_1$ are oxygen protecting group selected from the group consisting of alkyl ethers, benzyl ethers, silyl ethers, acetals, ketals, esters, carbamates, and carbonates;
$R_1$ is independently hydrogen, an oxygen protecting group selected from the group consisting of alkyl ethers, benzyl ethers, silyl ethers, acetals, ketals, esters, carbamates, and carbonates, or a carbohydrate having the structure of

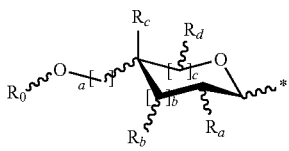

Where in:
  each occurrence of a, b, and c is independently 0 or 1;
  $R_0$ is independently hydrogen or an oxygen protecting group selected from the group consisting of alkyl ethers, benzyl ethers, silyl ethers, acetals, ketals, esters, carbamates, and carbonates;
  each occurrence of $R_a$, $R_b$, $R_c$, and $R_d$ is independently hydrogen, halogen, OH, OR, $OR^x$; each occurrence of $R^x$ are independently hydrogen or an oxygen protecting group selected from the group consisting of alkyl ethers, benzyl ethers, silyl ethers, acetals, ketals, esters, carbamates, and carbonates;
  $R_2$ is independently hydrogen, halogen, $CH_2OH$, or an optionally substituted group selected from low alkyl group; and
  LG is leaving group, may be, inter alia

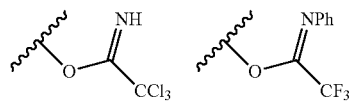

Definitions

As used herein, the following definitions shall apply unless otherwise indicated.

"Stereoisomer" or "stereoisomers" refer to compounds that differ in the chirality of one or more stereocenters. Stereoisomers include enantiomers and diastereomers.

"Subject" refers to mammals and includes humans and non-human mammals.

The term "aliphatic" or "aliphatic group" or "aliphatic moiety" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "cycloaliphatic" or "cycloalkyl") that has a single point of attachment to the rest of the molecule. Unless otherwise specified, aliphatic groups contain aliphatic carbon atoms. In some embodiments, aliphatic groups contain 1-12 aliphatic carbon atoms. In some embodiments, aliphatic groups contain 1-11 aliphatic carbon atoms. In other embodiments, aliphatic groups contain 1-10 aliphatic carbon atoms. In still other embodiments, aliphatic groups contain 1-9 aliphatic carbon atoms, and in yet other embodiments, aliphatic groups contain 1-8 aliphatic carbon atoms. In still other embodiments, aliphatic groups contain 1-7 aliphatic carbon atoms. In other embodiments, aliphatic groups contain 1-6 aliphatic carbon atoms. In other embodiments, aliphatic groups contain 1-5 aliphatic carbon atoms. In other embodiments, aliphatic groups contain 1-4 aliphatic carbon atoms. In other embodiments, aliphatic groups contain 1-3 aliphatic carbon atoms, and in yet other embodiments, aliphatic groups contain 1-2 aliphatic carbon atoms.

In some embodiments, cycloaliphatic (or "carbocycle" or "cycloalkyl") refers to a monocyclic C—C hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or, a substitutable nitrogen of a heterocyclic ring, for example N (as in 3,4-dihydro-2H-pyrrolyl), NH (as in pyrrolidinyl) or NR" (as in N-substituted pyrrolidinyl)).

The term "unsaturated" as used herein, means that a moiety has one or more double bond(s).

The term "halogen" means F, Cl, Br, or I.

The term "acyl" used alone or a part of a larger moiety, refers to groups formed by removing a hydroxy group from a carboxylic acid.

The terms "arylkyl" and "arylaliphatic" are used interchange ably and refer to aliphatic groups in which a hydrogen atom has been replaced with an aryl group. Such aryl groups include, without limitation, phenyl, biphenyl, naphthyl, cinnamyl and dihyrocinnamyl.

The term "aryl" used alone or as part of a larger moiety as in "aryl-aliphatic", "heteroaryl-aliphatic".

The term aryloxy-aliphatic (or "aralkoxy, or arylkoxy", or "aryloxyalkyl") refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, benzyl, phenyl, biphenyl, naphthyl, anthracyl and the like, which may bear one or more substituents. Also included within the scope of the term "aryl", as it is used herein, is a group in which an aromatic ring is fused to none or one or more non-aromatic rings, such as indanyl, phthalimidyl, naphthimidyl, phenanthridinyl, or tetrahydronaphthyl, and the like.

The terms "heteroaryl" used alone or as part of a larger moiety, e.g., "heteroaryloxy" or "heteroaryl-apliphatic", or "heteroarylkyl" refer to groups having 5 to 10 ring atoms, preferably 5, 6, or 9 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl pyrazolyl, triazolyl, tetrazolyl, oxazolyl, isoxazolyl, oxadiazolyl, thiazolyl, isothiazolyl, thiadiazolyl pyridyl, pyridazinyl, pyrimidinyl, pyrazinyl, indolizinyl, purinyl, naphthyridinyl, and pteridinyl.

The terms "heteroaryl" and "heteroar-", as used herein, also include groups in which a heteroaromatic ring is fused to one or more aryl, cycloaliphatic, or heterocyclyl rings, where the point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and 2H-pyrido [2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic" and any of which terms include rings that are optionally substituted. The terms "heteroaryl-apliphatic" and "heteroaryl-alkyl" refer to an aliphatic group substituted by a heteroaryl moiety, wherein the aliphatic and heteroaryl portions independently are optionally substituted.

The term "hetero-aliphatic" as used herein, means aliphatic groups wherein one or two carbon atoms are independently replaced by one or more of oxygen, sulfur, nitrogen, or phosphorous. Hetero-aliphatic groups may be substituted or unsubstituted, branched or unbranched, cyclic or acyclic, and include "heterocycle", "heterocyclyl", "heterocycloaliphatic", or "heterocyclic" groups.

As used herein, the terms "heterocycle", "heterocyclyl", and "heterocyclic ring are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

The terms "heterocycle", "heterocyclyl", "heterocyclyl ring", "heterocyclic group", and "heterocyclic moiety" are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono or bicyclic.

The term "heterocyclylaliphatic" refers to an alkyl group substituted by a heterocyclyl, wherein the aliphatic group and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present invention provides "pharmaceutically acceptable" compositions, which comprises a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by intramuscular, subcutaneous, intravenous or epidural injection as, for example, a sterile solution or suspension, or sustained release formulation; topical application, for example, as a cream, ointment, or a controlled-release spray or patch applied to the lungs, skin or oral cavity; intravaginally or intrarectally, for example, as a pessary, cream or foam; sublingually: ocularly; transdermally; or nasally, pulmonary and to other mucosal surfaces.

The phrase "pharmaceutically acceptable" is employed herein to refer to those compounds, compositions, materials, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle. Such as a liquid or solid filler, excipient, diluent, or solvent encapsulating material, involved in transporting or carrying the subject compound from one portion of the body, to another portion of the body. Each carrier must be "acceptable" in the sense of being compatible with the other ingredients of the formulation and not injurious to the patient. Some examples of materials which can serve as pharmaceutically-acceptable carriers include: sugars, such as glucose, lactose, sucrose; starches, such as corn starch and potato starch; cellulose, and its derivatives, such as sodium carboxymethyl cellulose, ethyl cellulose and cellulose acetate; powdered tragacanth; malt, gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols. Such as glycerin, sorbitol, mannitol and poly ethylene glycol; esters, such as ethyl oleate and ethyl laurate, agar, buffering agents, such as magnesium hydroxide and aluminum hydroxide; alginic acid; pyrogen-free water, isotonic saline: Ringer's solution: ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in. J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthale nesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N(C_{1-4}alkyl)$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counter ions such as halide, hydroxide, carboxylate, sulfate, phosphate, nitrate, lower alkyl sulfonate and aryl sulfonate. Representative organic amines useful for the formation of base addition salts include ethylamine, diethylamine, ethylenediamine, ethanolamine, diethanolamine, piperazine and the like.

Unless otherwise stated, structures depicted herein are also meant to include all isomeric (e.g., enantiomeric, diastereomeric, and geometric, conformational forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided compounds may comprise one or more saccharide moieties. Unless otherwise specified, both D- and L-configurations, and mixtures thereof, are within the scope of the invention. Unless otherwise specified, both C- and S-linked embodiments, and mixtures thereof, are contemplated by the present invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$- enriched carbon are within the scope of this invention. Such compounds are useful, for example, as analytical tools, as probes in biological assays, or as therapeutic agents in accordance with the present invention.

According to embodiments of the invention, the phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. Of course other appropreate protecting groupd may be used. Additionally, a variety of protecting groups are described by Greene and Wuts (supra).

In one embodiment of the invention, the protecting group may be, inter alia, a hydroxy protecting group. In one embodiment of the invention, the hydroxy protecting group may be, inter alia, an alkyl, aryl, aralkyl, silyl or acyl radical. In another embodiment, the protecting group may be, inter alia, trimethylsilyl, triethylsilyl, tert-butyldimethylsilyl (TBS), triisopropylsilyl (TIPS), or tert-butyldiphenylsilyl. Of course, any other appropriate protecting group may be used.

In one embodiment, the aralkyl may be unsubstituted or substituted. In another embodiment, the aralkyl may be, inter alia, arylmethyl. In another embodiment, the protecting group may be, inter alia, benzyl. In another embodiment, the protecting group may be, inter alia, methoxybenzyl. In another embodiment, the methoxybenzyl may be, inter alia, para-methoxybenzyl.

In one embodiment of the invention, the protecting group may be, inter alia, an amino protecting group. In one embodiment of the invention, the amino protecting group may be, inter alia, carbamate, an amide or an N-sulfonylamide. In another embodiment, the amino protecting group may be, inter alia, benzyloxycarbonyl (Cbz), 9-fluorenylmethyloxy carbonyl (Fmoc), t-butyloxycarbonyl, (tBoc), biphenyliso propyloxycarbonyl, t-amyloxycarbonylisobornyloxycarbonyl, alpha-dimethyl-3,5-dimethoxybenzyloxycarbonyl or 2-cyano-t-butyloxycarbonyl.

Furthermore, in one embodiment, the invention provides a method for stimulating, inhibiting, suppressing or modulating an immune response in a subject, the method may include, inter alia, administering to a subject any one of the compounds of this invention or any combination thereof.

Furthermore, in one embodiment, the invention provides a method for stimulating, inhibiting, suppressing or modulating an immune response in a subject, the method includes, inter alia, administering to a subject a pharmaceutical composition including, inter alia, any one of the compounds of this invention or any combination thereof, together with one or more pharmaceutically acceptable excipients.

Furthermore, in one embodiment, "pharmaceutical composition" can mean a therapeutically effective amount of one or more compounds of the present invention together with suitable excipients and/or carriers useful for stimulating, inhibiting, suppressing or modulating an immune response in a subject.

In one embodiment, "therapeutically effective amount" may refer to that amount that provides a therapeutic effect for a given condition and administration regimen. In one embodiment, such compositions can be administered by any method known in the art.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that resulted in the formation of stable or chemically feasible compounds.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration", "administered systemically", "peripheral administration" and "administered peripherally" as used herein mean the administration of a compound, drug or other material other than directly into the central nervous system, such that it enters the patient's system and, thus, is subjected to metabolism and other like processes, for example, subcutaneous administration.

The term "pure" refers to compounds that are substantially free of compounds of related non-target structure or chemical precursors (when chemically synthesized). This quality may be measured or expressed as "purity." In some embodiments, a target compound has less than about 30%, 20%, 10%, 5%, 2%, 1%, 0.5%, and 0.1% of non-target structures or chemical precursors.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, galactose, sucrose, ribose, mannose, arabinose, xylose, and fructose. Disaccharides are two joined monosaccharides. Exemplary disaccharides include sucrose, lactose, cellobiose, and maltose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose, wherein a hydroxyl group is removed, 2'-fluororibose, wherein a hydroxyl group is replace with a fluorine, or N-acetylglucosamine, a nitrogen-containing form of glucose. (e.g. 2'-fluororibose, deoxyribose, and hexose). Carbohydrates may exist in many different forms, for example, conformers, cyclic forms, acyclic forms, stereoisomers, tautomers, anomers, and isomers.

DETAILED DESCRIPTION OF CERTAIN EMBODIMENTS

Saponin Conjugate

Figure 1:
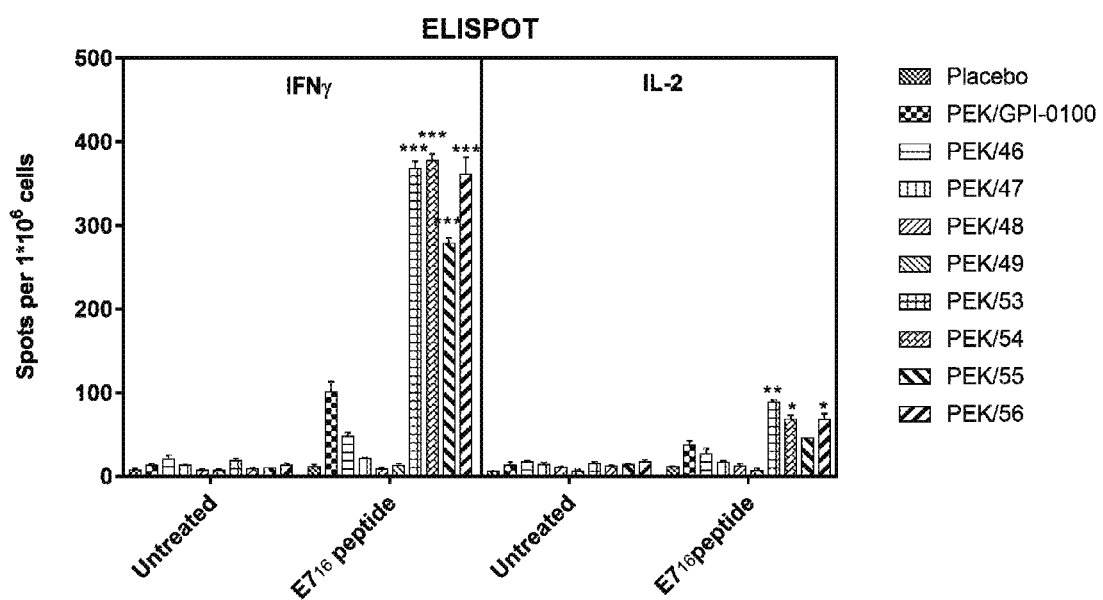
FIG. 1 demonstrates the IFNγ (left 2 groups) and IL-2 (right 2 groups) secretion profile obtained with saponins and PEK antigen or without PEK antigen, detected by ELISpot one week post-third dose.

The present invention relates to saponin conjugate of formula (I) defined as above, syntheses thereof, and intermediates thereto.

The saponin conjugate of formula (I) can be synthesized by the following synthesis steps.

Step 1-1: Synthesis of Trisaccharide Donor

The trisaccharide synthesis was started from the glycosylation of xylosyl imidate 1 and rhamnose acceptor 2 with catalytic amount of BF$_3$·OEt$_2$ to afford disaccharide 3 in 58% yield (Scheme 1). After that, the thio-disaccharide 3 was subsequently coupled with fucose 4α to furnish desired trisaccharide 5 in 58% yield. In addition, these two step glycosylations could also be performed in a one-pot fashion that disaccharide 3 was firstly conjugated then fucose 4α and NIS was successively added to the reaction mixture to afford trisaccharide 5. Trisaccharide 5 was selectively deprotected by using morpholine at rt and then acetylated by acetic anhydride. The resulting penta-acetylated trisaccharide 6 was proceeded under hydrogenolysis and imidate formation to furnish trisaccharide donor 10. An optimized trisacchairde approach was began with coupling of xylose 1 and rhamnose 7 to give quiantative yield of disaccharide 8, which following by hydrolysis and acetylation to gave 9. Glycosylation of disaccharide 9 and fucose 4α give trisaccharide 6 with excellent 96% yield. A arabinose containing trisaccharide 12 and its imidate derivative 13 were also synthesized by glycosylation of disaccharide 9 and arabinose 11a and the following hydrogenolysis and imidate reactions.

Scheme 1—Depicts Synthesis of Trisaccharide and Analogs Thereof.

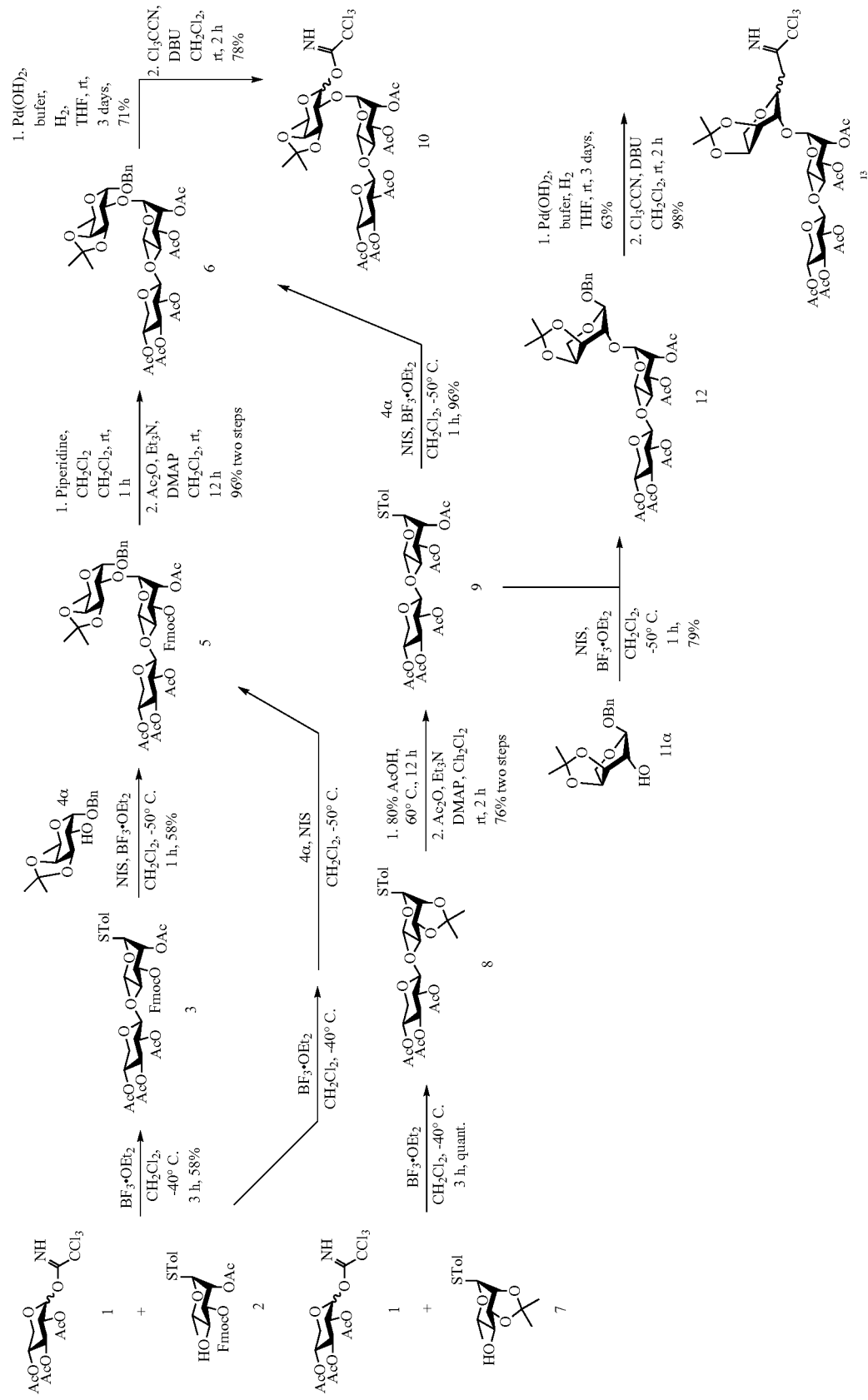

Step 1-2: Synthesis of Tetrasaccharide Donor

Synthesis of tetrasaccharide was achieved by treatment of glucosyl imidate 15 and rhamnoside 14 with TMSOTf resulted in disaccharide 16 with correct β-(1→3) connection in 51% yield (Scheme 2). After hydrolysis of thio group and imidate formation, disaccharide imidate donor 17 was obtained and then subsequently reacted with fucose 4α to afford trisaccharide 18, which was then treated with DDQ to remove PMB function. The resulting trisaccharide acceptor 19 was further conjugated with xylosyl donor 1 to achieve tetrasaccharide 20. After confirming the structure by NMR spectrums, tetrasaccharide 20 was proceeded under hydrogenolysis and imidate formation to furnish tetrasaccharide imidate 21 and 22.

Scheme 2—Depicts Synthesis of Tetrasaccharide and Analogs Thereof

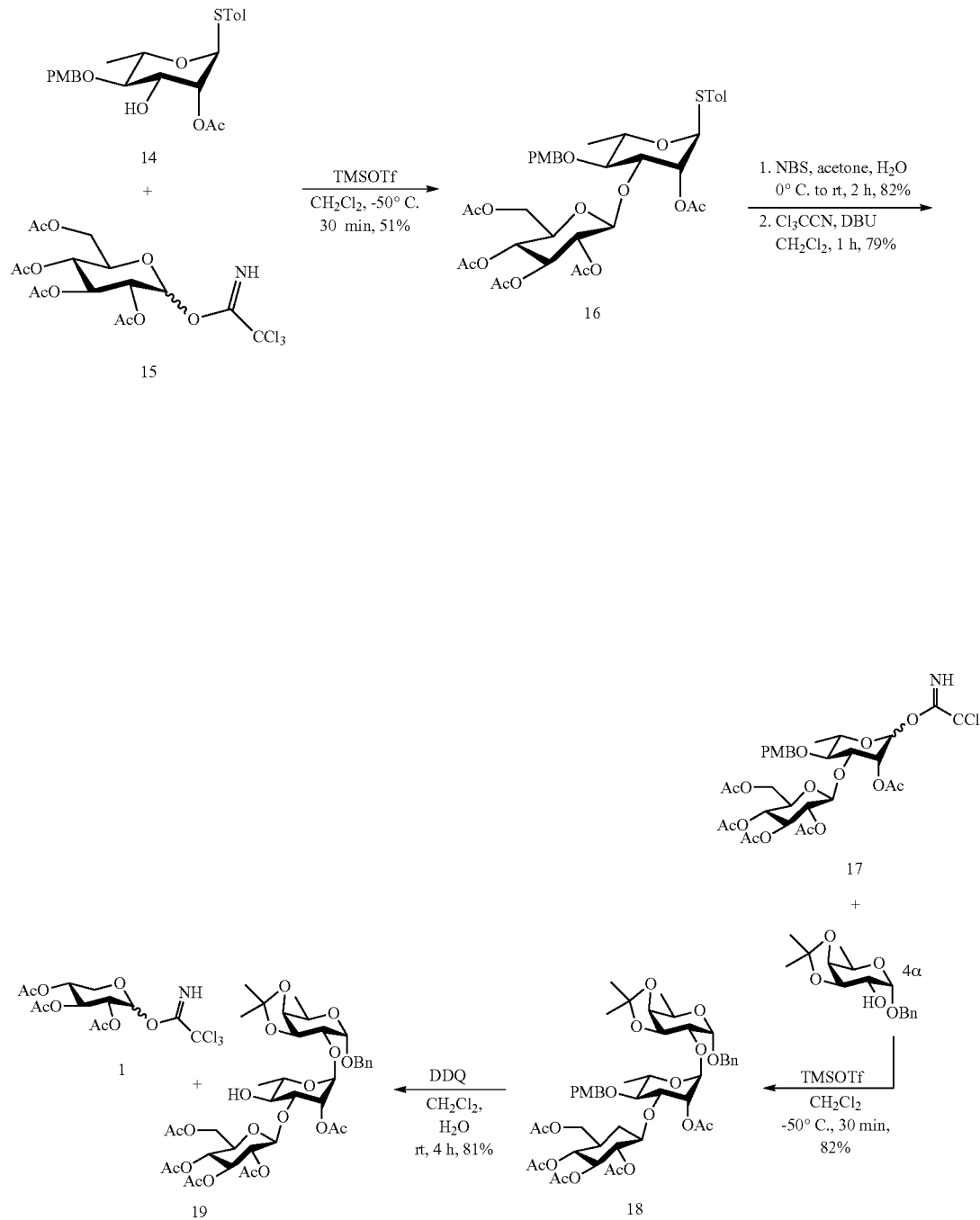

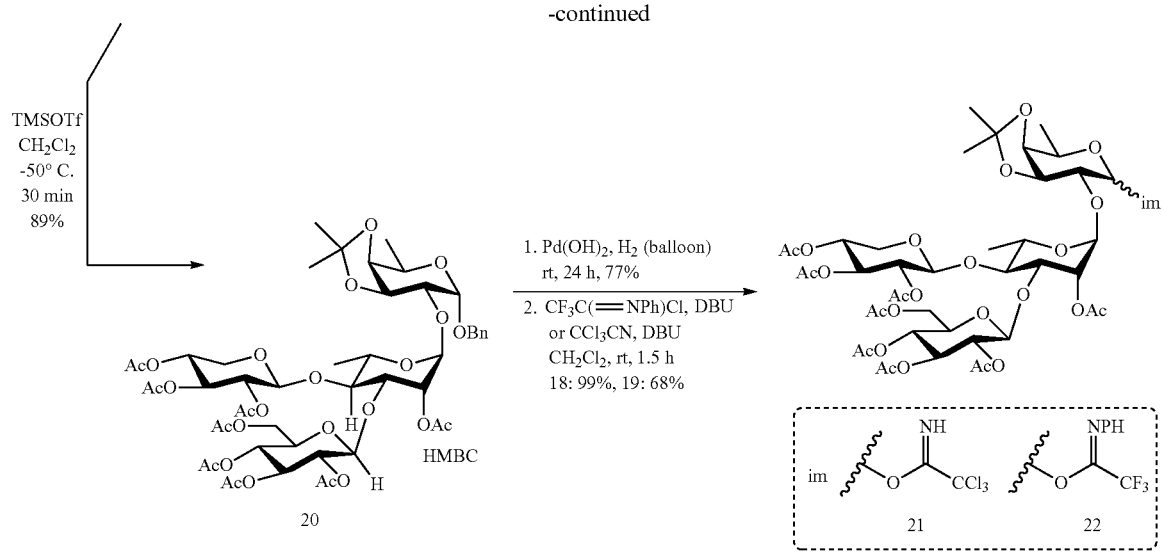

Step 2: Synthesis of Triterpene Building Block

Allylic group was firstly introduced to the C-28 carboxylic acid to afford quillaic ester 20 and echinocystic ester 21 (Scheme 3). In order to improve the selectivity of 3-O glycosylation, the 16-OH group on diol 20 was further protected by triethylsilyl (TES) group through three steps synthesis: selectively 3-O acetylation, TES installation on the 16-OH and then de-acetylation to afford alcohol 22 in 60% over 3 steps.

Scheme 3—Depicts Synthesis of Triterpene Building Block and Analogs Thereof

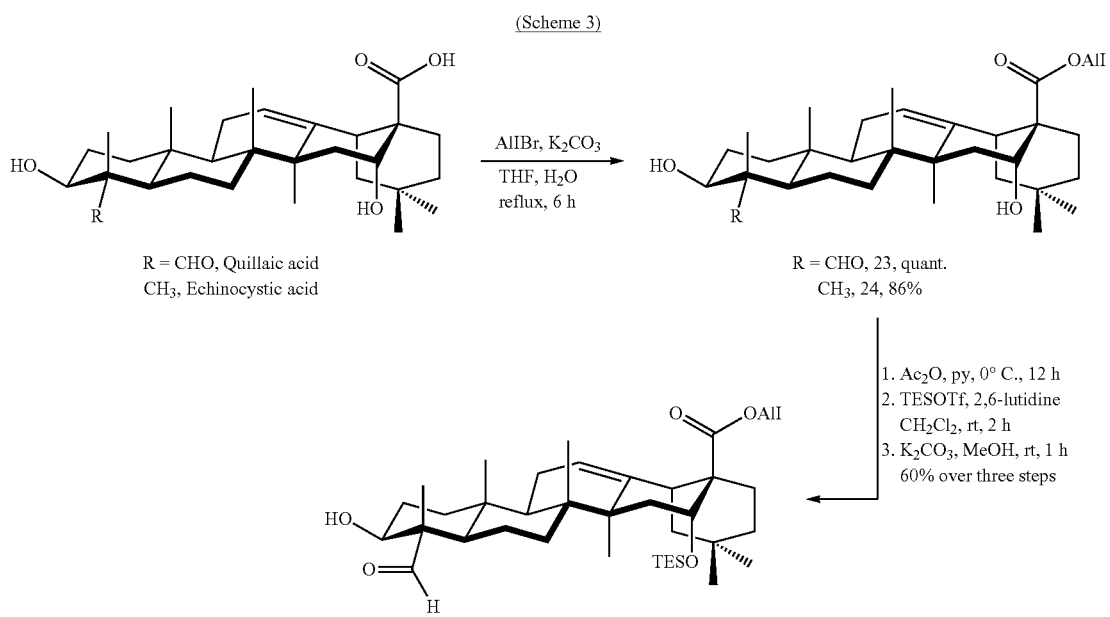

Step 3: Synthesis of Protected Bisdesmosidic Saponins

For the glucuronic acid building blocks, glucuronidie with benzoyl (Bz), isobutyryl (iPrCO) and pivaloyl (Piv) groups were synthesized. (Scheme 4). The reaction of glucoronate bromide 26 and thiotoluene brought thio-glucuronide 27. After that, compound 27 underwent de-acetylation and acylation with benzoyl, isobutyryl and pivaloyl chloride to obtain 28-30. Following by the oxidative removal of thio group and then trichloroacetimidate formation, glucuronate imidates 31-33 readily available to couple with quillaic acid. Coupling of benzoylated donor 31 and quillaic ester 23 was led to an orthoester predominated result. The increase amount of orthoester may resort to the flat conformation 2-O-benzoyl group. Therefore, isobutyrylated glucuronate 32 were introduced to build the barrier adjacent to the carbonyl position. As a result, the orthoester was still dominated in 47% along with the product was isolated in 21%. Even so, this result encouraged us to use a bulkier pivaloyl group. Finally, using pivaloylated donor 33 successfully brought conjugated product 34 in 48% yield with recovery of quillaic ester 23 in 29%. The reaction of echinocystic ester 24 with benzoylated glucoronate 31 was successfully resulted in 72% yield of product 36.

To unmask the C-28 carboxylic acid, firstly the benzoyl, pivaloyl, and methoxy groups were hydrolyzed under basic condition at elevated temperatures. The resulting intermediate was then proceeded under benzylation, and triethylsilylation afford the fully-protected quillaic ester 37 and echinocystic ester 38. Besides, we had noticed that the $^4C_1$ conformation of glucuronate was flipped into $^1C_4$ based on the coupling constant analysis of $^1H$ NMR. The original coupling constant between H-1'-H-2' of glucuronide 34 was dropped off from $J_{H-1'-H-2'}$=7.8 Hz to $J_{H-1'-H-2'}$=4.2 Hz of TES-protected compound 37. This coupling constant shrinking was also observed to the other hydrogens on the glucuronide. To further achieve glucuronide acceptors, the O-allyl ester was hydrolyzed by the catalysis of Pd(OAc)$_2$ under mild acidic environment to give compound 39 and 40. The conjugation of oligosaccharide 13 and glucuronide 39 was performed under the promotion of BF$_3$·OEt$_2$ at −75° C. and 41β was achieved consequently in excellent 94% yield. Coupling of arabinose-containing trisaccharide 13 with quillaic acid 39 brought 42β and 42α in 75% and 16%, respectively. Likewise, the echinocystic ester 43(β) was also obtained in excellent 96% yield by the glycosylation of imidate 10 with echinocystic acid 40. Applying the general coupling condition with tetrasaccharide donor 21 with quillaic acid 39 resulted in products 44 with anomeric ratio β/α~1/1 by TLC analysis. N-phenyl trifluoroacetimidate 22 was utilized afterward; as a result, saponin 44β was successfully achieved in 46% as a major product.

Scheme 4—Demonstrates the Preparation of Compounds 41-44.

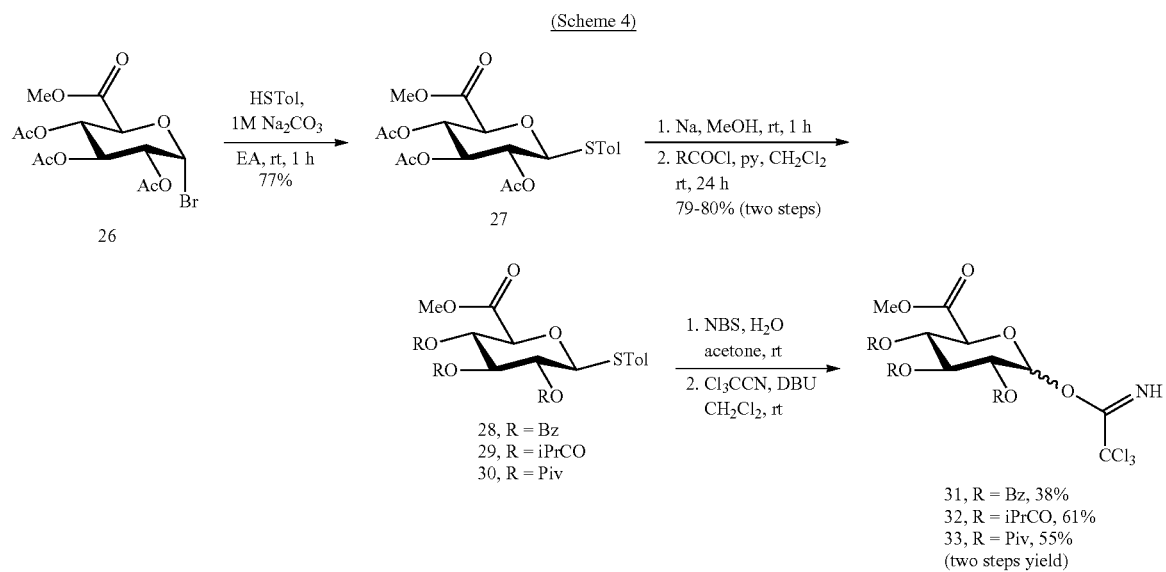

-continued
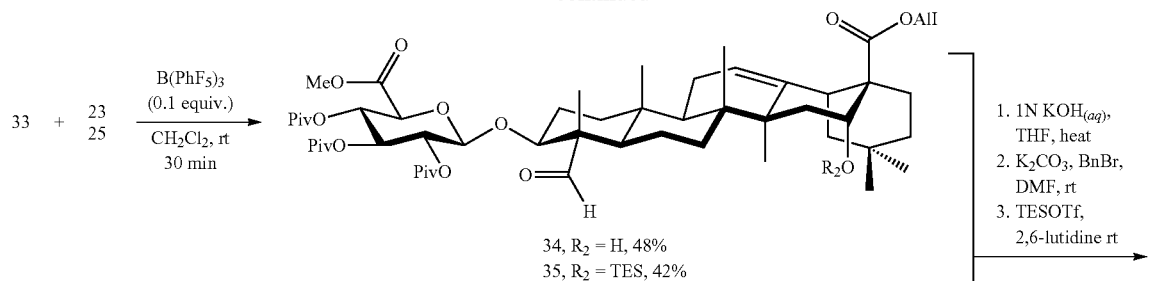
34, R$_2$ = H, 48%
35, R$_2$ = TES, 42%
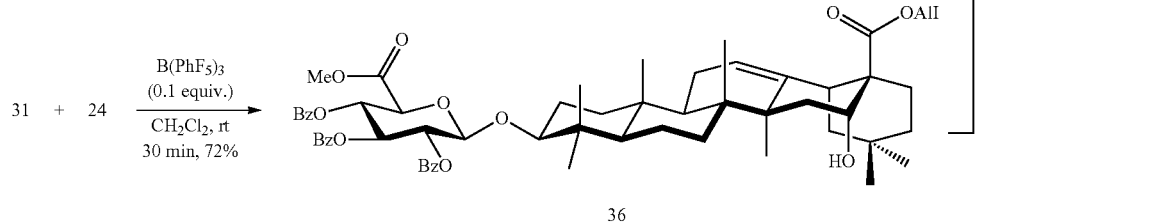
36
1. 1N KOH$_{(aq)}$, THF, heat
2. K$_2$CO$_3$, BnBr, DMF, rt
3. TESOTf, 2,6-lutidine rt
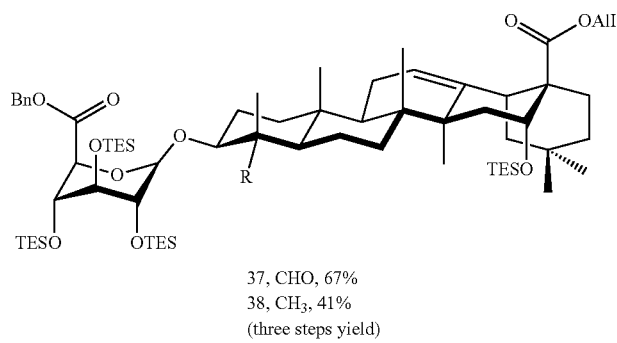
37, CHO, 67%
38, CH$_3$, 41%
(three steps yield)
Pd(OAc)$_2$, PPh$_3$, formic acid
Et$_3$N, 1,4-dioxane, rt
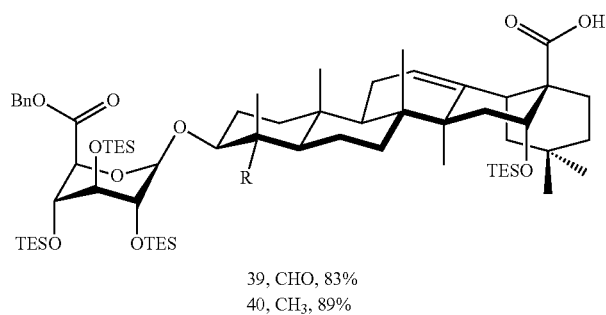
39, CHO, 83%
40, CH$_3$, 89%

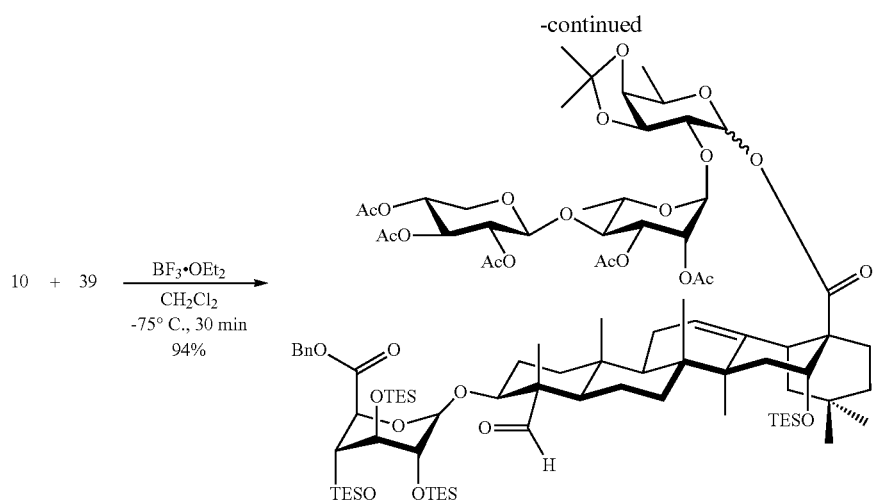
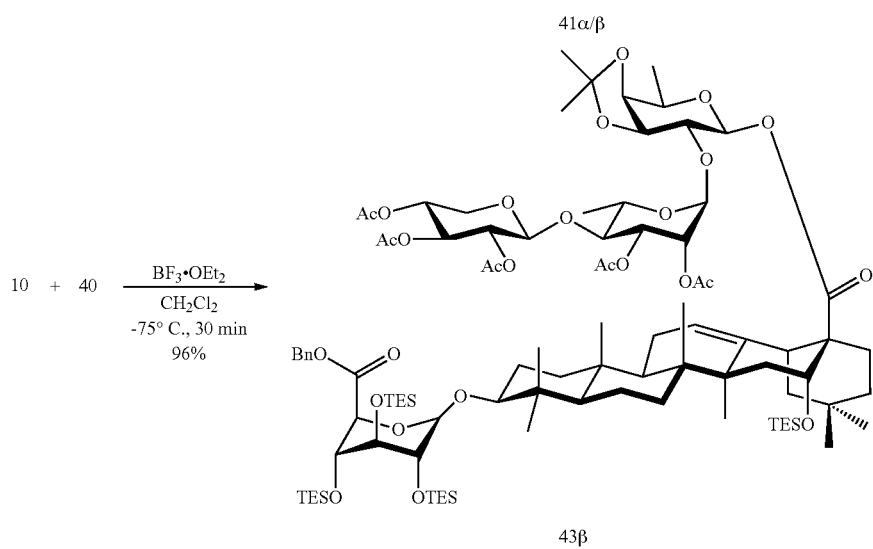
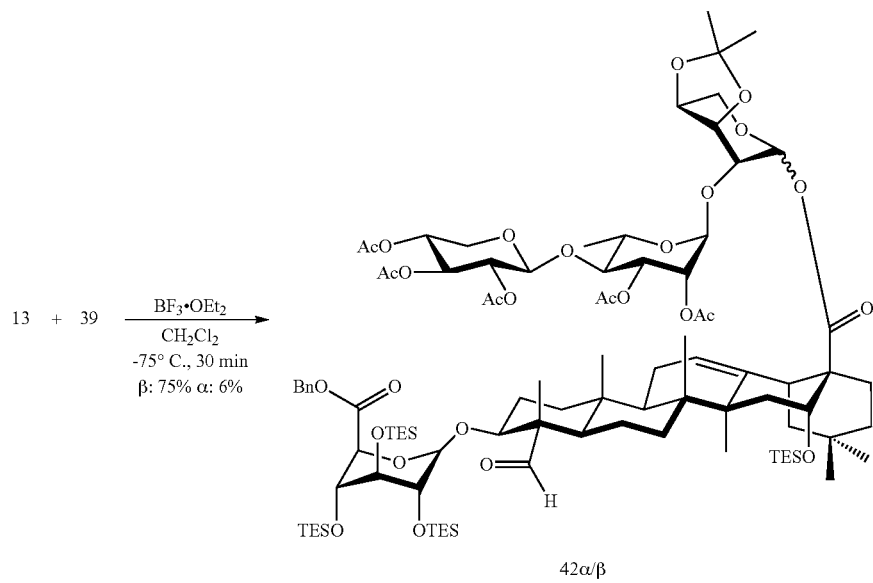

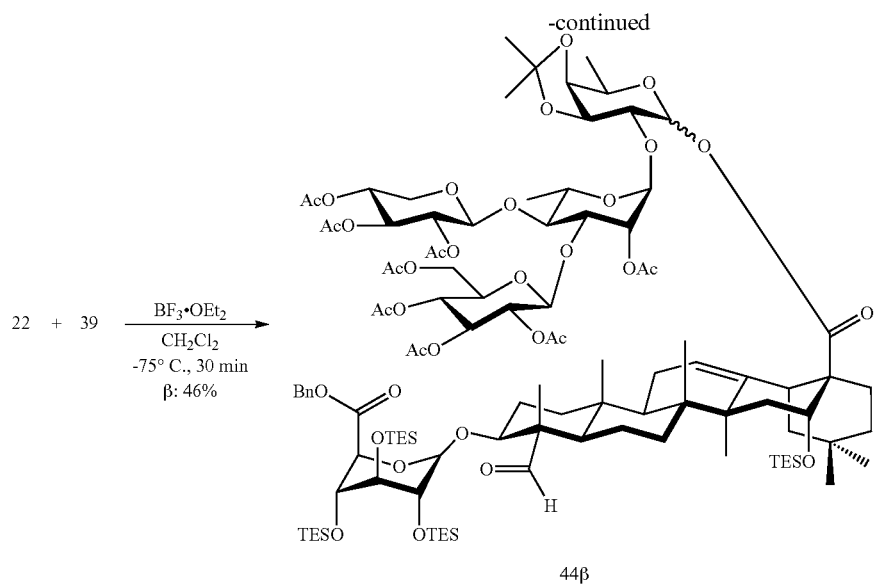

Step 4: Synthesis of Amide Conjugation and Fully Deprotected Saponins

After hydrogenolysis of 41β, the amide bond formation was successively carried out with HBTU/DIPEA coupling system to afford a series of conjugated amides. After that, the products were proceeded under acid hydrolysis and methanolysis to furnish our target saponins. Representative saponins in Scheme 5 contained aliphatic carbon chains in different lengths from methyl to octadecyl, various arylaliphatic, heteroarylalphatic, heterocylaliphatic compounds.

Scheme 5—Demonstrates the Preparation of Formula I According to Embodiments of the Invention

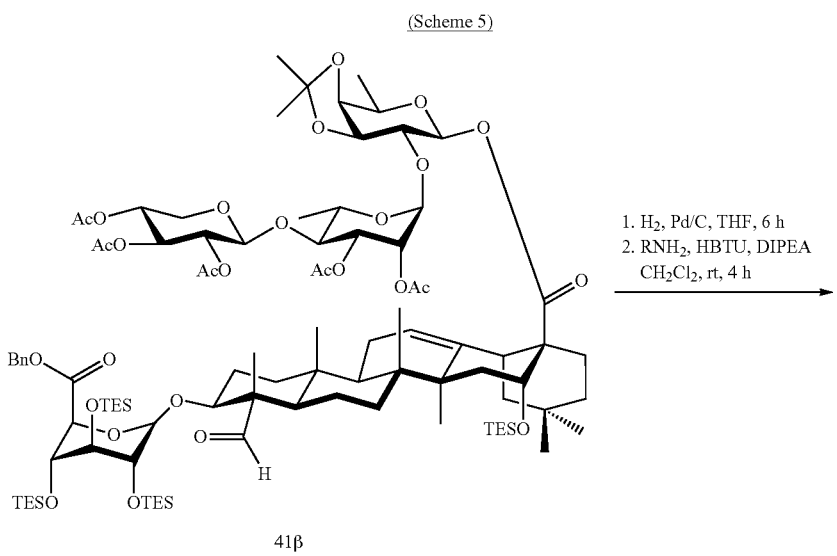

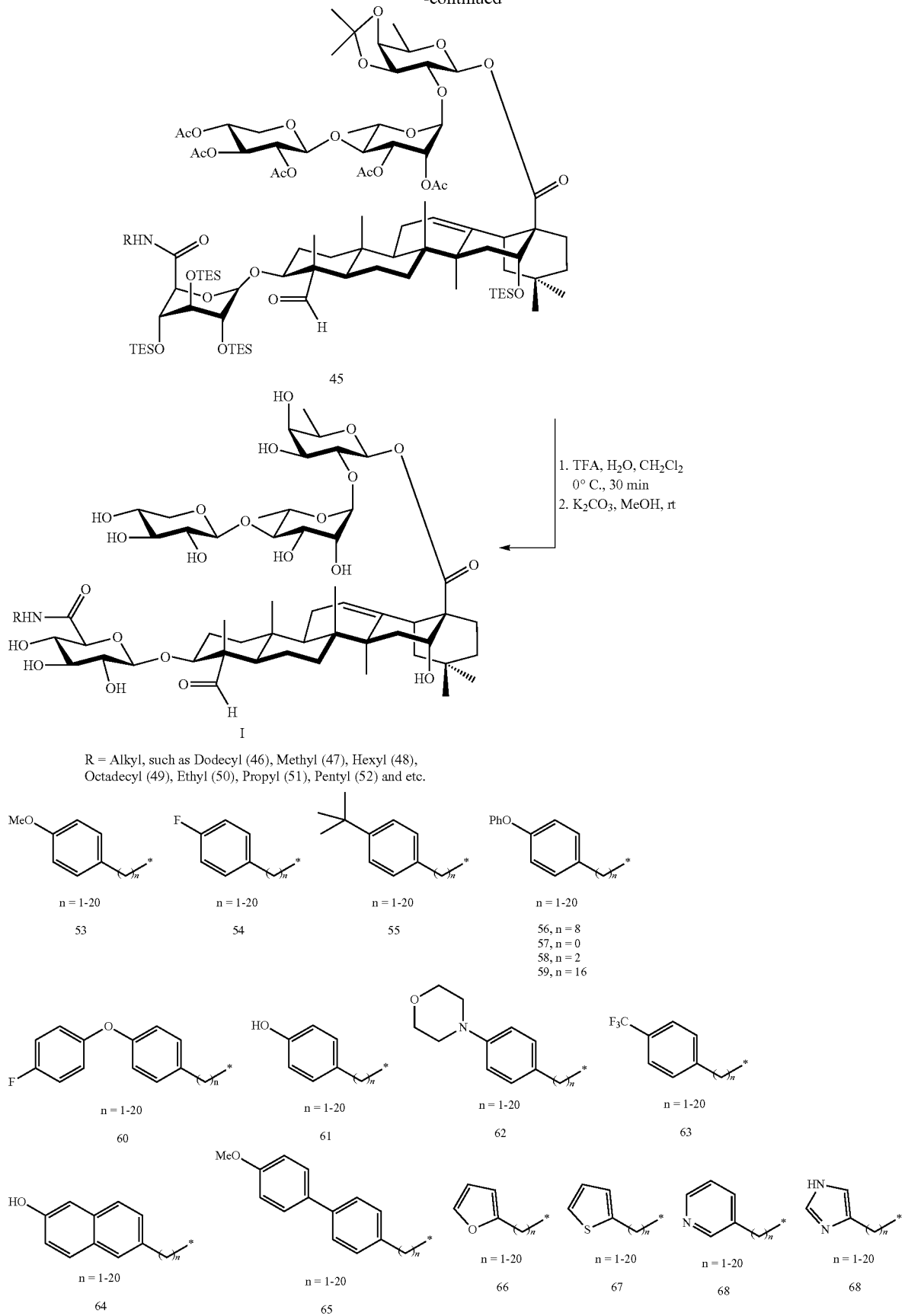

-continued

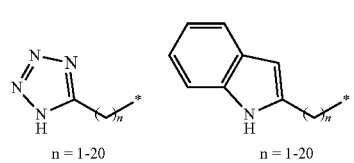

70     71     72     73     74     75

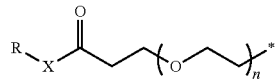

76

Step 5: Synthesis of Saponin Analogues

Synthesis of saponins contained a α-orientated trisaccharide moiety (compound 56α, Scheme 6). Replacing D-fucose by L-arabinose gave saponins 77α/β anomers. Echinocystic ester 78 was synthesized and b-linked tetrasaccharide ester 79 was also conducted.

Scheme 6—Demonstrates the Preparation of Saponin Analogues, According to Embodiments of the Invention

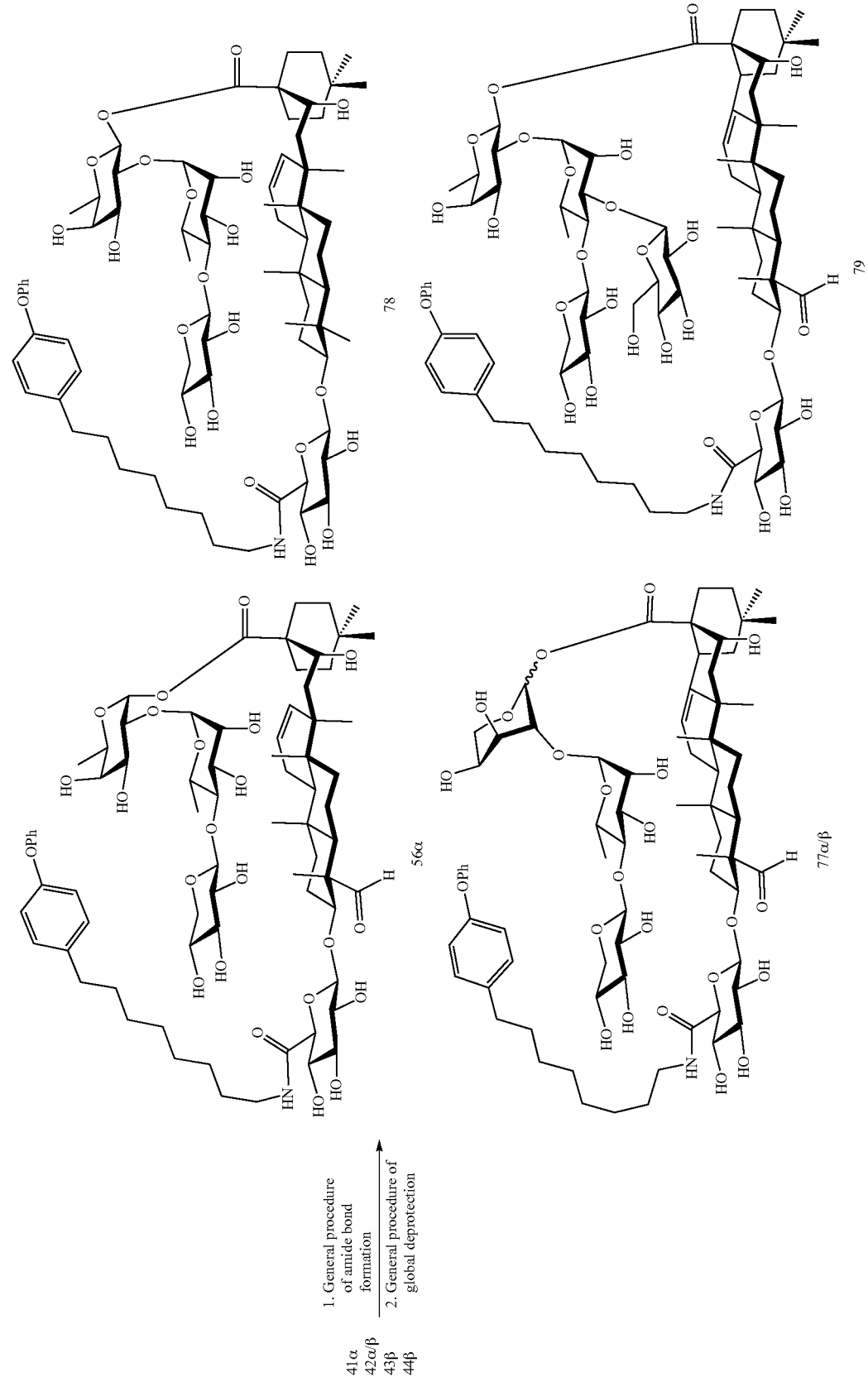

Vaccine Composition

Another aspect of the present application relates to a vaccine composition comprising an antigen and the saponin analogue of the present application as an adjuvant. In some embodiments, the vaccine composition further comprises additional adjuvants.

The vaccine compositions of the present application are useful as vaccines to induce active immunity towards antigens in subjects. Any animal that may experience the beneficial effects of the compositions of the present invention within the scope of subjects that may be treated. In some embodiments, the subjects are mammals. In some embodiments, the subjects are humans.

The administration of the vaccine (or the antisera which it elicits) may be for either a "prophylactic" or "therapeutic" purpose. The prophylactic administration of the vaccine(s) serves to prevent or attenuate any subsequent presentation of the disease. When provided prophylactically, the vaccine(s) are provided in advance of any symptoms of disease. When provided therapeutically, the vaccine(s) is provided upon or after the detection of symptoms which indicate that an animal may be infected with a pathogen or have a certain cancer. The therapeutic administration of the vaccine(s) serves to attenuate any actual disease presentation. Thus, the vaccines may be provided either prior to the onset of disease proliferation or after the initiation of an actual proliferation.

Thus, in one aspect the present invention provides vaccines comprising one or more bacterial, viral, protozoal, or tumor-related antigens in combination with one or more inventive compounds. In some embodiments, the vaccine comprises a single bacterial, protozoal, viral, or tumor-related antigen in combination with one inventive compound. In some embodiments, the vaccine comprises two or more bacterial, viral, protozoal, or tumor-related antigens in combination with a single inventive compound. In some embodiments, the vaccine comprises a single bacterial, viral, protozoal, or tumor-related antigen in combination with two or more inventive compounds.

In some embodiments, one or more antigens of provided vaccines are bacterial antigens. In certain embodiments, the bacterial antigens are antigens associated with a bacterium selected from the group consisting of *Bordetella pertussis, Bordetella parapertussis, Bordetella bronchiseptica, Borrelia burgdorferi, Borrelia* spp., *Chlamydia trachomatis, Helicobacter pylori, Chlamydia pneumoniae, Ureaplasma urealyticum, Mycoplasma pneumoniae, Staphylococcus* spp., *Staphylococcus aureus, Streptococcus pyogenes, Streptococcus* spp., *Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Campylobacter* spp., *Campylobacter jejuni, Clostridium* spp., *Clostridium difficile, Corynebacterium diphtheria, Mycobacterium* spp., *Mycobacterium tuberculosis, Pseudomonas aeruginosa, Treponema* spp., *Leptospria* spp., *Hemophilus ducreyi, hemophilus* influenza, *Escherichia coli, Shigella* spp., *Erlichia* spp., *Rickettsia* spp. and combinations thereof.

In certain embodiments, one or more antigens of provided vaccines are viral-associated antigens. In certain embodiments, the viral-associated antigens are antigens associated with a virus selected from the group consisting of influenza viruses, parainfluenza viruses, mumps virus, adenoviruses, respiratory syncytial virus, Epstein-Barr virus, rhinoviruses, polioviruses, coxsackieviruses, echo viruses, rubeola virus, rubella virus, varicell-zoster virus, herpes viruses, herpes simplex virus, parvoviruses, cytomegalovirus, hepatitis viruses, human papillomavirus, alphaviruses, flaviviruses, bunyaviruses, rabies virus, arenaviruses, filoviruses, HIV 1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, coronavirus, dengue virus, Favivirus and combinations thereof.

In certain embodiments, one or more antigens of provided vaccines are tumor-associated antigens. In some embodiments, the tumor-associated antigens are antigens selected from the group consisting of killed tumor cells and lysates thereof, MAGE-1, MAGE-3 and peptide fragments thereof; human chorionic gonadotropin and peptide fragments thereof; carcinoembryonic antigen and peptide fragments thereof, alpha fetoprotein and peptide fragments thereof; pancreatic oncofetal antigen and peptide fragments thereof; prostate-specific antigens and peptide fragments thereof; MUC-1 and peptide fragments thereof, CA 125, CA 15-3, CA 19-9, CA 549, CA 195 and peptide fragments thereof; prostate-specific membrane antigen and peptide fragments thereof; squamous cell carcinoma antigen and peptide fragments thereof; ovarian cancer antigen and peptide fragments thereof; pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein $p210^{BCR-ABL}$, STn, Tn, Lewis$^x$, Lewis$^y$, TF, GM1, GM2, GD2, GD3, Gb3, KH-1, Globo-H, SSEA-4; and mixtures thereof.

As described above, provided compounds may be used in cancer vaccines as adjuvants in combination with tumor-associated antigens. In certain embodiments, vaccines may be used in the treatment or prevention of tumors. In certain embodiments, the tumor is a benign neoplasm. In other embodiments, the tumor is a malignant neoplasm. Any cancer may be treated using compounds of the invention with an antigen.

Another aspect of the present application relates to methods for immunizing a subject with the vaccine composition of the present application.

Formulations

The saponin analogues of the present application may be combined with a pharmaceutically acceptable excipient to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the present invention include those suitable for oral, nasal, topical, rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

The preparations of the present application may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

Regardless of the route of administration selected, the saponin analogues of the present application, which may be used in a suitable hydrated form, and/or the pharmaceutical compositions of the present invention, are formulated into pharmaceutically-acceptable dosage forms by conventional methods known to those of skill in the art. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

EXAMPLES

The following examples are provided to illustrate certain aspects of the present invention and to aid those of skill in the art in practicing the invention. These examples are not intended to limit the scope of the invention.

All reagents and solvents were reagent grade and used without further purification, unless otherwise stated. Molecular sieves were activated at 200° C. prior to use.

Reaction progress was monitored by analytical TLC on 0.25 mm Merck Millipore silica gel 60 $F_{254}$ using p-anisaldehyde, ninhydrin, and ceriumammonium molybdate as visualizing agents. Flash column chromatography was performed employing 230-400 mesh silica gel.

Instrument

NMR spectra were acquired by using Bruker-AV-400 (400 MHz) and Bruker-AV-600 (600 MHz). Chemical shifts (δ) are given in ppm relative to $^1$H: 7.26 ppm, $^{13}$C: 77.0 ppm for CDCl$_3$; $^1$H: 3.31 ppm, $^{13}$C: 49.0 ppm for CD$_3$OD. Splitting patterns are reported as s (singlet), d (doublet), t (triplet), q (quartet) and m (multiplet). Coupling constants (J) are given in Hertz (Hz). Reverse phase HPLC purification and analyses were carried out on a HITACHI D-2000 Elite HPLC system equipped with autosampler L-2200, UV detector L-2420 and pump L-2130 or a SHIMADZU HPLC system equipped with system controller CBM-20A, photodiode array detector SPD-M20A, pump LC-20AT and autosampler SIL-20AHT. Exact mass measurements were performed on VG platform electrospray ESI/MS or BioTOF II.

Synthetic Example I

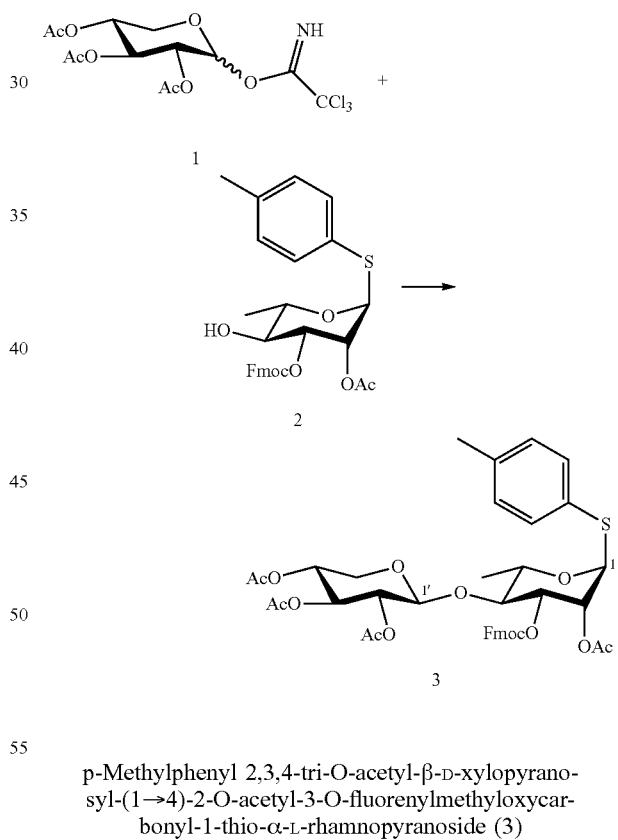

p-Methylphenyl 2,3,4-tri-O-acetyl-β-D-xylopyranosyl-(1→4)-2-O-acetyl-3-O-fluorenylmethyloxycarbonyl-1-thio-α-L-rhamnopyranoside (3)

To a stirred suspension of 1 (137 mg, 0.33 mmol), 2 (87 mg, 0.16 mmol), and activated 4 Å molecular sieve powder in anhydrous CH$_2$Cl$_2$ (1.6 mL) was added BF$_3$·OEt$_2$ (ca. 48%, 11 µL, 0.08 mmol) under N$_2$ atmosphere at −40° C. Upon completion of the reaction after 3 h, the mixture was quenched by addition of saturated NaHCO$_3$ and then warmed to rt. The resulting mixture was dried over MgSO$_4$ and concentrated under reduced pressure. The residue was purified by column chromatography (silica gel; EtOAc/hexanes=1/4 to 1/2) to give 3 (75 mg, 58%) as a colorless syrup: $R_f$ 0.36 (EtOAc/hexanes=1/2); $^1$H NMR (600 MHz, CDCl$_3$) δ 7.78 (d, J=7.5 Hz, 2H), 7.64 (dd, J=19.0, 7.4 Hz, 2H), 7.45-7.41 (m, 2H), 7.39-7.34 (m, 4H), 7.12 (d, J=8.0 Hz, 2H), 5.54 (dd, J=3.4, 1.4 Hz, 1H, H-2), 5.33 (d, J=1.4 Hz, 1H, H-1), 5.21 (t, J=9.4 Hz, 1H, H-3'), 5.08 (dd, J=9.6, 3.4 Hz, 1H, H-3), 4.99 (td, J=9.4, 5.4 Hz, 1H, H-4'), 4.95 (dd, J=9.4, 7.6 Hz, 1H, H-2'), 4.79 (d, J=7.6 Hz, 1H, H-1'), 4.57 (dd, J=13.4, 10.1 Hz, 1H, Fmoc C$\underline{H}_2$), 4.35-4.31 (m, 2H, Fmoc C$\underline{H}_2$ and C$\underline{H}$), 4.28-4.25 (m, 1H, H-5), 4.14 (dd, J=11.8, 5.4 Hz, 1H, H-5$_a$'), 3.84 (t, J=9.5 Hz, 1H, H-4'), 3.40 (dd, J=11.8, 9.5 Hz, 1H, H-5$_b$'), 2.33 (s, 3H), 2.16 (s, 3H), 2.05 (s, 3H), 2.03 (s, 3H), 1.91 (s, 3H), 1.35 (d, J=6.2 Hz, 3H, H-6); $^{13}$C NMR (151 MHz, CDCl$_3$) δ 167.0, 169.9, 169.8, 169.5, 154.0, 143.4, 143.1, 141.3, 141.2, 138.2, 132.6, 129.9, 129.3, 128.0, 127.3, 125.2, 125.0, 120.1, 120.0, 100.8 (C-1'), 85.8 (C-1), 76.1 (C-3), 75.9 (C-4), 72.2 (C-3'), 71.3 (C-2'), 71.2 (C-2), 70.6 (Fmoc C$\underline{H}_2$), 69.3 (C-4'), 68.1 (C-5), 62.5 (C-5'), 46.6 (Fmoc C$\underline{H}$), 21.1, 20.9, 20.7, 20.7, 20.5, 17.5 (C-6) ppm; HRMS (ESI-TOF) calcd. for C$_{41}$H$_{44}$O$_{14}$SNa [M+Na]$^+$ 815.2349, found 815.2352.

mixture was warmed to rt, stirred for 1 h and then filtered. Filtrate was diluted with CH$_2$Cl$_2$, washed by 10% Na$_2$S$_2$O$_3$ $_{(aq.)}$, saturated NaHCO$_3$, brine, dried over MgSO$_4$, and then concentrated under reduced pressure. The residue was purified by column chromatography (silica gel; EtOAc/CH$_2$Cl$_2$/hexanes=1/1/6 to 1/1/4) to give 5 (2.00 g, 58%) as a white foam: $R_f$ 0.44 (EtOAc/CH$_2$Cl$_2$/hexanes=1/1/2); $^1$H NMR (600 MHz, CDCl$_3$) δ 7.78 (d, J=7.5 Hz, 2H), 7.67 (d, J=7.4 Hz, 1H), 7.63 (d, J=7.5 Hz, 1H), 7.42 (t, J=7.4 Hz, 2H), 7.42 (t, J=7.4 Hz, 2H), 7.39-7.27 (m, 5H), 5.50-5.46 (m, 1H, H-2'), 5.19 (t, J=9.2 Hz, 1H, H-3"), 5.12-5.10 (m, 2H, H-1', H-3'), 4.99 (td, J=9.2, 5.5 Hz, 1H, H-4"), 4.94 (dd, J=9.2, 7.6 Hz, 1H, H-2"), 4.82 (d, J=3.5 Hz, 1H, H-1), 4.77 (d, J=7.5 Hz, 1H, H-1"), 4.71 (d, J=12.3 Hz, 1H, Bn C$\underline{H}_2$), 4.60-4.51 (m, 2H, Bn C$\underline{H}_2$, Fmoc C$\underline{H}_2$), 4.37-4.31 (m, 2H, H-3, Fmoc C$\underline{H}$), 4.28 (dd, J=10.0, 8.1 Hz, 1H, Fmoc C$\underline{H}_2$), 4.17-4.09 (m, 2H, H-5, H-5$_a$"), 4.02 (dd, J=5.3, 2.4 Hz, 1H, H-4), 3.76 (dd, J=8.1, 3.5 Hz, 1H, H-2), 3.72 (t, J=9.6 Hz, 1H, H-4'), 3.65-3.60 (m, 1H, H-5'), 3.40 (dd, J=11.6, 9.7 Hz, 1H, H-5$_b$"), 2.18 (s, 3H), 2.05 (s, 3H), 2.01 (s, 3H), 1.86 (s, 3H), 1.50 (s, 3H), 1.34 (d, J=6.7 Hz, 3H, H-6), 1.32 (s, 3H), 1.18 (d, J=6.2 Hz, 3H, H-6'); HRMS (ESI-TOF) calcd. for C$_{50}$H$_{58}$O$_{19}$Na [M+Na]$^+$ 985.3463, found 985.3476.

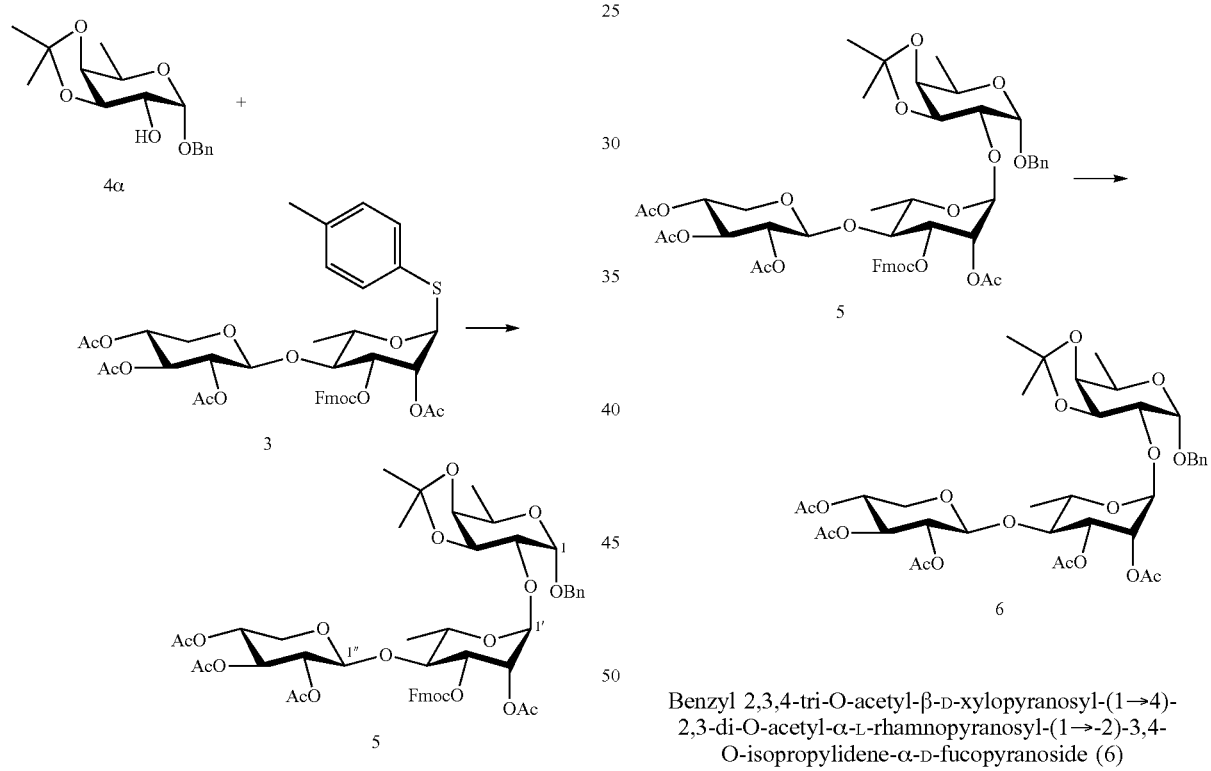

Benzyl 2,3,4-tri-O-acetyl-β-D-xylopyranosyl-(1→4)-2-O-acetyl-3-O-fluorenylmethyloxycarbonyl-α-L-rhamnopyranosyl-(1→2)-3,4-O-isopropylidene-α-D-fucopyranoside (5)

To a stirred suspension of 4a (1.05 g, 3.57 mmol), 3 (3.40 g, 4.28 mmol), and activated 4 Å molecular sieve powder in anhydrous CH$_2$Cl$_2$ (2 mL) was added NIS (1.12 g, 4.99 mmol) and BF$_3$·OEt$_2$ (0.38 mL, 1.42 mmol) under N$_2$ atmosphere at −50° C. Upon completion of the reaction after 1 h, the reaction was quenched by addition of saturated NaHCO$_3$ and 10% Na$_2$S$_2$O$_3$ aqueous solution. The reaction Benzyl 2,3,4-tri-O-acetyl-β-D-xylopyranosyl-(1→4)-2,3-di-O-acetyl-α-L-rhamnopyranosyl-(1→2)-3,4-O-isopropylidene-α-D-fucopyranoside (6)

To a stirred suspension of 5 (100 mg, 0.10 mmol) in CH$_2$Cl$_2$ (5 mL) was added morpholine (0.5 mL) at rt. Upon completion of the reaction after 1.5 h, the reaction mixture was diluted with CH$_2$Cl$_2$, washed by saturated NH$_4$Cl, saturated NaHCO$_3$, brine, dried over MgSO$_4$, and then concentrated under reduced pressure. The residue was purified by column chromatography (silica gel; EtOAc/hexanes=1/1 to 3/2) to give Fmoc-deprotected product (72 mg, 95%). To a stirred solution of Fmoc-deprotected product (462 mg, 0.48 mmol) in anhydrous CH$_2$Cl$_2$ (10 mL) was added Ac$_2$O (91 μL, 0.96 mmol), Et$_3$N (201 μL, 1.4 mmol) and DMAP (6 mg, 0.048 mmol) under N$_2$ atmosphere at rt. Upon completion of the reaction after 2 h, the reaction was diluted with CH$_2$Cl$_2$, washed by H$_2$O, brine, dried over MgSO$_4$, and them concentrated under reduced pressure. The residue was purified by column chromatography (silica gel; EtOAc/hexanes=2/3) to give 6 (391 mg, 96%) as a white foam: R$_f$ 0.48 (EtOAc/hexanes=1/1); $^1$H NMR (600 MHz, CDCl$_3$) δ 7.38-7.27 (m, 5H), 5.32 (dd, J=3.5, 1.6 Hz, 1H, H-2'), 5.26 (dd, J=9.3, 3.5 Hz, 1H, H-3'), 5.13 (t, J=9.3 Hz, 1H, H-3"), 5.05 (d, J=1.5 Hz, 1H, H-1'), 4.96 (td, J=9.3, 5.4 Hz, 1H, H-4"), 4.91-4.87 (dd, J=9.3, 7.6 Hz, 1H, H-2"), 4.80 (d, J=3.6 Hz, 1H, H-1), 4.71 (d, J=12.3 Hz, 1H, Bn C$\underline{H}_2$), 4.63 (d, J=7.6 Hz, 1H, H-1"), 4.54 (d, J=12.3 Hz, 1H, Bn C$\underline{H}_2$), 4.34 (dd, J=8.1, 5.4 Hz, 1H, H-3), 4.14 (qd, J=6.7, 2.5 Hz, 1H, H-5), 4.10 (dd, J=11.7, 5.4 Hz, 1H, H-5$_a$"), 4.02 (dd, J=5.4, 2.5 Hz, 1H, H-4), 3.74 (dd, J=8.1, 3.6 Hz, 1H, H-2), 3.62-3.54 (m, 2H, H-4', H-5'), 3.33 (dd, J=11.7, 9.5 Hz, 1H, H-5$_b$"), 2.13 (s, 3H), 2.08 (s, 3H), 2.03 (s, 3H), 2.01 (s, 6H), 1.49 (s, 3H), 1.34 (d, J=6.7 Hz, 3H, H-6), 1.32 (s, 3H), 1.14 (d, J=5.6 Hz, 3H, H-6') ppm; HRMS (ESI-TOF) calcd. for C$_{37}$H$_{50}$O$_{18}$Na [M+Na]$^+$ 805.2889, found 805.2898.

raphy (silica gel; EtOAc/hexanes=1/1 to 3/2, contained 0.5% Et$_3$N) to afford 10 (34 mg, 78%) as a yellow syrup. 10a: R$_f$ 0.46 (EtOAc/hexanes=1/1); $^1$H NMR (600 MHz, CDCl$_3$) δ 8.67 (s, 1H), 6.30 (d, J=3.5 Hz, 1H, H-1), 5.24 (dd, J=3.3, 1.8 Hz, 1H, H-2'), 5.14-5.08 (m, 2H, H-3', H-3"), 5.03 (d, J=1.8 Hz, 1H, H-1'), 4.93 (td, J=9.4, 5.4 Hz, 1H, H-4"), 4.86 (dd, J=9.4, 7.7 Hz, 1H, H-2"), 4.58 (d, J=7.7 Hz, 1H, H-1"), 4.40 (dd, J=7.8, 5.4 Hz, 1H, H-3), 4.32 (qd, J=6.7, 2.5 Hz, 1H, H-5), 4.12-4.07 (m, 2H, H-5$_a$", H-4), 3.91 (dd, J=7.8, 3.5 Hz, 1H, H-2), 3.81 (dq, J=9.6, 6.2 Hz, 1H, H-5'), 3.60 (t, J=9.6 Hz, 1H, H-4'), 3.31 (dd, J=11.7, 9.7 Hz, 1H, H-5$_b$"), 2.13 (s, 3H), 2.03 (s, 3H), 2.02 (s, 3H), 2.00 (s, 3H), 1.95 (s, 3H), 1.52 (s, 3H), 1.38 (d, J=6.7 Hz, 3H, H-6), 1.34 (s, 3H), 1.28 (d, J=6.2 Hz, 3H, H-6').

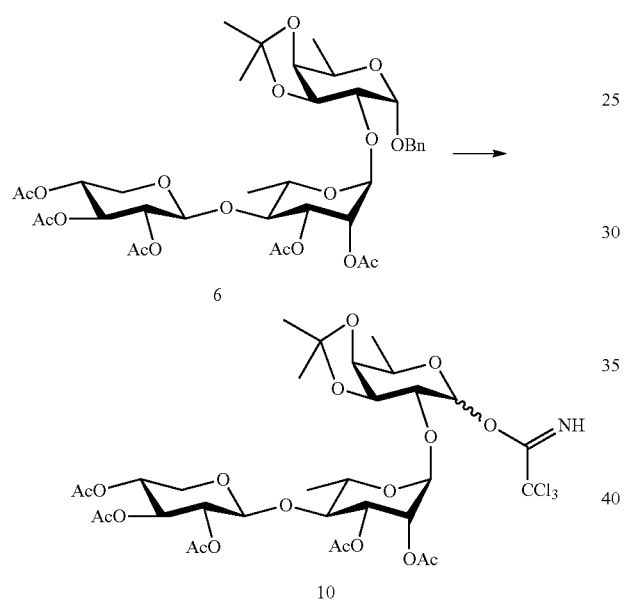

Trichloroacetimidoyl 2,3,4-Tri-O-acetyl-β-D-xylopyranosyl-(1→4)-2,3-di-O-acetyl-α-L-rhamnopyranosyl-(1→2)-3,4-O-isopropylidene-α/β-D-fucopyranoside (10)

To a suspension of 6 (1.26 g, 1.6 mmol) and 10% Pd/C (0.2 g) in phosphate buffer (100 mM Na$_2$HPO$_4$/NaH$_2$PO$_4$ (aq.), pH=7.0)/THF/MeOH=1/1/4 (30 mL) was stirred at rt under H$_2$ (balloon) atmosphere. After being stirred for 3 days, the mixture was filtered through celite and concentrated under reduced pressure. The residue diluted by CH$_2$Cl$_2$, washed by H$_2$O, brine, dried over MgSO$_4$, concentrated, and then purified by column chromatography (silica gel; EtOAc/hexanes=1/1 to 3/2) to afford hemiacetal (0.79 g, 71%) as a colorless syrup. To a stirred solution of hemiacetal (36 mg, 0.48 mmol) in anhydrous CH$_2$Cl$_2$ (1 mL) was added Cl$_3$CCN (16 μL, 0.16 mmol) and DBU (3 μL, 0.021 mmol) at rt under N$_2$ atmosphere. After being stirred for 1.5 h, the reaction was complete as indicated by TLC analysis, the mixture was concentrated under reduced pressure. The residue was purified by flash column chromatogp-Methylphenyl 2,3,4-tri-O-acetyl-β-D-xylopyranosyl-(1→4)-2,3-di-O-acetyl-1-thio-α-L-rhamnopyranoside (9)

To a stirred solution of 8 (4.6 g, 8.1 mmol) in 80% AcOH (100 mL) was heated to 60° C. for 12 h. The resulting mixture was evaporated and then azeotropic distilled with toluene (50 mL) twice under reduced pressure. After drying by high vacuum, the crude syrup was treated with Ac$_2$O (2.2 mL, 23 mmol), Et$_3$N (5.2 mL, 38 mmol) and DMAP (9 mg, 0.074 mmol) in CH$_2$Cl$_2$ under N$_2$ atmosphere at rt. Upon completion of the reaction after 2 h, the mixture was diluted with CH$_2$Cl$_2$, washed by H$_2$O, brine, dried over MgSO$_4$ and then concentrated under reduced pressure. The residue was purified by column chromatography (silica gel; EtOAc/hexanes=2/3) to give 9 (3.8 g, 76%) as a white solid: R$_f$ 0.19 (EtOAc/hexanes=1/2); $^1$H NMR (400 MHz, CDCl$_3$) δ 7.34 (d, J=7.9 Hz, 2H), 7.11 (d, J=7.8 Hz, 2H), 5.39 (brs, 1H, H-2), 5.26 (brs, 1H, H-1), 5.22 (dd, J=9.6, 3.1 Hz, 1H, H-3), 5.14 (t, J=9.2 Hz, 1H, H-3'), 5.00-4.93 (m, 1H, H-4'), 4.90 (dd, J=9.2, 7.6 Hz, 1H, H-2'), 4.66 (d, J=7.6 Hz, 1H, H-1'), 4.24 (dq, J=9.6, 6.1 Hz, 1H, H-5), 4.12 (dd, J=11.6, 5.3 Hz, 1H, H-5$_a$'), 3.72 (t, J=9.6 Hz, 1H, H-4), 3.39-3.30 (m, 1H, H-5$_b$'), 2.31 (s, 3H), 2.11 (s, 3H), 2.09 (s, 3H), 2.03 (s, 3H), 2.02 (s, 6H, Ac×2), 1.31 (d, J=6.1 Hz, 3H) ppm; HRMS (ESI-TOF) calcd. for C$_{28}$H$_{36}$O$_{13}$SNa [M+Na]$^+$ 635.1769, found 635.1774.

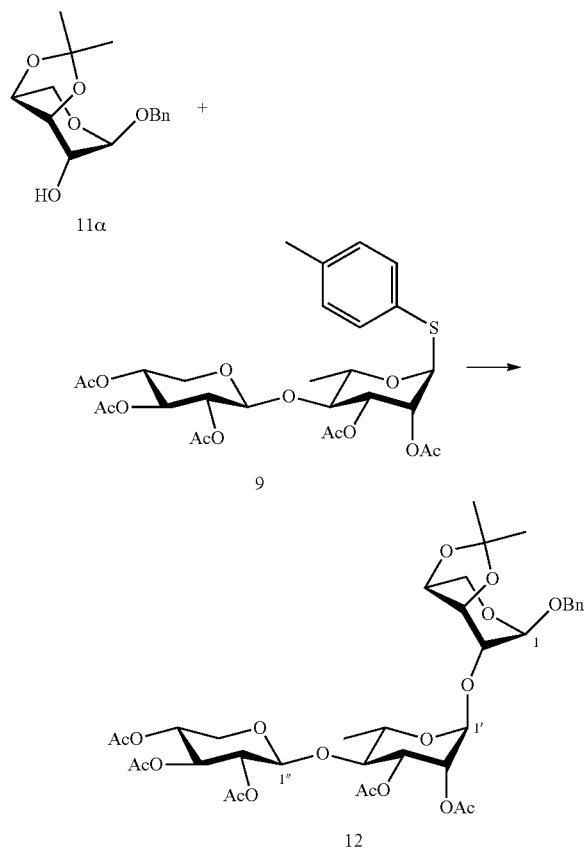

9

12

Benzyl 2,3,4-tri-O-acetyl-β-D-xylopyranosyl-(1→4)-2,3-di-O-acetyl-α-L-rhamnopyranosyl-(1-2)-3,4-O-isopropylidene-β-L-arabinopyranoside (12)

To a stirred suspension of 9 (500 mg, 0.82 mmol), 11a (190 mg, 0.68 mmol) and activated 4 Å molecular sieve powder in anhydrous $CH_2Cl_2$ (7 mL) was added NIS (0.23 g, 1.0 mmol) and TMSOTf (12 μL, 0.066 mmol) at −50° C. under $N_2$ atmosphere. Upon completion of the reaction after 0.5 h, the reaction was quenched by addition of $Et_3N$, saturated $NaHCO_3$ and 10% $Na_2S_2O_3$ aqueous solution. After warming and stirring at rt for 1 h, the reaction mixture was filtered, diluted with $CH_2Cl_2$, washed by 10% $Na_2S_2O_3$ aqueous solution, saturated $NaHCO_3$, brine, dried over $MgSO_4$, and concentrated under reduced pressure. The residue was purified by column chromatography (silica gel; EtOAc/hexanes=2/3 to 1/1) to give 12 (412 mg, 79%) as a white foam: $R_f$ 0.25 (EtOAc/hexanes=2/3); $^1H$ NMR (600 MHz, $CDCl_3$) δ 7.38-7.28 (m, 5H), 5.32 (dd, J=3.4, 1.4 Hz, 1H, H-2), 5.26 (dd, J=9.2, 3.4 Hz, 1H, H-3'), 5.13 (t, J=9.2 Hz, 1H, H-3"), 5.05 (s, 1H, H-1'), 4.96 (td, J=9.2, 5.5 Hz, 1H, H-4"), 4.90 (dd, J=9.2, 7.7 Hz, 1H, H-2"), 4.82 (d, J=3.4 Hz, 1H, H-1), 4.73 (d, J=12.3 Hz, 1H, Bn $CH_2$), 4.63 (d, J=7.7 Hz, 1H, H-1"), 4.53 (d, J=12.3 Hz, 1H, Bn $CH_2$), 4.36 (dd, J=7.9, 5.6 Hz, 1H, H-3), 4.20 (d, J=5.6 Hz, 1H, H-4), 4.10 (dd, J=11.7, 5.5 Hz, 1H, H-5$_a$"), 3.98 (brs, 2H, H-5), 3.75 (dd, J=7.9, 3.4 Hz, 1H, H-2), 3.61-3.54 (m, 2H, H-4', H-5'), 3.33 (dd, J=11.7, 9.6 Hz, 1H), 2.14 (s, 3H), 2.08 (s, 3H), 2.03 (s, 3H), 2.02-2.01 (m, 6H, Ac $CH_3 \times 2$), 1.50 (s, 3H), 1.32 (s, 3H), 1.14 (d, J=5.7 Hz, 311) ppm; HRMS (ESI-TOF) calcd. for $C_{36}H_{48}O_{18}Na$ $[M+Na]^+$ 791.2733, found 791.2735.

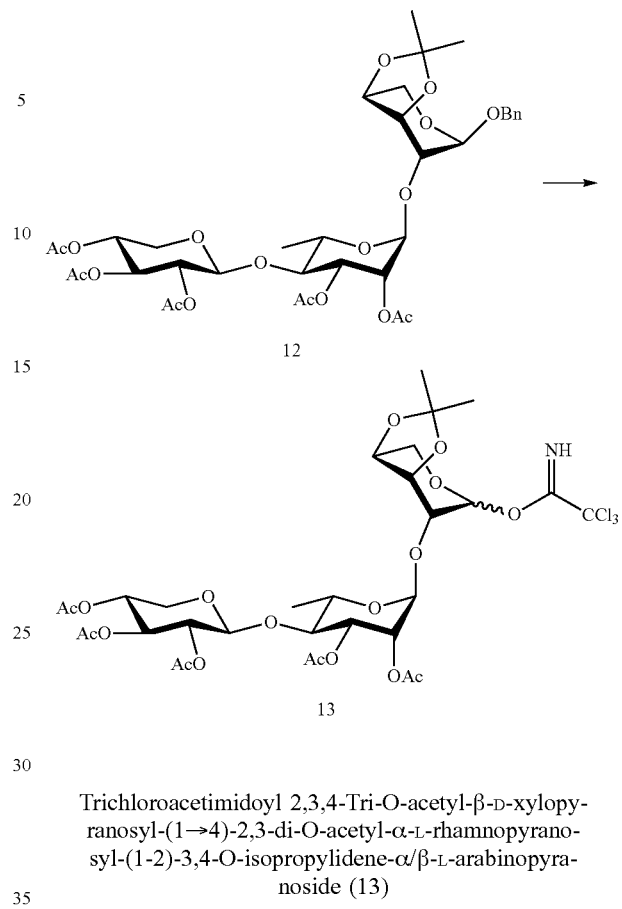

12

13

Trichloroacetimidoyl 2,3,4-Tri-O-acetyl-β-D-xylopyranosyl-(1→4)-2,3-di-O-acetyl-α-L-rhamnopyranosyl-(1-2)-3,4-O-isopropylidene-α/β-L-arabinopyranoside (13)

To a suspension of 12 (300 mg, 0.39 mmol) and 10% Pd/C (150 mg) in buffer (100 mM $Na_2HPO_4/NaH_2PO_4$(aq.), pH=7.0)/THF/MeOH=1/1/4 (30 mL) was stirred at rt under $H_2$ (balloon) atmosphere. After being stirred for 3.5 days, the mixture was filtered through celite and concentrated under reduced pressure. The residue was purified by column chromatography (silica gel; EtOAc/hexanes=1/1 to 3/2) to afford hemiacetal (166 mg, 63%) as a white foam. To a stirred solution of hemiacetal (50 mg, 0.074 mmol) in anhydrous $CH_2Cl_2$ (1.5 mL) was added $Cl_3CCN$ (22 μL, 0.22 mmol) and DBU (4.3 μL, 0.029 mmol) at rt under $N_2$ atmosphere. After being stirred for 16 h, the mixture was concentrated under reduced pressure. The resulting residue was purified by flash column chromatography (silica gel; EtOAc/hexanes=1/1, contained 0.5% $Et_3N$) to afford 13 (60 mg, 98%) as a colorless syrup. 100a: $R_f$ 0.43 (EtOAc/hexanes=1/1); $^1H$ NMR (600 MHz, $CDCl_3$) δ 8.69 (s, 1H, N$\underline{H}$), 6.30 (d, J=3.4 Hz, 1H, H-1), 5.24 (dd, J=3.2, 1.3 Hz, 1H, H-2'), 5.14-5.08 (m, 2H, H-3', H-3"), 5.02 (d, J=1.3 Hz, 1H, H-1'), 4.93 (td, J=9.4, 5.4 Hz, 1H, H-4"), 4.85 (dd, J=9.5, 7.7 Hz, 1H, H-2"), 4.58 (d, J=7.7 Hz, 1H, H-1"), 4.42 (dd, J=7.6, 5.7 Hz, 1H, H-3), 4.31-4.26 (m, 1H, H-4), 4.12 (d, J=1.8 Hz, 2H, H-5), 4.09 (dd, J=11.7, 5.4 Hz, 1H, H-5$_a$"), 3.91 (dd, J=7.6, 3.4 Hz, 1H, H-2), 3.80 (dq, J=9.5, 6.2 Hz, 1H, H-5'), 3.60 (t, J=9.5 Hz, 1H, H-4'), 3.31 (dd, J=11.7, 9.4 Hz, 1H, H-5$_b$"), 2.13 (s, 3H), 2.03 (s, 3H), 2.02 (s, 3H), 2.00 (s, 3H), 1.95 (s, 3H), 1.52 (s, 3H), 1.35 (s, 3H), 1.28 (d, J=6.2 Hz, 3H, H-6') ppm.

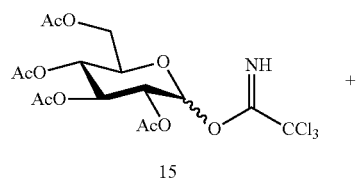

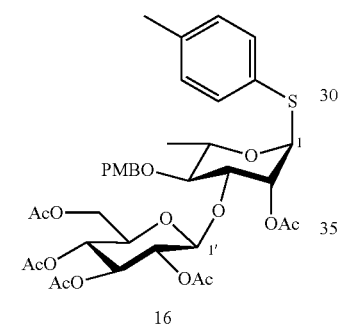

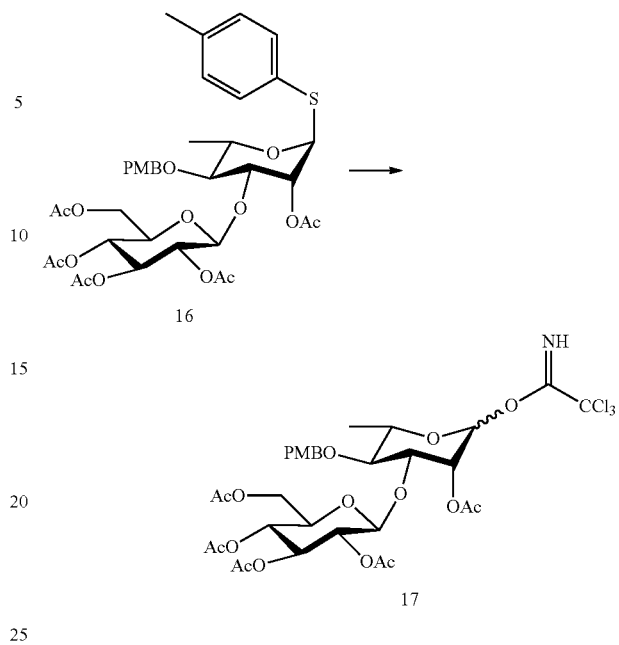

p-Methylphenyl 2,3,4,6-tetra-O-acetyl-β-D-glucopyranosyl-(1→3)-2-O-acetyl-4-O-(p-methoxybenzyl)-1-thio-α-L-rhamopyranoside (16)

To a stirred suspension of 15 (130 mg, 0.26 mmol), 14 (114 mg, 0.26 mmol), and activated 4 Å molecular sieve powder in anhydrous $CH_2Cl_2$ (2.5 mL) was added TMSOTf (10 µL, 0.052 mmol) at −50° C. under $N_2$ atmosphere. Upon completion of the reaction after 0.5 h, the reaction was quenched by addition of $Et_3N$, warmed to rt, filtered and then concentrated under reduced pressure. The residue was purified by column chromatography (silica gel; EtOAc/hexanes=1/2) to give 16 (102 mg, 51%) as a white foam: $R_f$ 0.24 (EtOAc/hexanes=1/2); $^1H$ NMR (600 MHz, $CDCl_3$) δ 7.29-7.27 (m, 4H), 7.08 (d, J=8.0 Hz, 2H), 6.89 (d, J=8.7 Hz, 2H), 5.39 (dd, J=3.4, 1.4 Hz, 1H, H-2), 5.30 (d, J=1.4 Hz, 1H, H-1), 5.18 (t, J=9.7 Hz, 1H, H-3'), 5.06 (dd, J=9.7, 8.0 Hz, 1H, H-2'), 5.03 (t, J=9.7 Hz, 1H, H-4'), 4.79 (d, J=8.0 Hz, 1H, H-1'), 4.71 (d, J=10.5 Hz, 1H), 4.46 (d, J=10.5 Hz, 1H), 4.19-4.13 (m, 2H), 4.09 (dd, J=12.2, 2.2 Hz, 1H'), 4.06 (dd, J=9.5, 3.4 Hz, 1H), 3.79 (s, 3H, 3.70 (ddd, J=9.7, 5.7, 2.2 Hz, 1H, H-5'), 3.48 (t, J=9.5 Hz, 1H, H-4), 2.29 (s, 3H), 2.10 (s, 3H), 2.09 (s, 3H), 2.01 (s, 3H), 1.98 (s, 3H), 1.83 (s, 3H), 1.25 (d, J=6.2 Hz, 3H, H-6) ppm; HRMS (ESI-TOF) calcd. for $C_{37}H_4O_{15}SNa$ $[M+Na]^+$ 785.2450, found 785.2457.

Trichloroacetimidoyl 2,3,4,6-tetra-O-acetyl-β-D-glucopyranosyl-(1→3)-2-O-acetyl-4-O-(p-methoxybenzyl)-α/β-L-rhamopyranoside (17)

To a stirred solution of 16 (37 mg, 0.049 mmol) in acetone/$H_2O$ (1 mL) was added NBS (35 mg, 0.19 mmol) at rt. After being stirred for 2 h, the mixture was quenched by addition of saturated $NaHCO_3$ and 10% $Na_2S_2O_{3(aq.)}$. The resulting mixture was stirred at rt for 1 h then the solvent was removed under reduced pressure. The residue was diluted with $CH_2Cl_2$, washed by 10% $Na_2S_2O_{3(aq.)}$, saturated $NaHCO_3$, brine, dried over $MgSO_4$, and then concentrated under reduced pressure. The residue was purified by column chromatography (silica gel; EtOAc/hexanes=3/2) to afford hemiacetal (26 mg, 82%) as a colorless syrup. To a stirred solution of hemiacetal (26 mg, 0.040 mmol) in anhydrous $CH_2Cl_2$ (1 mL) was added $Cl_3CCN$ (12 µL, 0.12 mmol) and DBU (2.4 µL, 0.016 mmol) at rt under $N_2$ atmosphere. After being stirred for 1 h, the mixture was concentrated under reduced pressure. The residue was purified by flash column chromatography (silica gel; EtOAc/hexanes=1/2, contained by 0.5% $Et_3N$) to afford 17 (25 mg, 79%) as a white foam. 17: $R_f$ 0.44 (EtOAc/hexanes=1/1); $^1H$ NMR (400 MHz, $CDCl_3$) δ 8.68 (s, 1H), 7.29 (d, J=8.4 Hz, 2H), 6.91 (d, J=8.4 Hz, 2H), 6.15 (s, 1H, H-1), 5.34 (s, 1H, H-2), 5.20 (t, J=9.4 Hz, 1H, H-3'), 5.12-5.06 (m, 2H, H-2', H-4'), 4.84 (d, J=7.9 Hz, 1H, H-1'), 4.72 (d, J=10.3 Hz, 1H, PMB C$\underline{H}_2$), 4.49 (d, J=10.3 Hz, 1H, PMB C$\underline{H}_2$), 4.21-4.13 (m, 2H, H-3, H-6$_a$'), 4.09 (t, J=11.0 Hz, 1H, H-6$_b$'), 3.89 (dq, J=9.6, 6.1 Hz, 1H, H-5), 3.81 (s, 3H, PMB OC$\underline{H}_3$), 3.66 (d, J=9.7 Hz, 1H, H-5'), 3.52 (t, J=9.6 Hz, 1H, H-4), 2.15 (s, 3H), 2.07 (s, 3H), 2.01 (s, 3H), 2.00 (s, 3H), 1.88 (s, 3H), 1.29 (d, J=6.1 Hz, 3H, H-6) ppm.

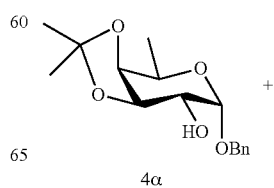

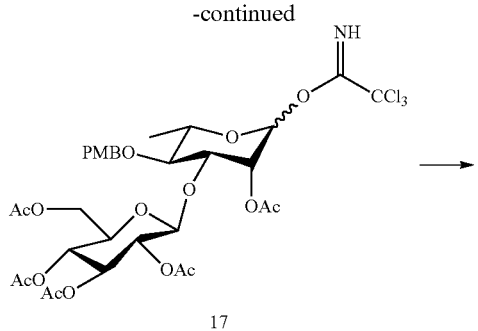

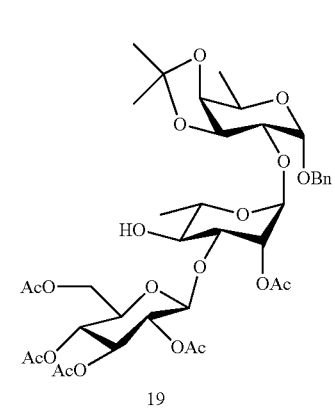

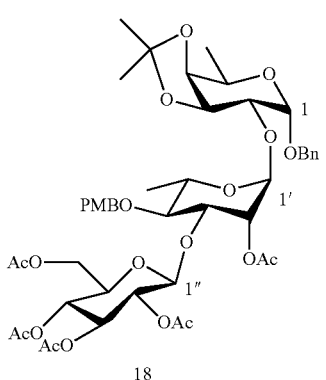

Benzyl 2,3,4,6-tetra-O-acetyl-β-D-glucopyranosyl-(1→3)-2-O-acetyl-4-O-(p-methoxybenzyl)-α-L-rhamnopyranosyl-(1→2)-3,4-O-isopropylidene-α-D-fucopyranoside (18)

To a stirred suspension of 17 (25 mg, 0.31 mmol), 4a (9 mg, 0.31 mmol), and activated 4 Å molecular sieve powder in anhydrous $CH_2Cl_2$ (1.5 mL) was added TMSOTf (1 μL, 0.0062 mmol) at −50° C. under $N_2$ atmosphere. Upon completion of the reaction after 1 h, the reaction was quenched by addition of $Et_3N$, warmed to rt, filtered and then concentrated under reduced pressure. The residue was purified by column chromatography (silica gel; EtOAc/hexanes=2/3) to give 18 (24 mg, 82%) as a white foam: $R_f$ 0.43 (EtOAc/hexanes=1/1); $^1H$ NMR (600 MHz, $CDCl_3$) δ 7.34 (d, J=7.2 Hz, 2H), 7.29 (t, J=7.5 Hz, 2H), 7.26-7.24 (m, 3H), 6.89 (d, J=8.7 Hz, 2H), 5.30 (dd, J=3.6, 1.7 Hz, 1H, H-2'), 5.16 (t, J=9.5 Hz, 1H, H-3"), 5.09-5.04 (m, H-2", H-4"), 5.03 (d, J=1.7 Hz, 1H, H-1'), 4.85 (d, J=3.6 Hz, 1H, H-1), 4.77 (d, J=7.9 Hz, 1H, H-1"), 4.70 (d, J=10.8 Hz, 1H, PMB C$\underline{H}_2$), 4.69 (d, J=12.2 Hz, 1H, Bn C$\underline{H}_2$), 4.51 (d, J=12.2 Hz, 1H, Bn C$\underline{H}_2$), 4.45 (d, J=10.8 Hz, 1H, PMB C$\underline{H}_2$), 4.29 (dd, J=8.1, 5.4 Hz, 1H, H-3), 4.21 (dd, J=12.2, 4.9 Hz, 1H, H-6$_a$"), 4.14-4.09 (m, 1H, H-5), 4.08 (dd, J=9.5, 3.6 Hz, 1H, H-3'), 4.04-3.99 (m, 2H, H-4, H-6$_b$"), 3.81 (s, 3H, PMB OC$\underline{H}_3$), 3.74 (dd, J=8.1, 3.6 Hz, 1H, H-2), 3.70-3.61 (m, 2H, H-5", H-5'), 3.40 (t, J=9.5 Hz, 1H, H-4'), 2.10 (s, 3H), 2.07 (s, 3H), 2.01 (s, 3H), 1.98 (s, 3H), 1.77 (s, 3H), 1.48 (s, 3H), 1.33 (d, J=6.7 Hz, 3H, H-6), 1.31 (s, 3H), 1.14 (d, J=6.2 Hz, 3H, H-6'); HRMS (ESI-TOF) calcd. for $C_{46}H_{60}O_{20}Na$ [M+Na]$^+$ 955.3570, found 955.3579.

Benzyl 2,3,4,6-tetra-O-acetyl-β-D-glucopyranosyl-(1→3)-2-O-acetyl-α-L-rhamnopyranosyl-(1→2)-3,4-O-isopropylidene-α-D-fucopyranoside (19)

To a stirred solution of 18 (24 mg, 0.026 mmol) in $CH_2Cl_2/H_2O=18/1$ (1 mL) was added DDQ (9 mg, 0.039 mmol) at rt. The reaction mixture was stirred for 3 h, and then quenched by saturated $NaHCO_3$. The resulting mixture was diluted with $CH_2Cl_2$, washed by saturated $NaHCO_3$, brine, dried over $MgSO_4$, and then concentrated under reduced pressure.

The residue was purified by column chromatography (silica gel, EtOAc/hexanes=1/1) to afford 19 (17 mg, 81%) as a colorless syrup: $R_f$ 0.30 (EtOAc/hexanes=1/1); $^1H$ NMR (600 MHz, $CDCl_3$) δ 7.37-7.29 (m, 5H), 5.24 (dd, J=3.6, 1.7 Hz, 1H, H-2'), 5.20 (t, J=9.6 Hz, 1H, H-3"), 5.04-4.99 (m, 3H, H-2", H-1', H-4"), 4.87 (d, J=3.6 Hz, 1H, H-1), 4.72 (d, J=12.1 Hz, 1H, Bn C$\underline{H}_2$), 4.70 (d, J=7.8 Hz, 1H, H-1"), 4.53 (d, J=12.1 Hz, 1H, Bn C$\underline{H}_2$), 4.30 (dd, J=8.2, 5.3 Hz, 1H, H-3), 4.22 (dd, J=12.3, 5.0 Hz, 1H, H-6$_a$"), 4.12 (qd, J=6.7, 2.6 Hz, 1H, H-5), 4.05-4.03 (m, 2H, H-4, H-6$_b$"), 3.85 (dd, J=9.0, 3.6 Hz, 1H, H-3'), 3.74 (dd, J=8.2, 3.6 Hz, 1H, H-2), 3.71 (ddd, J=10.1, 5.0, 2.2 Hz, 1H, H-5"), 3.63-3.56 (m, 2H, H-4', H-5'), 2.46 (d, J=2.2 Hz, 1H, O$\underline{H}$), 2.08 (s, 3H), 2.07 (s, 3H), 2.05 (s, 3H), 2.02 (s, 3H), 2.00 (s, 3H), 1.48 (s, 3H), 1.33 (d, J=6.7 Hz, 3H, H-6), 1.32 (s, 3H), 1.19 (d, J=5.7 Hz, 3H, H-6') ppm; HRMS (ESI-TOF) calcd. for $C_{38}H_{52}O_{19}Na$ [M+Na]$^+$ 835.2995, found 835.3000.

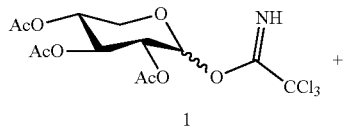

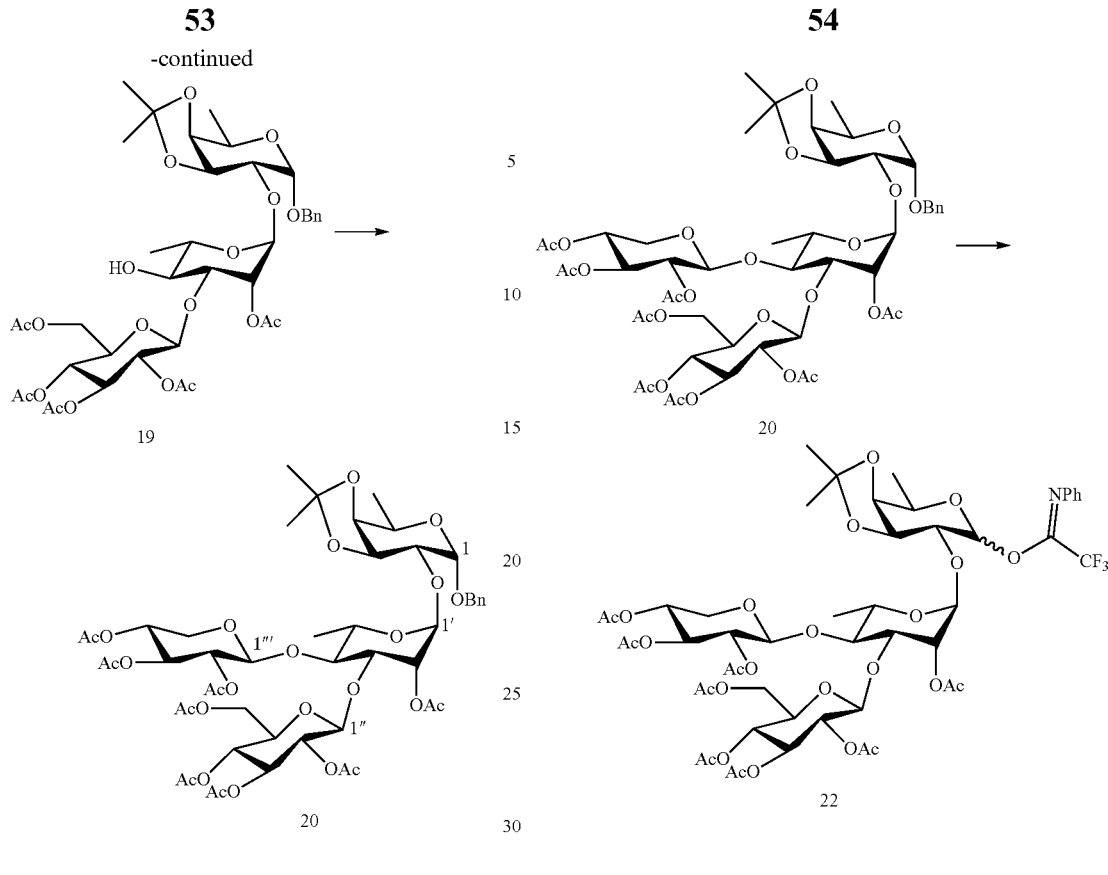

Benzyl 2,3,4,6-tetra-O-acetyl-β-D-glucopyranosyl-(1→3)-(2,3,4-tri-O-acetyl-β-D-xylopyranosyl-(1→4))-2-O-acetyl-α-L-rhamnopyranosyl-(1→2)-3,4-O-isopropylidene-α-D-fucopyranoside (20)

To a stirred suspension of 1 (13 mg, 0.031 mmol), 19 (17 mg, 0.021 mmol) and activated 4 Å molecular sieve powder in anhydrous CH$_2$Cl$_2$ (1 mL) was added TMSOTf (0.4 µL, 0.0021 mmol) at −50° C. under N$_2$ atmosphere. Upon completion of the reaction after 0.5 h, the reaction was quenched by addition of Et$_3$N, warmed to rt, filtered and then concentrated under reduced pressure. The residue was purified by column chromatography (silica gel; EtOAc/hexanes=1/1) to give 20 (20 mg, 89%) as a colorless syrup: R$_f$ 0.27 (EtOAc/hexanes=1/1); $^1$H NMR (600 MHz, CDCl$_3$) δ 7.39-7.30 (m, 5H), 5.30 (dd, J=3.6, 1.8 Hz, 1H, H-2'), 5.16 (t, J=9.5 Hz, 1H, H-4''), 5.11 (t, J=8.2 Hz, 1H, H-3'''), 5.04-4.98 (m, 2H, H-2'', H-3''), 4.96 (d, J=1.8 Hz, 1H, H-1'), 4.91 (td, J=8.3, 4.9 Hz, 1H, H-4'''), 4.86 (dd, J=8.2, 6.3 Hz, 1H, H-2'''), 4.82 (d, J=3.6 Hz, 1H, H-1), 4.80 (d, J=6.3 Hz, 1H, H-1'''), 4.73 (d, J=7.7 Hz, 1H, H-1''), 4.69 (d, J=12.1 Hz, 1H, Bn CH$_2$), 4.50 (d, J=12.1 Hz, 1H, Bn CH$_2$), 4.25 (dd, J=8.2, 5.3 Hz, 1H, H-3), 4.16-4.09 (m, 2H, H-6$_a$'', H-5), 4.09-4.03 (m, 2H, H-5$_a$''', H-3'), 4.03-3.99 (m, 2H, H-4, H-6$_b$''), 3.75 (t, J=9.5 Hz, 1H, H-4'), 3.71-3.66 (m, 2H, H-2, H-5''), 3.54 (dq, J=9.5, 6.2 Hz, 1H, H-5'), 3.37 (dd, J=11.9, 8.3 Hz, 1H, H-5$_b$'''), 2.19 (s, 3H), 2.08 (s, 3H), 2.08 (s, 3H), 2.08 (s, 3H), 2.04 (s, 3H), 2.01 (s, 3H), 1.99 (s, 3H), 1.97 (s, 3H), 1.46 (s, 3H), 1.33 (d, J=6.7 Hz, 3H, H-6), 1.29 (s, 3H), 1.10 (d, J=6.2 Hz, 3H, H-6') ppm; HRMS (ESI-TOF) calcd. for C$_{49}$H$_{66}$O$_{26}$Na [M+Na]$^+$ 1093.3735, found 1093.3734.

N-Penyl-2,2,2-Trifluoroacetimidoyl 2,3,4,6-tetra-O-acetyl-β-D-glucopyranosyl-(1→3)-(2,3,4-tri-O-acetyl-β-D-xylopyranosyl-(1→4))-2-O-acetyl-α-L-rhamopyranosyl-(1→2)-3,4-O-isopropylidene-α/β-D-fucopyranoside (22)

To a suspension of 20 (255 mg, 0.24 mmol) and 20% Pd(OH)$_2$/C (25 mg) in THF (5 mL) was stirred at rt under H$_2$ (balloon) atmosphere. After being stirred for 24 h, the mixture was filtered through celite and concentrated under reduced pressure. The residue was purified by column chromatography (silica gel; EtOAc/hexanes=3/2 to 2/1) to afford hemiacetal (180 mg, 77%) as a white foam. To a stirred solution of hemiacetal (20 mg, 0.020 mmol) in anhydrous CH$_2$Cl$_2$ (1 mL) was added N-phenyl-2,2,2-trifluoroacetimidoyl chloride (19 µL, 0.12 mmol) and DBU (3.7 µL, 0.024 mmol) at rt under N$_2$ atmosphere. After being stirred for 1.5 h, the mixture was concentrated under reduced pressure. The residue was purified by flash column chromatography (silica gel; EtOAc/hexanes=1/1 to 3/2, contained 0.5% Et$_3$N) to afford 22 (16 mg, 68%) as a colorless syrup. 22a: R$_f$ 0.61 (EtOAc/hexanes=3/2); $^1$H NMR (600 MHz, CDCl$_3$) δ 7.33 (t, J=7.8 Hz, 2H), 7.12 (t, J=7.4 Hz, 1H), 6.85 (d, J=7.6 Hz, 2H), 5.58 (brs, 1H, H-1), 5.20 (s, 1H, H-1'), 5.19-5.15 (m, 2H), 5.10 (t, J=9.7 Hz, 1H), 5.06 (t, J=7.0 Hz, 1H), 4.99 (dd, J=9.3, 7.9 Hz, 1H), 4.92 (d, J=5.1 Hz, 1H, H-1'''), 4.86 (td, J=6.9, 4.2 Hz, 1H), 4.80 (dd, J=6.7, 5.3 Hz, 1H), 4.72 (d, J=7.9 Hz, 1H, H-1''), 4.23-4.08 (m, 5H), 4.00-3.98 (m, 2H), 3.89 (brs, 1H), 3.84-3.77 (m, 2H), 3.66-3.63 (m, 1H), 3.45 (dd, J=12.1, 7.0 Hz, 1H), 2.16 (s, 3H), 2.11 (s, 3H), 2.09 (s, 3H), 2.06 (s, 3H), 2.04 (s, 4H), 2.02 (s, 3H), 1.99 (s, 3H), 1.99 (s, 3H), 1.53 (s, 3H), 1.39 (d, J=6.3 Hz, 3H), 1.32 (s, 3H), 1.27 (d, J=5.6 Hz, 3H) ppm.

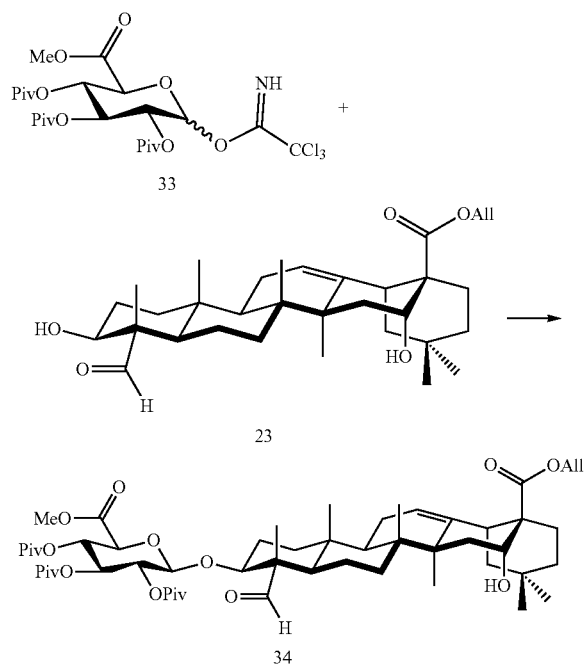

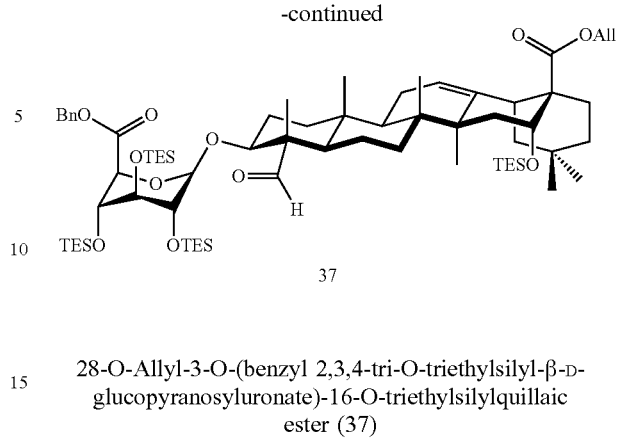

28-O-Allyl-3-O-(benzyl 2,3,4-tri-O-triethylsilyl-β-D-glucopyranosyluronate)-16-O-triethylsilylquillaic ester (37)

28-O-Allyl-3-O-(Methyl 2,3,4-tri-O-pivaloyl-β-D-glucopyranosyluronate)quillaic ester (34)

To a stirred suspension of 33 (500 mg, 0.83 mmol), 23 (435 mg, 0.83 mmol), and activated 4 Å molecular sieve powder in anhydrous $CH_2Cl_2$ (8 mL) was added $B(PhF_5)_3$ (42 mg, 0.083 mmol) at rt under $N_2$ atmosphere. Upon completion of the reaction after 0.5 h, the reaction was quenched by addition of $Et_3N$, filtered, and then concentrated under reduced pressure. The residue was purified by column chromatography (silica gel; EtOAc/$CH_2Cl_2$/hexanes=1/1/6) to give 34 (385 mg, 48%) as a white solid: $R_f$ 0.57 (EtOAc/hexanes=1:2); $^1H$ NMR (600 MHz, $CDCl_3$) δ 9.40 (s, 1H, H-23), 5.88-5.81 (m, 1H, All internal alkenyl C$\underline{H}$), 5.37 (t, J=3.3 Hz, 1H, H-12), 5.31-5.27 (m, 2H, H-3', All terminal alkenyl C$\underline{H}_a$), 5.20-5.16 (m, 2H, H-4', All terminal alkenyl C$\underline{H}_b$), 4.98 (t, J=8.0 Hz, H-2'), 4.52-4.44 (m, 4H, H-1', H-16, allylic C$\underline{H}_2$), 3.99 (d, J=10.0 Hz, 1H, H-5'), 3.84 (dd, J=11.8, 4.7 Hz, 1H, H-3), 3.72 (s, 3H, OC$\underline{H}_3$, 3.05 (dd, J=14.3, 4.1 Hz, 1H, H-18), 2.15 (t, J=13.6 Hz, 1H, H-19$_a$), 1.92-1.85 (m, 4H), 1.80-1.70 (m, 4H), 1.68-1.63 (m, 3H), 1.50-1.41 (m, 2H), 1.35-1.28 (m, 4H), 1.25-1.17 (m, 3H), 1.14 (s, 9H), 1.12-1.10 (m, 10H), 1.09-1.08 (m, 12H), 1.05-0.97 (m, 2H), 0.96 (s, 3H), 0.94 (s, 3H), 0.89 (s, 3H), 0.70 (s, 3H) ppm; HRMS (ESI-TOF) calcd. for $C_{55}H_{84}O_{14}Na$ [M+Na]$^+$ 991.5753, found 991.5758.

To a stirred solution of 34 (358 mg, 0.37 mmol) in THF (15 mL) was added 1.0 N KOH (3 mL) and heated under reflux 66° C. The reaction mixture was stirred for 24 h, and then cooled to rt. The reaction mixture was neutralized by amberlyst IR-120H$^+$, filtered, concentrated and dried under reduced pressure. The residue was then treated with benzyl bromide (88 μL, 0.73 mmol) and $K_2CO_3$ (102 mg, 0.73 mmol) in DMF (7 mL) at rt. After being stirred for 2 h, the reaction mixture was diluted with $CH_2Cl_2$, washed by $H_2O$, brine, dried over $MgSO_4$, and then concentrated under reduced pressure. The residue was purified by column chromatography (silica gel, MeOH/$CH_2Cl_2$=1/15) to afford benzyl ester as a yellow solid. To a stirred solution of benzyl ester (266 mg, 0.34 mmol) in anhydrous $CH_2Cl_2$ (5 mL) was added TESOTf (0.6 mL, 2.7 mmol) and 2,6-lutidine (0.4 mL, 3.4 mmol) under $N_2$ atmosphere at rt. The reaction mixture was stirred for 2 h, and then quenched by addition of saturated $NaHCO_3$. The mixture was diluted with $CH_2Cl_2$, washed by saturated $NaHCO_3$, brine, dried over $MgSO_4$, and then concentrated under reduced pressure. the residue was purified by column chromatography (silica gel, EtOAc/hexanes=1/40) to afford 37 (310 mg, 67% three steps) as a colorless syrup: $R_f$ 0.71 (EtOAc/hexanes=1/10); $^1H$ NMR (400 MHz, $CDCl_3$) δ 9.34 (s, 1H, H-23), 7.39-7.30 (m, 5H), 5.90-5.80 (m, 1H, All internal alkenyl C$\underline{H}$), 5.35 (s, 1H, H-12), 5.29 (d, J=17.2 Hz, 1H, All terminal alkenyl C$\underline{H}_a$), 5.20 (d, J=10.7 Hz, 1H, All terminal alkenyl C$\underline{H}_b$), 5.17-5.15 (m, 2H, Bn C$\underline{H}_2$), 4.58-4.57 (m, 2H, H-1', H-16), 4.53-4.40 (m, 2H, Allylic C$\underline{H}_2$), 4.27 (dd, J=6.2, 4.9 Hz, 1H, H-4'), 4.22 (d, J=6.2 Hz, 1H, H-5'), 3.81 (dd, J=11.4, 3.8 Hz, 1H, H-3), 3.61 (d, J=4.9 Hz, 1H, H-3'), 3.57 (d, J=3.4 Hz, 1H, H-2'), 3.02 (d, J=11.6 Hz, 1H, H-18), 2.23 (t, J=13.5 Hz, 1H, H-19), 1.99 (d, J=10.8 Hz, 1H), 1.91-1.79 (m, 4H), 1.75-1.53 (m, 5H), 1.48-1.31 (m, 5H), 1.30-1.22 (m, 1H), 1.20-1.23 (m, 3H), 1.11-1.06 (m, 4H), 1.03-0.85 (m, 47H), 0.72-0.52 (m, 27H) ppm; HRMS (ESI-TOF) calcd. for $C_{70}H_{120}O_{11}Si_4Na$ [M+Na]$^+$ 1271.7800, found 1271.7829.

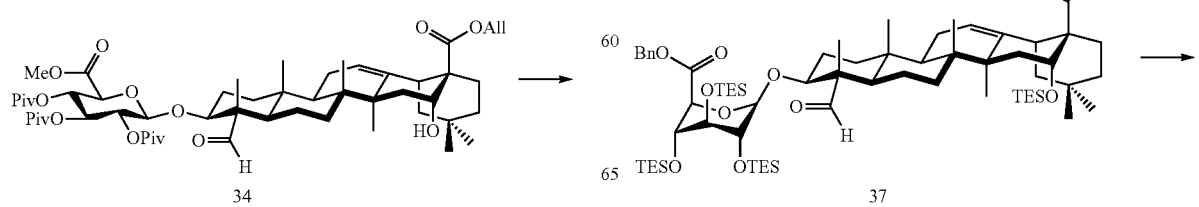

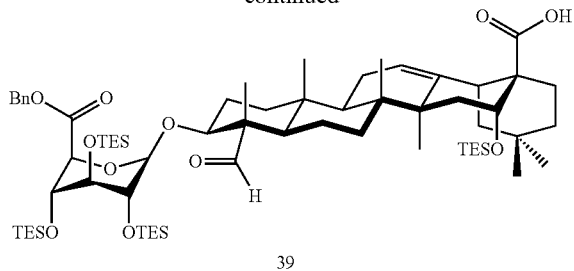

39

3-O-(Benzyl 2,3,4-tri-O-triethylsilyl-β-D-glucopyranosyluronate)-16-O-triethylsilylquillaic acid (39)

To a stirred solution of 37 (0.60 g, 0.48 mmol) and PPh$_3$ (0.31 g, 1.2 mmol) in 1,4-dioxane (5 mL) was added pre-mixed formic acid (0.38 mL, 10 mmol)/Et$_3$N (1.3 mL, 9.6 mmol) in 1,4-dioxane (2.5 mL) and Pd(OAc)$_2$ (54 mg, 0.24 mmol) in 1,4-dioxane (2.5 mL) at rt. The reaction mixture was stirred for 12 h, and then concentrated under reduced pressure. The residue was purified by column chromatography (silica gel, EtOAc/hexanes=1/6) to afford 39 (0.48 g, 83%) as white foam: R$_f$ 0.25 (EtOAc/hexanes=1/6); $^1$H NMR (600 MHz, CDCl$_3$) δ 9.36 (s, 1H, H-23), 7.37-7.30 (m, 5H), 5.34 (t, J=3.4 Hz, 1H, H-12), 5.16 (s, 2H, Bn CH$_2$), 4.59 (d, J=4.4 Hz, 1H, H-1'), 4.53 (s, 1H, H-16), 4.28 (dd, J=6.2, 5.3 Hz, 1H, H-4'), 4.22 (d, J=6.2 Hz, 1H, H-5'), 3.82 (dd, J=11.8, 4.6 Hz, 1H, H-3), 3.61 (d, J=5.3 Hz, 1H, H-3'), 3.58 (d, J=4.4 Hz, 1H, H-2'), 2.95 (dd, J=14.3, 4.0 Hz, 1H, H-18), 2.21 (t, J=13.6 Hz, 1H, H-19$_a$), 2.03-1.95 (m, 1H), 1.90-1.80 (m, 4H), 1.78-1.61 (m, 4H), 1.57 (d, J=13.4 Hz, 1H), 1.47-1.37 (m, 2H), 1.35 (s, 3H), 1.27 (d, J=13.6 Hz, 1H), 1.21-1.12 (m, 3H), 1.10-1.03 (m, 4H), 1.02-0.87 (m, 46H), 0.70-0.53 (m, 27H) ppm; HRMS (ESI-TOF) calcd. for C$_{67}$H$_{116}$O$_{11}$Si$_4$Na [M+Na]$^+$ 1231.7487, found 1231.7507.

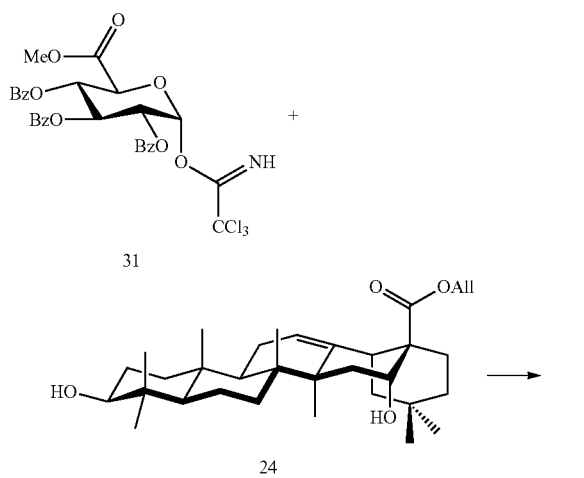

28-O-Allyl-3-O-(Methyl 2,3,4-tri-O-benzoyl-β-D-glucopyranosyluronate)echinocystic ester (36)

To a stirred suspension of 31 (20 mg, 0.030 mmol), 24 (7.7 mg, 0.015 mmol), and activated 4 Å molecular sieve powder in anhydrous CH$_2$Cl$_2$ (0.6 mL) was added B(PhF$_5$)$_3$ (1.5 mg, 0.0030 mmol) at rt under N$_2$ atmosphere. Upon completion of the reaction after 0.5 h, the reaction was quenched by addition of Et$_3$N, filtered, and then concentrated under reduced pressure. The residue was purified by column chromatography (silica gel; EtOAc/CH$_2$Cl$_2$/hexanes=1/1/6) to give 36 (11 mg, 72%) as a white solid: R$_f$ 0.42 (EtOAc/hexanes=1:2); $^1$H NMR (600 MHz, CDCl$_3$) δ 7.95-7.91 (m, 4H), 7.85 (dd, J=8.4, 1.3 Hz, 2H), 7.53-7.49 (m, 2H), 7.45-7.42 (m, 1H), 7.40-7.35 (m, 4H), 7.31-7.28 (m, 2H), 5.91 (t, J=9.7 Hz, 1H, H-3'), 5.89-5.82 (m, 1H, All internal alkenyl CH), 5.64 (t, J=9.7 Hz, 1H, H-4'), 5.59 (dd, J=9.7, 7.8 Hz, 1H, H-2'), 5.39 (t, J=3.6 Hz, 1H, H-12), 5.29 (dt, J=17.2, 1.5 Hz, 1H, All terminal alkenyl CH$_a$), 5.20 (dt, J=10.5, 1.3 Hz, 1H, All terminal alkenyl CH$_b$), 4.89 (d, J=7.8 Hz, 1H, H-1'), 4.53-4.45 (m, 3H, H-16, Allylic CH$_2$), 4.30 (d, J=9.7 Hz, 1H, H-5'), 3.69 (s, 3H, OCH$_3$), 3.16 (dd, J=11.7, 4.6 Hz, 1H, H-3), 3.06 (dd, J=14.4, 4.3 Hz, 1H, H-18), 2.14 (dd, J=13.7 Hz, 1H, H-19$_a$), 1.90-1.85 (m, 4H, H-2$_a$, H-11$_{ab}$, H-22$_a$), 1.82-1.71 (m, 4H, H-2$_b$, H-15$_a$, H-21$_a$, H-22$_b$), 1.65-1.61 (m, 1H, H-1$_a$), 1.55-1.52 (m, 2H, H-9, 16—OH), 1.44-1.34 (m, 2H, H-6$_a$, H-7$_a$), 1.34-1.30 (m, 4H, H-15$_b$, H-27), 1.26-1.19 (m, 3H, H-6$_b$, H-7$_b$, H-21$_b$), 1.14-1.10 (m, 1H, H-19$_b$), 0.97 (s, 3H, H-30), 0.94-0.92 (m, 1H, H-1$_b$), 0.90 (s, 3H, H-29), 0.88 (s, 3H, H-25), 0.71 (s, 3H, H-23), 0.70-0.65 (m, 4H, H-5, H-26), 0.62 (s, 3H, H-24) ppm; HRMS (ESI-TOF) calcd. for C$_{61}$H$_{74}$O$_{13}$Na [M+Na]$^+$ 1037.5022, found 1037.5026.

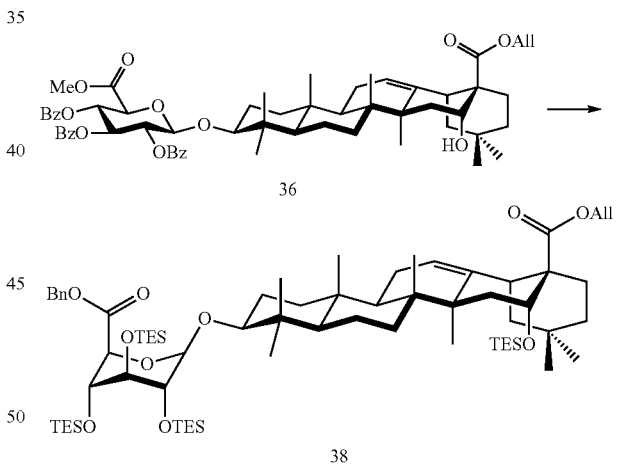

28-O-Allyl-3-O-(benzyl 2,3,4-tri-O-triethylsilyl-β-D-glucopyranosyluronate)-16-O-triethylsilylechinocystic ester (38)

To a stirred solution of 36 (0.45 g, 0.41 mmol) in THF (25 mL) was added 1.0 N KOH (5 mL) and heated under 45° C. The reaction mixture was stirred for 12 h, and then cooled to rt. The reaction mixture was neutralized by amberlyst IR-120H$^+$, filtered, concentrated, and then dried under reduced pressure. The residue was subsequently treated with benzyl bromide (98 µL, 0.82 mmol) and K$_2$CO$_3$ (113 mg, 0.82 mmol) in DMF (8 mL) at rt. After being stirred for 12 h, the reaction mixture was diluted with CH$_2$Cl$_2$, washed by H₂O, brine, dried over MgSO₄, and then concentrated under reduced pressure. The residue was purified by column chromatography (silica gel, MeOH/CH₂Cl₂=1/20) to afford benzyl ester. To a stirred solution of benzyl ester in anhydrous CH₂Cl₂ (8 mL) was added TESOTf (0.74 mL, 3.3 mmol) and 2,6-lutidine (0.48 mL, 4.1 mmol) under N₂ atmosphere at rt. The reaction mixture was stirred for 2 h, and then quenched by addition of saturated NaHCO₃. The mixture was diluted with CH₂Cl₂, washed by saturated NaHCO₃, brine, dried over MgSO₄, and then concentrated under reduced pressure. the residue was purified by column chromatography (silica gel, EtOAc/hexanes=1/40) to afford 38 (0.21 g, 41%) as a colorless syrup: Re 0.41 (EtOAc/hexanes=1/20); $^1$H NMR (400 MHz, CDCl₃) δ 7.39-7.28 (m, 5H), 5.92-5.82 (m, 1H, All internal alkenyl C$\underline{H}$), 5.35 (s, 1H, H-12), 5.33-5.27 (m, 1H, All terminal alkenyl C$\underline{H}$), 5.20 (d, J=10.3 Hz, 1H, All terminal alkenyl C$\underline{H}$), 5.16 (s, 2H, Bn C$\underline{H}_2$), 4.77 (d, J=4.2 Hz, 1H, H-1'), 4.59 (s, 1H, H-16), 4.53-4.43 (m, 2H All C$\underline{H}_2$), 4.34 (dd, J=6.1, 5.1 Hz, 1H, H-4'), 4.27 (d, J=6.1 Hz, 1H, H-5'), 3.73 (d, J=4.2 Hz, 1H, H-2'), 3.65 (d, J=5.1 Hz, 1H, H-3'), 3.06-2.98 (m, 2H, H-3, H-18), 2.23 (t, J=13.5 Hz, 1H, H-19$_a$), 1.96 (d, J=10.8 Hz, 1H), 1.89-1.80 (m, 4H), 1.77-1.62 (m, 3H), 1.58-1.40 (m, 4H), 1.34 (s, 3H), 1.31-1.23 (m, 3H), 1.16-1.04 (m, 2H), 1.04-0.90 (m, 42H), 0.89-0.84 (s, 7H), 0.78 (s, 3H), 0.72-0.55 (m, 28H) ppm; HRMS (ESI-TOF) calcd. for C₇₀H₁₂₂O₁₀Si₄Na [M+Na]⁺ 1257.8007, found 1257.8019.

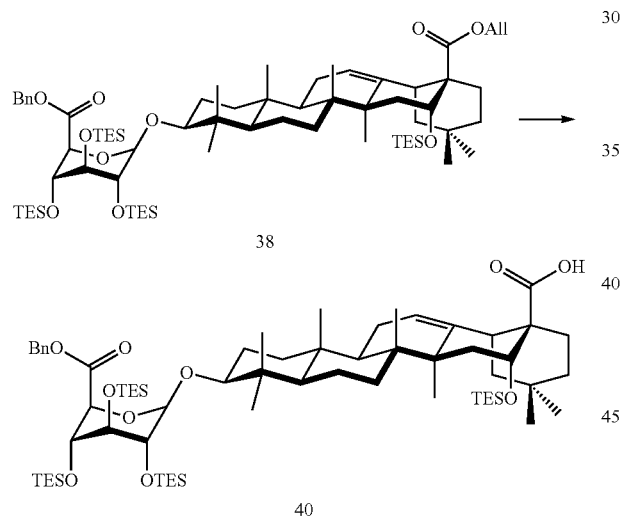

38

40

3-O-(Benzyl 2,3,4-tri-O-triethylsilyl-β-D-glucopyranosyluronate)-16-O-triethylsilylechinocystic acid (40)

To a stirred solution of 38 (194 mg, 0.16 mmol) and PPh₃ (1.03 mg, 0.39 mmol) in 1,4-dioxane (4 mL) was added pre-mixed formic acid (150 μL, 3.3 mmol)/Et₃N (430 μL, 3.1 mmol) in 1,4-dioxane (2 mL) and Pd(OAc)₂ (17 mg, 0.078 mmol) in 1,4-dioxane (2 mL) at rt. The reaction mixture was stirred for 12 h, and then concentrated under reduced pressure. The residue was purified by column chromatography (silica gel, EtOAc/hexanes=1/6) to afford 40 (168 mg, 89%) as white foam: R$_f$ 0.58 (EtOAc/hexanes=1/6); $^1$H NMR (400 MHz, CDCl₃) δ 7.40-7.28 (m, 5H), 5.34 (s, 1H, H-12), 5.16 (s, 2H, Bn C$\underline{H}_2$), 4.78 (d, J=4.3 Hz, 1H, H-1'), 4.55 (s, 1H, H-16), 4.34 (t, J=5.5 Hz, 1H, H-4'), 4.27 (d, J=5.8 Hz, 1H, H-5'), 3.73 (d, J=3.9 Hz, 1H, H-2'), 3.66 (d, J=5.0 Hz, 1H, H-3'), 3.02 (dd, J=11.5, 3.7 Hz, 1H, H-3), 2.95 (d, J=11.3 Hz, 1H, H-18), 2.21 (t, J=13.5 Hz, 1H, H-19$_a$), 1.96 (d, J=11.1 Hz, 1H), 1.92-1.62 (m, 7H), 1.62-1.40 (m, 4H), 1.34 (s, 3H), 1.31-1.23 (m, 3H), 1.17-1.04 (m, 2H), 1.02-0.91 (m, 42H), 0.90-0.84 (s, 7H), 0.79 (s, 3H), 0.73-0.55 (m, 28H) ppm; HRMS (ESI-TOF) calcd. for C₆₇H₁₁₈O₁₀Si₄Na [M+Na]⁺ 1217.7694, found 1217.7703.

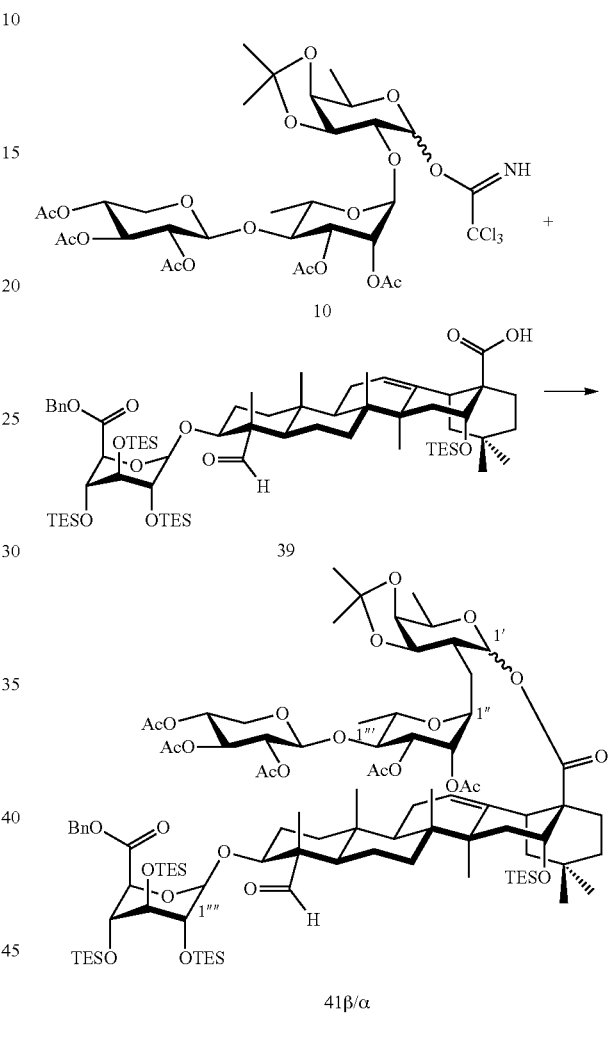

3-O-(benzyl 2,3,4-tri-O-triethylsilyl-β-D-glucopyranosyluronate)-28-O-(2,3,4-tri-O-acetyl-β-D-xylopyranosyl-(1→4)-2,3-di-O-acetyl-α-D-rhamnopyranosyl-(1→2)-3,4-O-isopropylidene-β/α-D-fucopyranosyl)-16-O-triethylsilylquillaic ester (41β/α)

To a stirred suspension of 10 (276 mg, 0.33 mmol), 39 (266 mg, 0.22 mmol) and activated 4 Å molecular sieve powder in anhydrous CH₂Cl₂ (11 mL) was added BF₃·OEt₂ (ca. 48%, 12 μL, 0.044 mmol) at −75° C. under N₂ atmosphere. Upon completion of the reaction after 0.5 h, the reaction was quenched by addition of Et₃N, warmed to rt, filtered and then concentrated under reduced pressure. The residue was purified by column chromatography (silica gel; EtOAc/CH₂Cl₂/hexanes=2/1/5) to give 41β (391 mg, 94%) as colorless syrups. 41β: R$_f$ 0.64 (EtOAc/hexanes=1:1); $^1$H NMR (600 MHz, CDCl₃) δ 9.35 (s, 1H, H-23), 7.40-7.28 (m, 5H), 5.41 (d, J=7.5 Hz, 1H, H-1'), 5.34 (t, J=3.5 Hz, 1H, H-12), 5.25 (dd, J=3.5, 1.6 Hz, 1H, H-2"), 5.21 (dd, J=9.8, 3.5 Hz, 1H, H-3"), 5.16 (s, 2H, Bn C$\underline{H}_2$), 5.13 (t, J=9.2 Hz, 1H, H-3'''), 4.98 (d, J=1.6 Hz, 1H, H-1"), 4.96 (td, J=9.2, 5.5 Hz, 1H, H-4'''), 4.85 (dd, J=9.2, 7.7 Hz, 1H, H-2'''), 4.63 (d, J=7.7 Hz, 1H, H-1'''), 4.58 (d, J=4.3 Hz, 1H, H-1''''), 4.49 (s, 1H, H-16), 4.27 (t, J=6.3 Hz, 1H, H-4''''), 4.22 (d, J=6.3 Hz, 1H, H-5''''), 4.18 (t, J=6.0 Hz, 1H, H-3'), 4.13 (dd, J=11.7, 5.4 Hz, 1H, H-5$_a$'''), 4.01 (dd, J=6.0, 2.0 Hz, 1H, H-4'), 3.87 (qd, J=6.5, 2.0 Hz, 1H, H-5'), 3.84-3.79 (m, 2H, H-3, H-5"), 3.66 (dd, J=7.5, 6.3 Hz, 1H, H-2'), 3.64-3.60 (m, 2H, H-3'''', H-4"), 3.57 (dd, J=4.3, 0.9 Hz, 1H, H-2''''), 3.34 (dd, J=11.7, 9.3 Hz, 1H, H-5$_b$'''), 2.94 (dd, J=14.2, 4.0 Hz, 1H, H-18), 2.23 (t, J=13.6 Hz, 1H, H-19$_a$), 2.13 (s, 3H), 2.06 (s, 3H), 2.03 (s, 3H), 2.00 (s, 3H), 1.99-1.97 (m, 4H, H-2, Ac C$\underline{H}_3$), 1.88-1.75 (m, 5H, H-11$_{ab}$, H-21$_a$, H-22$_{ab}$), 1.73-1.65 (m, 2H, H-2$_a$, H-15$_a$), 1.63-1.60 (m, 1H, H-9), 1.57-1.55 (m, 1H, H-1$_a$), 1.53 (s, 3H, isopropylidene C$\underline{H}_3$), 1.47-1.40 (m, 2H, H-6$_a$, H-7$_a$), 1.35 (s, 3H, H-27), 1.34 (s, 3H, isopropylidene C$\underline{H}_3$), 1.29 (d, J=6.5 Hz, 4H, H-6'), 1.27-1.24 (m, H-6", H-15$_b$), 1.19-1.16 (m, 2H, H-5, H-6$_b$), 1.12 (d, J=7.8 Hz, 1H, H-21$_b$), 1.09 (s, 3H, H-24), 1.05 (dd, J=12.1, 4.0 Hz, 1H, H-19$_b$), 1.01-0.89 (m, 44H, TES C$\underline{H}_3$, H-1$_b$, H-7$_b$, H-25, H-30), 0.89 (s, 3H, H-29), 0.73 (s, 3H, H-26), 0.69-0.55 (m, 24H, TES C$\underline{H}_2$) ppm; FIRMS (ESI-TOF) calcd. for C$_{97}$H$_{158}$O$_{28}$Si$_4$Na [M+Na]⁺ 1906.9937, found 1906.9959.

41α: R$_f$ 0.69 (EtOAc/hexanes=1:1), ¹H NMR (600 MHz, CDCl₃) δ 9.34 (s, 1H, H-23), 7.37-7.30 (m, 5H), 6.02 (d, J=3.7 Hz, 1H, H-1'), 5.39 (t, J=3.6 Hz, 1H, H-12), 5.21 (dd, J=3.5, 1.7 Hz, 1H, H-2'''), 5.16 (s, 2H, Bn C$\underline{H}_2$), 5.11 (t, J=9.0 Hz, 1H, H-3''''), 5.08-5.06 (m, 2H, H-1''', H-3'''), 4.93 (td, J=9.0, 5.3 Hz, 1H, H-4''''), 4.80 (dd, J=9.0, 7.4 Hz, 1H, H-2''''), 4.66 (d, J=7.4 Hz, 1H, H-1'''), 4.58 (d, J=4.4 Hz, 1H, H-1'), 4.56 (s, 1H, H-16), 4.27 (t, J=6.3 Hz, 1H, H-4'), 4.21 (d, J=6.3 Hz, 1H, H-5'), 4.19 (dd, J=8.0, 5.1 Hz, 11H, H-3"), 4.13-4.09 (dd, J=11.8, 5.2 Hz, 1H, H-5$_a$''''), 4.06-4.01 (m, 2H, H-4", H-5"), 3.87 (dd, J=8.0, 3.7 Hz, 1H, H-2"), 3.81 (dd, J=11.8, 4.7 Hz, 1H, H-3), 3.70-3.64 (m, 1H, H-5'''), 3.63-3.58 (m, 2H, H-4''', H-3'), 3.57 (dd, J=4.4, 1.1 Hz, 1H, H-2'), 3.35 (dd, J=11.8, 9.0 Hz, 1H, H-5$_b$''''), 3.00 (dd, J=14.3, 4.1 Hz, 111, H-18), 2.19 (t, J=13.2 Hz, 1H, H-19$_a$), 2.13 (s, 3H), 2.03 (s, 3H), 2.02 (s, 3H), 2.02 (s, 3H), 2.00-1.97 (m, 1H, H-2$_a$), 1.96 (s, 3H), 1.95-1.83 (m, 3H, H-22$_a$, H-11$_{ab}$), 1.81-1.65 (m, 3H, H-21$_a$, H-22$_b$, H-2$_b$), 1.62-1.52 (m, 3H, H-9, H-1$_a$, H-15$_a$), 1.51 (s, 3H, isopropylidene C$\underline{H}_3$), 1.48-1.40 (m, 2H, H-6$_a$, H-7$_a$), 1.35 (s, 3H, H-27), 1.34 (s, 3H, isopropylidene C$\underline{H}_3$), 1.32 (d, J=6.5 Hz, 3H, H-6"), 1.29-1.27 (m, 4H, H-15$_b$, H-6'''), 1.23-1.11 (m, 3H, H-21$_b$, H-5, H-6$_b$), 1.09-1.05 (m, 4H, H-24, H-19$_b$), 1.01 (m, TES C$\underline{H}_3$×3), 0.96-0.90 (m, 35H, H-1$_b$, H-7$_b$, H-25, H-30, TES C$\underline{H}_3$×9), 0.88 (s, 3H, H-29), 0.73 (s, 3H, H-26), 0.67 (m, 6H, TES C$\underline{H}_2$×3), 0.62-0.54 (m, 18H, TES C$\underline{H}_2$×9) ppm; HRMS (ESI-TOF) calcd. for C$_{97}$H$_{158}$O$_{28}$Si$_4$Na [M+Na]⁺ 1906.9937, found 1906.9967.

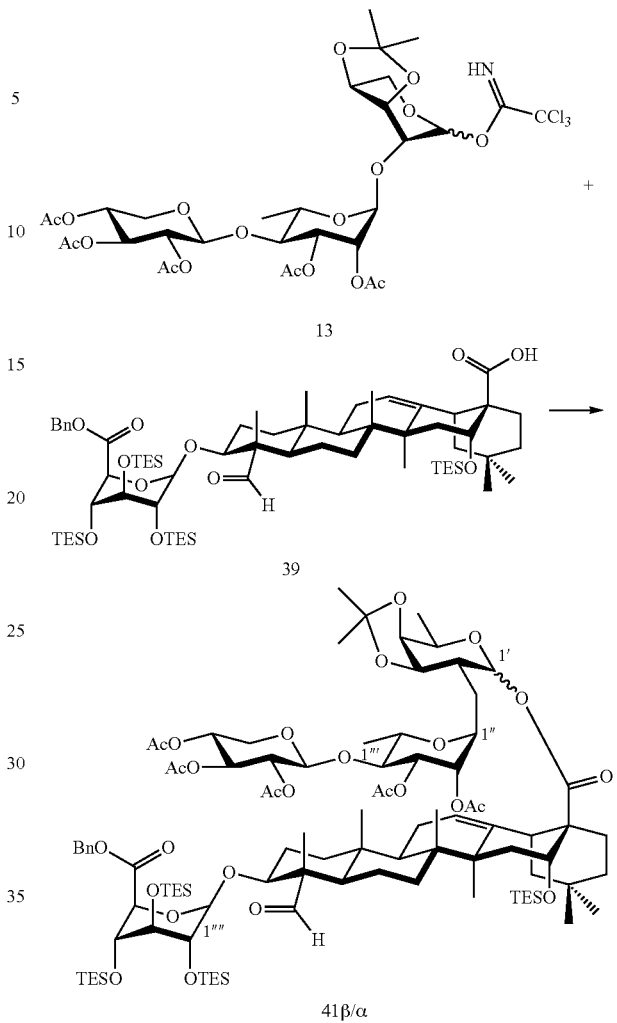

3-O-(Benzyl 2,3,4-tri-O-triethylsilyl-β-D-glucopyranosyluronate)-28-O-(2,3,4-tri-O-acetyl-β-D-xylopyranosyl-(1→4)-2,3-di-O-acetyl-α-L-rhamnopyranosyl-(1→2)-3,4-O-isopropylidene-β/α-L-arabinopyranosyl)-16-O-triethylsilylquillaic ester (42β/α)

To a stirred suspension of 13 (67 mg, 0.081 mmol), 39 (65 mg, 0.054 mmol) and activated 4 Å molecular sieve powder in anhydrous CH₂Cl₂ (6 mL) was added BF₃·OEt₂ (ca. 48%, 1.5 μL, 0.0058 mmol) at −75° C. under N₂ atmosphere. Upon completion of the reaction after 0.5 h, the reaction was quenched by Et₃N, warmed to rt. The resulting mixture was diluted with CH₂Cl₂, washed by saturated NaHCO₃, brine, dried over MgSO₄, and then concentrated under reduced pressure. The residue was purified by column chromatography (silica gel; EtOAc/CH₂Cl₂/hexanes=2/1/5) to give 101 (101β: 76 mg, 75%, 101α: 15 mg, 16%) as colorless syrups. 42β: R$_f$ 0.24 (EtOAc/CH₂Cl₂/hexanes=2/1/5); ¹H NMR (600 MHz, CDCl₃) δ 9.36 (s, 1H, H-23), 7.39-7.29 (m, 5H), 5.76 (d, J=3.8 Hz, 1H, H-1'), 5.35 (s, 1H, H-12), 5.21 (s, 1H, H-2"), 5.19-5.15 (m, 3H, H-3", Bn C$\underline{H}_2$), 5.13 (t, J=9.2 Hz, 1H, H-3'''), 4.97→4.92 (m, 2H, H-1", H-4"), 4.86 (dd, J=9.2, 7.6 Hz, 1H, H-2'''), 4.63 (d, J=7.6 Hz, 1H, H-1'''), 4.58 (d, J=4.2 Hz, 1H, H-1''''), 4.55 (s, 1H, H-16), 4.35 (q, J=6.2 Hz, 1H, H-4'), 4.27 (t, J=5.8 Hz, 1H, H-4''''), 4.21 (d, J=6.3 Hz, 1H, H-5''''), 4.17 (t, J=5.4 Hz, 1H, H-3'), 4.12 (dd, J=11.5, 5.1 Hz, 1H, H-5$_a$'''), 3.85-3.76 (m, 4H, H-3, H-2', H-5$_a$', H-5''), 3.71 (dd, J=11.7, 8.2 Hz, 1H, H-5$_b$'), 3.64-3.60 (m, 2H, H-4'', H-3''''), 3.57 (d, J=4.2 Hz, 1H, H-2''''), 3.33 (t, J=10.6 Hz, 1H, H-5$_b$''), 2.98 (d, J=11.8 Hz, 1H, H-18), 2.24 (t, J=13.5 Hz, 1H, H-19$_a$), 2.13 (s, 3H), 2.07 (s, 3H), 2.03 (s, 3H), 2.01 (s, 3H), 2.00-1.97 (m, 4H, Ac CH$_3$, H-2$_a$), 1.89-1.65 (m, 7H, H-2$_b$, H-11$_{ab}$, H-15$_a$, H-21$_a$, H-22$_{ab}$), 1.63-1.60 (m, 1H, H-9), 1.56 (d, J=13.5 Hz, 1H, H-1$_a$), 1.51 (s, 3H, CH$_3$) 1.48-1.40 (m, 2H, H-6$_a$, H-7$_a$), 1.35 (s, 6H, H-27, CH$_3$), 1.27-1.24 (m, 4H, H-15$_b$, H-6''), 1.20-1.12 (m, 3H, H-5, H-6$_b$, H-21$_b$), 1.09 (s, 3H, H-24), 1.06 (d, J=13.2 Hz, 1H, H-19$_b$), 1.01-0.90 (m, 44H, H-1$_b$, H-7$_b$, H-25, H-30, TES CH$_3$), 0.89 (s, 3H, H-29), 0.72 (s, 3H, H-26), 0.69-0.53 (m, 24H) ppm; HRMS (ESI-TOF) calcd. for C$_{96}$H$_{156}$O$_{28}$Si$_4$Na [M+Na]$^+$ 1892.9793, found 1892.9791.

42α: R$_f$ 0.29 (EtOAc/CH$_2$Cl$_2$/hexanes=2/1/5); $^1$H NMR (600 MHz, CDCl$_3$) δ 9.35 (s, 1H, H-23), 7.39-7.30 (m, 5H), 6.07 (d, J=3.3 Hz, 1H, H-1''), 5.39 (t, J=3.5 Hz, 1H, H-12), 5.22 (dd, J=3.5, 1.3 Hz, 1H, H-2'''), 5.16 (s, 2H, Bn CH$_2$), 5.11 (t, J=8.9 Hz, 1H, H-3''''), 5.07 (dd, J=9.7, 3.5 Hz, 1H, H-3'), 5.05 (d, J=1.3 Hz, 1H, H-1'''), 4.94 (td, J=8.9, 5.3 Hz, 1H, H-4''''), 4.81 (dd, J=8.9, 7.4 Hz, 1H, H-2''''), 4.67 (d, J=7.4 Hz, 1H, H-1''''), 4.58 (d, J=4.4 Hz, 1H, H-1'), 4.57 (s, 1H, H-16), 4.27 (t, J=5.8 Hz, 1H, H-4'), 4.25-4.20 (m, 3H, H-3'', H-4', H-5'), 4.11 (dd, J=11.8, 5.3 Hz, 1H, H-5$_a$''''), 4.05-4.01 (d, J=13.4 Hz, 1H, H-5$_a$''), 3.91-3.84 (m, 2H, H-2'', H-5$_b$''), 3.81 (dd, J=11.8, 4.6 Hz, 1H, H-3), 3.69 (dq, J=9.5, 6.1 Hz, 1H, H-5'''), 3.64-3.59 (m, 2H, H-4''', H-3'), 3.57 (d, J=4.4 Hz, 1H, H-2'), 3.36 (dd, J=11.8, 9.1 Hz, 1H, H-5$_b$''''), 2.99 (dd, J=14.4, 4.0 Hz, 1H, H-18), 2.20 (t, J=13.6 Hz, 1H, H-19$_a$), 2.14 (s, 3H), 2.04 (s, 3H), 2.03 (s, 3H), 2.02 (s, 3H), 2.00-1.99 (m, 1H, H-2$_a$), 1.97 (s, 3H), 1.95-1.83 (m, 3H, H-22$_a$, H-11$_{ab}$), 1.81-1.65 (m, 3H, H-21$_a$, H-22$_b$, H-2$_b$), 1.65-1.62 (m, 1H, H-9), 1.58-1.53 (m, 2H, H-1$_a$, H-15$_a$), 1.51 (s, 3H, isopropylidene CH$_3$), 1.45-1.40 (m, 2H, H-6$_a$, H-7$_a$), 1.36-1.35 (m, 6H, H-27, isopropylidene CH$_3$), 1.32 (dd, J=14.5, 1.6 Hz, 1H, H-15$_b$), 1.29 (d, J=6.1 Hz, 3H, H-6'''), 1.23-1.15 (m, 3H, H-5, H-6$_b$, H-21$_b$), 1.10-1.05 (m, 4H, H-19$_b$, H-24), 1.04-0.89 (m, 44H, H-1$_b$, H-7$_b$, H-25, H-30, TES CH$_3$×12), 0.88 (s, 3H, H-29), 0.73 (s, 3H, H-26), 0.71-0.54 (m, 24H, TES CH$_2$×12) ppm; HRMS (ESI-TOF) calcd. for C$_{96}$H$_{156}$O$_{28}$Si$_4$Na [M+Na]$^+$ 1892.9793, found 1892.9780.

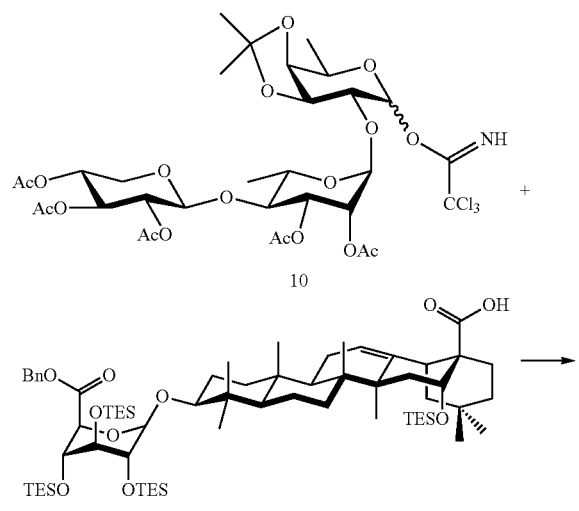

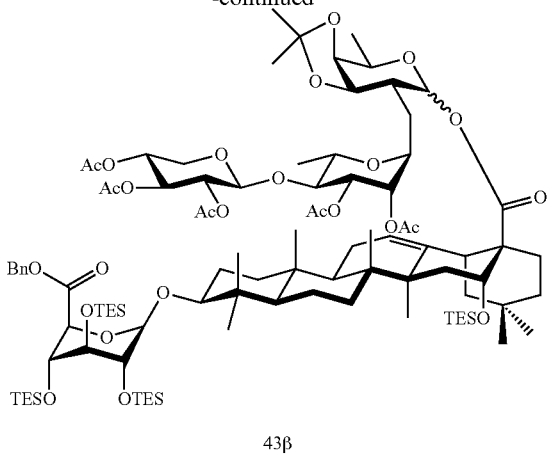

43β

3-O-(Benzyl 2,3,4-tri-O-triethylsilyl-β-D-glucopyranosyluronate)-28-O-(2,3,4-tri-O-acetyl-β-D-xylopyranosyl-(1→4)-2,3-di-O-acetyl-α-L-rhamnopyranosyl-(1→2)-3,4-O-isopropylidene-β-D-fucopyranosyl)-16-O-triethylsilylechinocystic ester (43β)

To a stirred suspension of 10 (166 mg, 0.20 mmol), 40 (158 mg, 0.13 mmol) and activated 4 Å molecular sieve powder in anhydrous CH$_2$Cl$_2$ (6.5 mL) was added BF$_3$·OEt$_2$ (ca. 48%, 7.0 μL, 0.026 mmol) at −75° C. under N$_2$ atmosphere. Upon completion of the reaction after 0.5 h, the reaction was quenched by Et$_3$N, warmed to rt. The resulting mixture was diluted with CH$_2$Cl$_2$, washed by saturated NaHCO$_3$, brine, dried over MgSO$_4$ and then concentrated under reduced pressure. The residue was purified by column chromatography (silica gel; EtOAc/CH$_2$Cl$_2$/hexanes=2/1/5) to give 43β (237 mg, 96%) as colorless syrups. 102β: R$_f$ 0.23 (EtOAc/CH$_2$Cl$_2$/hexanes=2/1/5); $^1$H NMR (600 MHz, CDCl$_3$) δ 7.37-7.29 (m, 5H), 5.42 (d, J=7.5 Hz, 1H, H-1'), 5.34 (s, 1H, H-12), 5.26 (dd, J=3.4, 1.5 Hz, 1H, H-2'''), 5.21 (dd, J=9.8, 3.4 Hz, 1H, H-3'), 5.16 (d, J=3.2 Hz, 2H, Bn CH$_2$), 5.13 (t, J=9.3 Hz, 1H, H-3''''), 4.99 (d, J=1.5 Hz, 1H, H-1'''), 4.95 (td, J=9.3, 5.4 Hz, 1H, H-4''''), 4.85 (dd, J=9.3, 7.6 Hz, 1H, H-2''''), 4.77 (d, J=4.4 Hz, 1H, H-1''''), 4.64 (d, J=7.6 Hz, 1H, H-1'''), 4.50 (s, 1H, H-16), 4.33 (dd, J=6.1, 5.8 Hz, 1H, H-4''''), 4.26 (d, J=6.1 Hz, 1H, H-5''''), 4.18 (t, J=6.0 Hz, 1H, H-3'), 4.12 (dd, J=11.7, 5.4 Hz, 1H, H-5$_a$'''), 4.01 (dd, J=6.0, 1.8 Hz, 1H, H-4'), 3.89-3.81 (m, 2H, H-5', H-5''), 3.72 (d, J=4.4 Hz, 1H, H-2''''), 3.68-3.61 (m, 3H, H-2', H-3'''', H-4''), 3.34 (dd, J=11.9, 9.3 Hz, 1H, H-5$_b$'''), 3.01 (dd, J=11.7, 4.3 Hz, 1H, H-3), 2.93 (dd, J=14.2, 3.7 Hz, 1H, H-18), 2.23 (t, J=13.5 Hz, 1H, H-19$_a$), 2.13 (s, 3H), 2.07 (s, 3H), 2.03 (s, 3H), 2.00 (s, 3H), 1.98 (s, 3H), 1.97-1.93 (m, 1H, H-2$_a$), 1.86-1.76 (m, 6H, H-1$_{ab}$, H-22α, H-21, H-22$_b$), 1.76-1.71 (m, 1H, H-15$_a$), 1.67-1.65 (m, 1H, H-2$_b$), 1.54 (s, 3H, isopropylidene CH$_3$), 1.53-1.42 (m, 4H, H-9, H-1$_a$, H-6$_a$, H-7$_a$), 1.34-1.33 (m, 6H, H-27, isopropylidene CH$_3$), 1.31-1.24 (m, 9H, H-6', H-6'', H-6$_b$, H-7$_b$, H-15$_b$), 1.11-1.10 (m, 1H, H-21$_b$), 1.07-1.02 (m, 2H, H-19$_b$), 1.01-0.91 (m, 42H, H-23, H-30, TES CH$_3$), 0.89 (s, 3H, H-25), 0.88 (s, 5H, H-29), 0.79 (s, 3H, H-24), 0.73 (s, 3H, H-26), 0.70-0.55 (m, 25H, H-5, TES CH$_2$) ppm; HRMS (ESI-TOF) calcd. for C$_{97}$H$_{160}$O$_{27}$Si$_4$Na [M+Na]$^+$ 1893.0144, found 1893.0150.

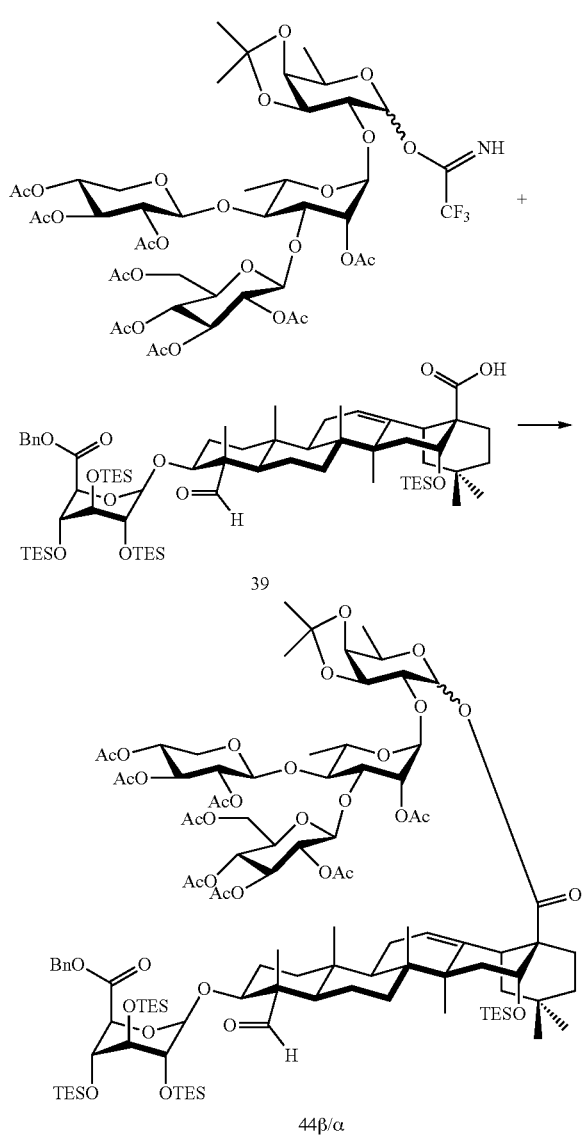

3-O-(benzyl 2,3,4-tri-O-triethylsilyl-β-D-glucopyranosyluronate)-28-O-(2,3,4,6-tetra-O-acetyl-β-D-glucopyranosyl-(1→3)-(2,3,4-tri-O-acetyl-β-D-xylopyranosyl-(1→4))-2-O-acetyl-α-L-rhamopyranosyl-(1-2)-3,4-O-isopropylidene-β-D-fucopyranosyl)-16-O-triethylsilylquillaic ester (44β)

To a stirred suspension of 22 (22 mg, 0.019 mmol), 39 (23 mg, 0.019 mmol) and activated 4 Å molecular sieve powder in anhydrous $CH_2Cl_2$ (1 mL) was added $BF_3$—$OEt_2$ (ca. 48%, 2.0 µL, 0.0076 mmol) at −75° C. under $N_2$ atmosphere. Upon completion of the reaction after 0.5 h, the reaction was quenched by addition of saturated $NaHCO_3$, warmed to rt. The resulting mixture was diluted with $CH_2Cl_2$, washed by saturated $NaHCO_3$, brine, dried over $MgSO_4$ and then concentrated under reduced pressure. The residue was purified by column chromatography (silica gel; $EtOAc/CH_2Cl_2$/hexanes=4/1/7) to give 103 (44β: 19 mg, 46%; 44α: 2 mg, 5%) as colorless syrups. 44β: $R_f$ 0.60 (EtOAc/hexanes=1/1); $^1$H NMR (600 MHz, $CDCl_3$) δ 9.36 (s, 1H, H-23), 7.38-7.30 (m, 5H), 5.39 (d, J=7.3 Hz, 1H, H-1'), 5.32 (t, J=3.6 Hz, 1H, H-12), 5.17 (dd, J=3.5, 1.8 Hz, 1H, H-2″), 5.16 (d, J=1.8 Hz, 2H, Bn C$\underline{H}_2$), 5.15-5.09 (m, 3H, H-3‴, H-4‴, H-3″″), 5.02 (m, J=7.8 Hz, 1H, H-2‴), 4.95 (d, J=1.8 Hz, 1H, H-1″), 4.91 (td, J=8.0, 4.9 Hz, 1H, H-4″″), 4.85-4.81 (m, 2H, H-2″″, H-1″″), 4.68 (d, J=7.8 Hz, 1H, H-1‴), 4.58 (d, J=4.4 Hz, 1H, H-1‴″), 4.47 (s, 1H, H-16), 4.28-4.25 (m, 2H, H-4″″, H-6$_a$″), 4.21 (d, J=6.3 Hz, 1H, H-5″″), 4.16 (t, J=6.0 Hz, 1H, H-3'), 4.14-4.09 (m, 2H, H-6$_b$‴, H-5$_a$″″), 4.03 (dd, J=6.0, 1.9 Hz, 1H, H-4'), 3.99 (dd, J=9.4, 3.5 Hz, 1H, H-3″), 3.86 (qd, J=6.5, 1.9 Hz, 1H, H-5'), 3.81 (dd, J=11.8, 4.6 Hz, 1H, H-3), 3.76 (t, J=9.4 Hz, 1H, H-4″), 3.71-3.62 (m, 3H, H-5″, H-2', H-5″″), 3.61 (dd, J=5.4, 1.2 Hz, 1H, H-3″″″), 3.57 (dd, J=4.4, 1.2 Hz, 1H, H-2″″″), 3.40 (dd, J=11.9, 8.1 Hz, 1H, H-5$_b$″″), 2.91 (dd, J=14.4, 4.2 Hz, 1H, H-18), 2.22 (t, J=13.5 Hz, 1H, H-19$_a$), 2.18 (s, 3H), 2.11 (s, 3H), 2.09 (s, 6H), 2.04 (s, 3H), 2.03 (s, 3H), 2.01 (s, 3H), 2.00 (s, 3H), 1.99-1.97 (m, 1H, H-2$_a$), 1.87-1.84 (m, 2H, H-11$_{ab}$), 1.80 (s, 3H, H-21$_a$, H-22$_{ab}$), 1.70-1.68 (m, 2H, H-2$_b$, H-15$_a$), 1.59-1.56 (m, 2H, H-9, H-1$_a$), 1.54 (s, 3H, isopropylidene C$\underline{H}_3$), 1.45-1.41 (m, 2H, H-6$_b$, H-7$_a$), 1.34 (s, 6H, H-27, isopropylidene C$\underline{H}_3$), 1.28 (d, J=6.5 Hz, 3H, H-6'), 1.26-1.24 (m, 1H, H-15$_b$), 1.22 (d, J=6.1 Hz, 3H, H-6″), 1.18-1.16 (m, 2H, H-5, H-6$_b$), 1.13-1.11 (m, 1H, H-21$_b$), 1.08 (s, 3H, H-24), 1.06-1.02 (m, 1H, H-19$_b$), 1.00-0.92 (m, 44H, H-1$_b$, H-7$_b$, H-25, H-30, TES C$\underline{H}_3$), 0.88 (s, 3H, H-29), 0.74 (s, 3H, H-26), 0.68-0.55 (m, 24H, TES C$\underline{H}_2$) ppm; HRMS (ESI-TOF) calcd. for $C_{109}H_{174}O_{36}Si_4Na$ [M+Na]$^+$ 2195.0788, found 2195.0785.

General Procedure of Amide Bond Formation:

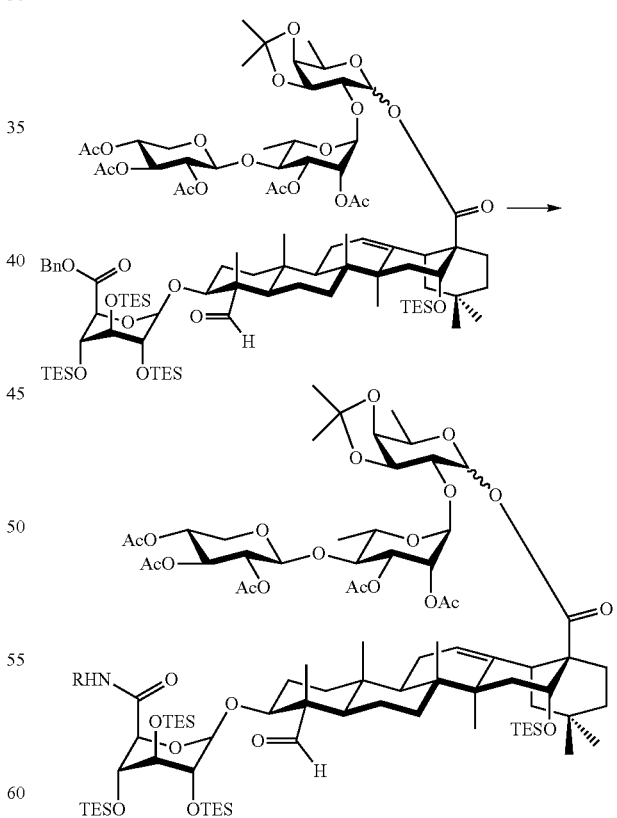

To a suspension of benzyl ester starting material (1 equiv.) and 10% Pd/C (10% w/v) in THF (50 mM) was stirred at rt under $H_2$ atmosphere (balloon). The reaction mixture was stirred for 12 to 24 h. The resulting mixture was filtered through celite, concentrated, and then dried under reduced pressure to afford crude acid intermediate. To a stirred solution of crude acid intermediate, HBTU (3 equiv.) and DIPEA (3 equiv.) in anhydrous CH$_2$Cl$_2$ (50 mM) was added alkyl amine (3 equiv.) under N$_2$ atmosphere at rt. The reaction mixture was stirred for 4 h. The resulting mixture was concentrated, and then purified by column chromatography (silica gel, EtOAc/CH$_2$Cl$_2$/Hexanes=2/1/5 to 1/1/2) to afford amide product in 61-95% two steps yield.

In some embodiments, silyl groups were deprotected randomly under hydrogenolysis condition that resulted unseparable mixture in the following amide coupling step. Thus, after filtration by short column (silica, EtOAc/CH$_2$Cl$_2$/Hexanes=1/1/2), the mixture was directly proceeded toward global deprotection steps without structural characterizations.

General Procedure of Global Deprotection:

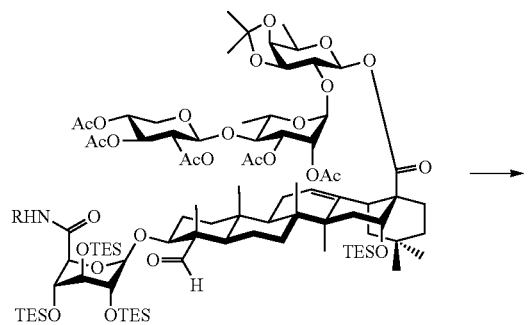

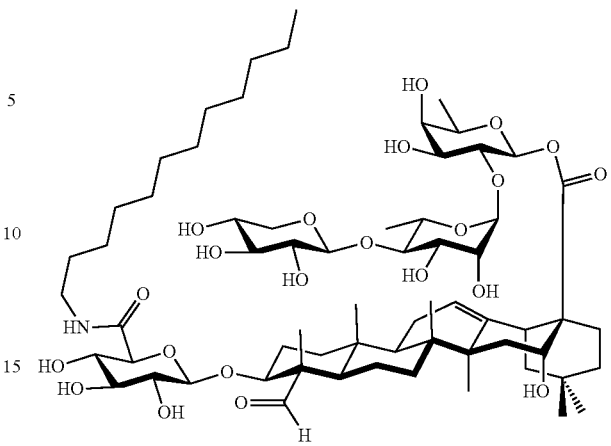

3-O—(N-((Dodecyl)-β-D-glucopyranosyluronamide)-28-O-(β-D-xylopyranosyl-(1-4)-α-L-rhamnopyranosyl-(1→2)-β-D-fucopyranosyl) quillaic ester (46)

Following the general procedure of global deprotection, 46 was obtained in 68% yield as a white solid: $[\alpha]_D^{20}$ −68.0 (c 0.15, MeOH); $^1$H NMR (600 MHz, MeOD) δ 9.43 (s, 1H, H-23), 8.55 (s, 1H, amide NH), 5.41 (d, J=1.7 Hz, 1H, H-1"), 5.31 (t, J=3.5 Hz, 1H, H-12), 5.28 (d, J=8.2 Hz, 1H, H-1'), 4.49-4.48 (m, 2H, H-1''', H-16), 4.26 (d, J=7.8 Hz, 1H, H-1''''), 3.92-3.79 (m, 6H, H-2", H-3, H-5''', H-3", H-2', H-5"), 3.69-3.64 (m, 3H, H-5', H-3', H-5''''), 3.57-3.53 (m, 2H, H-4', H-4"), 3.49-3.42 (m, 2H, H-4''', H-4''''), 3.33-3-30 (m, 2H, H-3''', H-3''''), 3.28-3.26 (m, 1H, —NHCH$_a$—), 3.24-3.17 (m, 3H, —NHCH$_b$—, H-2''', H-5'''), 3.14 (dd, J=9.2, 7.8 Hz, 1H, H-2''''), 2.94 (dd, J=14.1, 4.3 Hz, 1H, H-18), 2.30 (t, J=13.6 Hz, 1H, H-19$_a$), 1.97-1.89 (m, 5H, H-2$_a$, H-11$_{ab}$, H-21$_a$, H-22$_a$), 1.84-1.64 (m, 5H, H-2$_b$, H-22$_b$, H-9, H-1$_a$, H-15$_a$), 1.58-1.48 (m, 4H, H-6$_a$, H-7$_a$, carbon chain CH$_2$), 1.45 (dd, J=14.8, 2.7 Hz, 1H, H-15$_b$), 1.40 (s, 3H, H-27), 1.37-1.27 (m, 23H, H-5, H-6$_b$, H-6", carbon chain CH$_2$×9), 1.22 (d, J=6.4 Hz, 3H, H-6'), 1.19-1.16 (m, 1H, H-21$_b$), 1.14 (s, 3H, H-24), 1.12-1.09 (m, 1H, H-1$_b$), 1.07-1.04 (m, 1H, H-19$_b$), 1.02 (s, 3H, H-25), 0.98-0.94 (m, 4H, H-7$_b$, H-30), 0.91 (t, J=7.0 Hz, 3H, carbon chain CH$_3$), 0.88 (s, 3H, H-29), 0.77 (s, 3H, H-26); $^{13}$C NMR (151 MHz, MeOD) δ 209.2 (C-23), 177.2 (C-28), 171.5, 144.9 (C-13), 123.1 (C-12), 107.0 (C-1'''), 105.1 (C-1''''), 101.1 (C-1"), 95.2 (C-1'), 84.0 (C-4"), 83.5 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5"), 72.2 (C-3"), 71.9 (C-2"), 71.1 (C-4'''), 68.8 (C-5'), 67.3 (C-5"), 56.1 (C-4), 50.0 (C-17), 49.6 (C-5), 48.1 (C-9), 48.0 (C-19), 42.8 (C-14), 42.4 (C-18), 41.1 (C-8), 40.1 (carbon chain CH$_2$), 39.5 (C-1), 37.1 (C-10), 36.5 (C-21), 36.5 (C-15), 33.6 (C-6), 33.4 (C-29), 33.1 (carbon chain CH$_2$), 32.0 (C-22), 31.3 (C-20), 30.9 (carbon chain CH$_2$), 30.9 (carbon chain CH$_2$), 30.8 (carbon chain CH$_2$), 30.8 (carbon chain CH$_2$), 30.6 (carbon chain CH$_2$), 30.5 (carbon chain CH$_2$), 30.3 (carbon chain CH$_2$), 28.0 (carbon chain CH$_2$), 27.2 (C-27), 26.0 (C-2), 24.8 (C-30), 24.5 (C-11), 23.8 (carbon chain CH$_2$), 21.6 (C-7), 18.3 (C-6"), 17.7 (C-26), 16.5 (C-6'), 16.4 (C-25), 14.5 (carbon chain CH$_3$), 10.6 (C-24) ppm; HRMS (ESI-TOF) calcd. for C$_{65}$H$_{107}$NO$_{22}$Na [M+Na]$^+$ 1276.7177, found 1276.7209.

To a solution of starting material in CH$_2$Cl$_2$ (10 mM) was added pre-cooled TFA/H$_2$O=4/1 solution (50% v/v to CH$_2$Cl$_2$) at 0° C. and stirred for 30 min. The solvent was evaporated under reduced pressure (<1 torr) at 0° C., and then dried under high vacuum at rt for 1 h. To a solution of the residue in MeOH (10 mM) was added K$_2$CO$_3$ (20 equiv.) and stirred at rt for 12 h. The suspension was centrifuged, and then the liquid was purified by HPLC to afford products in 30-75% two steps yield. (HPLC column: SUPELCO Ascentis C18 25 cm×10 mm, 5 m; mobile phase: 20% ACN/H$_2$O gradient to 90% ACN/H$_2$O in 20 min, and then 90% ACN/H$_2$O isocratic for 15 min; flow rate: 5 mL/min).

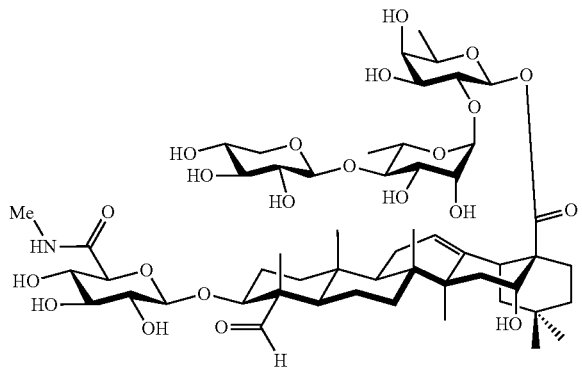
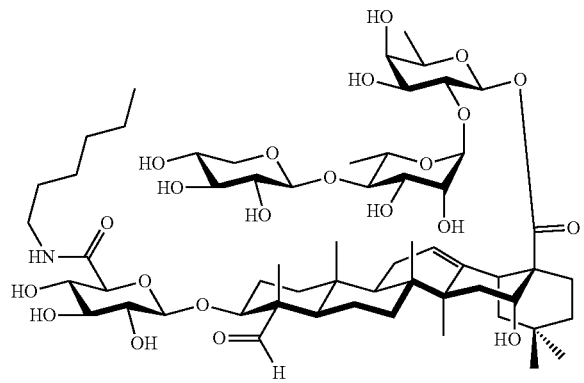

3-O—(N-(Methyl)-β-D-glucopyranosyluronamide)-28-β-(β-D-xylopyranosyl-(1→4)-α-L-rhamnopyranosyl-(1→2)-β-D-fucopyranosyl) quillaic ester (47)

Following the general procedure of global deprotection, 47 was obtained in 36% yield as a white solid: $[\alpha]_D^{20}$ −26.8 (c 0.22, MeOH); $^1$H NMR (600 MHz, MeOD) δ 9.42 (s, 1H, H-23), 8.52 (s, 1H, amide NH̲), 5.40 (d, J=1.7 Hz, 1H, H-1''), 5.31 (t, 1H, J=3.5 Hz, H-12), 5.28 (d, J=8.2 Hz, 1H, H-1'), 4.49-4.47 (m, 2H, H-1''', H-16), 4.24 (d, J=7.9 Hz, 1H, H-1''''), 3.90 (dd, J=3.3, 1.7 Hz, 1H, H-2''), 3.89-3.79 (m, 5H, H-3, H-5a''', H-3'', H-2', H-5''), 3.69-3.64 (m, 3H, H-5', H-3', H-5''''), 3.56-3.53 (m, 2H, H-4', H-4''), 3.46 (ddd, J=10.4, 8.8, 5.4 Hz, 1H, H-4''''), 3.41 (t, J=9.1 Hz. 1H, H-4'''), 3.33-3.30 (m, 2H, H-3''', H-3''''), 3.23-3.17 (m, 2H, H-2''', H-5'''), 3.13 (dd, J=9.2, 7.9 Hz, 1H, H-2''''), 2.94 (dd, J=14.6, 4.1 Hz, 1H, H-18), 2.80 (s, 3H, —NHCH̲$_3$), 2.30 (t, J=13.7 Hz, 1H, H-19$_a$), 1.94-1.91 (m, 5H, H-2$_a$, H-11$_{ab}$, H-21$_a$, H-22$_a$), 1.81-1.66 (m, 5H, H-2$_b$, H-22$_b$, H-9, H-1$_a$, H-15$_a$), 1.55-1.43 (m, 3H, H-6$_a$, H-7$_a$, H-15$_b$), 1.40 (s, 3H, H-27), 1.35-1.31 (m, 5H, H-5, H-6$_b$, H-6''), 1.22 (d, J=6.4 Hz, 3H, H-6'), 1.18 (d, J=10.3, 2.5 Hz, 1H, H-21$_b$), 1.13 (s, 3H, H-24), 1.10 (dd, J=13.2, 4.02 Hz, 1H, H-1$_b$), 1.05 (dd, J=13.4, 3.5 Hz, 1H, H-19$_b$), 1.02 (s, 3H, H-25), 0.97-0.95 (m, 4H, H-7$_b$, H-30), 0.88 (s, 3H, H-29), 0.77 (s, 3H, H-26); $^{13}$C NMR (151 MHz, MeOD) δ 209.3 (C-23), 177.2 (C-28), 172.3, 144.8 (C-13), 123.2 (C-12), 107.0 (C-1'''), 104.8 (C-1''''), 101.1 (C-1''), 95.2 (C-1'), 84.1 (C-4''), 83.3 (C-3), 78.2 (C-3'''), 77.5 (C-3''''), 76.7 (C-3'), 76.5 (C-5''''), 76.1 (C-2'''), 74.7 (C-2''''), 74.6 (C-16), 74.0 (C-2'), 73.6 (C-4'), 73.4 (C-4''''), 72.7 (C-5'), 72.2 (C-3''), 71.9 (C-2''), 71.1 (C-4'''), 68.8 (C-5''), 67.3 (C-5'''), 56.1 (C-4), 50.0 (C-17), 49.6 (C-5), 48.0 (C-9), 48.0 (C-19), 42.8 (C-14), 42.4 (C-18), 41.1 (C-8), 39.3 (C-1), 37.1 (C-10), 36.5 (C-21), 36.5 (C-15), 33.6 (C-6), 33.4 (C-29), 32.0 (C-22), 31.3 (C-20), 27.2 (C-27), 26.2 (—NHCH̲$_3$), 25.8 (C-2), 24.8 (C-30), 24.5 (C-11), 21.5 (C-7), 18.3 (C-6''), 17.7 (C-26), 16.5 (C-6'), 16.3 (C-25), 10.5 (C-24) ppm; HRMS (ESI-TOF) calcd. for C$_{54}$H$_{86}$NO$_{22}$ [M+H]$^+$ 1100.5636 found 1100.5667.

3-O—(N-(Hexyl)-β-D-glucopyranosyluronamide)-28-O-(β-D-xylopyranoyl-(1→4)-α-L-rhamnopyranosyl-(1→2)-β-D-fucopyranosyl) quillaic ester (48)

Following the general procedure of global deprotection, 48 was obtained in 45% yield as a white solid: $[\alpha]_D^{20}$ −17.35 (c 0.34, MeOH); $^1$H NMR (600 MHz, MeOD) δ 9.42 (s, 1H, H-23), 8.55 (s, 1H, amide NH̲), 5.40 (d, J=1.6 Hz, 1H, H-1''), 5.31 (t, J=3.4 Hz, 1H, H-12), 5.28 (d, J=8.2 Hz, 1H, H-1'), 4.49-4.48 (m, 2H, H-16, H-1'''), 4.26 (d, J=7.9 Hz, 1H, H-1''''), 3.92-3.77 (m, 6H, H-2'', H-3, H-5$_a$''', H-3'', H-2', H-5''), 3.70-3.62 (m, 3H, H-5', H-3', H-5''''), 3.56-3.53 (m, 2H, H-4', H-4''), 3.49-3.41 (m, 2H, H-4''', H-4''''), 3.33-3.30 (m, 2H, H-3''', H-3''''), 3.29-3.17 (m, 4H, —NHCH̲$_2$—, H-2''', H-5$_b$'''), 3.14 (dd, J=9.2, 7.9 Hz, 1H, H-2''''), 2.94 (dd, J=14.1, 4.0 Hz, 1H, H-18), 2.30 (t, J=13.8 Hz, 1H, H-19$_a$), 1.96-1.90 (m, 5H, H-2$_a$, H-11$_{ab}$, H-21$_a$, H-22$_a$), 1.84-1.64 (m, 5H, H-2$_b$, H-22$_b$, H-9, H-1$_a$, H-15$_a$), 1.55-1.49 (m, 4H, H-6$_a$, H-7$_a$, carbon chain CH̲$_2$), 1.45 (dd, J=14.8, 2.7 Hz, 1H, H-15$_b$), 1.40 (s, 3H, H-27), 1.36-1.29 (m, 13H, H-5, H-6$_b$, H-6'', carbon chain CH̲$_2$×4), 1.22 (d, J=6.4 Hz, 3H, H-6'), 1.18-1.17 (m, 1H, H-21$_b$), 1.13 (s, 3H, H-24), 1.12-1.09 (m, 1H, H-1$_b$), 1.05 (dd, J=12.6, 3.0 Hz, 1H, H-19$_b$), 1.01 (s, 3H, H-25), 0.95 (s, 4H, H-7$_b$, H-30), 0.92 (t, J=7.0 Hz, 3H, carbon chain CH̲$_3$), 0.88 (s, 3H, H-29), 0.77 (s, 3H, H-26); $^{13}$C NMR (151 MHz, MeOD) δ 209.3 (C-23), 177.2 (C-28), 171.5, 144.8 (C-13), 123.2 (C-12), 106.9 (C-1'''), 104.9 (C-1''''), 101.1 (C-1''), 95.2 (C-1'), 84.0 (C-4''), 83.3 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.1 (C-2'), 73.6 (C-4'), 73.2 (C-4''''), 72.7 (C-5'), 72.2 (C-3''), 71.9 (C-2''), 71.1 (C-4'''), 68.8 (C-5''), 67.3 (C-5'''), 56.1 (C-4), 50.0 (C-17), 49.6 (C-5), 48.0 (C-9, C-19), 42.8 (C-14), 42.4 (C-18), 41.1 (C-8), 40.1 (carbon chain CH̲$_2$), 39.4 (C-1), 37.1 (C-10), 36.5 (C-21), 36.5 (C-15), 33.6 (C-6), 33.4 (C-29), 32.8 (carbon chain CH̲$_2$), 32.0 (C-22), 31.3 (C-20), 30.3 (carbon chain CH̲$_2$), 27.6 (carbon chain CH̲$_2$), 27.2 (C-27), 25.9 (C-2), 24.8 (C-30), 24.5 (C-11), 23.8 (carbon chain CH̲$_2$), 21.5 (C-7), 18.3 (C-6''), 17.7 (C-26), 16.5 (C-6'), 16.3 (C-25), 14.5 (carbon chain CH̲$_3$), 10.6 (C-24) ppm; HRMS (ESI-TOF) calcd. for C$_{59}$H$_{96}$NO$_{22}$ [M+H]$^+$ 1170.6418, found 1170.6448.

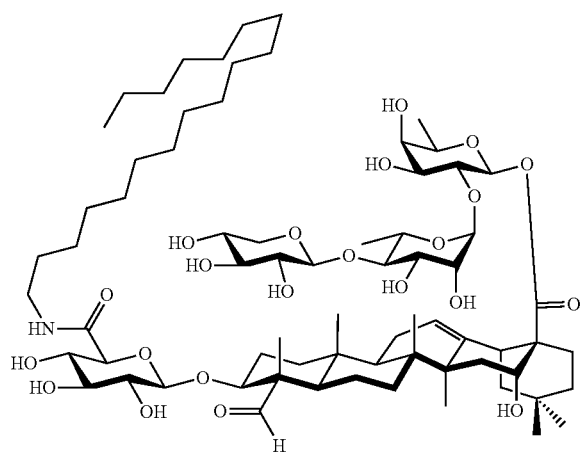

3-O—(N-(Octadecyl)-β-D-glucopyranosyluronamide)-28-O-(β-D-xylopyranosyl-(1→4)-α-L-rhamnopyranosyl-(1→2)-β-D-fucopyranosyl) quillaic ester (49)

Following the general procedure of global deprotection (HPLC column: Alltima C8 150 mm×4.6 mm, 5 m, flow rate: 1 mL/min), 49 was obtained in 30% yield as a white solid: $[\alpha]_D^{20}$ −27.4 (c 0.27, MeOH); $^1$H NMR (600 MHz, MeOD) δ 9.43 (s, 1H, H-23), 8.55 (s, 1H, amide NH), 5.41 (d, J=1.6 Hz, 1H, H-1"), 5.31 (t, J=3.4 Hz, 1H, H-12), 5.28 (d, J=8.2 Hz, 1H, H-1'), 4.49 (d, J=7.6 Hz, 2H, H-16, H-1'''), 4.26 (d, J=7.9 Hz, 1H, H-1''''), 3.92-3.77 (m, 6H, H-2'', H-3, H-5$_a$''', H-3'', H-2', H-5''), 3.69-3.63 (m, 3H, H-5', H-3', H-5''''), 3.57-3.53 (m, 2H, H-4', H-4''), 3.49-3.41 (m, 2H, H-4''', H-4''''), 3.33-3.27 (m, 3H, H-3''', H-3''''', —NH-CH$_a$—), 3.24-3.17 (m, 3H, H-2''', H-5$_b$'''', —NHCH$_b$—), 3.14 (dd, J=9.2, 7.9 Hz, 1H, H-2''''), 2.94 (dd, J=14.3, 4.1 Hz, 1H, H-18), 2.30 (t, J=13.6 Hz, 1H, H-19$_a$), 1.98-1.89 (m, 5H, H-2$_a$, H-11$_{ab}$, H-21$_a$, H-22$_a$), 1.84-1.64 (m, 5H, H-2$_b$, H-9, H-22$_b$, H-1$_a$, H-15$_a$), 1.55-1.49 (m, 4H, H-6$_a$, H-7$_a$, carbon chain CH$_2$), 1.45 (dd, J=14.8, 2.5 Hz, 1H, H-15$_b$), 1.40 (s, 3H, H-27), 1.37-1.25 (m, 35H, H-5, H-6$_b$, H-6'', carbon chain CH$_2$×15), 1.22 (d, J=6.4 Hz, 3H, H-6'), 1.20-1.15 (m, 1H, H-21$_b$), 1.14 (s, 3H, H-24), 1.13-1.08 (m, 1H, H-1$_b$), 1.06 (dd, J=12.6, 3.0 Hz, 1H, H-19$_b$), 1.02 (s, 3H, H-25), 0.97-0.95 (m, 4H, H-7$_b$, H-30), 0.90 (t, J=7.0 Hz, 3H, carbon chain CH$_3$), 0.88 (s, 3H, H-29), 0.77 (s, 3H, H-26); $^{13}$C NMR (151 MHz, MeOD) δ 209.2 (C-23), 177.2 (C-28), 171.5, 144.9 (C-13), 123.1 (C-12), 107.0 (C-1'''), 105.1 (C-1''''), 101.1 (C-1''), 95.7 (C-1'), 84.0 (C-4''), 83.5 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5'), 72.2 (C-3''), 71.9 (C-2''), 71.1 (C-4'''), 68.7 (C-5''), 67.3 (C-5'''), 56.1 (C-4), 50.0 (C-17), 49.6 (C-5), 48.1 (C-9), 48.0 (C-19), 42.8 (C-14), 42.3 (C-18), 41.1 (C-8), 40.0 (carbon chain CH$_2$), 39.5 (C-1), 37.1 (C-10), 36.5 (C-21), 36.5 (C-15), 33.6 (C-6), 33.4 (C-29), 33.1 (carbon chain CH$_2$), 32.0 (C-22), 31.4 (C-20), 30.9 (carbon chain CH$_2$), 30.9 (carbon chain CH$_2$), 30.8 (carbon chain CH$_2$), 30.8 (carbon chain CH$_2$), 30.6 (carbon chain CH$_2$), 30.5 (carbon chain CH$_2$), 30.3 (carbon chain CH$_2$), 28.0 (carbon chain CH$_2$), 27.2 (C-27), 26.0 (C-2), 24.9 (C-30), 24.5 (C-11), 23.8 (carbon chain CH$_2$), 21.6 (C-7), 18.3 (C-6''), 17.7 (C-26), 16.5 (C-6'), 16.4 (C-25), 14.5 (carbon chain CH$_3$), 10.6 (C-24) ppm; HRMS (ESI-TOF) calcd. for C$_{71}$H$_{120}$NO$_{22}$ [M+H]$^+$ 1338.8297, found 1338.3327.

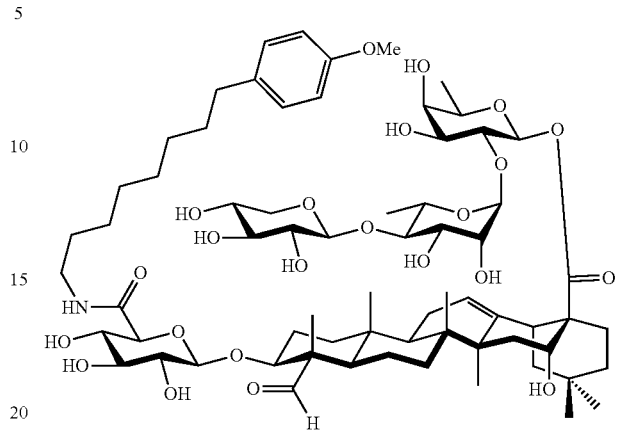

3-O—(N-(8-(4-Methoxyphenyl)octyl)-β-D-glucopyranosyluronamide)-28-O-(β-D-xylopyranosyl-(1→4)-α-L-rhamnopyranosyl-(1→2)-β-D-fucopyranosyl) quillaic ester (53)

Following the general procedure of global deprotection, 53 was obtained in 54% yield as a white solid: $[\alpha]_D^{20}$ −123.3 (c 0.06, MeOH); $^1$H NMR (600 MHz, MeOD) δ 9.42 (s, 1H, H-23), 8.55 (s, 1H, amide NH), 7.07 (d, J=8.7 Hz, 2H), 6.82 (d, J=8.7 Hz, 2H), 5.41 (d, J=1.8 Hz, 1H, H-1"), 5.30-5.27 (m, 2H, H-12, H-1'), 4.49-4.48 (m, 2H, H-16, H-1'''), 4.26 (d, J=7.8 Hz, 1H, H-1''''), 3.91 (dd, J=3.3, 1.8 Hz, 1H, H-2''), 3.90-3.79 (m, 5H, H-3, H-5$_a$''', H-3'', H-2', H-5''), 3.76 (s, 3H, OCH$_3$), 3.69-3.66 (m, 2H, H-5', H-3'), 3.64 (d, J=9.7 Hz, 1H, H-5''''), 3.58-3.53 (m, 2H, H-4', H-4''), 3.49-3.42 (m, 2H, H-4''', H-4''''), 3.33-3.30 (m, 2H, H-3''', H-3''''), 3.28-3.25 (m, 1H, —NHCH$_a$—), 3.24-3.17 (m, 3H, H-2''', H-5$_b$'''', —NHCH$_b$—), 3.14 (dd, J=9.2, 7.8 Hz, 1H, H-2''''), 2.94 (dd, J=14.3, 4.1 Hz, 1H, H-18), 2.54 (t, J=7.4 Hz 2H, carbon chain CH$_2$Ph), 2.30 (t, J=13.6 Hz, 1H, H-19$_a$), 1.97-1.88 (m, 5H, H-2$_a$, H-11$_{ab}$, H-21$_a$, H-22$_a$), 1.84-1.72 (m, 3H, H-2$_b$, H-9, H-22$_b$), 1.71-1.66 m, 2H, H-1$_a$, H-15$_a$), 1.62-1.47 (m, 6H, carbon chain CH$_2$×2, H-6$_a$, H-7$_a$), 1.47-1.43 (m, 1H, H-15$_b$), 1.40 (s, 3H, H-27), 1.37-1.30 (m, 13H, H-5, H-6$_b$, H-6'', carbon chain CH$_2$×4), 1.22 (d, J=6.4 Hz, 3H, H-6'), 1.18-1.16 (m, 1H, H-21$_b$), 1.13 (s, 3H, H-24), 1.10-1.08 (m, 1H, H-1$_b$), 1.05 (dd, J=12.1, 3.6 Hz, 1H, H-19$_b$), 1.00 (s, 3H, H-25), 0.97-0.94 (m, 4H, H-7$_b$, H-30), 0.87 (s, 3H, H-29), 0.77 (s, 3H, H-26); $^{13}$C NMR (151 MHz, MeOD) δ 209.2 (C-23), 177.2 (C-28), 171.5, 159.2, 144.8 (C-13), 135.9, 130.3, 123.1 (C-12), 114.8, 107.0 (C-1'''), 105.0 (C-1''''), 101.1 (C-1''), 95.2 (C-1'), 84.0 (C-4''), 83.5 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5'), 72.2 (C-3''), 71.9 (C-2''), 71.1 (C-4'''), 68.8 (C-5''), 67.3 (C-5'''), 56.1 (C-4), 55.7 (OCH$_3$), 50.0 (C-17), 49.6 (C-5), 48.1 (C-19), 48.0 (C-9), 42.8 (C-14), 42.3 (C-18), 41.1 (C-8), 40.0 (carbon chain CH$_2$), 39.4 (C-1), 37.1 (C-10), 36.5 (C-21), 36.5 (C-15), 36.7 (carbon chain CH$_2$), 33.6 (C-6), 33.4 (C-29), 33.0 (carbon chain CH$_2$), 32.0 (C-22), 31.3 (C-20), 30.7 (carbon chain CH$_2$), 30.5 (carbon chain CH$_2$), 30.3 (carbon chain CH$_2$), 30.2 (carbon chain CH$_2$), 27.9 (carbon chain CH$_2$), 27.2 (C-27), 26.0 (C-2), 24.8 (C-30), 24.5 (C-11), 21.6 (C-7), 18.3 (C-6''), 17.7 (C-26), 16.5 (C-6'), 16.4 (C-25), 10.6 (C-24) ppm; HRMS (ESI-TOF) calcd. for $C_{68}H_{106}NO_{23}$ [M+H]$^+$ 1326.6970, found 1326.6978.

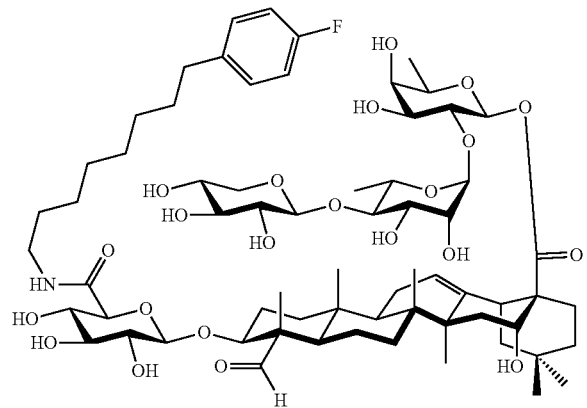

3-O—(N-(8-(4-Fluorophenyl)octyl)-β-D-glucopyranosyluronamide)-28-O-(β-D-xylopyranosyl-(1→4)-α-L-rhamnopyranosyl-(1→2)-β-D-fucopyranosyl) quillaic ester (54)

Following the general procedure of global deprotection, 54 was obtained in 56% yield as a white solid: $[\alpha]_D^{20}$ −28.3 (c 0.18, MeOH); $^1$H NMR (600 MHz, MeOD) δ 9.42 (s, 1H, H-23), 8.55 (s, 1H, amide N$\underline{H}$), 7.17 (dd, J=8.8, 5.4 Hz, 2H), 6.98 (t, J=8.8 Hz, 2H), 5.41 (d, J=1.7 Hz, 1H, H-1''), 5.29-5.27 (m, 2H, H-12, H-1'), 4.49-4.48 (m, 2H, H-16, H-1'''), 4.26 (d, J=7.9 Hz, 1H, H-1''''), 3.92-3.78 (m, 6H, H-2'', H-3, H-5$_a$''', H-3'', H-2', H-5''), 3.70-3.63 (m, 3H, H-5', H-3', H-5''''), 3.57-3.52 (m, 2H, H-4', H-4''), 3.48-3.41 (m, 2H, H-4''', H-4''''), 3.33-3.30 (m, 2H, H-3''', H-3''''), 3.28-3.25 (m, 1H, —NHC$\underline{H}_a$—), 3.24-3.16 (m, 3H, H-2''', H-5$_b$''', —NHC$\underline{H}_b$—), 3.13 (dd, J=9.2, 7.9 Hz, 1H, H-2''''), 2.94 (dd, J=14.3, 4.5 Hz, 1H, H-18), 2.59 (t, J=7.6 Hz, 2H, carbon chain C$\underline{H}_2$Ph), 2.29 (t, J=13.6 Hz, 1H, H-19$_a$), 1.96-1.89 (m, 5H, H-2$_a$, H-1$_{ab}$, H-21$_a$, H-22$_a$), 1.83-1.72 (m, 3H, H-2$_b$, H-9, H-22$_b$), 1.72-1.64 (m, 2H, H-1$_a$, H-15$_a$), 1.63-1.58 (m, 2H, carbon chain C$\underline{H}_2$), 1.56-1.48 (m, 4H, H-6$_a$, H-7$_a$), 1.45 (dd, J=14.9, 2.6 Hz, 1H, H-15$_b$), 1.40 (s, 3H, H-27), 1.36-1.31 (m, 13H, H-5, H-6$_b$, H-6'', carbon chain C$\underline{H}_2$×4), 1.22 (d, J=6.4 Hz, 3H, H-6'), 1.18-1.16 (m, 1H, H-21$_b$), 1.13 (s, 3H, H-24), 1.11-1.08 (m, 1H, H-1$_b$), 1.05-1.03 (m, 1H, H-19$_b$), 1.00 (s, 3H, H-25), 0.96-0.94 (m, 4H, H-7$_b$, H-30), 0.86 (s, 3H, H-29), 0.77 (s, 3H, H-26); $^{13}$C NMR (151 MHz, MeOD) δ 209.2 (C-23), 177.2 (C-28), 171.5, 162.6 (J=241 Hz), 144.9 (C-13), 139.8, 130.9 (J=8 Hz), 123.1 (C-12), 115.8 (J=21 Hz), 107.0 (C-1'''), 105.0 (C-1''''), 101.1 (C-1''), 95.2 (C-1'), 84.0 (C-4''), 83.4 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5'), 72.2 (C-3''), 71.9 (C-2''), 71.1 (C-4'''), 68.8 (C-5''), 67.3 (C-5'''), 56.1 (C-4), 50.0 (C-17), 49.6 (C-5), 48.1 (C-9), 48.0 (C-19), 42.8 (C-14), 42.4 (C-18), 41.1 (C-8), 40.0 (carbon chain C$\underline{H}_2$), 39.4 (C-1), 37.1 (C-10), 36.5 (C-21), 36.5 (C-15), 36.1 (carbon chain C$\underline{H}_2$), 33.6 (C-6), 33.4 (C-29), 32.9 (C-), 32.0 (C-22), 31.3 (C-20), 30.7 (carbon chain C$\underline{H}_2$), 30.5 (carbon chain C$\underline{H}_2$), 30.3 (carbon chain C$\underline{H}_2$), 30.3 (carbon chain C$\underline{H}_2$), 30.2 (carbon chain C$\underline{H}_2$), 27.9 (carbon chain C$\underline{H}_2$), 27.2 (C-27), 26.0 (C-2), 24.8 (C-30), 24.5 (C-11), 21.5 (C-7), 18.3 (C-6''), 17.7 (C-26), 16.5 (C-6'), 16.4 (C-25), 10.6 (C-24) ppm; HRMS (ESI-TOF) calcd. for $C_{67}H_{102}FNO_{22}Na$ [M+Na]$^+$ 1314.6770, found 1314.6794.

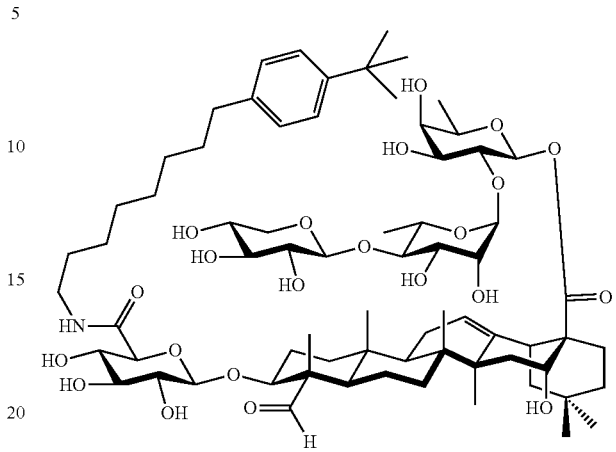

3-O—(N-(8-(4-Fluorophenyl)octyl)-β-D-glucopyranosyluronamide)-28-O-(β-D-xylopyranosyl-(1→4)-α-L-rhamnopyranosyl-(1→2)-β-D-fucopyranosyl) quillaic ester (55)

Following the general procedure of global deprotection, 55 was obtained in 75% yield as a white solid: $[\alpha]_D^{20}$ −32.5 (c 0.24, MeOH); $^1$H NMR (600 MHz, MeOD) δ 9.42 (s, 1H, H-23), 8.55 (s, 1H, amide N$\underline{H}$), 7.29 (d, J=8.3 Hz, 2H), 7.08 (d, J=8.3 Hz, 2H), 5.41 (d, J=1.7 Hz, 1H, H-1''), 5.31 (t, J=3.6 Hz, 1H, H-12), 5.29 (d, J=8.2 Hz, 1H, H-1'), 4.49-4.48 (m, 2H, H-1''', H-16), 4.26 (d, J=7.8 Hz, 1H, H-1''''), 3.91-3.78 (m, 6H, H-2'', H-3, H-5$_a$''', H-3'', H-2', H-5''), 3.69-3.63 (m, 3H, H-5', H-3', H-5''''), 3.57-3.53 (m, 2H, H-4', H-4''), 3.48-3.42 (m, 2H, H-4''', H-4''''), 3.33-3.30 (m, 2H, H-3''', H-3''''), 3.29-3.25 (m, 1H, —NHC$\underline{H}_a$—), 3.23-3.17 (m, 3H, H-2''', H-5$_b$''', —NHC$\underline{H}_a$—), 3.14 (dd, J=9.2, 7.8 Hz, 1H, H-2''''), 2.94 (dd, J=14.5, 4.3 Hz, 1H, H-18), 2.57 (m, J=7.6 Hz, 2H, carbon chain C$\underline{H}_2$Ph), 2.30 (t, J=13.6 Hz, 1H, H-19$_a$), 1.97-1.89 (m, 5H, H-2$_a$, H-11$_{ab}$, H-21$_a$, H-22$_a$), 1.83-1.72 (m, 3H, H-2$_b$, H-9, H-22$_b$), 1.72-1.64 (m, 2H, H-1$_a$, H-15$_a$), 1.63-1.57 (m, 2H, carbon chain C$\underline{H}_2$), 1.56-1.47 (m, 4H, H-6$_a$, H-7$_a$, carbon chain C$\underline{H}_2$), 1.47-1.43 (m, 1H, H-15$_b$), 1.40 (s, 3H, H-27), 1.36-1.28 (m, 22H, H-5, H-6$_b$, H-6'', carbon chain C$\underline{H}_2$×4, tBu C$\underline{H}_3$×3), 1.22 (d, J=6.4 Hz, 3H, H-6'), 1.19-1.15 (m, 1H, H-21$_b$), 1.13 (s, 3H, H-24), 1.11-1.08 (m, 1H, H-1$_b$), 1.08-1.03 (m, 1H, H-19$_b$), 1.00 (s, 3H, H-25), 0.96-0.94 (m, 4H, H-7$_b$, H-30), 0.86 (s, 3H, H-29), 0.77 (s, 3H, H-26); $^{13}$C NMR (151 MHz, MeOD) δ 209.2 (C-23), 177.2 (C-28), 171.5, 149.5, 144.8 (C-13), 140.8, 129.1, 126.1, 123.1 (C-12), 107.0 (C-1'''), 105.0 (C-1''''), 101.1 (C-1''), 95.2 (C-1'), 84.1 (C-4''), 83.5 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5'), 72.2 (C-3''), 71.9 (C-2''), 71.1 (C-4'''), 68.8 (C-5''), 67.1 (C-5'''), 56.1 (C-4), 50.0 (C-17), 49.6 (C-5), 48.1 (C-9), 48.0 (C-19), 42.8 (C-14), 42.4 (C-18), 41.1 (C-8), 40.0 (carbon chain C$\underline{H}_2$), 39.4 (C-1), 37.1 (C-10), 36.4 (C-15, C-21, carbon chain C$\underline{H}_2$), 35.2 (tBu 4° C.), 33.6 (C-6), 33.4 (C-29), 32.8 (carbon chain C$\underline{H}_2$), 31.9 (C-22, tBu C$\underline{H}_3$×3), 31.3 (C-20), 30.7 (carbon chain C$\underline{H}_2$), 30.5 (carbon chain C$\underline{H}_2$), 30.4 (carbon chain C$\underline{H}_2$), 30.2 (carbon chain C$\underline{H}_2$), 27.9 (carbon chain C$\underline{H}_2$), 27.2

(C-27), 26.0 (C-2), 24.8 (C-30), 24.5 (C-11), 21.6 (C-7), 18.3 (C-6''), 17.7 (C-26), 16.5 (C-6'), 16.4 (C-25), 10.6 (C-24) ppm; HRMS (ESI-TOF) calcd. for $C_{71}H_{111}NO_{22}Na$ [M+Na]$^+$ 1352.7490, found 1352.7515.

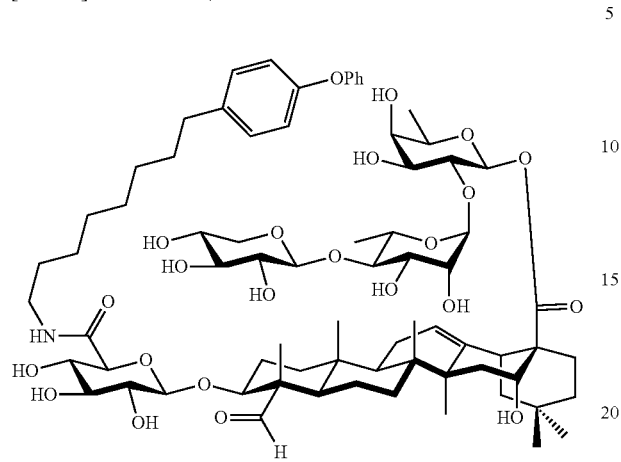

3-O—(N-(8-(4-Phenoxyhenyl)octyl)-β-D-glucopyranosyluronamide)-28-O-(β-D-xylopyranosyl-(1→4)-α-L-rhamnopyranosyl-(1→2)-β-D-fucopyranosyl) quillaic ester (56)

Following the general procedure of global deprotection, 56 was obtained in 46% yield as a white solid: $[\alpha]_D^{20}$ −71.4 (c 0.07, MeOH); $^1$H NMR (600 MHz, MeOD) δ 9.42 (s, 1H, H-23), 8.55 (s, 1H, amide NH), 7.32 (dd, J=8.6, 7.5 Hz, 2H), 7.17 (dd, J=8.6, 1.0 Hz, 2H), 7.07 (tt, J=7.5, 1.0 Hz, 1H), 6.95 (d, J=8.6 Hz, 2H), 6.91 (d, J=8.6 Hz, 2H), 5.41 (d, J=1.7 Hz, 1H, H-1''), 5.30 (s, 1H, H-12), 5.27 (d, J=8.2 Hz, 1H, H-1'), 4.49-4.47 (m, 2H, H-16, H-1'''), 4.26 (d, J=7.8 Hz, 1H, H-1''''), 3.91-3.79 (m, 6H, H-2'', H-3, H-5$_a$''', H-3'', H-2', H-5''), 3.67-3.63 (m, 3H, H-5', H-3', H-5''''), 3.56-3.53 (m, 2H, H-4', H-4''), 3.49-3.42 (m, 2H, H-4''', H-4''''), 3.33-3.25 (m, 3H, H-3''', H-3'''', —NHCH$_a$), 3.23-3.17 (m, 3H, H-2''', H-5$_b$''', —NHCH$_b$—), 3.14 (dd, J=9.2, 7.8 Hz, 1H, H-2''''), 2.94 (dd, J=14.2, 4.4 Hz, 1H, H-18), 2.60 (t, J=7.5 Hz, 2H, carbon chain CH$_2$Ph), 2.29 (t, J=13.1 Hz, 1H, H-19$_a$), 1.98-1.87 (m, 5H, H-2$_a$, H-11$_{ab}$, H-21$_a$, H-22$_a$), 1.82-1.76 (m, 3H, H-2$_b$, H-9, H-22$_b$), 1.71-1.65 (m, 2H, H-1$_a$, H-15$_a$), 1.64-1.60 (m, 2H, carbon chain CH$_2$), 1.56-1.48 (m, 4H, H-6$_a$, H-7$_a$), 1.45 (dd, J=14.9, 2.6 Hz, 1H, H-15$_b$), 1.40 (s, 3H, H-27), 1.37-1.31 (m, 13H, H-5, H-6$_b$, H-6'', carbon chain CH$_2$), 1.21 (d, J=6.4 Hz, 3H, H-6'), 1.18-1.15 (m, 1H, H-21$_b$), 1.13 (s, 3H, H-24), 1.11-1.08 (m, 1H, H-1$_b$), 1.06-1.03 (m, 1H, H-19$_b$), 1.00 (s, 3H, H-25), 0.97-0.93 (m, 4H, H-7$_b$, H-30), 0.85 (s, 3H, H-29), 0.77 (s, 3H, H-26); $^{13}$C NMR (151 MHz, MeOD) δ 209.2 (C-23), 177.1 (C-28), 171.5, 159.2, 156.5, 144.9 (C-13), 139.2, 130.8, 130.7, 124.0, 123.1 (C-12), 120.0, 119.4, 107.0 (C-1'''), 105.0 (C-1''''), 101.1 (C-1''), 95.2 (C-1'), 84.1 (C-4''), 83.5 (C-3), 78.2 (C-3'''), 77.6 (C-3''''), 76.7 (C-3'), 76.6 (C-5''''), 76.1 (C-2'''), 74.7 (C-2''''), 74.6 (C-16), 74.0 (C-2'), 73.6 (C-4'), 73.2 (C-4''''), 72.7 (C-5'), 72.2 (C-3''), 71.9 (C-2''), 71.1 (C-4'''), 68.7 (C-5''), 67.3 (C-5'''), 56.1 (C-4), 50.0 (C-17), 49.6 (C-5), 48.1 (C-9), 48.0 (C-19), 42.8 (C-14), 42.4 (C-18), 41.1 (C-8), 40.0 (carbon chain CH$_2$), 39.4 (C-1), 37.1 (C-10), 36.5 (C-21), 36.5 (C-15), 36.2 (carbon chain CH$_2$), 33.6 (C-6), 33.4 (C-29), 32.9 (carbon chain CH$_2$), 32.0 (C-22), 31.3 (C-20), 30.7 (carbon chain CH$_2$), 30.5 (carbon chain CH$_2$), 30.4 (carbon chain CH$_2$), 30.3 (carbon chain CH$_2$), 27.9 (carbon chain CH$_2$), 27.2 (C-27), 26.0 (C-2), 24.8 (C-30), 24.5 (C-11), 21.6 (C-7), 18.3 (C-6''), 17.7 (C-26), 16.5 (C-6'), 16.4 (C-25), 10.6 (C-24) ppm; HRMS (ESI-TOF) calcd. for $C_{73}H_{107}NO_{23}Na$ [M+Na]$^+$ 1388.7126, found 1388.7172.

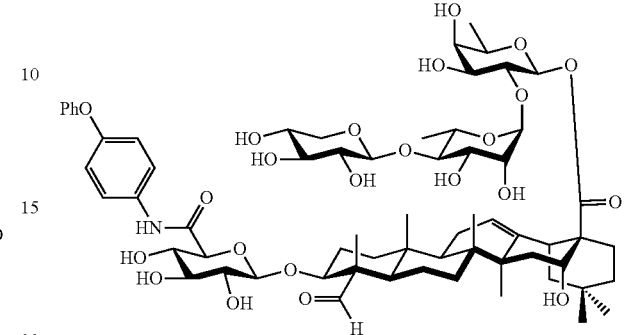

3-O—(N-(4-phenoxyphen-1-yl)-β-D-glucopyranosyluronamide)-28-O-(β-D-xylopyranosyl-(1→4)-α-L-rhamnopyranosyl-(1→2)-β-D-fucopyranosyl) quillaic ester (57)

Following the general procedure of global deprotection, 57 was obtained in 23% yield as a white solid: $^1$H NMR (600 MHz, CD$_3$OD) δ 9.45 (s, 1H), 8.55 (s, 1H), 7.61 (d, J=8.9 Hz, 2H), 7.34 (t, J=7.7 Hz, 2H), 7.09 (t, J=7.1 Hz, 1H), 7.00-6.95 (m, 4H), 5.41 (d, J=1.6 Hz, 1H), 5.30 (t, J=3.6 Hz, 1H), 5.28 (d, J=8.2 Hz, 1H), 4.50-4.47 (m, 2H), 4.32 (d, J=7.8 Hz, 1H), 3.93 (dd, J=11.8, 4.6 Hz, 1H), 3.90 (dd, J=3.2, 1.8 Hz, 1H), 3.87-3.77 (m, 5H), 3.67-3.65 (m, 2H), 3.60-3.53 (m, 3H), 3.46 (ddd, J=10.4, 9.0, 5.4 Hz, 1H), 3.36 (t, J=9.0 Hz, 1H), 3.33-3.30 (m, 1H) 3.24-3.17 (m, 3H), 2.93 (dd, J=14.4, 4.3 Hz, 1H), 2.29 (t, J=13.6 Hz, 1H), 2.00-1.90 (m, 5H), 1.86-1.64 (m, 5H), 1.61-1.48 (m, 2H), 1.45 (dd, J=14.8, 2.6 Hz, 1H), 1.39 (s, 3H), 1.37-1.33 (m, 2H), 1.31 (d, J=6.2 Hz, 3H), 1.21 (d, J=6.4 Hz, 3H), 1.20-1.16 (m, 1H), 1.15 (s, 3H), 1.13-1.08 (m, 1H), 1.06-1.02 (m, 1H), 1.01 (s, 3H), 0.97-0.94 (m, 4H), 0.87 (s, 3H), 0.77 (s, 3H); $^{13}$C NMR (151 MHz, CD$_3$OD) δ 209.4, 177.2, 170.3, 169.4, 159.0, 155.2, 144.7, 134.8, 130.9, 124.3, 123.2, 120.3, 119.5, 106.9, 105.2, 101.1, 95.2, 84.0, 83.4, 78.2, 77.6, 77.6, 77.6, 76.7, 76.1, 74.7, 74.6, 74.0, 73.6, 73.0, 72.7, 72.2, 71.9, 71.1, 68.7, 67.3, 56.2, 50.0, 49.6, 48.0, 48.0, 42.8, 42.3, 41.1, 39.3, 37.1, 36.5, 36.5, 36.5, 33.4, 32.0, 31.3, 27.2, 24.8, 21.6, 18.3, 17.7, 16.5, 16.3, 10.6 ppm; HRMS (ESI-TOF) calcd. for $C_{65}H_{92}NO_{23}$ [M+H]$^+$ 1254.6055, found 1254.6060.

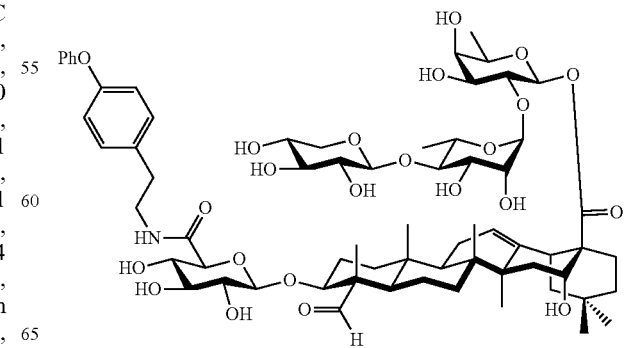

3-O—(N-(2-(4-phenoxyphen-1-yl)ethyl)-β-D-glucopyranosyluronamide)-28-O-(β-D-xylopyranosyl-(1→4)-α-L-rhamnopyranosyl-(1→2)-β-D-fucopyranosyl) quillaic ester (58)

Following the general procedure of global deprotection, 58 was obtained in 58% yield as a white solid: $^1$H NMR (600 MHz, CD$_3$OD) δ 9.40 (s, 1H), 8.55 (s, 1H), 7.33 (dd, J=8.5, 7.5 Hz, 2H), 7.23 (d, J=8.5 Hz, 2H), 7.09 (t, J=7.5 Hz, 1H), 6.95 (d, J=8.5 Hz, 2H), 6.93 (d, J=8.6 Hz, 2H), 5.41 (d, J=1.7 Hz, 1H), 5.30-5.27 (m, 2H), 4.50-4.47 (m, 2H), 4.23 (d, J=7.9 Hz, 1H), 3.91 (dd, J=3.2, 1.7 Hz, 1H), 3.87-3.77 (m, 5H), 3.70-3.65 (m, 2H), 3.63 (d, J=9.7 Hz, 1H), 3.57-3.50 (m, 3H), 3.50-3.43 (m, 2H), 3.40 (t, J=9.3 Hz, 1H), 3.33-3.29 (m, 2H), 3.23-3.17 (m, 2H), 3.11 (dd, J=9.2, 7.9 Hz, 1H), 2.94 (dd, J=14.3, 4.1 Hz, 1H), 2.83 (t, J=6.8 Hz, 2H), 2.30 (t, J=13.6 Hz, 1H), 1.98-1.79 (m, 8H), 1.77 (dd, J=13.8, 4.3 Hz, 1H), 1.74-1.64 (m, 4H), 1.58-1.41 (m, 3H), 1.39 (s, 3H), 1.35 (d, J=11.7 Hz, 1H), 1.34-1.28 (m, 5H), 1.22 (d, J=6.4 Hz, 3H), 1.18 (d, J=12.8 Hz, 1H), 1.11 (s, 3H), 1.08-1.02 (m, 2H), 0.97 (s, 3H), 0.96-0.92 (m, 4H), 0.89 (s, 3H), 0.76 (s, 3H); BBD $^{13}$C NMR (151 MHz, MeOD) δ 209.3, 177.2, 171.7, 159.0, 157.0, 144.7, 135.6, 131.3, 130.9, 124.2, 123.2, 120.2, 119.5, 106.9, 104.9, 101.1, 95.2, 84.0, 83.5, 78.2, 77.5, 76.7, 76.4, 76.1, 74.7, 74.6, 74.0, 73.6, 73.4, 72.7, 72.2, 71.9, 71.1, 68.7, 67.3, 56.1, 50.0, 49.6, 48.0, 48.0, 42.8, 42.3, 41.5, 41.1, 39.4, 37.0, 36.5, 36.5, 35.4, 33.6, 33.4, 32.0, 31.3, 27.2, 25.9, 24.8, 24.6, 21.5, 18.3, 17.7, 16.5, 16.3, 10.6 ppm; HRMS (ESI-TOF) calcd. for C$_{67}$H$_{96}$NO$_{23}$ [M+H]$^+$ 1282.6368, found 1282.6370.

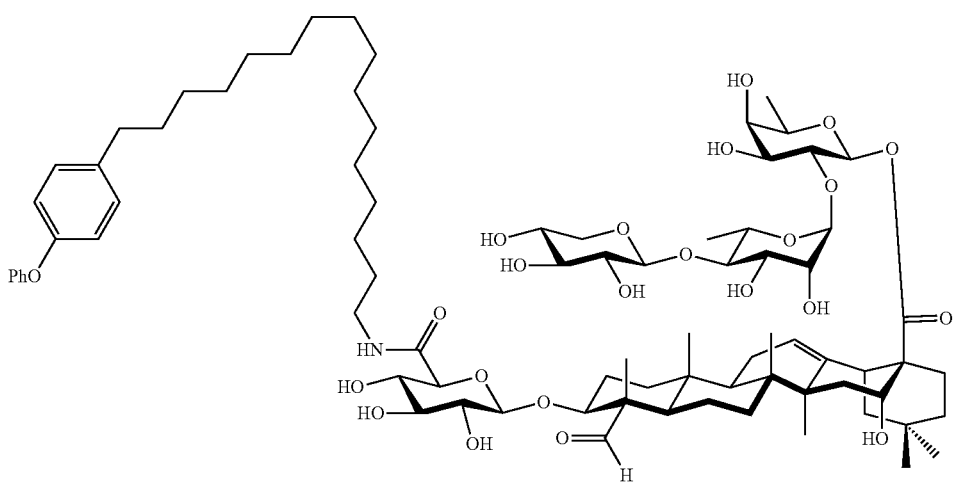

3-O—(N-(16-(4-phenoxyphen-1-yl)hexadecyl)-β-D-glucopyranosyluronamide)-28-O-(β-D-xylopyranosyl-(1→4)-α-L-rhamnopyranosyl-(1→2)-β-D-fucopyranosyl) quillaic ester. (59)

Following the general procedure of global deprotection (HPLC column: Alltima C8 150 mm×4.6 mm, 5 m, flow rate: 1 mL/min), 59 was obtained in 34% yield as a white solid: $^1$H NMR (600 MHz, CD$_3$OD) δ 9.42 (s, 1H), 8.55 (s, 1H), 7.32 (dd, J=8.5, 7.5 Hz, 2H), 7.16 (d, J=8.5 Hz, 2H), 7.07 (t, J=7.5 Hz, 1H), 6.94 (d, J=8.5 Hz, 2H), 6.89 (d, J=8.5 Hz, 2H), 5.41 (d, J=1.6 Hz, 1H), 5.31 (brs, 1H), 5.28 (d, J=8.2 Hz, 1H), 4.50-4.47 (m, 2H), 4.26 (d, J=7.8 Hz, 1H), 3.92-3.78 (m, 6H), 3.68-3.63 (m, 3H), 3.57-3.53 (m, 2H), 3.48-3.42 (m, 2H), 3.35-3.27 (m, 3H), 3.24-3.16 (m, 3H), 3.14 (dd, J=9.2, 7.8 Hz, 1H), 2.97-2.92 (m, 1H), 2.60 (t, J=7.7 Hz, 2H), 2.30 (t, J=13.6 Hz, 1H), 1.97-1.90 (m, 5H), 1.83-1.65 (m, 5H), 1.63-1.59 (m, 2H), 1.56-1.43 (m, 5H), 1.40 (s, 3H), 1.38-1.27 (m, 29H), 1.21 (d, J=6.4 Hz, 3H), 1.17 (d, J=12.6 Hz, 1H), 1.13 (s, 3H), 1.09 (d, J=13.4 Hz, 1H), 1.07-1.03 (m, 1H), 1.01 (s, 3H), 0.97-0.92 (m, 4H), 0.87 (s, 3H), 0.77 (s, 3H); BBD $^{13}$C NMR (151 MHz, CD$_3$OD) δ 209.2, 177.1, 171.5, 159.2, 156.4, 144.9, 139.3, 130.8, 130.7, 124.0, 123.1, 112.0, 119.4, 106.9, 105.1, 101.1, 95.2, 84.0, 83.5, 78.2, 77.8, 76.7, 76.7, 76.6, 76.1, 74.7, 74.6, 73.9, 73.6, 73.2, 72.7, 72.2, 71.9, 71.2, 68.7, 67.3, 56.1, 50.0, 49.6, 48.1, 48.0, 42.8, 42.3, 41.1, 40.0, 37.1, 36.5, 36.5, 36.2, 33.6, 33.4, 32.8, 31.4, 30.9, 30.9, 30.9, 30.8, 30.8, 30.7, 30.7, 30.6, 30.6, 30.5, 30.3, 28.0, 27.2, 26.0, 24.9, 24.5, 21.6, 18.3, 17.7, 16.5, 16.4, 10.6 ppm; HRMS (ESI-TOF) calcd. for $C_{81}H_{124}NO_{23}$ [M+H]$^+$ 1478.8559, found 1478.8560.

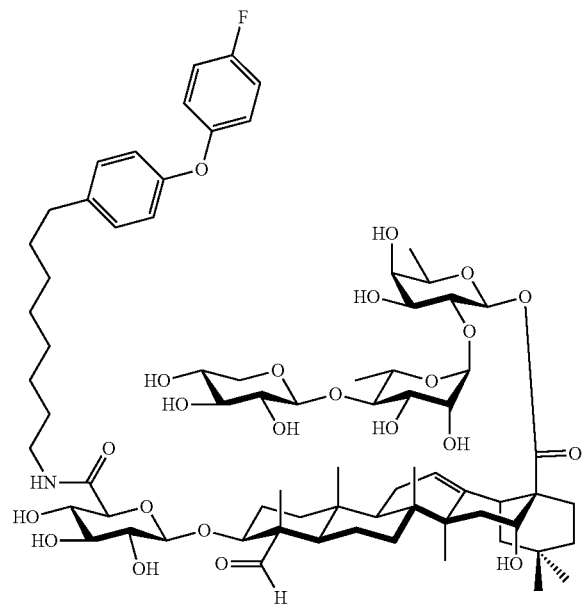

3-O—(N-(8-(4-(4-Fluorophenoxy)phen-1-yl)octyl)-β-D-glucopyranosyluronamide)-28-O-(β-D-xylopyranosyl-(1→4)-α-D-rhamnopyranosyl-(1→2)-β-D-fucopyranosyl) quillaic ester (60)

Following the general procedure of amide bond formation and global deprotection, 60 was obtained in 40% yield as a white solid: $^1$H NMR (600 MHz, CD$_3$OD) δ 9.42 (s, 1H), 7.16 (d, J=8.5 Hz, 2H), 7.09-7.04 (m, 2H), 6.99-6.95 (m, 2H), 6.88 (d, J=8.5 Hz, 2H), 5.41 (d, J=1.6 Hz, 1H), 5.29-5.27 (m, 2H), 4.50-4.48 (m, 2H), 4.26 (d, J=7.8 Hz, 1H), 3.92-3.77 (m, 6H), 3.67-3.63 (m, 3H), 3.57-3.52 (m, 2H), 3.48-3.43 (m, 2H), 3.33-3.30 (m, 2H), 3.29-3.26 (m, 1H), 3.23-3.17 (m, 3H), 3.14 (dd, J=9.2, 7.8 Hz, 1H), 2.93 (dd, J=14.3, 4.1 Hz, 1H), 2.60 (t, J=7.6 Hz, 2H), 2.29 (t, J=13.6 Hz, 1H), 1.97-1.88 (m, 5H), 1.83-1.64 (m, 5H), 1.63-1.59 (m, 2H), 1.57-1.48 (m, 4H), 1.45 (dd, J=14.7, 2.4 Hz, 1H), 1.39 (s, 3H), 1.38-1.30 (m, 13H), 1.21 (d, J=6.4 Hz, 3H), 1.19-1.15 (m, 1H), 1.13 (s, 3H), 1.11-1.07 (m, 1H), 1.04 (dd, J=13.6, 3.7 Hz, 1H), 0.99 (s, 3H), 0.96 (d, J=11.6 Hz, 1H), 0.92 (s, 3H), 0.85 (s, 3H), 0.76 (s, 3H); $^{13}$C NMR (151 MHz, CD$_3$OD) δ 209.2, 177.1, 171.5, 160.8, 159.2, 156.9, 155.1, 144.9, 139.1, 130.8, 123.1, 121.2, 121.2, 119.5, 117.3, 117.1, 106.9, 105.1, 101.0, 95.2, 84.0, 83.5, 78.2, 77.6, 76.7, 76.6, 76.1, 74.7, 74.6, 73.9, 73.6, 73.2, 72.7, 72.2, 71.9, 71.1, 68.7, 67.3, 56.1, 50.0, 49.6, 48.1, 48.0, 42.8, 42.3, 41.1, 40.0, 39.4, 37.1, 36.5, 36.5, 36.2, 33.6, 33.4, 32.9, 32.0, 31.3, 30.7, 30.5, 30.4, 30.2, 27.9, 27.2, 26.0, 24.8, 24.5, 21.5, 18.3, 17.7, 16.5, 16.4, 10.6 ppm; HRMS (ESI-TOF) calcd. for $C_{73}H_{107}FNO_{23}$ [M+H]$^+$ 1384.7212, found 1384.7224.

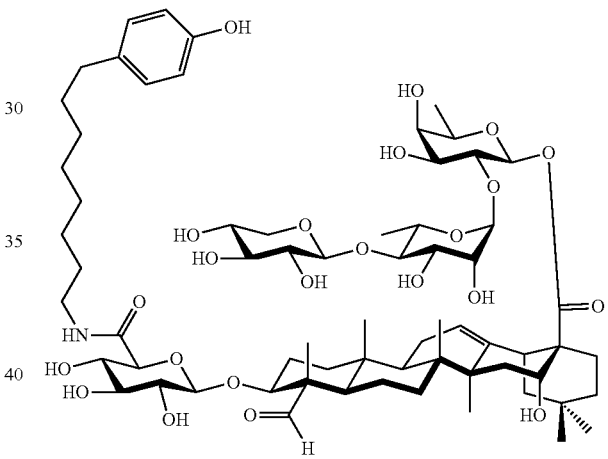

3-O—(N-(8-(4-Hydroxyphen-1-yl)octyl)-β-D-glucopyranosyluronamide)-28-O-(β-D-xylopyranosyl-(1-4)-α-L-rhamnopyranosyl-(1-2)-β-D-fucopyranosyl) quillaic ester (61)

Following the general procedure of global deprotection, 61 was obtained in 23% yield as a white solid: $^1$H NMR (600 MHz, CD$_3$OD) δ 9.42 (s, 1H), 8.55 (s, 1H), 6.97 (d, J=8.5 Hz, 2H), 6.69 (d, J=8.5 Hz, 2H), 5.41 (d, J=1.7 Hz, 1H), 5.30 (t, J=3.1 Hz, 1H), 5.29 (d, J=8.2 Hz, 1H), 4.49 (d, J=7.7 Hz, 2H), 4.26 (d, J=7.8 Hz, 1H), 3.93-3.77 (m, 6H), 3.69-3.63 (m, 3H), 3.58-3.52 (m, 2H), 3.49-3.41 (m, 2H), 3.33-3.25 (m, 3H), 3.24-3.16 (m, 3H), 3.14 (dd, J=9.2, 7.8 Hz, 1H), 2.94 (dd, J=14.2, 4.2 Hz, 1H), 2.50 (t, J=7.5 Hz, 2H), 2.30 (t, J=13.6 Hz, 1H), 1.98-1.88 (m, 5H), 1.83-1.64 (m, 5H), 1.60-1.48 (m, 6H), 1.47-1.43 (m, 1H), 1.40 (s, 3H), 1.37-1.27 (m, 13H), 1.22 (d, J=6.4 Hz, 3H), 1.18-1.16 (m, 1H), 1.13 (s, 3H), 1.11-1.03 (m, 2H), 1.00 (s, 3H), 0.96-0.95 (m, 4H), 0.87 (s, 3H), 0.77 (s, 3H); BBD $^{13}$C NMR (151 MHz, CD$_3$OD) δ 209.2, 177.2, 171.5, 156.3, 144.8, 134.8, 130.3, 123.2, 116.1, 106.9, 105.0, 101.1, 95.2, 84.0, 83.4, 78.2, 77.6, 76.7, 76.6, 76.1, 74.7, 74.6, 74.0, 73.6, 73.2, 72.7, 72.2, 71.9, 71.1, 68.7, 67.3, 56.1, 50.0, 49.6, 48.0, 42.8, 42.3, 41.1, 40.0, 39.4, 37.1, 36.5, 36.5, 36.1, 33.6, 33.4, 33.1, 32.0, 31.3, 30.7, 30.5, 30.3, 30.3, 27.9, 27.2, 26.0, 24.8, 24.5, 21.5, 18.3, 17.7, 16.5, 16.4, 10.6 ppm; HRMS (ESI-TOF) calcd. for $C_{67}H_{104}NO_{23}$ [M+H]$^+$ 1290.6994, found 19690.7008.

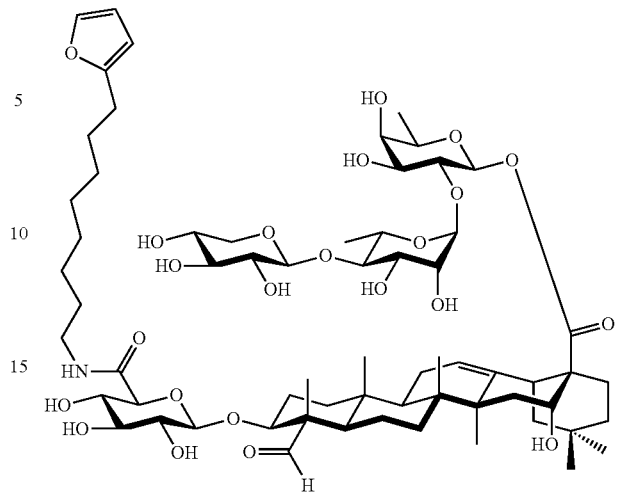

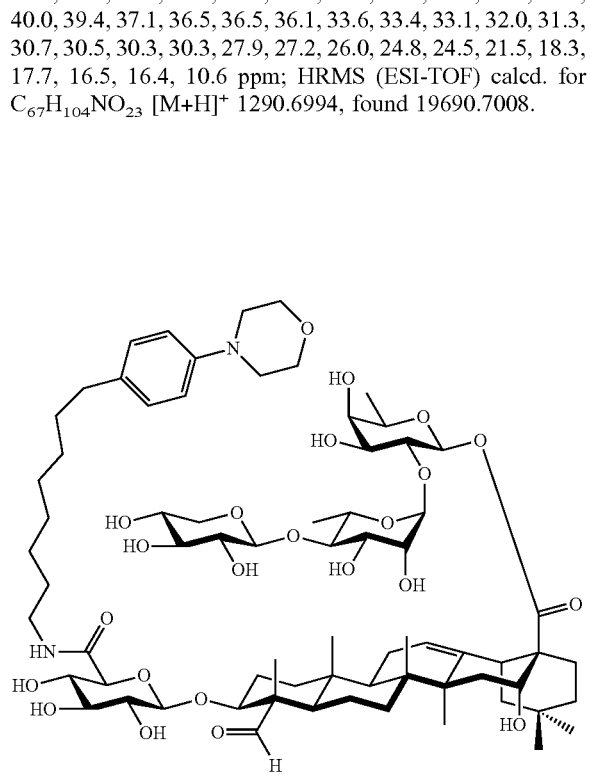

3-O—(N-(8-(4-morpholinophen-1-yl)octyl)-β-D-glucopyranosyluronamide)-28-O-(β-D-xylopyranosyl-(1→4)-α-L-rhamnopyranosyl-(1-2)-β-D-fucopyranosyl) quillaic ester (62)

Following the general procedure of global deprotection, 62 was obtained in 43% yield as a white solid: $^1$H NMR (600 MHz, MeOD) δ 9.42 (s, 1H), 8.55 (s, 1H), 7.07 (d, J=8.5 Hz, 2H), 6.90 (d, J=8.5 Hz, 2H), 5.41 (d, J=1.1 Hz, 1H), 5.31-5.27 (m, 2H), 4.49 (d, J=7.6 Hz, 1H), 4.48 (brs, 1H) 4.26 (d, J=7.8 Hz, 1H), 3.92-3.90 (m, 1H), 3.89-3.77 (m, 9H), 3.69-3.63 (m, 3H), 3.57-3.52 (m, 2H), 3.49-3.42 (m, 2H), 3.33-3.26 (m, 3H), 3.24-3.16 (m, 3H), 3.13 (dd, J=9.2, 7.8 Hz, 1H), 3.11-3.08 (m, 4H), 2.94 (dd, J=14.3, 4.0 Hz, 1H), 2.53 (t, J=7.6 Hz, 2H), 2.29 (t, J=13.6 Hz, 1H), 1.98-1.86 (m, 5H), 1.82-1.63 (m, 5H), 1.62-61.47 (m, 6H), 1.47-1.43 (m, 1H), 1.40 (s, 3H), 1.37-1.29 (m, 13H), 1.22 (d, J=6.4 Hz, 3H), 1.17 (d, J=13.4 Hz, 1H), 1.13 (s, 3H), 1.11-1.02 (m, 2H), 0.99 (s, 3H), 0.96-0.94 (m, 4H), 0.87 (s, 3H), 0.76 (s, 3H); BBD $^{13}$C NMR (151 MHz, CD$_3$OD) δ 209.2, 177.1, 171.5, 150.9, 144.8, 135.9, 130.0, 123.1, 117.4, 106.9, 105.1, 101.1, 95.1, 84.0, 83.6, 78.2, 77.6, 76.7, 76.6, 76.1, 74.7, 74.6, 74.0, 73.6, 73.2, 72.7, 72.2, 71.9, 71.1, 68.7, 68.0, 67.3, 56.1, 51.4, 50.0, 49.6, 48.1, 48.0, 42.8, 42.3, 41.1, 40.0, 39.4, 37.1, 36.5, 36.5, 36.1, 33.6, 33.4, 33.0, 32.0, 31.3, 30.8, 30.5, 30.3, 30.2, 27.9, 27.2, 26.0, 24.9, 24.1, 21.5, 18.3, 17.8, 16.5, 16.4, 10.6 ppm; HRMS (ESI-TOF) calcd. for $C_{71}H_{111}N_2O_{23}$ [M+H]$^+$ 1359.7572, found 1359.7580.

3-O—(N-(8-(furan-2-yl)octyl)-β-D-glucopyranosyluronamide)-28-O-(β-D-xylopyranosyl-(1→4)-α-L-rhamnopyranosyl-(1→2)-β-D-fucopyranosyl) quillaic ester (66)

Following the general procedure of global deprotection, 66 was obtained in 23% yield as a white solid: $^1$H NMR (600 MHz, CD$_3$OD) δ 9.42 (s, 1H), 8.55 (s, 1H), 7.33 (d, J=1.1 Hz, 1H), 6.30-6.26 (m, 1H), 5.99 (d, J=3.1 Hz, 1H), 5.41 (d, J=1.4 Hz, 1H), 5.30-5.27 (m, 2H), 4.50-4.47 (m, 2H), 4.26 (d, J=7.8 Hz, 1H), 3.93-3.76 (m, 6H), 3.71-3.62 (m, 3H), 3.58-3.50 (m, 2H), 3.48-3.42 (m, 2H), 3.33-3.25 (m, 3H), 3.23-3.16 (m, 3H), 3.13 (dd, J=9.0, 7.8 Hz, 1H), 2.94 (dd, J=14.3, 4.2 Hz, 1H), 2.62 (d, J=7.5 Hz, 2H), 2.31 (d, J=13.4 Hz, 1H), 1.99-1.87 (m, 5H), 1.84-1.59 (m, 7H), 1.59-1.48 (m, 4H), 1.45 (dd, J=14.8, 2.5 Hz, 1H), 1.40 (s, 3H), 1.37-1.30 (m, 13H), 1.22 (d, J=6.4 Hz, 3H), 1.18 (d, J=11.0 Hz, 1H), 1.13 (s, 3H), 1.12-1.08 (m, 1H), 1.07-1.03 (m, 1H), 1.01 (s, 3H), 0.97-1.94 (m, 4H), 0.87 (s, 3H), 0.77 (s, 3H); BBD $^{13}$C NMR (151 MHz, CD$_3$OD) δ 209.2, 177.2, 171.5, 157.5, 144.8, 141.9, 123.2, 111.0, 106.9, 105.7, 105.0, 101.1, 95.2, 84.0, 83.4, 78.2, 77.6, 76.7, 76.6, 76.1, 74.7, 74.6, 74.0, 73.6, 73.2, 72.7, 72.2, 71.9, 71.1, 68.7, 67.3, 56.1, 50.0, 49.8, 48.0, 42.8, 42.3, 41.1, 40.0, 39.4, 37.1, 36.5, 36.5, 33.6, 33.4, 32.0, 31.3, 30.6, 30.5, 30.2, 29.3, 28.9, 27.9, 27.2, 26.0, 24.8, 24.5, 21.5, 18.3, 17.7, 16.5, 16.3, 10.6 ppm; HRMS (ESI-TOF) calcd. for $C_{65}H_{102}NO_{23}$ [M+H]$^+$ 1264.6837, found 1264.6846.

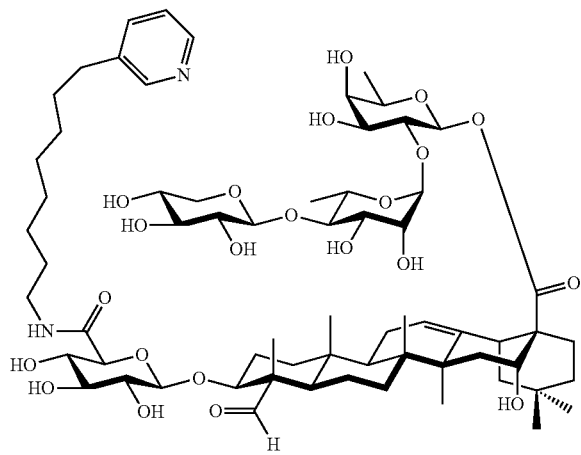

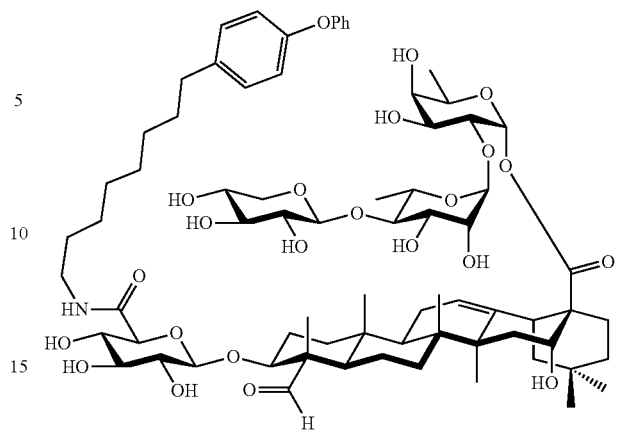

3-O—(N-(8-(pyridin-3-yl)octyl)-β-D-glucopyranosyluronamide)-28-O-(β-D-xylopyranosyl-(1→4)-α-L-rhamnopyranosyl-(1→2)-β-D-fucopyranosyl) quillaic ester (68)

Following the general procedure of amide bond formation and global deprotection, 68 was obtained in 42% yield as a white solid: $^1$H NMR (600 MHz, CD$_3$OD) δ 9.42 (s, 1H), 8.55 (s, 1H), 8.38 (d, J=1.8 Hz, 1H), 8.36 (dd, J=4.8, 1.8 Hz, 1H), 7.70 (dt, J=7.8, 1.8 Hz, 1H), 7.37 (dd, J=7.7, 4.8 Hz, 1H), 5.41 (d, J=1.6 Hz, 1H), 5.29-5.27 (m, 2H), 4.50-4.47 (m, 2H), 4.26 (d, J=7.8 Hz, 1H), 3.92-3.77 (m, 6H), 3.69-3.63 (m, 3H), 3.56-3.53 (m, 2H), 3.49-3.42 (m, 2H), 3.33-3.25 (m, 3H), 3.23-3.17 (m, 3H), 3.14 (dd, J=9.2, 7.8 Hz, 1H), 2.93 (dd, J=14.3, 4.2 Hz, 1H), 2.67 (t, J=7.6 Hz, 2H), 2.29 (t, J=13.6 Hz, 1H), 1.98-1.87 (m, 5H), 1.83-1.62 (m, 7H), 1.56-1.48 (m, 4H), 1.45 (dd, J=14.7, 2.4 Hz, 1H), 1.39 (s, 3H), 1.38-1.28 (m, 13H), 1.22 (d, J=6.4 Hz, 3H), 1.19-1.15 (m, 1H), 1.13 (s, 3H), 1.10 (d, J=13.5 Hz, 1H), 1.06-1.01 (m, 1H), 1.00 (s, 3H), 0.96-0.94 (m, 4H), 0.86 (s, 3H), 0.76 (s, 3H); $^{13}$C NMR (151 MHz, CD$_3$OD) δ 209.2, 177.2, 171.5, 170.3, 150.0, 147.5, 144.8, 140.3, 138.3, 130.9, 125.2, 123.1, 106.9, 105.0, 101.1, 95.2, 84.08, 83.4, 78.2, 77.6, 76.7, 76.6, 76.1, 74.7, 74.6, 74.0, 73.6, 73.2, 72.7, 72.2, 71.9, 71.2, 68.7, 67.3, 56.1, 50.0, 49.6, 48.1, 48.0, 42.8, 42.3, 41.1, 40.0, 39.4, 37.1, 36.5, 36.4, 33.8, 33.6, 33.4, 32.4, 32.0, 31.3, 30.8, 30.8, 30.6, 30.4, 30.3, 30.2, 27.9, 27.2, 26.0, 24.8, 24.5, 21.5, 18.3, 17.7, 16.5, 16.4, 10.6 ppm; HRMS (ESI-TOF) calcd. for C$_{66}$H$_{103}$N$_2$O$_{22}$ [M+H]$^+$ 1275.6997, found 1275.7031.

3-O—(N-(8-(4-Phenoxyhenyl)octyl)-β-D-glucopyranosyluronamide)-28-O-(β-D-xylopyranosyl-(1→4)-α-L-rhamnopyranosyl-(1→2)-α-D-fucopyranosyl) quillaic ester (56α)

Following the general procedure of global deprotection, 56α was obtained in 47% yield as a white solid: $^1$H NMR (600 MHz, MeOD) δ 9.41 (s, 1H, H-23), 8.55 (s, 1H, amide NH), 7.32 (dd, J=8.6, 7.5 Hz, 2H), 7.16 (d, J=8.6 Hz, 2H), 7.07 (t, J=7.4 Hz, 1H), 6.95 (d, J=8.5 Hz, 2H), 6.90 (d, J=8.5 Hz, 2H), 6.06 (d, J=3.7 Hz, 1H, H-1'), 5.33 (t, J=3.4 Hz, 1H, H-12), 4.87 (d, J=1.7 Hz, 1H, H-1''') 4.49 (s, 1H, H-16), 4.42 (d, J=7.7 Hz, 1H, H-1'''), 4.26 (d, J=7.8 Hz, 1H, H-1''''), 3.97 (dd, J=3.2, 1.7 Hz, 1H, H-2''), 3.92-3.86 (m, 3H, H-3, H-2', H-5'), 3.85-3.80 (m, 2H, H-3', H-5$_a$'''), 3.77 (dd, J=9.4, 3.2 Hz, 1H, H-3''), 3.72 (d, J=3.0 Hz, 1H, H-4'), 3.65 (d, J=9.7 Hz, 1H, H-5''''), 3.53 (dq, J=9.4, 6.0 Hz, 1H, H-5''), 3.49 (t, J=9.4 Hz, 1H, H-4''), 3.45-3.41 (m, 2H, H-4''', H-4''''), 3.33-3.25 (m, 3H, H-3''', H-3'''', —NHCH$_a$—), 3.23-3.16 (m, 3H, H-2''', H-5$_b$''', —NHCH$_b$—), 3.14 (dd, J=9.2, 7.8 Hz, 1H, H-2''''), 2.98 (dd, J=14.3, 4.1 Hz, 1H, H-18), 2.60 (t, J=7.7 Hz, 2H, carbon chain CH$_2$Ph), 2.26 (t, J=13.7 Hz, 1H), 2.01-1.88 (m, 5H, H-2$_a$, H-11$_{ab}$, H-21$_a$, H-22$_a$), 1.83-1.74 (m, 3H, H-2$_b$, H-22$_b$, H-9), 1.70 (d, J=13.4 Hz, 1H, H-1$_a$), 1.65-1.59 (m, 2H, H-15$_a$, carbon chain CH$_2$), 1.58-1.47 (m, 4H, H-6$_a$, H-7$_a$, carbon chain CH$_2$), 1.41-1.38 (m, 4H, H-15$_b$, H-27), 1.37-1.31 (m, 9H, H-5, carbon chain CH$_2$×4), 1.24 (d, J=6.0 Hz, 3H, H-6''), 1.23-1.19 (m, 2H, H-6$_b$, H-21$_b$), 1.17 (d, J=6.5 Hz, 3H, H-6'), 1.12 (s, 3H, H-24), 1.11-1.08 (m, H-1$_b$), 1.05 (dd, J=11.7, 4.3 Hz, 1H, H-19$_b$), 1.01 (s, 3H, H-25), 0.95-0.91 (m, 4H, H-7$_b$, H-30), 0.87 (s, 3H, H-29), 0.79 (s, 3H, H-26); $^{13}$C NMR (151 MHz, MeOD) δ 209.1 (C-23), 176.8 (C-28), 171.5, 159.2, 156.5, 144.7 (C-13), 139.1, 130.8, 130.7, 124.0, 123.4 (C-12), 120.0, 119.4, 107.1 (C-1'''), 105.0 (C-1''''), 104.5 (C-1'), 93.0 (C-1'), 84.5 (C-4''), 83.3 (C-3), 78.4 (C-3'''), 77.6 (C-3''''), 76.9 (C-2'), 76.6 (C-5''''), 76.1 (C-2'''), 75.0 (C-16), 74.7 (C-2''''), 73.5 (C-4'), 73.2 (C-4''''), 72.5 (C-3''), 71.6 (C-2''), 71.0 (C-4'''), 71.0 (C-3'), 70.5 (C-5'), 68.8 (C-5''), 67.2 (C-5'''), 56.1 (C-4), 50.6 (C-17), 49.6 (C-5), 48.0 (C-9), 48.0 (C-19), 42.8 (C-14), 42.1 (C-18), 41.0 (C-8), 40.0, 39.4 (C-1), 37.1 (C-10), 36.3 (C-21, C-15), 36.2, 33.6 (C-6), 33.4 (C-29), 32.9, 32.4 (C-22), 31.4 (C-20), 30.7, 30.4, 30.3, 30.2, 27.9, 27.2 (C-27), 26.0 (C-2), 25.3 (C-30), 24.5 (C-11), 21.4 (C-7), 18.0 (C-26), 17.9 (C-6''), 16.8 (C-6'), 16.3 (C-25), 10.5 (C-29) ppm; HRMS (ESI-TOF) calcd. for C$_{73}$H$_{108}$NO$_{23}$ [M+H]$^+$ 1366.7307, found 1366.7318.

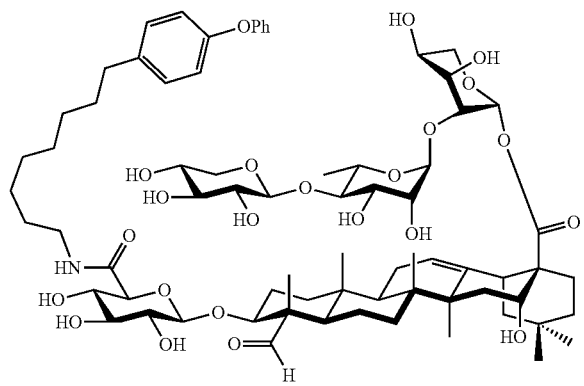
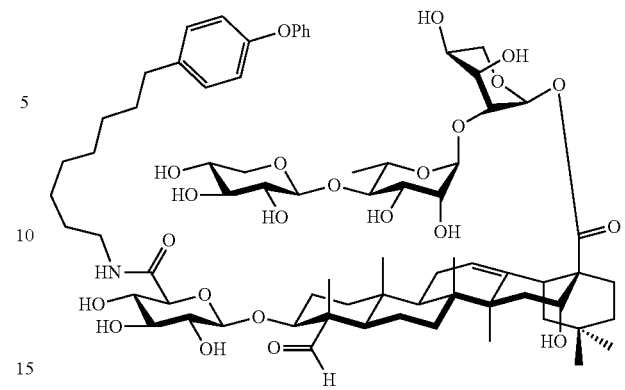

3-O—(N-(8-(4-Phenoxyhenyl)octyl)-β-D-glucopyranosyluronamide)-28-O-(β-D-xylopyranosyl-(1→4)-α-L-rhamnopyranoyl-(1→2)-β-L-arabinopyranosyl) quillaic ester (77β)

Following the general procedure of global deprotection, 77β was obtained in 67% yield as a white solid: $^1$H NMR (600 MHz, MeOD) δ 9.42 (s, 1H, H-23), 8.55 (s, 1H, amide NH), 7.32 (dd, J=8.5, 7.4 Hz, 2H), 7.16 (dd, J=8.5, 1.0 Hz, 2H), 7.07 (tt, J=7.6, 1.0 Hz, 1H), 6.95 (d, J=8.5 Hz, 2H), 6.90 (d, J=8.5 Hz, 2H), 5.61 (d, J=3.7 Hz, 1H, H-1'), 5.35 (t, J=3.5 Hz, 1H, H-12), 5.02 (s, 1H, H-1''), 4.51 (d, J=7.7 Hz, 1H, H-1''''), 4.49 (s, 1H, H-16), 4.26 (d, J=7.8 Hz, 1H, H-1''''), 3.92-3.79 (m, 7H, H-5$_a$', H-3, H-3', H-2'', H-3'', H-5$_a$''', H-4'), 3.77 (dd, J=5.2, 3.7 Hz, 1H, H-2'), 3.73-3.67 (m, 1H, H-5''), 3.65 (d, J=9.7 Hz, 1H, H-5''''), 3.57 (t, J=9.1 Hz, 1H, H-4''), 3.50-3.41 (m, 3H, H-5$_b$', H-4''', H-4''''), 3.33-3.26 (m, 3H, H-3''', H-3'''', —NHCH$_a$—), 3.23-3.16 (m, 3H, H-2''', H-5$_b$''', —NHCH$_b$—), 3.14 (dd, J=9.2, 7.8 Hz, 1H, H-2''''), 3.05 (dd, J=14.3, 4.2 Hz, 1H, H-18), 2.60 (t, J=7.6 Hz, 2H, carbon chain CH$_2$Ph), 2.28 (t, J=13.6 Hz, 1H, H-19$_a$), 1.97-1.87 (m, 5H, H-2$_a$, H-11$_b$, H-21$_a$, H-22$_a$), 1.84-1.66 (m, 5H, H-2$_a$, H-22$_b$, H-9, H-15$_a$, H-1$_a$), 1.66-1.59 (m, 2H, carbon chain CH$_2$), 1.59-1.50 (m, 3H, H-6$_a$, carbon chain CH$_2$), 1.42-1.37 (m, 4H, H-15$_b$, H-27), 1.36-1.32 (m, 9H, H-5, carbon chain CH$_2$×4), 1.31-1.27 (m, 5H, H-6$_b$, H-7$_a$, H-6''), 1.17-1.12 (m, 4H, H-21$_b$, H-24), 1.12-1.07 (m, 1H, H-1$_b$), 1.04 (dd, J=12.7, 3.1 Hz, 1H, H-19$_b$), 1.00 (s, 3H, H-25), 0.97-0.92 (m, 4H, H-30, H-7$_b$), 0.86 (s, 3H, H-29), 0.77 (s, 3H, H-26); $^{13}$C NMR (151 MHz, MeOD) δ 209.1 (C-23), 176.9 (C-28), 171.5, 159.2, 156.5, 144.9 (C-13), 139.1, 130.8, 130.7, 124.0, 123.4 (C-12), 120.0, 119.4, 106.6 (C-1'''), 105.0 (C-1''''), 101.3 (C-1''), 94.0 (C-1'), 83.4 (C-3), 83.3 (C-4''), 78.1 (C-3'''), 77.6 (C-3''''), 76.6 (C-5''''), 76.0 (C-2'''), 75.5 (C-2'), 74.7 (C-2''''), 74.6 (C-16), 73.2 (C-4''''), 72.3 (C-3''), 72.1 (C-2''), 71.1 (C-3', C-4'''), 69.0 (C-5''), 67.2 (C-5'''), 67.0 (C-4'), 63.7 (C-5'), 56.1 (C-4), 50.2 (C-17), 49.6 (C-5), 48.1 (C-9), 47.7 (C-19), 42.8 (C-14), 42.1 (C-18), 41.1 (C-8), 40.0 (carbon chain CH$_2$), 39.4 (C-1), 37.1 (C-10), 36.4 (C-21), 36.3 (C-15), 36.2 (carbon chain CH$_2$), 33.5 (C-6), 33.4 (C-29), 32.9 (carbon chain CH$_2$), 32.0 (C-22), 31.4 (C-20), 30.7 (carbon chain CH$_2$), 30.5 (carbon chain CH$_2$), 30.3 (carbon chain CH$_2$), 30.3 (carbon chain CH$_2$), 27.9 (carbon chain CH$_2$), 27.3 (C-27), 26.0 (C-2), 25.1 (C-30), 24.5 (C-11), 21.5 (C-7), 18.1 (C-6''), 17.9 (C-26), 16.4 (C-25), 10.6 (C-24) ppm; HRMS (ESI-TOF) calcd. for $C_{72}H_{105}NO_{23}$ $[M+H]^+$ 1352.7150, found 1352.7167.

3-O—(N-(8-(4-Phenoxyhenyl)octyl)-β-D-glucopyranosyluronamide)-28-O-(β-D-xylopyranosyl-(1→4)-α-L-rhamnopyranosyl-(1→2)-α-L-arabinopyranosyl) quillaic ester (77α)

Following the general procedure of global deprotection, 77a was obtained in 35% yield as a white solid: $^1$H NMR (600 MHz, MeOD) δ 9.41 (s, 1H, H-23), 8.55 (s, 1H, amide NH), 7.32 (dd, J=8.6, 7.4 Hz, 2H), 7.16 (d, J=8.6 Hz, 2H), 7.07 (t, J=7.4 Hz, 1H), 6.95 (d, J=8.6 Hz, 2H), 6.90 (d, J=8.6 Hz, 2H), 6.09 (d, J=3.6 Hz, 1H, H-1'), 5.34 (t, J=3.5 Hz, 1H, H-12), 4.89 (d, J=1.7 Hz, 1H, H-1'') 4.49 (s, 1H, H-16), 4.43 (d, J=7.7 Hz, 1H, H-1''''), 4.26 (d, J=7.8 Hz, 1H, H-1'''), 3.96 (dd, J=3.1, 1.7 Hz, 1H, H-2''), 3.94 (dd, J=10.1, 3.6 Hz, 1H, H-2'), 3.92-3.90 (m, H-4'), 3.89 (dd, J=11.8, 4.7 Hz, 1H, H-3), 3.85 (dd, J=10.1, 3.3 Hz, 1H, H-3'), 3.83 (dd, J=11.4, 5.4 Hz, 1H, H-5$_a$'''), 3.80-3.76 (m, 2H, H-5$_a$', H-3), 3.67 (dd, J=12.4, 1.8 Hz, 1H, H-5$_b$'), 3.65 (d, J=9.7 Hz, 1H, H-5''''), 3.58-3.53 (m, 1H, H-5''), 3.49 (t, J=9.4 Hz, 1H, H-4''), 3.46-3.41 (m, 2H, H-4''', H-4''''), 3.33-3.26 (m, 3H, H-3''', H-3'''', —NHCH$_a$—), 3.23-3.12 (m, 4H, H-2''', H-5$_b$''', H-2'''', —NHCH$_b$—), 2.98 (dd, J=14.4, 4.2 Hz, 1H, H-18), 2.60 (t, J=7.6 Hz, 2H, carbon chain CH$_2$Ph), 2.26 (t, J=13.6 Hz, 1H, H-19$_a$), 2.00-1.87 (m, 5H, H-2$_a$, H-11$_{ab}$, H-21$_a$, H-22$_a$), 1.83-1.78 (m, 2H, H-2$_b$, H-22$_b$), 1.75 (dd, J=10.9, 6.7 Hz, 1H, H-9), 1.73-1.65 (m, 2H, H-1$_a$, H-15$_a$), 1.65-1.60 (m, 2H, carbon chain CH$_2$), 1.60-1.46 (m, 4H, H-6$_a$, H-7$_a$, carbon chain CH$_2$), 1.43-1.38 (m, 4H, H-15$_b$, H-27), 1.37-1.32 (m, 9H, H-5, carbon chain CH$_2$×4), 1.26-1.24 (m, 4H, H-6$_b$, H-6''), 1.21 (d, J=12.5 Hz, 1H, H-21$_b$), 1.12 (s, 3H, H-24), 1.10 (dd, J=13.7, 3.6 Hz, 1H, H-1$_b$), 1.05 (dd, J=12.4, 3.7 Hz, 1H, H-19$_b$), 1.01 (s, 3H, H-25), 0.95-0.91 (m, 4H, H-7$_b$, H-30), 0.87 (s, 3H, H-29), 0.77 (s, 3H, H-26); $^3$C NMR (151 MHz, MeOD) δ 209.0 (C-23), 176.8 (C-28), 171.5, 170.3, 159.2, 156.5, 144.5 (C-13), 139.2, 130.8, 130.7, 124.0, 123.5 (C-12), 120.0, 119.4, 107.1 (C-1'''), 105.0 (C-1''''), 104.3 (C-1''), 93.5 (C-1'), 84.4 (C-4''), 83.3 (C-3), 78.4 (C-3'''), 77.6 (C-3''''), 77.0 (C-2'), 76.6 (C-5''''), 76.1 (C-2'''), 74.9 (C-16), 74.7 (C-2''''), 73.2 (C-4''''), 72.5 (C-3''), 71.6 (C-2''), 71.0 (C-4'''), 70.7 (C-4'), 70.1 (C-3'), 68.8 (C-5''), 67.2 (C-5'''), 66.5 (C-5'), 56.1 (C-4), 50.7 (C-17), 49.6 (C-5), 48.0 (C-9), 47.9 (C-19), 42.8 (C-14), 42.2 (C-18), 41.1 (C-8), 40.0 (carbon chain CH$_2$), 39.4 (C-1), 37.1 (C-10), 36.4 (C-21), 36.3 (C-15), 36.2 (carbon chain CH$_2$), 33.7 (C-6), 33.3 (C-29), 32.9 (carbon chain CH$_2$), 32.3 (C-22), 31.4 (C-20), 30.7 (carbon chain CH$_2$), 30.4 (carbon chain CH$_2$), 30.3 (carbon chain CH$_2$), 30.2 (carbon chain CH$_2$), 27.9 (carbon chain CH$_2$), 27.2 (C-27), 26.0 (C-2), 25.3 (C-30), 24.5 (C-11), 21.4 (C-7), 17.9 (C-6″), 17.9 (C-26), 16.3 (C-25), 10.5 (C-24) ppm; HRMS (ESI-TOF) calcd. for $C_{72}H_{106}NO_{23}$ [M+H]$^+$ 1352.7150, found 1352.7159.

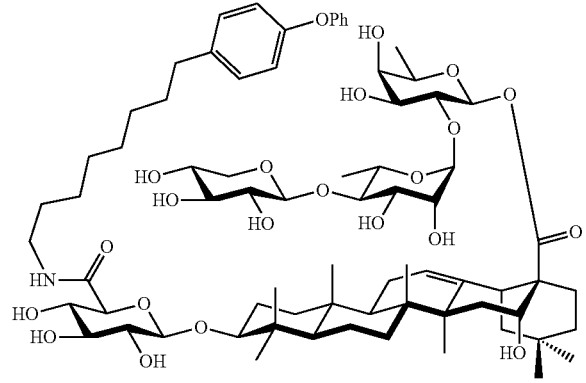

3-O—(N-(8-(4-Phenoxyhenyl)octyl)-β-D-glucopyranosyluronamide)-28-O-(β-D-xylopyranosyl-(1→4)-α-L-rhamnopyranosyl-(1→2)-β-D-fucopyranosyl) echinocystic ester (78)

Following the general procedure of global deprotection, 78 was obtained in 69% yield as a white solid: $^1$H NMR (600 MHz, MeOD) δ 8.55 (s, 1H, amide NH), 7.32 (dd, J=8.6, 7.4 Hz, 2H), 7.16 (dd, J=8.6, 1.0 Hz, 2H), 7.06 (tt, J=7.4, 1.0 Hz, 1H), 6.95 (d, J=8.6 Hz, 2H), 6.90 (d, J=8.6 Hz, 2H), 5.41 (d, J=1.7 Hz, 1H, H-1″), 5.30-5.27 (m, 2H, H-12, H-1′), 4.51-4.48 (m, 2H, H-1‴, H-16), 4.40 (d, J=7.8 Hz, 1H, H-1″″), 3.92 (dd, J=3.3, 1.7 Hz, 1H, H-2″), 3.88-3.79 (m, 4H, H-5$_a$‴, H-3″, H-2′, H-5″), 3.69-3.62 (m, 3H, H-5″″, H-3′, H-5′), 3.58-3.53 (m, 2H, H-4″, H-4′), 3.50-3.45 (m, 2H, H-4‴, H-4″″), 3.38 (t, J=9.1 Hz, 1H, H-3″″), 3.35-3.28 (m, 2H, H-3‴, —NHCH$_a$—), 3.27-3.24 (m, 2H, H-2″, H-2″″), 3.23-3.17 (m, 3H, H-3, H-5$_b$‴, —NHCH$_b$—), 2.93 (dd, J=14.3, 4.2 Hz, 1H, H-18), 2.60 (m, J=7.5 Hz, 2H, carbon chain CH$_2$Ph), 2.29 (t, J=13.6 Hz, 1H, H-19$_a$), 1.96-1.82 (m, 5H, H-2$_a$, H-1$_{ab}$, H-21$_a$, H-22$_a$), 1.80-1.66 (m, 3H, H-22$_b$, H-2$_b$, H-15$_a$), 1.66-1.55 (m, 5H, H-1$_a$, H-7$_a$, H-9, carbon chain CH$_2$), 1.55-1.49 (m, 3H, H-6$_a$, carbon chain CH$_2$), 1.48-1.41 (m, 2H, H-15$_b$, H-6$_b$), 1.40-1.36 (m, 4H, H-7$_b$, H-27), 1.36-1.32 (m, 11H, H-6″, carbon chain CH$_2$×4), 1.21 (d, J=6.4 Hz, 3H, H-6′), 1.16 (dd, J=10.8, 3.8 Hz, 1H, H-21$_b$), 1.06 (s, 3H, H-23), 1.03 (dd, J=12.1, 8.9 Hz, 1H, H-19$_b$), 0.98 (dd, J=13.4, 3.5 Hz, 1H, H-1$_b$), 0.95 (s, 3H, H-25), 0.92 (s, 3H, H-30), 0.86 (s, 3H, H-24), 0.85 (s, 3H, H-29), 0.78 (d, J=12.0 Hz, 1H, H-5), 0.76 (s, 3H, H-26); $^{13}$C NMR (151 MHz, MeOD) δ 177.1 (C-28), 171.7, 159.2, 156.5, 144.8 (C-13), 139.1, 130.8, 130.7, 124.0, 123.4 (C-12), 120.1, 119.4, 107.0 (C-1‴), 106.8 (C-1″″), 101.1 (C-1″), 95.2 (C-1′), 91.0 (C-3), 84.1 (C-4″), 78.1 (C-3‴), 77.8 (C-3″″), 76.7 (C-3′), 76.5 (C-5″″), 76.1 (C-2″), 75.2 (C-2″″), 74.7 (C-16), 74.0 (C-2′), 73.6 (C-4′), 73.4 (C-4″″), 72.7 (C-5′), 72.2 (C-3″), 71.9 (C-2″), 71.1 (C-4‴), 68.7 (C-5″), 67.3 (C-5‴), 57.2 (C-5), 50.0 (C-17), 48.1 (C-9), 48.1 (C-19), 42.7 (C-14), 42.3 (C-18), 40.8 (C-8), 40.2 (C-4), 40.0 (C-1), 39.9, 37.9 (C-10), 36.5 (C-21), 36.5 (C-15), 36.4, 34.3 (C-6), 33.4 (C-29), 32.9, 32.0 (C-22), 31.3 (C-20), 30.7, 30.6, 30.4, 30.3, 28.5 (C-23), 27.9, 27.3 (C-2), 27.2 (C-27), 24.8 (C-30), 24.6 (C-11), 19.4 (C-7), 18.3 (C-6″), 17.8 (C-26), 17.0 (C-24), 16.5 (C-6′), 16.3 (C-25) ppm; HRMS (ESI-TOF) calcd. for $C_{73}H_{110}NO_{22}$ [M+H]$^+$ 1352.7514, found 1352.7532.

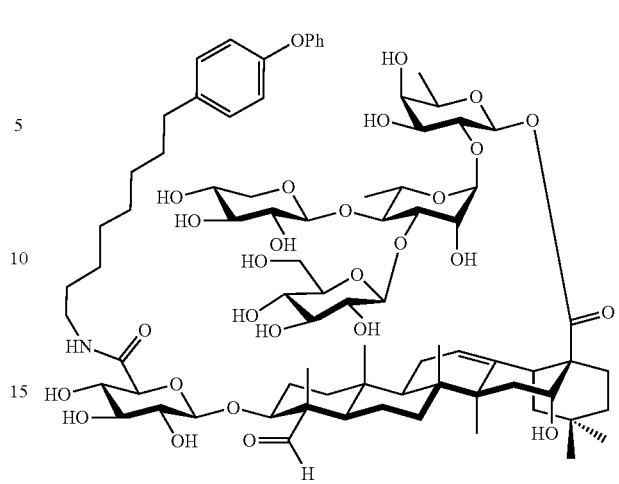

3-O—(N-(8-(4-Phenoxyhenyl)octyl)-β-D-glucopyranosyluronamide)-28-O-(β-D-glucopyranosyl-(1→3)-(β-D-xylopyranosyl-(1-4))-α-L-rhamnopyranosyl-(1→2)-β-D-fucopyranosyl) quillaic ester (79)

Following the general procedure of global deprotection, 79 was obtained in 33% yield as a white solid: 1H NMR (600 MHz, MeOD) δ 9.42 (s, 1H, H-23), 8.55 (s, 1H, amide NH), 7.32 (dd, J=8.5, 7.5 Hz, 2H), 7.17 (d, J=8.5 Hz, 2H), 7.07 (t, J=7.5 Hz, 1H), 6.95 (d, J=8.5 Hz, 2H), 6.90 (d, J=8.5 Hz, 2H), 5.29 (s, 1H, H-12), 5.26 (d, J=8.1 Hz, 1H, H-1′), 5.23 (s, 1H, H-1″), 4.70 (d, J=7.9 Hz, 1H, H-1″″), 4.53 (d, J=7.3 Hz, 1H, H-1‴), 4.46 (s, 1H, H-16), 4.27-4.25 (m, 2H, H-2″, H-1″″′), 3.95 (dd, J=9.5, 3.0 Hz, 1H, H-3″), 3.90-3.81 (m, 4H, H-5″, H-3, H-6$_a$‴, H-5$_a$‴), 3.74 (dd, J=10.2, 8.1 Hz, 1H, H-2′), 3.71-3.60 (m, 5H, H-4″, H-6$_b$‴, H-5″″, H-5′, H-3′), 3.55 (d, J=2.6 Hz, 1H, H-4′), 3.49-3.41 (m, 2H, H-4‴, H-4″″), 3.33-3.25 (m, 7H, H-2″, H-3″, H-4‴, H-5″″, H-3″″, H-3″″′, —NHCH$_a$—), 3.23-3.08 (m, 4H, H-2‴, H-5$_b$″″, H-2″″′), 2.95-2.88 (m, 1H, H-18), 2.60 (t, J=7.6 Hz, 2H, carbon chain CH$_2$Ph), 2.28 (t, J=13.6 Hz, 1H, H-19$_a$), 1.98-1.86 (m, 5H, H-2$_a$, H-21$_a$, H-22$_a$, H-11$_{ab}$), 1.86-1.77 (m, 2H, H-22$_b$, H-2$_b$), 1.76-1.67 (m, 3H, H-9, H-15$_a$, H-1$_a$), 1.65-1.59 (m, 2H, carbon chain CH$_2$), 1.58-1.48 (m, 4H, H-6$_a$, H-7$_a$, carbon chain CH$_2$), 1.41-1.38 (m, 4H, H-15$_b$, H-27), 1.37-1.31 (m, 9H, H-5, carbon chain CH$_2$×4), 1.30-1.26 (m, 4H, H-6$_b$, H-6″), 1.21 (d, J=6.3 Hz, 3H, H-6′), 1.16 (d, J=11.2 Hz, 1H, H-21$_b$), 1.14 (s, 3H, H-24), 1.10 (d, J=16.7 Hz, 2H, H-1$_b$), 1.04 (d, J=10.1 Hz, 1H, H-19$_b$), 1.00 (s, 3H, H-25), 0.96-0.94 (m, 1H, H-7$_b$), 0.93 (s, 3H, H-30), 0.85 (s, 3H, H-29), 0.79 (s, 3H, H-26); $^{13}$C NMR (151 MHz, MeOD) δ 209.4 (C-23), 177.2 (C-28), 171.5, 159.2, 156.5, 144.8 (C-13), 139.2, 130.8, 130.7, 124.0, 123.1 (C-12), 120.0, 119.4, 105.4 (C-1‴), 105.1 (C-1″″), 105.0 (C-1″″′), 101.5 (C-1″), 95.4 (C-1′), 83.5 (C-3), 83.0 (C-3″), 78.7 (C-4″), 78.6 (C-3‴), 78.3 (C-3″″), 77.8 (C-2″), 77.6 (C-3″″′), 76.6 (C-5″″′), 75.9 (C-3′), 75.7 (C-2″″), 75.3 (C-4″), 74.9 (C-2′), 74.8 (C-16), 74.7 (C-2″″′), 73.5 (C-4′), 73.2 (C-4″″′), 72.7 (C-5′), 71.5 (C-4″″), 71.3 (C-2″), 71.1 (C-5‴), 69.1 (C-5″), 67.0 (C-5″″), 62.4 (C-6‴), 56.1 (C-4), 49.9 (C-17), 49.5 (C-5), 48.1 (C-19), 48.0 (C-9), 42.8 (C-14), 42.4 (C-18), 41.1 (C-8), 40.0, 39.4 (C-1), 37.1 (C-10), 36.5 (C-15, C-21), 36.2, 33.8 (C-6), 33.4 (C-29), 32.9, 31.8 (C-22), 31.3 (C-20), 30.7, 30.5, 30.4, 30.3, 27.9, 27.3 (C-27), 26.0 (C-2), 24.9 (C-30), 24.5 (C-11), 21.4 (C-7), 18.6 (C-6″), 17.8 (C-26), 16.5 (C-6′), 16.4 (C-25), 10.6 (C-24); HRMS (ESI-TOF) calcd. for $C_{79}H_{118}NO_{28}$ [M+H]$^+$ 1528.7835, found 1528.7847.

Synthetic Example II

Prosapogenins Couples with Trisaccharides.

Considering the lengthy route to conjugate glucuronate and qullaic ester, we further applied semi-synthetic approach to achieve saponin core. The starting material *Quillaja* Ultra Dry100-Q (Desert King, Batch: QDU-100-121213-2) was proceeded under alkaline condition to hydrolyze the C-28 linked oligosaccharide. Following by triethylsilylation and selective benzylation, the prosapogenins core was afforded in three steps (Scheme 7).

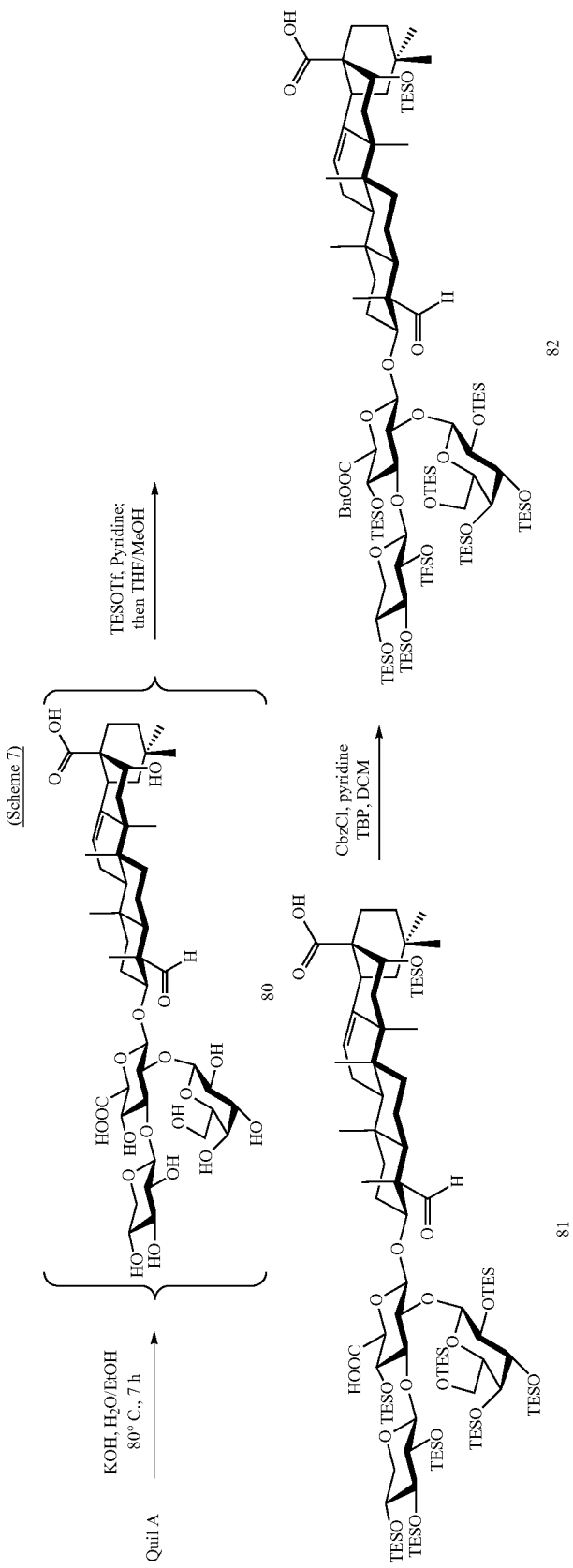

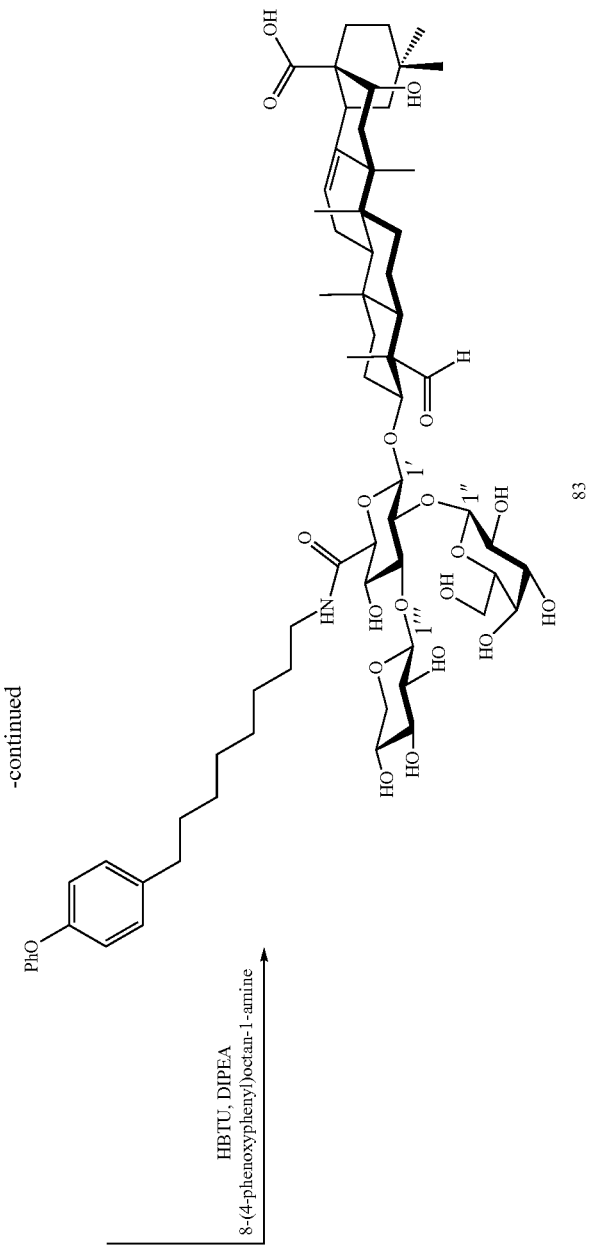

Scheme 7—Isolation and Selective Protection of Branched Trisaccharide-Triterpene Saponin.

Amide Bond Formation of Diversed Linker on Prosapogenins.

The coupling of tisaccharide and prosapogenin can be readily achieved to afford saponin core. Following by deprotection and amide bond formation, target saponins with diversified carbon chain were furnished.

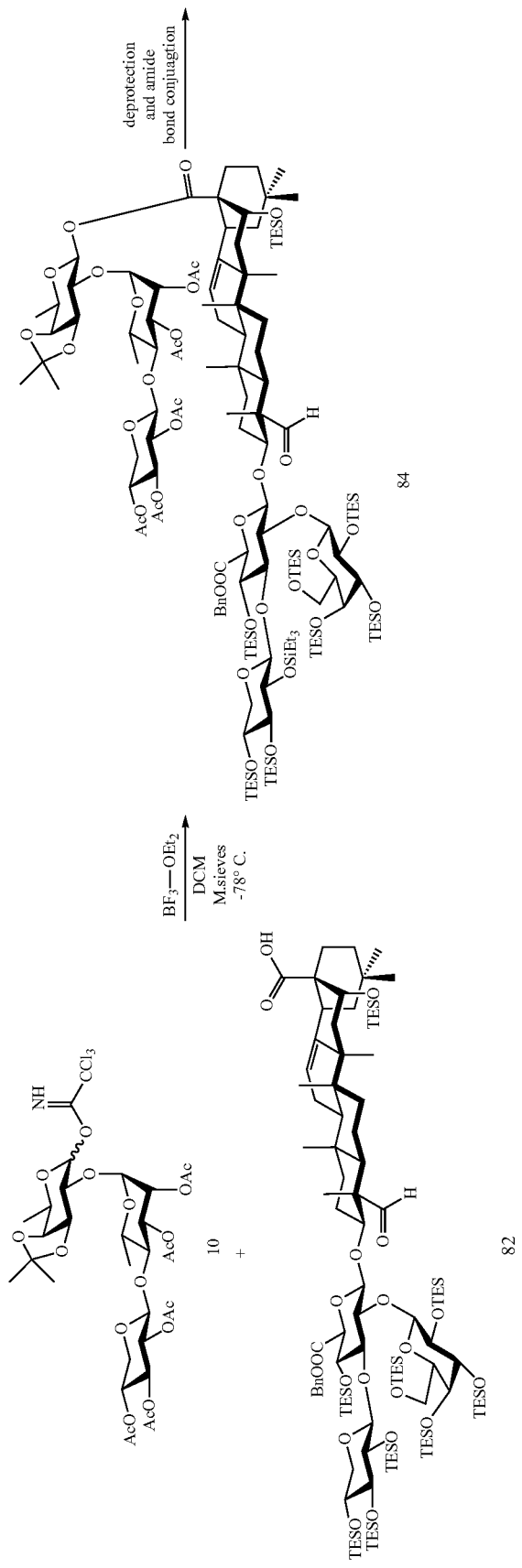

-continued
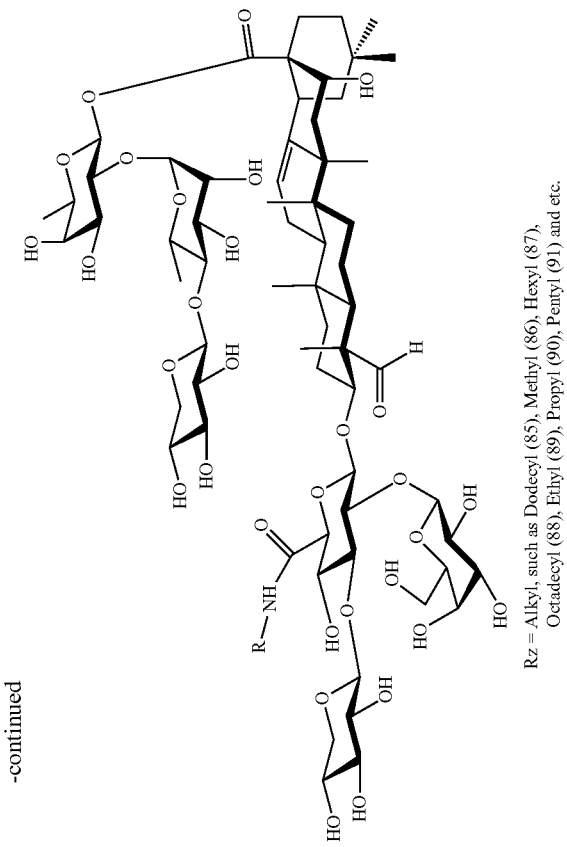
Rz = Alkyl, such as Dodecyl (85), Methyl (86), Hexyl (87), Octadecyl (88), Ethyl (89), Propyl (90), Pentyl (91) and etc.

-continued

Scheme 8—Demonstrates the Preparation of Saponin Analogues, According to Embodiments of the Invention.

Experimental Details

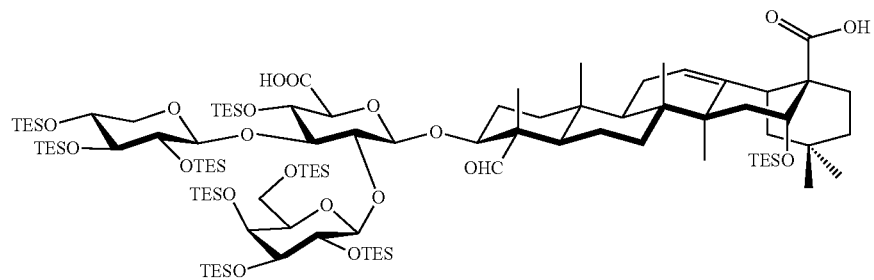

3-O-(2,3,4,6-tetra-O-triethylsilyl-α-D-galactopyranosyl-(1→2)-(2,3,4-tri-O-triethylsilyl-β-D-Xylopyranosyl-(1→3))-3-O-triethylsilyl-β-D-glucopyranosyluronic acid))-16-O-triethylsilylquillaic acid (81)

To a stirred suspension of prosapogenins (1.72 g) in anhydrous pyridine (25 mL) was added TESOTf (5.0 mL, 22.1 mmol) at room temperature under $N_2$ atmosphere. The reaction mixture was stirred for 2 days, then TESOTf (1.3 mL, 5.8 mmol) was added, followed by 1 further addition (1.0 mL, 4.4 mmol) after 24 h later. The reaction mixture was stirred for 5 days in total. The resulting mixtures was concentrated and passed through a short plug of silica gel eluted with Hexanes/EtOAc (2:1). The eluate was concentrated and dried under reduced pressure to afford yellow oil. The resulting yellow oil was dissolved in MeOH/THF (1:1) (80 mL), and the solution was stirred for 3 days at room temperature. The reaction mixture was concentrated under reduced pressure, and then purified by column chromatography (silica gel, EtOAc/Hexanes=1/6 to 1/4) to afford 81 (0.66 g, ~19%) as a white solid foams. $R_f$ 0.47 (EtOAc/Benzene=1/4); $^1$H NMR (600 MHz, CDCl$_3$) δ 9.68 (s, 1H), 5.35 (br. s, 1H, H-12), 4.56 (br. s, 1H, H-16), 4.54 (d, J=7.4 Hz, 1H, H-1'''), 4.42 (d, J=7.4 Hz, 1H, H-1''), 4.41 (d, J=6.4 Hz, 1H, H-1'), 3.96-3.88 (m, 4H, H-4'', H-3', H-5', H-3''), 3.84-3.82 (m, 2H, H-5$_a$'', H-2'), 3.77 (t, J=9.2 Hz, 1H, H-6$_a$''), 3.65-3.61 (m, 3H, H-3, H-2'', H-6$_b$''), 3.52-3.49 (m, 1H, H-4'''), 3.53-3.51 (m, 1H, H-4'), 3.42-3.35 (m, 2H, H-3''', H-5'), 3.27 (t, J=7.8 Hz, 1H, H-2'''), 3.12 (t, J=10.7 Hz, 1H, H-5'''), 2.96 (dd, J=13.3 Hz, J=3.1 Hz, 1H, H-18), 2.22 (t, J=13.8 Hz, 1H, H-19), 1.92-1.86 (m, 4H), 1.84-1.71 (m, 4H), 1.68 (t, J=8.9 Hz, 1H, H-19$_a$), 1.63-1.31 (m, 1H, H-1), 1.57-1.50 (m, 1H), 1.49-1.41 (m, 2H, H-6), 1.39-1.36 (m, 5H, H-5, H-27), 1.29-1.25 (m, 5H, H-15, H-24), 1.12-1.15 (m, 2H, H-21), 1.11-1.07 (m, 1H, H-9), 1.04-0.94 (m, 94H), 0.91 (s, 3H, H-29), 0.75-0.62 (m, 54H) ppm; HRMS (ESI-TOF) calcd. for $C_{101}H_{199}O_{20}Si_9$ [M+H]$^+$ 1986.2504, found 1986.3361.

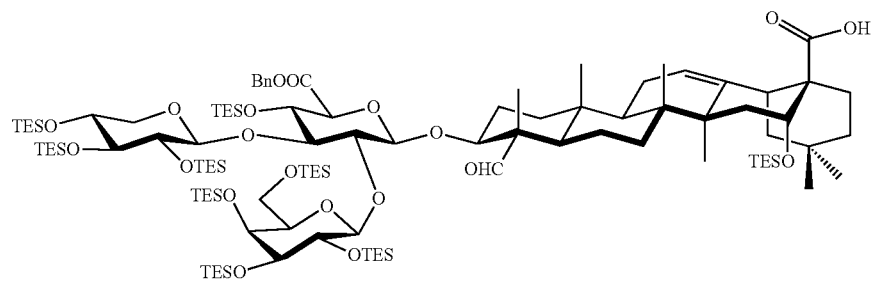

3-O-(benzyl 2,3,4,6-tetra-O-triethylsilyl-β-D-galactopyranosyl-(1→2)-(2,3,4-tri-O-triethylsilyl-β-D-xylopyranosyl-(1→3))-3-O-triethylsilyl-β-D-glucopyranosyluronate))-16-O-triethylsilylquillaic acid (82)

To a stirred suspension of 81 (253 mg, 127 µmol), TBP (319 mg, 1.29 mmol) and anhydrous pyridine (94 µL, 1.2 mmol) in CH$_2$Cl$_2$ (2.2 mL) was added CBzCl (47 µL, 0.33 mmol) under N$_2$ atmosphere. Upon the completion of the reaction after 14 h, the reaction mixture was concentrated under reduced pressure. The residue was purified by column chromatography (silica gel; EtOAc/hexanes=1/20 to 1/10) to give 82 (207 mg, 65%) as white solid foams. R$_f$ 0.74 (EtOAc/Benzene=1/9); $^1$H NMR (400 MHz, CDCl$_3$) δ 9.68 (s, 1H), 7.33-7.29 (m, 5H), 5.31 (br. s, 1H, H-12), 5.23 (d, J=12.4 Hz, 1H Bn CH$_2$), 5.07 (d, J=12.0 Hz, 1H Bn CH$_2$), 4.53 (d, J=7.6 Hz, 1H, H-1"), 4.51 (br. s, 1H, H-16), 4.40 (d, J=7.2 Hz, 1H, H-1"'), 4.12 (d, J=7.2 Hz, 1H, H-1'), 3.93-3.79 (m, 4H, H-4", H-3', H-5', H-3"'), 3.878-3.74 (m, 2H, H-5$_a$', H-2'), 3.72 (t, J=9.1 Hz, 1H, H-6$_a$"), 3.61-3.52 (m, 3H, H-3, H-2", H-6$_b$"), 3.49-3.42 (m, 1H, H-4"'), 3.40-3.35 (m, 1H, H-4'), 3.39-3.29 (m, 2H, H-3"', H-5"), 3.23 (t, J=7.7 Hz, 1H, H-2"'), 3.11 (t, J=11.0 Hz, 1H, H-5$_b$"'), 2.91 (dd, J=13.8 Hz, J=3.6 Hz, 1H, H-18), 2.19 (t, J=13.6 Hz, 1H, H-19), 1.89-1.79 (m, 4H), 1.55-1.45 (m, 4H), 1.42-1.30 (m, 5H, H-5, H-27), 1.30-1.23 (m, 5H, H-15, H-24), 1.16-1.09 (m, 2H, H-21), 1.08-1.01 (m, 1H, H-9), 1.00-0.90 (m, 94H), 0.88 (s, 3H, H-29), 0.73-0.57 (m, 54H) ppm; HRMS (ESI-TOF) calcd. for C$_{108}$H$_{204}$O$_{20}$Si$_9$Na [M+Na]$^+$ 2099.2803, found 2099.3005.

mL) was added DIPEA (5 µL, 25 µmol) then 8-(4-phenoxyphenyl)octan-1-amine (4 mg, 14 gmol) under N$_2$ atmosphere. Upon the completion of the reaction after 1 h, the reaction mixture was concentrated under reduced pressure, diluted with CH$_2$Cl$_2$, washed by H$_2$O for two times, brine, dried over MgSO$_4$, and then concentrated under pressure. The residue was then purified through flash column (silica gel, EtOAc/hexanes=1/20 to 1/10). The crude product was then dissolved in 1 mL THF, and stirring under pH 1 acid condition for 6 hours. After neutralized with NaHCO$_3$, the mixtures were filter though 0.22 µmm filter plate and the filtrate was concentrated then purified by HPLC to afford product 83 (2 mg) in 80% as a whit e solid (HPLC column: SUPELCO Ascentis C18 25 cm×10 mm, 5 µm; mobile phase: 20% A CN/H$_2$O gradient to 90% ACN/H$_2$O in 20 min, and then 90% ACN/H$_2$O isocratic for 15 min; flow rate: 4 mL/min): $^1$H NMR (600 MHz, CD$_3$OD) δ 9.44 (s, 1H, H-23), 7.32 (t, J=7.7 Hz, 2H), 7.16 (d, J=8.3 Hz, 2H), 7.07 (t, J=7.2 Hz, 1H), 6.95 (d, J=8.2 Hz, 2H), 6.90 (d, J=8.2 Hz, 1H), 5.28 (br.s, 1H, H-12), 4.79 (d, J=7.1 Hz, 1H, H-1"), 4.45 (s, 1H, H-16), 4.57 (d, J=7.7 Hz, 1H, H-1"'), 4.43 (d, J=7.4 Hz, 1H, H-1'), 3.89 (dd, J=11.5 & 5.5 Hz, 1H, H-3), 3.85 (dd, J=11.8 & 4.4 Hz, 1H, H-5$_a$"'), 3.81 (d, J=2.5 Hz, 1H, H-4") 3.75 (d, J=6.2 Hz, 2H, H-6"), 3.70-3.63 (m, 4H, H-2"', H-2', H-5', H-3'), 3.56-3.41 (m, 5H, H-2", H-3', H-4', H-5", H-4"'), 3.26-3.19 (m, 4H, H-3"', H-5$_b$"', —NHCH$_2$—), 3.00 (dd, J=14.1 Hz & 4.1 Hz, 1H, H-18), 2.60 (t, J=7.6 Hz, 2H, carbon chain CH$_2$Ph), 2.29 (t, J=13.4 Hz, 1H, H-19$_a$),

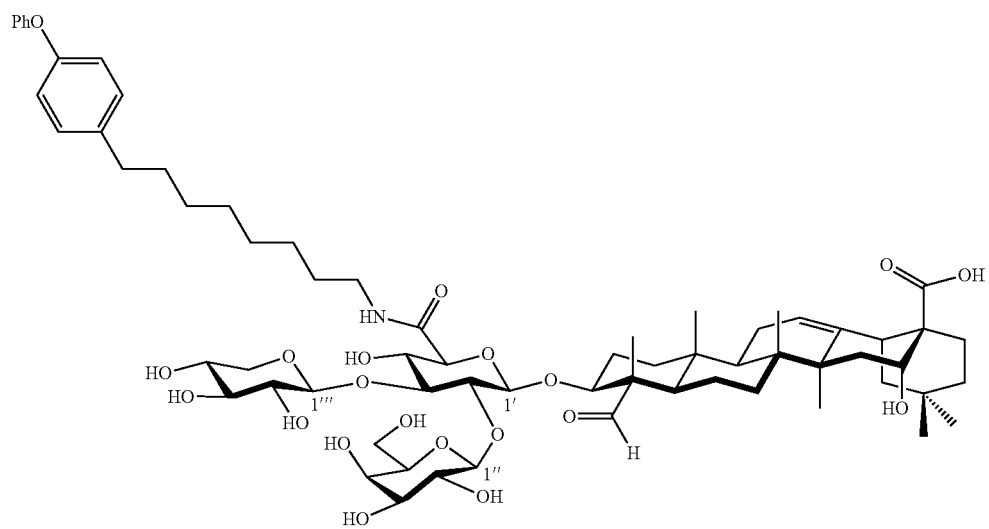

3-O—(N-(8-(4-phenoxyphenyl)octyl)-β-D-galactopyranosyl-(1→2)-(β-D-xylopyranosyl-(1-3))-β-D-glucopyranosyluroamide)-quillaic acid (83)

To a stirred suspension of of saponin diacid (26 mg, 13 µmol) and HBTU (7 mg, 25 µmol) in a anhydrous THE (1

1.99-1.87 (m, 5H), 1.80-1.72 (m, 3H), 1.71-1.66 (m, 1H), 1.65-1.60 (m, 2H), 1.55-1.49 (m, 3H), 1.38 (s, 1H, H-27), 1.36-1.29 (m, 14H), 1.15 (s, 3H, H-23), 1.02 (m=3H), 0.98 (s, 3H, H-25), 0.95 (s, 3H, H-30), 0.86 (s, 3H, H-24), 0.78 (s, 3H, H-26) ppm; HRMS$^+$ (ESI-TOF) calcd. for C$_{67}$H$_{97}$NO$_{20}$ Na [M+Na]$^+$ 1258.6496, found 1258.6510.

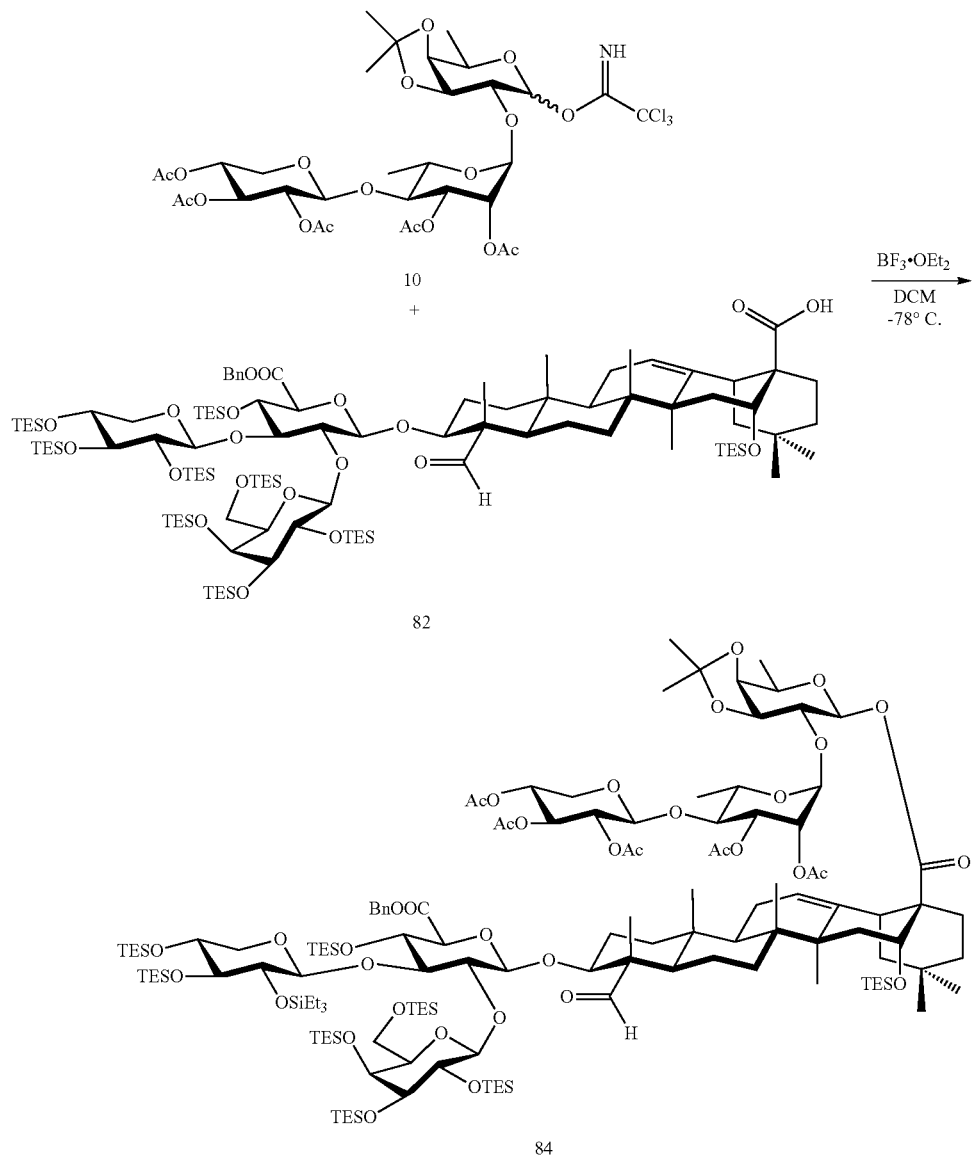

3-O-(benzyl 2,3,4,6-tetra-O-triethylsilyl-β-D-galactopyranosyl-(1→2)-(2,3,4-tri-O-triethylsilyl-β-D-xylopyranosyl-(1→3))-(3-O-triethylsilyl-β-D-glucopyranosyluronate))-28-O-(2,3,4-tri-O-acetyl-β-D-xylopyranosyl-(1→4)-2,3-di-O-acetyl-α-L-rhamnopyranosyl-(1→2)-3,4-O-isopropylidene-β-D-fucopyranosyl)-16-O-triethylsilylquillaic ester (84)

To a stirred suspension of 10 (68.8 mg, 83.6 μmol), 82 (130 mg, 62.3 μmol) and activated 4 Å molecular sieve powder in anhydrous $CH_2Cl_2$ (3.0 mL) was added $BF_3$—$OEt_2$ (ca. 48%, 4 μL, 24 μmol) at −75° C. under $N_2$ atmosphere. Upon completion of the reaction after 0.5 h, the reaction was quenched by $Et_3N$, warmed to room temperature. The resulting mixture was diluted with $CH_2Cl_2$ and filtered through 5 m filter paper. The resulting filtrate was concentrated under reduced pressure. The residue was purified by column chromatography (silica gel; $EtOAc/CH_2Cl_2$/hexanes=1/1/6 to 1/1/4) to give 84 (160 mg, 93%) as white solid foams. $R_f$ 0.63 (EtOAc/hexanes=1/1); $^1H$ NMR (600 MHz, $CDCl_3$) δ 9.67 (s, 1H), 7.32-7.29 (m, 5H), 5.38 (d, J=7.4 Hz, 1H, H-1''''), 5.30 (t, J=3.71H, H-12), 5.26 (d, J=12.0 Hz, 1H Bn $CH_2$), 5.23-5.21 (m, 1H, H-2''''), 5.19 (dd, J=9.8 Hz, J=3.5 Hz, 1H, H-3''''), 5.07 (d, J=12.4 Hz, 1H Bn $CH_2$), 4.97 (d, J=0.8 Hz, 1H, H-1''''), 4.93 (dt, J=9.2 Hz, J=5.5 Hz, 1H, H-4''''), 4.83 (dd, J=9.2 Hz, J=5.5 Hz, 1H, H-2''''), 4.61 (d, J=7.8 Hz, 1H, H-1''''), 4.53 (d, J=7.8 Hz, 1H, H-1'''), 4.46 (s, 1H, H-16), 4.39 (d, J=7.2 Hz, 1H, H-1''), 4.17-4.14 (m, 2H, H-1', H-3'''), 4.12-4.07 (m, 2H, H-3', H-5a''''), 3.99 (dd, J=5.8 Hz, J=1.9 Hz, 1H, H-4''''), 3.91-3.88 (m, 2H, H-4', H-5'), 3.86-3.81 (m, 3H, H-4'', H-5'''', H-3''), 3.81-3.75 (m, 3H, H-5''', H-5$_a$''', H-2'), 3.72 (t, J=9.2 Hz, 1H, H-6$_a$''), 3.66-3.60 (m, 2H, H-2'''', H-5''''), 3.59-3.53 (m, 3H, H-2''', H-6$_b$'', H-3), 3.47-3.42 (m, 1H, H-4'''), 3.36 (dd, J=9.4 Hz, J=2.2 Hz, 1H, H-4''''), 3.34-3.29 (m, 3H, H-3''', H-5'', H-5$_b$''''), 3.22 (t, J=7.4 Hz, 1H, H-2''), 3.10, (t, J=11.0 Hz, 1H, H-5$_b$'''), 2.90 (dd, J=14.1 Hz, J=3.7 Hz, 1H, H-18), 2.21 (t, J=13.7 Hz, 1H, H-19), 2.11 (s, 3H), 2.04 (s, 3H), 2.01 (s, 3H), 1.99 (s, 3H), 1.95 (s, 3H), 1.83-1.77 (m, 4H, H-11, H-22), 1.76-1.62 (m, 4H), 1.62-1.55 (m, 3H), 1.52 (s, 3H, H-27), 1.50-1.47 (m, 1H), 1.33 (s, 1H, H-5), 1.31 (s, 6H, isopropylidene CH$_3$), 1.27 (s, 3H, H-24), 1.26-1.25 (m, 3H, H-6''''), 1.25-1.24 (d, 3H, H-6''''), 1.24-1.22 (m, 4H), 0.98-0.91 (m, 94H), 0.91-0.89 (m, 10H, H-1, H-7, H-15, H-20), 0.69-0.56 (m, 54H) ppm; HRMS (ESI-TOF) calcd. for C$_{138}$H$_{246}$O$_{37}$Si$_9$Na [M+Na]$^+$ 2772.5224, found 2772.5586.

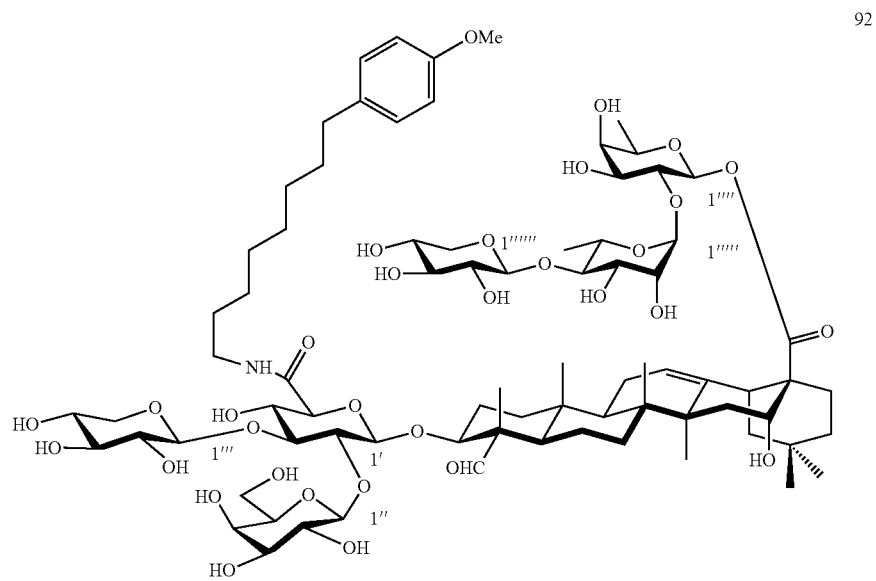

92

3-O—{β-D-galactopyranosyl-(1→2)-[β-D-xylopyra-nosyl-(1→3)]-[N-(8-(4-methoxyphenyl)octyl)-β-D-glucuropyranosyluroamide]}-28-O-[β-D-xylopyrano-syl-(1→4)-α-L-rhamnopyranosyl-(1→2)-β-D-fucopyranosyl]quillaic ester (92)

To a stirred suspension of 50 (8 mg, 6 mol), 8-(4-methoxyphenyl)octan-1-amine (13 mg, 58 μmol), and HBTU (22 mg, 58 μmol) in anhydrous DMA (0.5 mL) was added DIPEA (10 L, 58 μmol) under N$_2$ atmosphere. Upon the completion of the reaction after 24 h, the reaction mixture was concentrated under reduced pressure, diluted with MeOH then filtered through 5 μm filter paper. The filtrate was concentrated then purified by HPLC to afford product 51b (2 mg) in 30% as a white solid (HPLC column: SUPELCO Ascentis C18 25 cm×10 mm, 5 m; mobile phase: 30% ACN/H$_2$O gradient to 80% ACN/H$_2$O in 20 min, and then 90% ACN/H$_2$O isocratic for 15 min; flow rate: 5 mL/min); HRMS (ESI-TOF) calcd. for C$_{79}$H$_{123}$NO$_{32}$Na [M+Na]$^+$ 1620.7920, found 1620.7920.

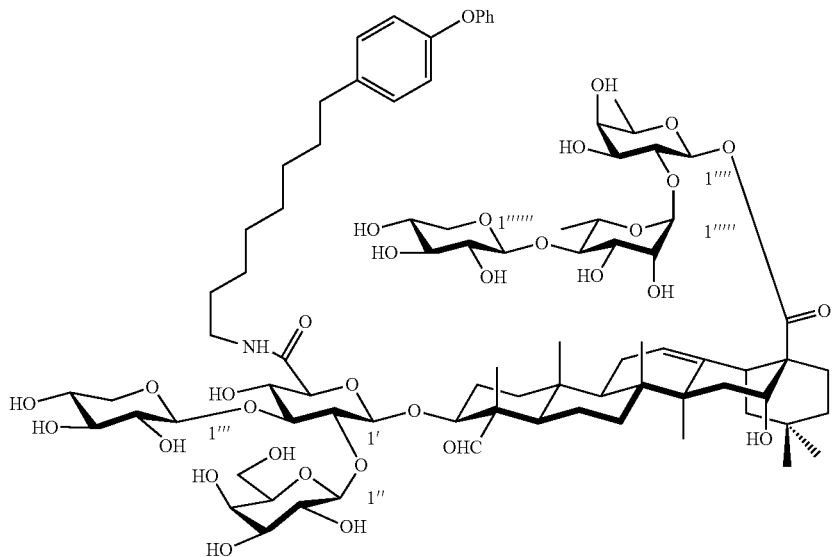

95

3-O—{β-D-galactopyranosyl-(1→2)-[β-D-xylopyranosyl-(1→3)]-[N-(8-(4-phenoxyphenyl)octyl)-β-D-glucuropyranosyluroamide]}-28-O-[β-D-xylopyranosyl-(1→4)-α-L-rhamnopyranosyl-(1→2)-β-D-fucopyranosyl]quillaic ester (95)

To a stirred suspension of 50 (5 mg, 4 μmol), 8-(4-phenoxyphenyl)octan-1-amine (10 mg, 40 μmol), and HBTU (12 mg, 40 mol) in anhydrous DMA (0.5 mL) was added DIPEA (6 μL, 40 μmol) under $N_2$ atmosphere. Upon the completion of the reaction after 24 h, the reaction mixture was concentrated under reduced pressure, diluted with MeOH then filtered through 5 μm filter paper. The filtrate was concentrated then purified by HPLC to afford product 51a (2 mg) in 80% as a white solid (HPLC column: SUPELCO Ascentis C18 25 cm×10 mm, 5 μm; mobile phase: 20% ACN/$H_2O$ gradient to 90% ACN/$H_2O$ in 20 min, and then 90% ACN/$H_2O$ isocratic for 15 min; flow rate: 2.4 mL/min): $^1$H NMR (600 MHz, $CD_3OD$) δ 9.45 (s, 1H, H-23), 8.54 (s, 1H, amide NH), 7.33 (dd, J=8.5 Hz &7.6 Hz, 2H), 7.18 (d, J=8.5 Hz, 2H), 7.08 (t, J=7.4 Hz, 1H), 6.95 (d, J=7.8 Hz, 2H), 6.91 (d, J=8.5 Hz, 1H), 5.37 (d, J=1.5 Hz, 1H, H-1''''''), 5.28 (t, J=3.4 Hz, 1H, H-12), 5.27 (d, J=8.2 Hz, 1H, H-1''''), 4.79 (d, J=7.1 Hz, 1H, H-1''), 4.62 (s, 1H, H-16), 4.57 (d, J=7.7 Hz, 1H, H-1'''), 4.47 (d, J=7.7 Hz, 1H, H-1'''''), 4.43 (d, J=7.4 Hz, 1H, H-1'), 3.93 (m, 1H, H-2'''''), 3.89 (m, 1H, H-5a'''), 3.82 (m, 6H, H-4'', H-2'''', H-3'''', H-3''''', H-5''''', H-5$_a$''''''), 3.75 (m, 2H, H-6''), 3.69 (m, 1H, H-2'''), 3.65 (m, 5H, H-2', H-5', H-3'', H-4'''', H-5'''''), 3.49 (m, 9H, H-3, H-3', H-4', H-5'', H-4'''', H-3''''', H-4'''', H-2'''', H-4''''''), 3.22 (m, 6H, H-2'', H-3''', H-5$_b$''', H-3''''', H-5$_b$'''''', —NHC$\underline{H}_a$—), 2.95 (m, 2H, H-18, —NHC$\underline{H}_b$), 2.60 (t, J=7.6 Hz, 2H, carbon chain C$\underline{H}_2$Ph), 2.29 (t, J=13.4 Hz, 1H, H-19$_a$), 1.95 (m, 2H), 1.90 (m, 4H), 1.76 (m, 3H), 1.69 (m, 2H), 1.63 (m, 4H), 1.53 (m, 3H), 1.46 (m, 3H), 1.38 (s, 1H, H-27), 1.34 (m, 13H), 1.30 (m, 11H), 1.20 (d, J=6.4 Hz, 3H, H-6'''''), 1.16 (s, 3H, H-23), 1.15 (m, 1H), 1.08 (m, 3H), 0.98 (s, 3H, H-25), 0.92 (s, 3H, H-30), 0.90 (m, 2H), 0.86 (s, 3H, H-24), 0.74 (s, 3H, H-26); HRMS (ESI-TOF) calcd. for $C_{84}H_{25}NO_{32}Na$ [M+Na]$^+$ 1682.8077, found 1682.8079.

6-N-glycosyl Quillaic ester

The conjugation of quillaic ester with azido-glucose was successfully resulted in 70% yield of product 117. Interestingly, this result revealed the selectivity of 3-O glycosylation over 16-O position.

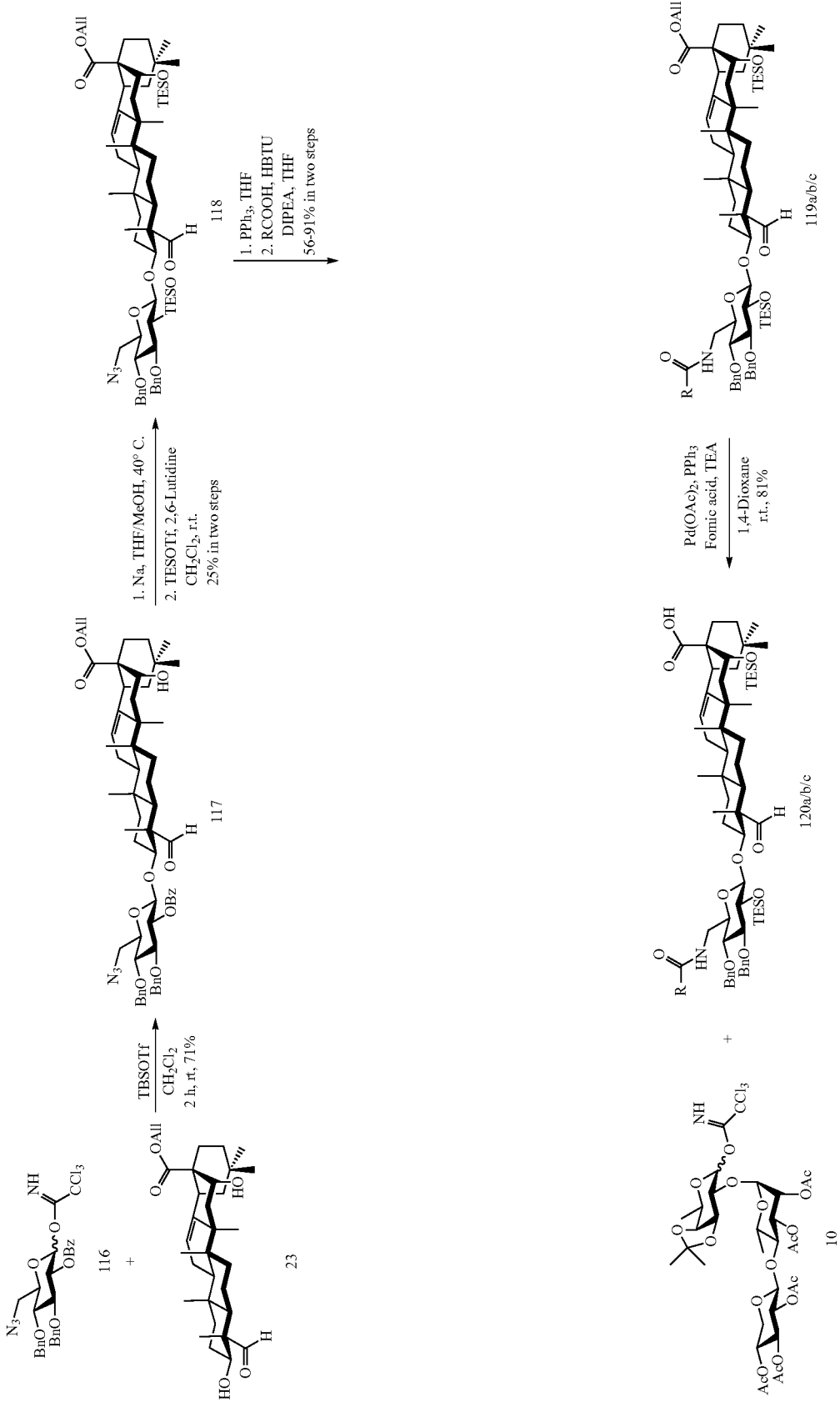

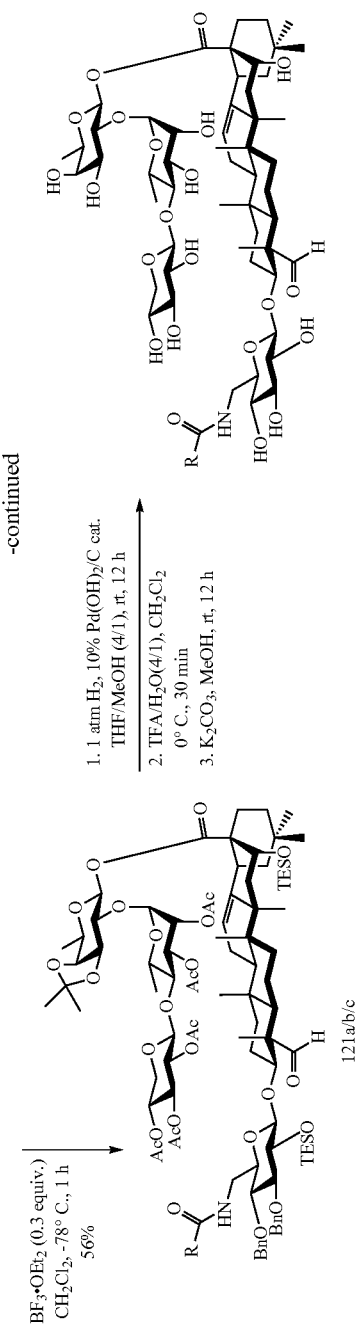
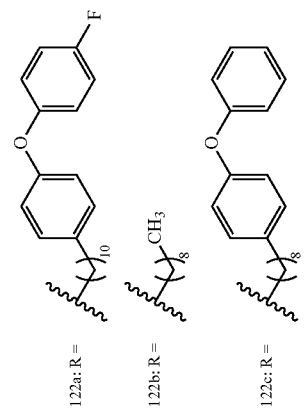

With the glycoside 117 in hand, further modifications had been conducted to unmask the C-28 carboxylic acid. First, the benzoyl group was hydrolyzed under basic condition at elevated temperatures. Surprisingly, 28-O-allyl ester was not affected under this harsh environment. After triethylsilylation of the resulting azido-glycoside, the azide group was reduce to amine then forming amide by coupling with lipophilic long chain acid to afford fully-protected quillaic ester 119a/b/c. The O-allyl ester 119a/b/c was hydrolyzed by the catalysis of Pd(OAc)$_2$ under mild acidic environment to give glycoside acceptor 120a/b. Under the catalysis of Lewis acid at −78° C., the monoacid 120a/b/c was conjugated with trisaccharide 10 to obtain 121a/b/c in 56% yield. The fully protected saponin 121a/b/c was suspended with Pd(OH)$_2$ in THF/MeOH under H$_2$ atmosphere to hydrolyze the benzyl groups on 3-O and 4-O of glucose. Upon complement of acidic hydrolysis and basic methanolysis, 122a/b/c was obtained in 13, 16, 30% yield after HPLC purification

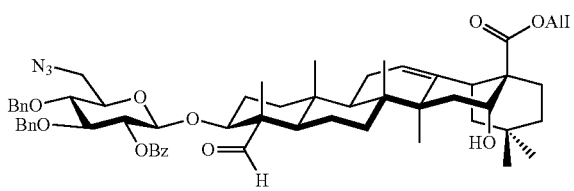

3-O-(6-Azido-2-O-benzoyl-3,4-di-O-benzyl-6-deoxy-β-D-glucopyranosyl)-28-O-Allyl-quillaic ester (117): $^1$H NMR (600 MHz, CDCl$_3$) δ 9.17 (s, 1H, H-23), 8.04-8.01 (m, 2H, Bz), 7.61-7.56 (m, 1H, Bz), 7.48-7.44 (m, 2H, Bz), 7.36-7.24 (m, 5H, Bn), 7.14-7.09 (m, 5H, Bn), 5.88-5.80 (m, 1H, All internal alkenyl CH), 5.33 (t, J=3.5 Hz, 1H, H-12), 5.28 (d, J=17.6 Hz, 1H, All terminal alkenyl CH$_a$), 5.21-15 (m, 2H, H-2', All terminal alkenyl CH$_b$), 4.85 (d, J=11.2 Hz, 1H, Bn CH$_a$), 4.68 (d, J=11.1 Hz, 1H, Bn CH$_b$), 4.62 (d, J=11.1 Hz, 1H, Bn CH$_a$), 4.57 (d, J=11.2 Hz, 1H, Bn CH$_b$), 4.52-4.45 (m, 3H, H-16, allylic CH$_2$), 4.43 (d, J=7.9 Hz 1H, H-1'), 3.80-3.73 (m, 2H, H-3, H-3'), 3.53-3.50 (m, 1H, H-4', H-5'), 3.41-3.38 (m, 1H, H-6$_a$'), 3.32-3.28 (m, 1H, H-6$_b$'), 3.05 (dd, J=14.4, 4.4 Hz, 1H, H-18), 2.13 (t, J=13.4 Hz, 1H, H-19), 1.93-1.82 (m, 4H), 1.80-1.69 (m, 4H), 1.66-1.60 (m, 3H), 1.59 (br. s, 3H), 1.43-1.33 (m, 2H), 1.31 (s, 3H), 1.30-1.26 (m, 1H), 1.21-1.14 (m, 3H), 1.10 (dd, J=12.8, 3.6 Hz, 1H), 1.03-0.99 (m, 1H), 0.97-0.94 (m, 6H), 0.90-0.88 (m, 6H) ppm; HRMS (ESI-TOF) calcd. for C$_{60}$H$_{75}$N$_3$O$_{10}$Na [M+Na]$^+$ 1020.5345, found 1020.5350.

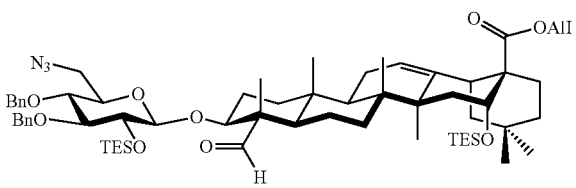

3-O-(6-Azido-3,4-di-O-benzyl-6-deoxy-2-O-triethyl-silyl-β-D-glucopyranosyl)-16-O-triethylsilyl-28-O-Allyl-quillaic ester (118)

$^1$H NMR (400 MHz, CDCl$_3$) δ 9.45 (s, 1H, H-23), 7.61-7.56 (m, 1H, Bz), 7.48-7.44 (m, 2H, Bz), 7.36-7.26 (m, 8H, Bn), 7.18-7.12 (m, 2H, Bn), 5.92-5.80 (m, 1H, All internal alkenyl CH), 5.40-5.26 (m, 2H, H-12, All terminal alkenyl CH$_a$), 5.21 (d, J=10.4 Hz, 1H, All terminal alkenyl CH$_b$), 4.85 (br. s, 2H, Bn CH$_2$), 4.73 (d, J=11.0 Hz, 1H, Bn CH$_b$), 4.59 (br. s, 1H, Bn CH$_a$), 4.55-4.41 (m, 3H, H-16, allylic CH$_2$), 4.14 (d, J=6.2 Hz 1H, H-1'), 3.99 (dd, J=11.1, 4.6 Hz, 1H, H-3), 3.50-3.34 (m, 5H, H-2', H-3', H-4', H-5', H-6$_a$'), 3.32-3.23 (m, 1H, H-6$_b$'), 3.07-2.99 (m, 1H, H-18), 2.23 (t, J=13.3 Hz, 1H, H-19), 1.93-1.80 (m, 5H), 1.78-1.59 (m, 6H), 1.54-1.40 (m, 2H), 1.37 (br. s, 3H), 1.32-1.18 (m, 4H), 1.15 (br. s, 5H), 1.06-0.88 (m, 30H), 0.73-0.59 (m, 15H) ppm; HRMS (ESI-TOF) calcd. for C$_{65}$H$_{100}$N$_3$O$_9$Si$_2$ [M+H]$^+$ 1233.6993, found 1122.7010.

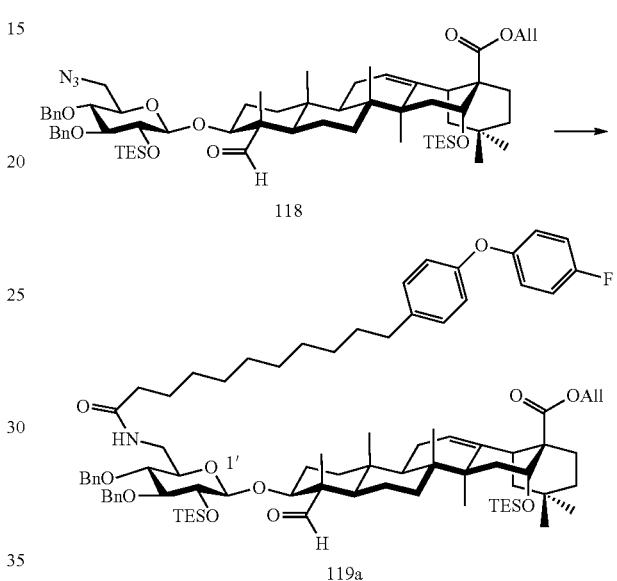

3-O-(3,4-di-O-benzyl-6-deoxy-6-(11-(4-(4-fluoro-phenoxyl)phenyl)undecanamido)-2-O-triethylsilyl-β-D-glucopyranosyl)-16-O-triethylsilyl-28-O-allyl-quillaic ester (119a)

To a stirred solution of 118 (282 mg, 0.25 mmol) in THF (15 mL) was added PPh$_3$ (200 mg, 0.76 mmol). After stirring the mixture for 12 h, 0.5 mL of H$_2$O was added, then removed THF under reduced pressure at 35° C. The resulting residue was diluted by CH$_2$Cl$_2$ then washed by H$_2$O, brine, MgSO$_4$ dried over and then concentrated under pressure. To a stirred solution of the resulting mixture in THF (7 mL), was treated with a premixed suspension of 11-(4-(4-fluorophenoxy)phenyl)undecanoic acid (187 mg, 0.50 mmol), HBTU (286 mg, 0.75 mmol), DIPEA (132 μL, 0.75 mmol) and THF (7 mL). Upon the completion of the reaction after 2 hours of stirring at 30° C., the residue was concentrated under reduced pressure to remove THF. The residue was diluted with CH$_2$Cl$_2$, washed by H$_2$O, brine, dried over MgSO$_4$, and then concentrated under pressure. The residue was purified by column chromatography (silica gel, EtOAc// hexanes=1/8) to afford 119a (349 mg, 96%) as white foam solid: R$_f$ 0.29 (EtOAc/hexanes=1/5); $^1$H NMR (600 MHz, CDCl$_3$) δ 9.45 (s, 1H, H-23), 7.33-7.26 (m, 4H), 7.22-7.17 (m, 2H), 7.10 (d, J=8.5 Hz, 2H), 7.01-6.96 (m, 2H), 6.95-6.91 (m, 2H), 6.86 (d, J=8.5 Hz, 2H), 5.87-5.81 (m, 1H, internal alkenyl CH), 5.32 (t, J=3.7 Hz, 1H, H-12), 5.28 (dq, J=17.0 Hz & 1.2 Hz, 1H, terminal alkenyl CH$_a$), 5.18 (dt, J=10.6 Hz & 1.2 Hz, 1H, terminal alkenyl CH$_b$), 4.83 (q, J=10.5 Hz, 2H, Bn C$\underline{H}_2$), 4.67 (d, J=10.5 Hz, 1H, Bn C$\underline{H}_a$), 4.56 (br. s, 1H, H-16), 4.51 (d, J=10.6 Hz, 1H, Bn C$\underline{H}_b$), 4.45 (dt, J=19.9 Hz & 1.4 Hz, 2H, allylic C$\underline{H}_2$), 4.02 (d, J=6.8 Hz, 1H, H-1'), 3.93 (dd, J=11.2 Hz & 5.2 Hz, 1H, H-3), 3.59 (dt, J=13.9 Hz & 5.9 Hz, 1H, H-6a'), 3.47 (dt, J=13.9 Hz & 5.9 Hz, 1H, H-6$_b$'), 3.43-3.37 (m, 2H, H-2', H-4'), 3.36-3.22 (m, 2H, H-3', H-5'), 3.00 (dd, J=14.3 Hz & 4.0 Hz, 1H, H-18), 2.54 (t, J=6.7 Hz, 2H, C$\underline{H}_2$PhOPhF), 2.32 (t, J=7.6 Hz, 1H, NHC$\underline{H}_a$), 2.20 (m, 1H, H-19$_a$), 2.15 (td, J=13.6 Hz & 3.1 Hz, 1H, H-19$_b$), 1.90-1.85 (m, 2H), 1.84-1.76 (m, 3H), 1.72-1.65 (m, 3H), 1.64-1.53 (m, 9H), 1.48-1.40 (m, 2H), 1.34 (s, 2H), 1.31-1.23 (m, 22H), 1.16 (s, 2H), 1.13-1.08 (m, 2H), 1.06-1.02 (m, 2H), 1.00-0.95 (m, 10H), 0.95-0.92 (m, 4H), 0.92-0.91 (m, 2H), 0.91-0.90 (m, 3H), 0.89-0.88 (m, 2H), 0.87-0.85 (m, 4H), 0.69-0.63 (m, 8H), 0.63-0.57 (m, 6H) ppm; HRMS$^+$ (ESI-TOF) calcd. for C$_{88}$H$_{129}$FNO$_{11}$Si$_2$ [M+Na]$^+$ 1451.9113, found 1451.9095.

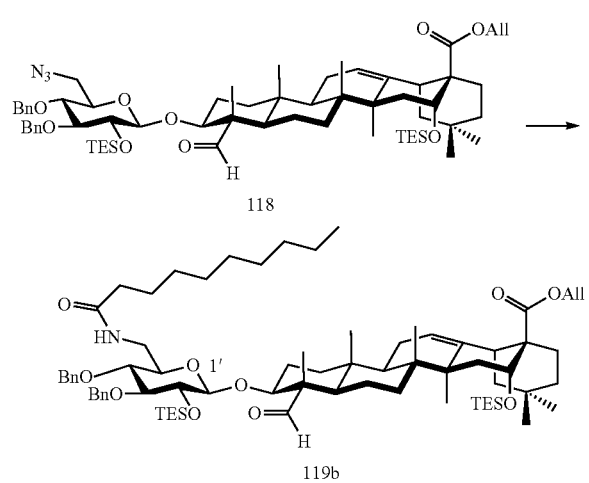

3-O-(3,4-di-O-benzyl-6-decanamido-6-deoxy-2-O-triethylsilyl-β-D-glucopyranosyl)-16-O-triethylsilyl-28-O-allyl-quillaic ester (119b)

Following the procedure of azide reduction and amide formation as described above, 119b was obtained in 56% as white solid: $^1$H NMR (600 MHz, CDCl$_3$) δ 9.40 (s, 1H, H-23), 7.33-7.24 (m, 5H), 7.24-7.15 (m, 5H), 5.87-5.80 (m, 1H, internal alkenyl C$\underline{H}$), 5.31 (t, J=3.4 Hz, 1H, H-12), 5.30-5.25 (m, 2H, terminal alkenyl C$\underline{H}_a$, NHC$\underline{H}_2$), 5.18 (dd, J=10.5 Hz & 1.1 Hz, 1H, terminal alkenyl C$\underline{H}_b$), 4.87-4.80 (m, 2H, Bn C$\underline{H}_2$), 4.65 (d, J=10.4 Hz, 1H, Bn C$\underline{H}_a$), 4.58-4.52 (m, 2H, H-16, Bn C$\underline{H}_b$), 4.46 (qd, J=13.6 Hz & 1.1 Hz, 2H, allylic C$\underline{H}_2$), 4.07 (d, J=6.8 Hz, 1H, H-1'), 3.98-3.91 (m, 1H, H-3), 3.65-3.54 (m, 1H, H-4'), 3.50-3.30 (m, 4H, H-2', H-5', H-6'), 3.29-3.22 (m, 1H, H-3'), 3.00 (dd, J=14.2 Hz & 3.8 Hz, 1H, H-18), 2.31 (t, J=7.4 Hz, 1H, NHC$\underline{H}_a$), 2.20 (t, J=12.8 Hz, 1H, H-19$_a$), 1.90-1.75 (m, 7H), 1.72-1.63 (m, 4H), 1.63-1.58 (m, 3H), 1.45-1.40 (m, 2H), 1.39 (s, 3H), 1.31-1.21 (m, 16H), 1.78-1.15 (m, 1H), 1.12 (s, 3H), 1.06-1.02 (m, 2H), 0.98 (t, J=3.7 Hz, 3H), 0.97 (s, 3H), 0.96 (br. s, 2H), 0.95-0.92 (m, 6H), 0.91 (br. s, 2H), 0.90 (s, 3H), 0.89 (s, 3H), 0.87-0.84 (m, 6H), 0.67-0.62 (m, 9H), 0.62-0.56 (m, 6H) ppm; HRMS$^+$ (ESI-TOF) calcd. for C$_{75}$H$_{120}$NO$_{10}$Si$_2$ [M+H]$^+$ 1251.8475, found 1251.8426.

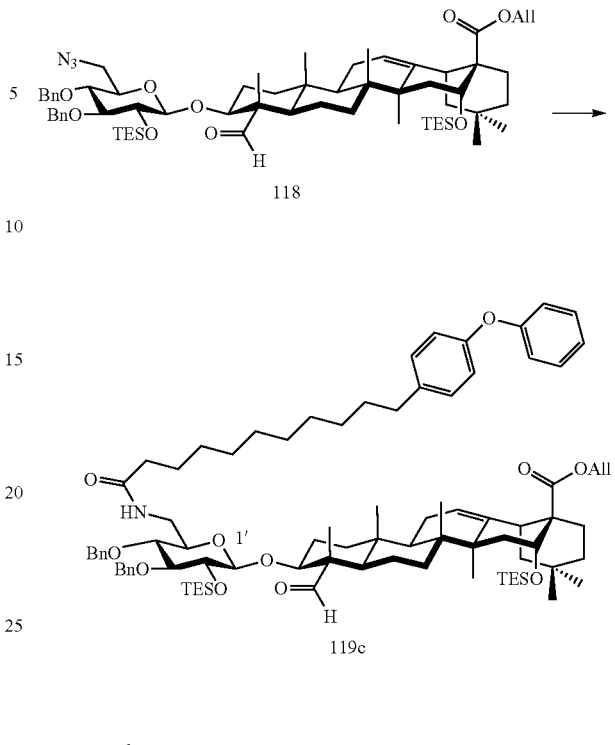

3-O-{2-O-triethylsilyl-3,4-di-O-benzyl-6-[9-(4-phenoxyl-phenyl)nonanamide]-6-deoxy-β-D-glucopyranosyl}-16-O-triethylsilyl-28-O-allyl-quillaic ester (119c)

Following the procedure of azide reduction and amide formation as described above, 119b was obtained in 56% as white solid: $^1$H NMR (400 MHz, CDCl$_3$) δ 9.45 (s, 1H, H-23), 7.31-7.21 (m, 2H), 7.10 (d, J=8.4 Hz, 2H), 7.04 (t, J=7.4 Hz, 2H), 6.96 (dd, J=8.7 Hz & 1.0 Hz, 2H), 6.90 (d, J=8.5 Hz, 2H), 5.89-5.80 (m, 2H, Amide N$\underline{H}$, internal alkenyl C$\underline{H}$), 5.32 (t, J=3.7 Hz, 1H, H-12), 5.28 (d, J=18.2 Hz, 1H, terminal alkenyl C$\underline{H}_a$), 5.17 (dd, J=10.4 Hz & 1.3 Hz, 1H, terminal alkenyl C$\underline{H}_b$), 4.83 (q, J=11.7 Hz, 2H, Bn C$\underline{H}_2$), 4.67 (d, J=10.4 Hz, 1H, Bn C$\underline{H}_a$), 4.57 (br. s, 1H, H-16), 4.51 (d, J=10.4 Hz, 1H, Bn C$\underline{H}_b$), 4.45 (ddt, J=11.4 Hz & 5.6 Hz & 1.1 Hz, 2H, allylic C$\underline{H}_2$), 4.02 (d, J=6.8 Hz, 1H, H-1'), 3.94 (dd, J=10.2 Hz & 5.8 Hz, 1H, H-3), 3.63-3.56 (m, 1H), 3.51-3.39 (m, 3H), 3.32-3.21 (m, 2H), 3.00 (dd, J=14.2 Hz & 3.9 Hz, 1H, H-18), 2.55 (t, J=7.5 Hz, 2H, C$\underline{H}_2$PhOPh), 2.33-2.13 (m, 3H, H-19$_a$, NHCOC$\underline{H}_2$), 1.91-1.83 (m, 3H), 1.83-1.76 (m, 3H), 1.75-1.52 (m, 11H), 1.49-1.40 (m, 2H), 1.34 (s, 3H), 1.29 (br. s, 11H), 1.23 (s, 3H), 1.15 (s, 3H), 1.14-1.00 (m, 4H), 0.98-0.86 (m, 31H), 0.69-0.57 (m, 16H); BBD $^{13}$C NMR (100 MHz, CDCl$_3$) δ 207.5 (C-23), 176.4 (C-28), 173.1 (NHC$\underline{C}$O), 157.7, 154.8, 143.5 (C-13), 138.5, 137.8, 137.5, 132.2, 129.6 129.4, 128.4, 128.2, 128.1, 127.9, 127.2, 126.8, 122.7, 121.7 (C-12), 118.9, 118.4, 117.8 (All terminal alkenyl C$\underline{H}_2$), 101.0 (C-1'), 85.5 (C-3), 79.3, 79.0, 75.2 (Bn C$\underline{H}_2$), 75.0, 75.0 (Bn C$\underline{H}_2$), 74.9 (C-16), 73.1, 65.0 (C-6'), 54.5, 48.9, 48.8, 46.6, 46.3, 41.3, 40.4, 40.0, 39.5, 38.1, 36.7, 36.0, 35.2, 35.1, 34.5, 33.8, 32.7, 32.3, 31.5×2, 30.5, 29.6, 29.3×2, 29.2, 29.1, 29.0, 26.3, 25.7, 24.7, 24.6, 24.2, 23.2, 20.1, 16.9, 15.5, 10.4, 7.1, 6.9, 5.0, 4.9 ppm; HRMS$^+$ (ESI-TOF) calcd. for C$_{86}$H$_{125}$NO$_{11}$Si$_2$ [M+H]$^+$ 140.8894, found 1405.8984.

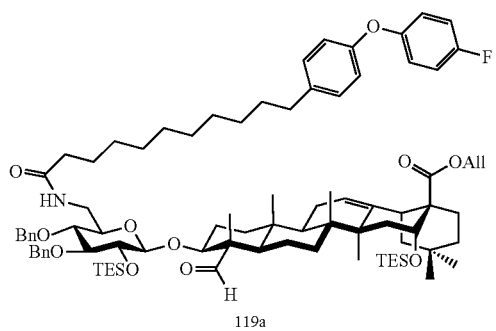

119a

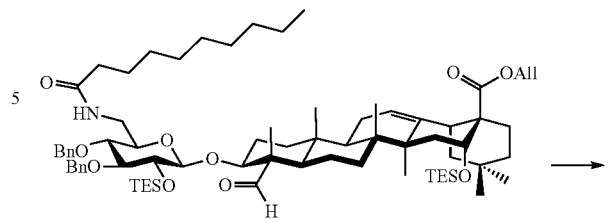

119b

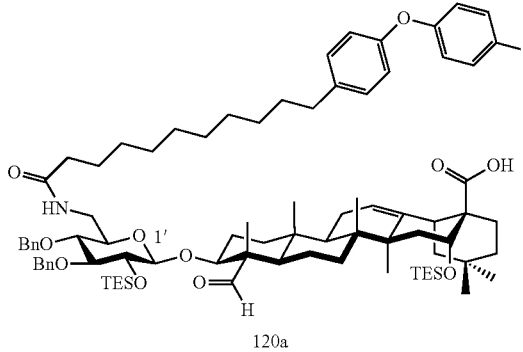

120a

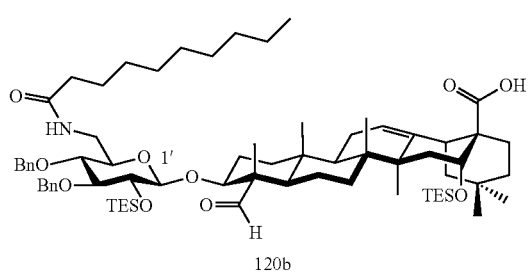

120b

3-O-(3,4-di-O-benzyl-6-deoxy-6-(11-(4-(4-fluorophenoxyl)phenyl)undecanamido)-2-O-triethylsilyl-β-D-glucopyranosyl)-16-O-triethylsilyl-quillaic acid (120a)

To a stirred solution of 119a (237 mg, 0.16 mmol) and PPh$_3$ (107 mg, 0.41 mmol) in 1,4-dioxane (4 mL) was added pre-mixed formic acid (129 µL, 3.4 mmol)/Et$_3$N (456 µL, 3.2 mmol) in 1,4-dioxane (2 mL) and Pd(OAc)$_2$ (18 mg, 0.08 mmol) in 1,4-dioxane (2 mL) at rt. The reaction mixture was stirred for 12 h, and then concentrated under reduced pressure. The residue was purified by column chromatography (silica gel, EtOAc/hexanes=1/4 to 1/2) to afford 120a (186 mg, 81%) as white solid: R$_f$ 0.36 (EtOAc/hexanes=1/2); $^1$H NMR (600 MHz, CDCl$_3$) δ 9.41 (s, 1H, H-23), 7.27-7.26 (m, 1H), 7.25 (br. s, 1H), 7.34-7.25 (m, 6H), 7.06 (d, J=8.4 Hz, 1H), 6.98-6.64 (m, 6H), 6.82 (d, J=8.4 Hz, 1H), 5.82 (t, J=5.2 Hz, Amide NH), 5.30 (br. s, 1H, H-12), 4.83-4.76 (m, 2H, Bn CH$_2$), 4.63 (d, J=10.3 Hz, 1H, Bn CH$_a$), 4.50-4.53 (m, 2H, H-16, Bn CH$_b$), 3.98 (d, J=6.6 Hz, 1H, H-1'), 3.90 (dd, J=11.2 Hz & 4.9 Hz, 1H, H-3), 3.60-3.53 (m, 1H, H-6$_a$'), 3.48-3.41 (m, 1H, H-6$_b$'), 3.41-3.34 (m, 2H, H-2', H-4'), 3.27-3.19 (m, 2H, H-3', H-5'), 2.90 (dd, J=14.1 Hz & 3.6 Hz, 1H, H-18), 2.50 (t, J=7.6 Hz, 2H, CH$_2$PhOPhF), 2.31 (t, J=7.4 Hz, 1H, NHCH$_a$), 2.19-2.09 (m, 3H), 1.87-1.68 (m, 7H), 1.68-1.59 (m, 3H), 1.59-1.49 (m, 4H), 1.44-1.36 (m, 2H), 1.30 (s, 3H, H-27), 1.28-1.16 (m, 17H), 1.11 (s, 3H, H-29), 1.09-1.08 (m, 1H), 1.03-0.97 (m, 2H), 0.94 (s, 2H), 0.93 (s, 3H), 0.92 (s, 3H), 0.89-0.87 (m, 5H), 0.87 (s, 3H), 0.85 (s, 2H), 0.82 (s, 3H), 0.66-0.53 (m, 17H) ppm; HRMS$^+$ (ESI-TOF) calcd. for C$_{85}$H$_{125}$FNO$_{11}$Si$_2$ [M+H]$^+$ 1411.8800, found 1411.8742.

3-O-(2-O-triethylsilyl-3,4-di-O-benzyl-6-decanamido-6-deoxy-β-D-glucopyranosyl)-16-O-triethylsilyl-28-O-allyl-quillaic acid (120b)

To a stirred solution of 119b (200 mg, 0.16 mmol) and PPh$_3$ (107 mg, 0.41 mmol) in 1,4-dioxane (4 mL) was added pre-mixed formic acid (129 µL, 3.4 mmol)/Et$_3$N (456 µL, 3.2 mmol) in 1,4-dioxane (2 mL) and Pd(OAc)$_2$ (18 mg, 0.08 mmol) in 1,4-dioxane (2 mL) at rt. The reaction mixture was stirred for 12 h, and then concentrated under reduced pressure. The residue was purified by column chromatography (silica gel, EtOAc/hexanes=1/4 to 1/2) to afford 120b (154 mg, 80%) as white solid: R$_f$ 0.36 (EtOAc/hexanes=1/2); $^1$H NMR (600 MHz, CDCl$_3$) δ 9.45 (s, 1H, H-23), 7.32-7.24 (m, 6H), 7.24-7.19 (m, 4H), 5.85 (t, J=5.0 Hz, Amide NH), 5.30 (t, J=3.7 Hz 1H, H-12), 4.86-4.80 (m, 2H, Bn CH$_2$), 4.66 (d, J=10.4 Hz, 1H, Bn CH$_a$), 4.54-4.49 (m, 2H, H-16, Bn CH$_b$), 4.03 (d, J=6.8 Hz, 1H, H-1'), 3.94 (dd, J=11.2 Hz & 4.9 Hz, 1H, H-3), 3.59-3.55 (m, 1H), 3.52-3.46 (m, 1H), 3.44-3.38 (m, 2H), 3.31-3.24 (m, 2H), 2.94 (dd, J=14.2 Hz & 4.0 Hz, 1H, H-18), 2.31 (t, J=7.5 Hz, 1H, NHCH$_a$), 2.19-2.09 (m, 3H), 1.87-1.68 (m, 7H), 1.68-1.59 (m, 3H), 1.59-1.49 (m, 4H), 1.44-1.36 (m, 2H), 1.30 (s, 3H, H-27), 1.28-1.16 (m, 17H), 1.11 (s, 3H), 1.09-1.08 (m, 1H), 1.03-0.97 (m, 2H), 0.94 (s, 2H), 0.93 (s, 3H), 0.92 (s, 3H), 0.89-0.87 (m, 5H), 0.87 (s, 3H), 0.85 (s, 2H), 0.82 (s, 3H), 0.66-0.53 (m, 17H); BBD $^{13}$C NMR (150 MHz, CDCl$_3$) δ 207.4 (C-23), 182.7 (C-28), 173.3 (NHCO), 143.3 (C-13), 138.6, 137.6, 128.4, 128.2, 126.9, 121.8 (C-12), 101.1 (C-1'), 85.5, 79.5, 79.2 (C-3), 75.2 (Bn CH$_2$), 75.0 (Bn CH$_2$), 74.9, 74.8 (C-16), 73.2, 54.5, 49.0, 48.6, 46.6, 46.3, 41.3, 40.1 (C-6'), 39.5 (C-8), 38.2, 36.8 (—NHCOCH$_2$—), 36.1, 35.1, 34.6, 34.0, 32.6, 32.7, 31.8, 31.6, 30.5, 29.5, 29.4, 29.3, 29.2, 29.0, 26.4, 25.8, 24.7, 24.2, 23.2, 22.7, 20.1, 16.9, 15.5, 14.1, 10.4, 7.1, 7.0, 5.1, 5.0 ppm ppm; HRMS$^+$ (ESI-TOF) calcd. for C$_{72}$H$_{116}$NO$_{10}$Si$_2$ [M+H]$^+$ 1210.8132, found 1210.8108.

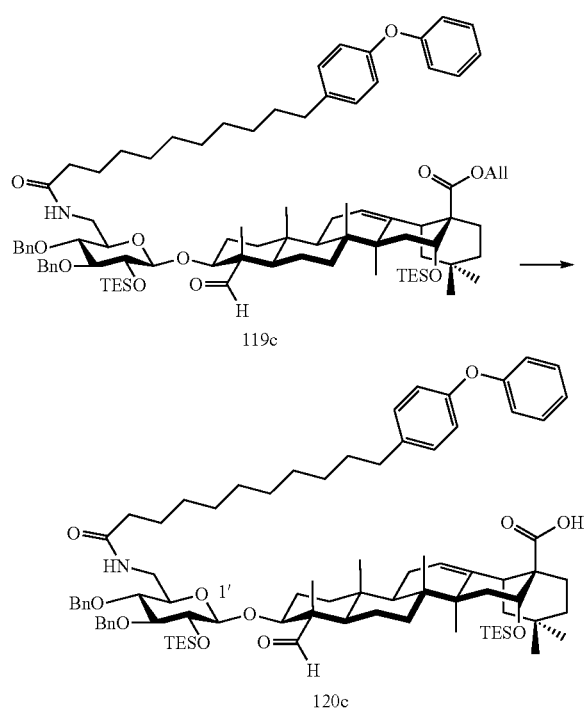

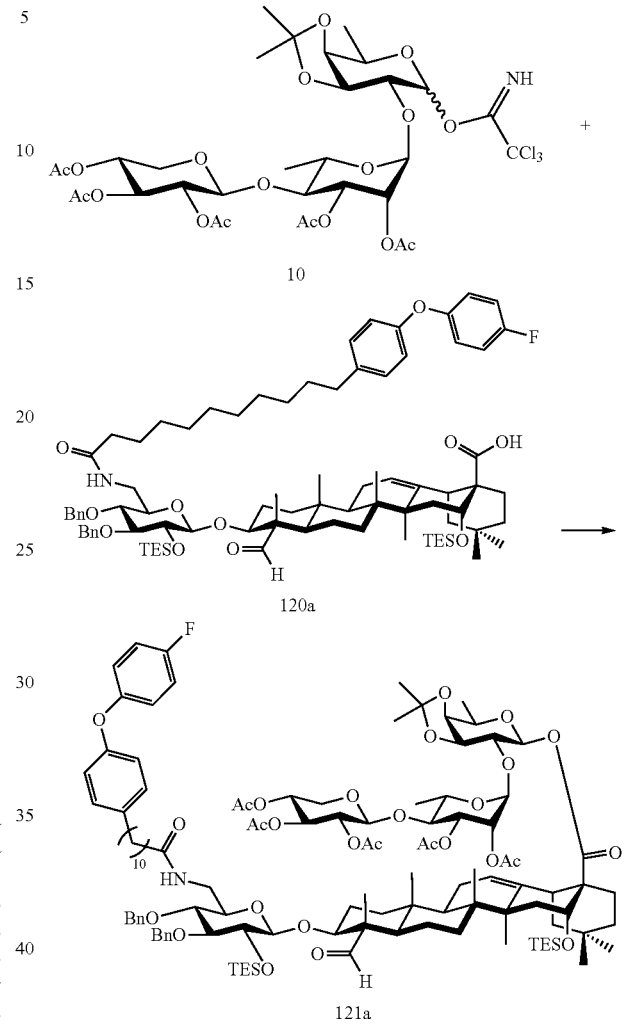

3-O-{2-O-triethylsilyl-3,4-di-O-benzyl-6-[9-(4-phenoxyl-phenyl)nonanamide]-6-deoxy-β-D-glucopyranosyl}-16-O-triethylsilyl-28 quillaic acid (120c)

To a stirred solution of 119c (224 mg, 0.16 mmol) and PPh$_3$ (107 mg, 0.41 mmol) in 1,4-dioxane (4 mL) was added pre-mixed formic acid (129 µL, 3.4 mmol)/Et$_3$N (456 µL, 3.2 mmol) in 1,4-dioxane (2 mL) and Pd(OAc)$_2$ (18 mg, 0.08 mmol) in 1,4-dioxane (2 mL) at rt. The reaction mixture was stirred for 12 h, and then concentrated under reduced pressure. The residue was purified by column chromatography (silica gel, EtOAc/hexanes=1/4 to 1/2) to afford 120c (154 mg, 80%) as white solid: R$_f$ 0.36 (EtOAc/hexanes=1/2) $^1$H NMR (400 MHz, CDCl$_3$) δ 9.45 (s, 1H, H-23), 7.31-7.21 (m, 2H), 7.10 (d, J=8.4 Hz, 2H), 7.04 (t, J=7.4 Hz, 2H), 6.96 (dd, J=8.7 Hz & 1.0 Hz, 2H), 6.90 (d, J=8.5 Hz, 2H), 5.89-5.80 (m, 2H, Amide N$\underline{H}$, internal alkenyl C$\underline{H}$), 5.32 (t, J=3.7 Hz, 1H, H-12), 4.83 (q, J=11.7 Hz, 2H, Bn C$\underline{H}_2$), 4.67 (d, J=10.4 Hz, 1H, Bn C$\underline{H}_a$), 4.57 (br. s, 1H, H-16), 4.51 (d, J=10.4 Hz, 1H, Bn C$\underline{H}_b$), 4.02 (d, J=6.8 Hz, 1H, H-1'), 3.94 (dd, J=10.2 Hz & 5.8 Hz, 1H, H-3), 3.63-3.56 (m, 1H), 3.51-3.39 (m, 3H), 3.32-3.21 (m, 2H), 3.00 (dd, J=14.2 Hz & 3.9 Hz, 1H, H-18), 2.55 (t, J=7.5 Hz, 2H, C$\underline{H}_2$PhOPh), 2.33-2.13 (m, 3H, H-19$_a$, NHCOC$\underline{H}_2$), 1.91-1.83 (m, 3H), 1.83-1.76 (m, 3H), 1.75-1.52 (m, 11H), 1.49-1.40 (m, 2H), 1.34 (s, 3H), 1.29 (br. s, 11H), 1.23 (s, 3H), 1.15 (s, 3H), 1.14-1.00 (m, 4H), 0.98-0.86 (m, 31H), 0.69-0.57 (m, 16H); BBD $^{13}$C NMR (100 MHz, CDCl$_3$) δ 207.5 (C-23), 182.0 (C-28), 173.2 (NH$\underline{C}$O), 157.7, 154.8, 143.5 (C-13), 138.5, 137.5, 132.2, 129.6, 129.4, 128.4, 128.2, 128.1, 127.9, 127.2, 126.8, 122.7, 121.7 (C-12), 118.9, 118.4, 101.0 (C-1'), 85.5 (C-3), 79.3, 79.0, 75.2 (Bn $\underline{C}$H$_2$), 75.0, 75.0 (Bn $\underline{C}$H$_2$), 74.9 (C-16), 73.1, 65.0 (C-6'), 54.5, 48.9, 48.8, 46.6, 46.3, 41.3, 40.4, 40.0, 39.5, 38.1, 36.7, 36.0, 35.2, 35.1, 34.5, 33.8, 32.7, 32.3, 31.5×2, 30.5, 29.6, 29.3×2, 29.2, 29.1, 29.0, 26.3, 25.7, 24.7, 24.6, 24.2, 23.2, 20.1, 16.9, 15.5, 10.4, 7.1, 6.9, 5.0, 4.9 ppm;

HRMS$^+$ (ESI-TOF) calcd. for C$_{83}$H$_{122}$NO$_{11}$Si$_2$ [M+H]$^+$ 1364.8551, found 1364.8567.

3-O-(3,4-di-O-benzyl-6-deoxy-6-(11-(4-(4-fluorophenoxyl)phenyl)undecanamido)-2-O-triethylsilyl-β-D-glucopyranosyl)-28-O-(2,3,4-tri-O-acetyl-β-D-xylopyranosyl-(1→4)-2,3-di-O-acetyl-α-L-rhamnopyranosyl-(1→2)-3,4-O-isopropylidene-β-D-fucopyranosyl)-16-O-triethylsilylquillaic ester (121a)

To a stirred suspension of 10 (40 mg, 48 µmol), 120a (50 mg, 35 µmol) and activated 4 Å molecular sieve powder in anhydrous CH$_2$Cl$_2$ (0.5 mL) was added BF$_3$·OEt$_2$ (ca. 48%, 4 µL, 24 mol) at −75° C. under N$_2$. Upon completion of the reaction after 0.5 h, the reaction was quenched by Et$_3$N, and warmed to room temperature. The resulting mixture was diluted with CH$_2$Cl$_2$ and filtered through 5 µm filter paper. The resulting filtrate was concentrated under reduced pressure. The residue was purified by column chromatography (silica gel; EtOAc/hexanes=1/5 to 1/2) to give 121a (37 mg, 50%) as white solid foams. R$_f$ 0.56 (EtOAc/hexanes=1/1); $^1$H NMR (600 MHz, CDCl$_3$) δ 9.49 (s, 1H, H-23), 7.33-7.26 (m, 6H), 7.26-7.21 (m, 4H), 7.12 (d, J=8.4 Hz, 1H), 7.02-7.00 (m, 2H), 6.96-6.93 (m, 2H), 6.88 (d, J=8.6 Hz, 1H), 6.82 (d, J=8.4 Hz, 1H), 5.86 (t, J=5.1 Hz, Amide N$\underline{H}$), 5.41 (d, J=7.6 Hz, 1H, H-1″), 5.33 (t, J=3.4 Hz, 1H, H-1̄2), 5.25 (dd, J=3.4 Hz & 1.3 Hz, 1H, H-2‴), 5.20 (dd, J=9.8 Hz & 3.5 Hz, 1H, H-3‴), 5.13 (t, J=9.4 Hz, 1H, H-3″″), 4.98 (d, J=1.3 Hz, 1H, H-1‴), 4.97-4.94 (m, 1H, H-4″″), 4.88-4.82 (m, 3H, H-2″″, Bn C$\underline{H}_2$), 5.68 (d, J=10.4 Hz, 1H, Bn C$\underline{H}_a$), 4.63 (d, J=7.7 Hz, 1H, H-1″″), 4.53 (d, J=10.4 Hz, 1H, Bn C$\underline{H}_b$), 4.50 (br. s, 1H, H-16), 4.17 (t, J=6.0 Hz, 1H, H-3″), 4.12-4.10 (m, 1H, H-5″″), 4.04-4.00 (m, 2H, H-1′, H-4″), 3.98-3.94 (m, 1H, H-3), 3.89-3.84 (m, 1H, H-5″), 3.84-3.79 (m, 1H, H-5‴), 3.68-3.64 (m, 1H, H-2″), 3.64-3.59 (m, 2H, H-6$_a$′, H-4′), 3.49 (dt, J=13.9 Hz, & 3.8 Hz, 1H H-6$_b$′), 3.45-3.39 (m, 2H, H-2′, H-4′), 3.36-3.24 (m, 3H, H-3′, H-5′, H-5$_b$″″), 2.93 (dd, J=14.2 Hz & 3.8 Hz, 1H, H-18), 2.56 (t, J=7.6 Hz, 2H, C$\underline{H}_2$PhOPhF), 2.22 (in, 1H, H-19$_a$), 2.17 (td, J=7.5 Hz & 3.4 Hz, 2H, —NHCOC$\underline{H}_2$—), 2.13 (s, 3H), 2.06 (s, 3H), 2.03 (s, 3H), 2.01 (s, 3H), 1.98 (s, 3H), 1.90-1.86 (m, 2H), 1.86-1.82 (m, 1H), 1.83-1.76 (m, 3H), 1.74-1.67 (m, 4H), 1.67-1.56 (m, 5H), 1.52 (s, 3H, isopropylidne C$\underline{H}_3$), 1.52-1.49 (m, 1H), 1.34 (s, 3H, H-27), 1.33 (s, 3H, isopropylidene C$\underline{H}_3$), 1.30-1.25 (m, 24H), 1.23-1.32 (m, 1H), 1.19 (s, 3H, H-24), 1.13-1.10 (m, 1H), 1.05-1.03 (m, 1H), 1.03-1.01 (m, 1H), 1.01-0.96 (m, 15H, H-25, TES C$\underline{H}_3$×4), 0.92 (s, H, H-30), 0.91 (s, 3H, TES C$\underline{H}_3$), 0.90 (s, 3H, TES C$\underline{H}_3$), 0.88 (s, 3H, H-29), 0.74 (s, 3H, H-26), 0.68-0.58 (m, 12H, TES C$\underline{H}_2$×6) ppm; HRMS$^+$ (ESI-TOF) calcd. for $C_{115}H_{167}FNO_{28}Si_2$ [M+H]$^+$ 2086.1223, found 2086.1222.

3-O-(3,4-di-O-benzyl-6-decanamido-6-deoxy-β-D-glucopyranosyl}-28-O-(2,3,4-tri-O-acetyl-β-D-xylopyranosyl-(1→4)-2,3-di-O-acetyl-α-L-rhamnopyranosyl-(1→2)-3,4-O-isopropylidene-β-D-fucopyranosyl)-16-O-triethylsilylquillaic ester (121b)

To a stirred suspension of 10 (40 mg, 48 μmol), 120b (42 mg, 35 μmol) and activated 4 Å molecular sieve powder in anhydrous $CH_2Cl_2$ (0.5 mL) was added $BF_3 \cdot OEt_2$ (ca. 48%, 4 μL, 24 mol) at −75° C. under $N_2$. Upon completion of the reaction after 0.5 h, the reaction was quenched by $Et_3N$, and warmed to room temperature. The resulting mixture was diluted with $CH_2Cl_2$ and filtered through 5 m filter paper. The resulting filtrate was concentrated under reduced pressure. The residue was purified by column chromatography (silica gel; EtOAc/hexanes=1/5 to 1/2) to give 121b (37 mg, 50%) as white solid foams. $R_f$ 0.56 (EtOAc/hexanes=1/1); to give 121b α/β mixtures as white solid foams.

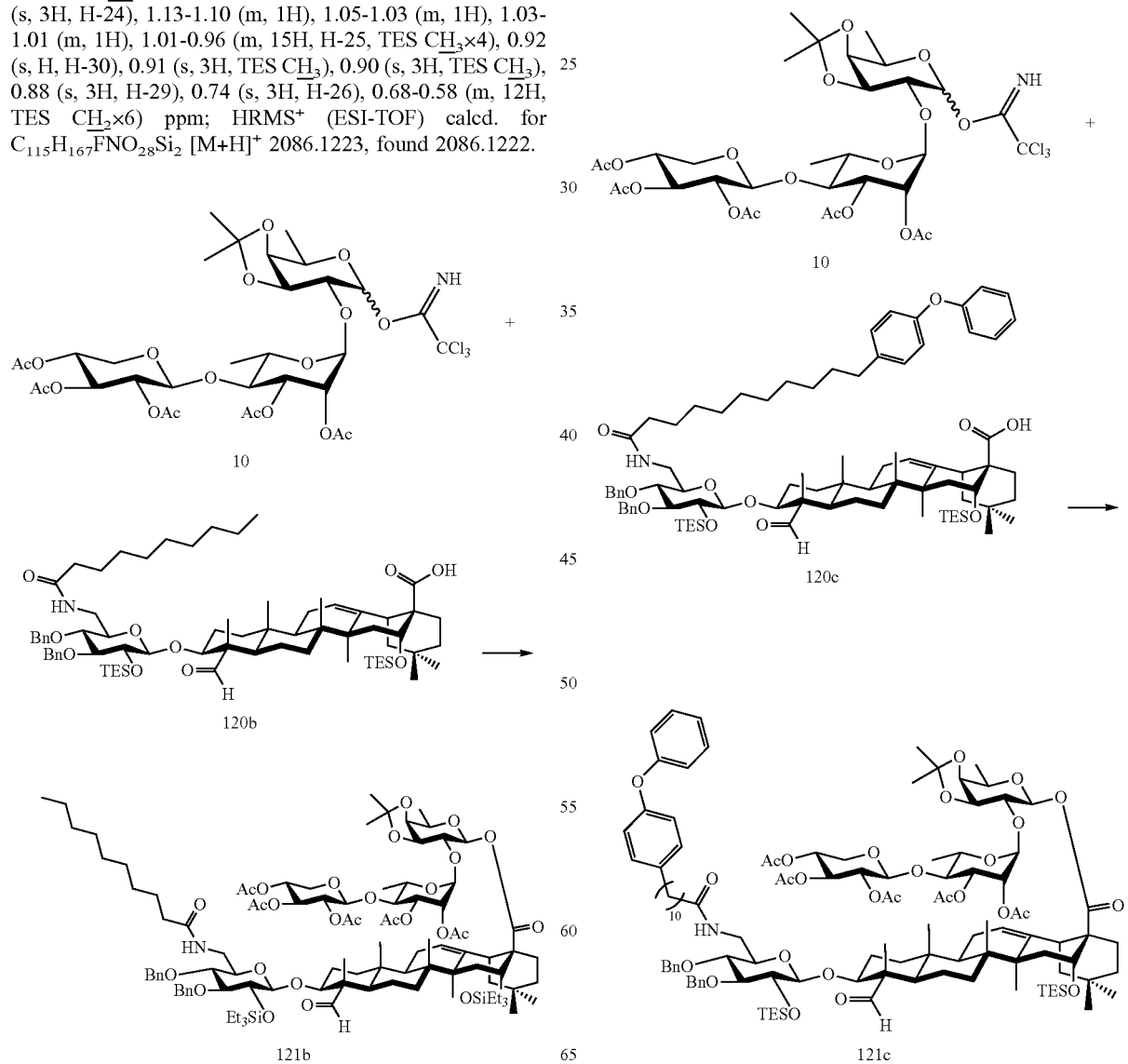

3-O-(2-O-triethylsilyl-3,4-di-O-benzyl-6-[9-(4-phenoxyl-phenyl)nonanamide}-28-O-(2,3,4-tri-O-acetyl-β-D-xylopyranosyl-(1→4)-2,3-di-O-acetyl-α-L-rhamnopyranosyl-(1→2)-3,4-O-isopropylidene-β-D-fucopyranosyl)-16-O-triethylsilylquillaic ester (121c)

To a stirred suspension of 10 (40 mg, 48 gmol), 120c (42 mg, 35 gmol) and activated 4 Å molecular sieve powder in anhydrous $CH_2Cl_2$ (0.5 mL) was added $BF_3$—$OEt_2$ (ca. 48%, 4 μL, 24 gmol) at −75° C. under $N_2$. Upon completion of the reaction after 0.5 h, the reaction was quenched by $Et_3N$, and warmed to room temperature. The resulting mixture was diluted with $CH_2Cl_2$ and filtered through 5 μm filter paper. The resulting filtrate was concentrated under reduced pressure. The residue was purified by column chromatography (silica gel; EtOAc/hexanes=1/5 to 1/2) to give 121c (37 mg, 50%) as white solid foams. $R_f$ 0.56 (EtOAc/hexanes=1/1); to give 121c a/s mixtures as white solid foams.

3-O-(6-deoxy-6-(11-(4-(4-fluorophenoxyl)phenyl)undecanamido)-β-D-glucopyranosyl)-28-O-(β-D-xylopyranosyl-(1→4)-α-L-rhamnopyranosyl-(1→2)-β-D-fucopyranosyl) quillaic ester (122a)

To a suspension of 121a (32 mg, 15 μmol) and 10% Pd(OH)$_2$/C (5 mg, 4 μmol) in THF/MeOH=4/1 (1.5 mL) was stirred at rt under 1 atm $H_2$ atmosphere. The reaction mixture was stirred for 12 h. To a stirred solution of crude tetrasaccharide saponin in $CH_2Cl_2$ (0.5 mL) was added pre-cooled TFA/$H_2O$=4/1 (0.5 mL) at 0° C., and stirred for 30 min. The solvent was evaporated under reduced pressure (<1 torr) at 0° C., and then dried under high vacuum at rt for 1 h. To a stirred solution of the residue in MeOH (1 mL) was added $K_2CO_3$ (40 mg, 300 μmol) and stirred for 12 h. The suspension was filtered, concentrated then purified by HPLC to afford product 122a (3.6 mg) in 16% as a white solid (HPLC column: SUPELCO Ascentis C18 25 cm×10 mm, 5 μm; mobile phase: 20% ACN/$H_2O$ gradient to 90% ACN/$H_2O$ in 25 min, and then 90% ACN/$H_2O$ isocratic for 15 min; flow rate: 5 mL/min): $^1H$ NMR (600 MHz, $CD_3OD$) δ 9.41 (s, 1H, H-23), 7.16 (d, J=8.4 Hz, 2H), 7.07 (t, J=8.8 Hz, 2H), 6.98-6.95 (m, 4H), 6.87 (d, J=8.6 Hz, 2H), 5.40 (d, J=1.4 Hz, 1H, H-1'''), 5.31 (br. s, 1H, H-12), 5.29 (d, J=8.2 Hz, 1H, H-1''), 4.50-4.47 (m, 2H, H-16, H-1''''), 4.14 (d, J=7.7 Hz, 1H, H-1'), 3.91-3.89 (m, 1H, H-2'''), 3.86-3.78 (m, 5H, H-3, H-2'', H-3''', H-5''', H-5$_a$''''), 3.68-3.64 (m, 2H, H-3'', H-5''), 3.60-3.56 (m, 1H, H-6$_a$'), 3.56-3.53 (m, 2H, H-4'', H-4'''), 3.49-3.42 (m, 2H, H-5', H-4''''), 3.29-3.25 (m, 3H, H-3', H-6$_b$', H-3''''), 3.23-3.16 (m, 2H, H-2'''', H-5$_b$''''), 3.09-3.05 (m, 2H, H-2', H-4'), 2.45 (dd, J=13.4 Hz & 3.2 Hz, H-18), 2.60 (t, J=7.6 Hz, 2H, C$\underline{H}_2$PhOPhF), 2.30 (m, 1H, H-19$_a$), 2.21 (t, J=7.6 Hz, 2H, —NHCOC$\underline{H}_2$—), 1.99-1.95 (m, 1H), 1.95-1.91 (m, 1H), 1.80-1.71 (m, 4H), 1.70-1.65 (m, 1H), 1.64-1.59 (m, 4H), 1.55-1.50 (m, 2H) 1.49-1.44 (m, 1H), 1.40 (s, 3H, H-27), 1.36-1.29 (m, 19H, H-6''', carbon chain C$\underline{H}_2$×8), 1.20 (d, J=6.5 Hz, 3H, H-6''), 1.12 (s, 3H, H-24), 1.10-1.06 (m, 1H), 1.01 (s, 3H, 25), 0.99-0.96 (m, 1H), 0.93 (s, 3H, H-30), 0.92-0.89 (m, 1H), 0.87 (s, 3H, H-29), 0.77 (s, 3H, H-26); BBD $^{13}C$ NMR (150 MHz, $CD_3OD$) δ 209.3 (C-23), 177.1 (C-28), 176.7 (Amide NHC̲O), 160 (d, J=240 Hz), 156.8, 155.1, 144.9 (C-13), 139.2, 130.8, 123.1 (C-12), 121.2 (d, J=8 Hz), 119.5, 117.2 (d, J=23 Hz), 107.0, (C-1''''), 105.0 (C-1'), 101.1 (C-1'''), 95.2 (C-1''), 84.0 (C-4''''), 83.4 (C-3), 78.2 (C-3''''), 77.6 (C-3'), 76.7 (C-3''), 76.1 (C-2'''), 75.6 (C-2'), 75.2 (C-5'), 74.6 (C-16), 74.0 (C-2''), 73.6 (C-4''), 73.3 (C-4'), 72.7 (C-5''), 72.2 (C-3'''), 71.9 (C-2'''), 71.1 (C-4''''), 68.7 (C-5'''), 67.3 (C-5''''), 56.1 (C-5), 50.0 (C-17), 48.1 (C-19, C-9), 42.8 (C-14), 42.4 (C-18), 41.9 (C-6'), 41.1 (C-8), 39.6 (C-1), 37.3 (C-1), 36.8 (—NHCOC̲H$_2$—), 37.1 (C-10), 36.5 (C-21), 36.2 (—C̲H$_2$PhOPhF), 33.6 (C-16), 3.4 (C-29), 32.9 (C-6), 32.0 (C-22), 31.4 (C-20), 30.8, 30.7, 30.6, 30.4, 27.3 (C-2), 20.2 (C-27), 26.0, 25.9 (C-2), 24.9 (C-30), 24.6 (C-11), 21.6, (C-7), 18.3 (C-6'''), 17.7 (C-26), 16.5 (C-6''), 16.4 (C-25), 10.6 (C-24) ppm; HRMS$^+$ (ESI-TOF) calcd. for $C_{76}H_{112}FNO_{23}Si_2Na[M+H]^+$ 1448.7501, found 1448.7558.

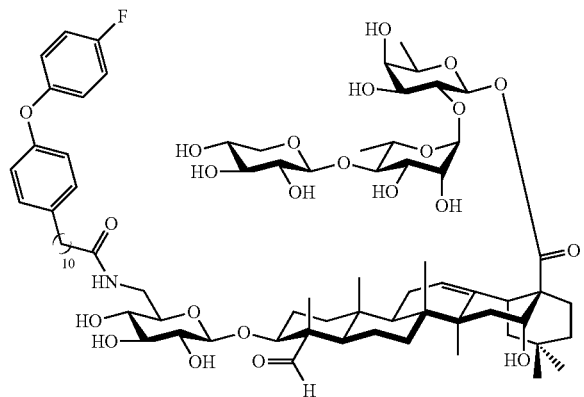

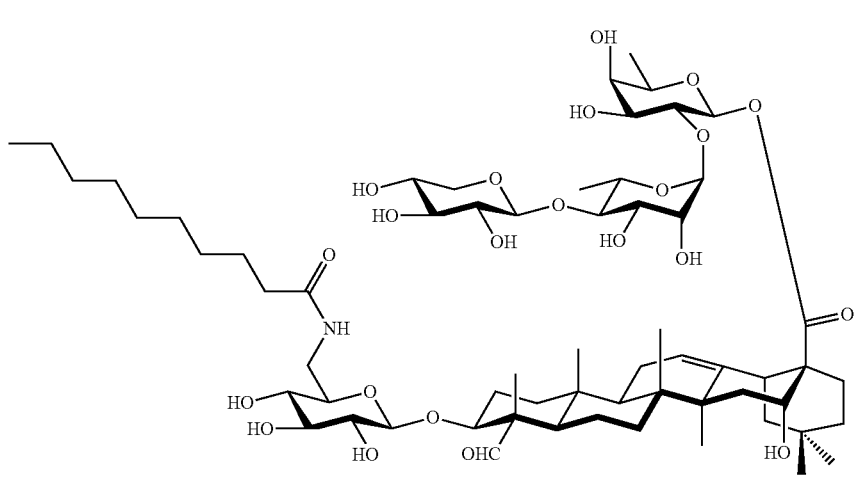

3-O-{6-decanamido-6-deoxy-β-D-glucopyranosyl}-28-O-[β-D-xylopyranosyl-(1→4)-α-L-rhamnopyranosyl-(1→2)-β-D-fucopyranosyl] quillaic ester. (122b)

To a suspension of 121b (28 mg, 15 μmol) and 10% Pd(OH)$_2$/C (5 mg, 4 gmol) in THF/MeOH=4/1 (1.5 mL) was stirred at rt under 1 atm H$_2$ atmosphere. The reaction mixture was stirred for 12 h. To a stirred solution of crude tetrasaccharide saponin in CH$_2$Cl$_2$ (0.5 mL) was added pre-cooled TFA/H$_2$O=4/1 (0.5 mL) at 0° C., and stirred for 30 min. The solvent was evaporated under reduced pressure (<1 torr) at 0° C., and then dried under high vacuum at rt for 1 h. To a stirred solution of the residue in MeOH (1 mL) was added K$_2$CO$_3$ (40 mg, 300 μmol) and stirred for 12 h. The suspension was filtered, concentrated then purified by HPLC to afford product 122b (2.3 mg) in 13% as a white solid (HPLC column: SUPELCO Ascentis C18 25 cm×10 mm, 5 μm; mobile phase: 20% ACN/H$_2$O gradient to 90% ACN/H$_2$O in 25 min, and then 90% ACN/H$_2$O isocratic for 15 min; flow rate: 5 mL/min): 1H NMR (600 MHz, CD$_3$OD) δ 9.42 (s, 1H, H-23), 5.40 (s, 1H, H-1'''), 5.31 (br. s, 1H, H-12), 5.29 (d, J=8.2 Hz, 1H, H-1''), 4.51-4.46 (m, 2H, H-16, H-1''''), 4.15 (d, J=7.7 Hz, 1H, H-1'), 3.93-3.90 (m, 1H), 3.87-3.78 (m, 5H), 3.71-3.66 (m, 2H), 3.60-3.53 (m, 3H), 3.49-3.41 (m, 2H), 3.29-3.25 (m, 3H), 3.24-3.17 (m, 2H), 3.09-3.04 (m, 2H), 2.95 (d, J=14.1 Hz, 1H, H-18), 2.30 (m, 1H, H-19$_a$), 2.21 (t, J=7.6 Hz, 2H, —NHCOC$\underline{H_2}$—), 2.04-1.88 (m, 3H), 1.69-1.60 (m, 3H), 1.55-1.44 (m, $\overline{4H}$), 1.40 (s, 3H, H-27), 1.35-1.29 (m, 18H), 1.20 (d, J=6.5 Hz, 3H, H-6''), 1.12 (s, 3H), 1.10-1.06 (m, 1H), 1.01 (s, 3H), 0.99-0.96 (m, 1H), 0.95 (s, 3H), 0.93-0.89 (m, 3H), 0.88 (s, 3H), 0.77 (s, 3H); BBD 13C NMR (150 MHz, CD3OD) δ 209.4 (C-23), 177.2 (C-28), 176.7 (Amide NHCO), 144.9 (C-13), 123.1 (C-12), 106.9, (C-1''''), 105.0 (C-1'), 101.1 (C-1'''), 95.2 (C-1''), 84.0 (C-4'''), 83.3 (C-3), 78.1 (C-3''''), 77.6, 76.6, 76.1, 75.6, 75, 74.6 (C-16), 74.0, 73.6, 73.3, 72.7, 72.2, 71.9, 71.0, 68.7, 67.3, 56.1, 50.0, 48.1, 42.8, 42.3 (C-18), 41.8 (C-6'), 41.1, 39.6, 37.3, 37.1, 36.8 (—NHCOCH2-), 36.5, 36.4, 33.6, 33.4, 33.1, 32.0, 31.3, 30.8, 30.7, 30.6, 30.5, 27.3, 27.2, 26.0, 24.8, 24.5, 23.8, 21.6, 18.3 (C-6'''), 17.7, 16.5 (C-6''), 16.3, 14.6 (carbon chain terminal —CH3), 10.6 ppm; HRMS+ (ESI-TOF) calcd. for C63H104NO22 [M+H]+ 1226.7059, found 1226.7059.

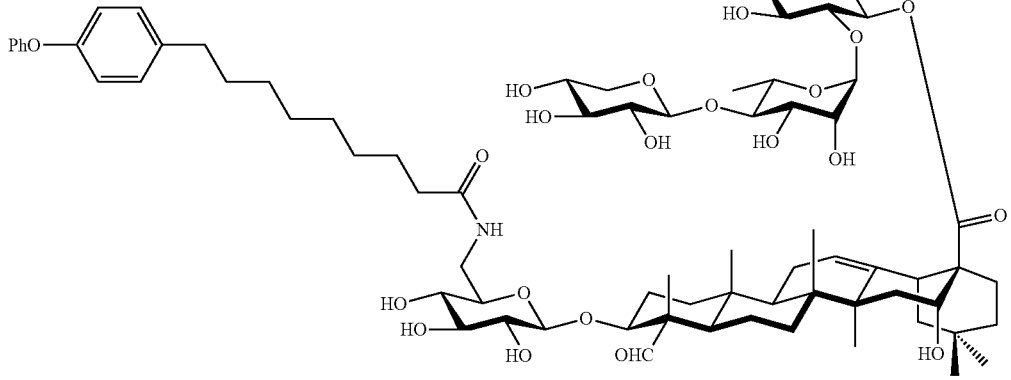

3-O-{[9-(4-phenoxyl-phenyl)nonanamido]-6-deoxy-β-D-glucopyranosyl}-28-O—[β-D-xylopyranosyl-(1→4)-α-L-rhamnoyranosyl-(1→2)-β-D-fucopyranosyl]quillaic ester. (122c)

To a suspension of 121c (20 mg, 15 μmol) and 10% Pd(OH)$_2$/C (5 mg, 4 mol) in THF/MeOH=4/1 (1.5 mL) was stirred at rt under 1 atm H$_2$ atmosphere. The reaction mixture was stirred for 12 h. To a stirred solution of crude tetrasaccharide saponin in CH$_2$Cl$_2$ (0.5 mL) was added pre-cooled TFA/H2O=4/1 (0.5 mL) at 0° C., and stirred for 30 min. The solvent was evaporated under reduced pressure (<1 torr) at 0° C., and then dried under high vacuum at rt for 1 h. To a stirred solution of the residue in MeOH (1 mL) was added K$_2$CO$_3$ (40 mg, 300 μmol) and stirred for 12 h. The suspension was filtered, concentrated then purified by HPLC to afford product 122c (6.2 mg) in 30% as a white solid (HPLC column: SUPELCO Ascentis C18 25 cm×10 mm, 5 μm; mobile phase: 20% ACN/H$_2$O gradient to 90% ACN/H$_2$O in 25 min, and then 90% ACN/H$_2$O isocratic for 15 min; flow rate: 5 mL/min): 1H NMR (600 MHz, CD$_3$OD) δ 9.41 (s, 1H, H-23), 7.32 (t, J=8.2 Hz, 2H), 7.17 (d, J=8.4 Hz, 2H), 7.06 (t, J=7.5 Hz, 1H), 6.94 (d, J=8.2 Hz, 2H), 6.90 (d, J=8.2 Hz, 2H), 5.40 (br.s, 1H, H-1''''), 5.31 (br. s, 1H, H-12), 5.28 (d, J=8.2 Hz, 1H, H-1''), 4.50-4.46 (m, 2H, H-16, H-1'''), 4.15 (d, J=7.8 Hz, 1H, H-1'), 3.92-3.90 (m, 1H, H-2'''), 3.87-3.79 (m, 5H), 3.67-3.64 (m, 2H), 3.60-3.56 (m, 1H, H-6$_a$'), 3.56-3.53 (m, 2H), 3.49-3.42 (m, 1H, H-4''''), 3.36-3.33 (m, 1H), 3.30-3.16 (m, 5H), 3.09-3.05 (m, 2H), 2.97-2.92 (m, 1H, H-18), 2.61 (t, J=7.8 Hz, 2H, CH$_2$PhOPh), 2.30 (m, 1H, H-19$_d$), 2.21 (t, J=7.7 Hz, 2H, —NHCOCH$_2$—), 1.98-1.88 (m, 5H), 1.80-1.69 (m, 4H), 1.67-1.59 (m, 4H), 1.55-1.43 (m, 3H), 1.40 (s, 3H, H-27), 1.39-1.33 (m, 10H), 1.31 (d, J=6.2 Hz, 3H, H-6'''), 1.29 (s, 1H), 1.20 (d, J=6.4 Hz, 3H, H-6''), 1.13 (s, 3H), 1.10-1.03 (m, 2H), 1.00 (s, 3H), 0.98-0.94 (m, 1H), 0.92 (s, 3H), 0.85 (s, 3H), 0.77 (s, 3H); BBD $^{13}$C NMR (150 MHz, CD$_3$OD) δ 209.4 (C-23), 177.2 (C-28), 176.7 (Amide NHCO), 159.3, 156.5, 155.1, 144.9 (C-13), 139.2, 130.8, 124.0, 123.1 (C-12), 120.0, 119.4, 107.0, (C-1''''), 104.9 (C-1'), 101.1 (C-1'''), 95.2 (C-1''), 84.2, 83.3 (C-3), 78.2, 77.7 (C-3'), 76.6, 76.2, 75.6, 75.3, 74.6 (C-16), 74.0, 73.6, 73.3, 72.7, 72.3, 71.9, 71.1, 68.8, 67.2, 56.1, 50.1, 48.1, 42.8, 42.4 (C-18), 41.9 (C-6'), 41.2, 39.6, 37.1, 37.3, 36.5 (—NHCOCH$_2$—), 36.5, 36.2 (—CH$_2$PhOPh), 33.6, 33.4, 32.8, 31.9, 31.3, 30.7, 30.5, 30.3, 27.3, 27.2, 26.0, 25.0, 24.6, 21.6, 18.3 (C-6''''), 17.8, 16.5 (C-6''), 16.4, 10.6 ppm; HRMS$^+$ (ESI-TOF) calcd. for C$_{74}$H$_{110}$NO$_{23}$ [M+H]$^+$ 1380.7463, found 1380.7476.

Experimental Example I—Immunological Evaluation of Saponins

Material and Method

Adjuvant Stock

Dissolve sample powder in DMSO to 20 mg/mL. Before administration, dilute stock with 0.5% (w/w) Tween-20 to 0.5 mg/mL and filtered through PTFE (0.1 m). Reconstitute PEK lyophilized cake (1 mg/mL PEK and 0.5 mg/mL adjuvant) or OVA (100 mg) and placebo is PBS.

Animal and Vaccinations

C57BL/6 mice were obtained from NLAC Taiwan. Mice between 4 and 8 weeks of age were vaccinated with 100 μL via the subcutaneous (SC) route and one dose per week for three weeks. Mice was sacrificed one week after the third vaccination, serum and splenocytes were harvested.

Splenocytes Sample Prepare and Flow Cytometry Analysis

Spleen tissue was isolated from mice and processed into single cell suspensions using PP micro centrifuge sample pestle. Splenocytes were seeding on 6 well plate at 2×10$^7$/2 mL, stimulate with or without HPV16E7-peptide and cultivation for 2 h in a CO$_2$ incubator. After 2 h, treated cell with protein transport inhibitor Monensin (Invitrogen, Cat. no. 00-4505-51) and Brefeldin (Invitrogen, Cat. no. 00-4506-51) for 4 hours at 37° C. Afterward, cells were harvested then washed twice with PBS and then stained for surface CD3 (BioLegend, Cat. no. 100290), CD4 (Invitrogen, Cat. no. 56-0041-82), CD8 (Invitrogen, Cat. no. 12-0081-82) for 30 minutes at 4° C. After washing, cells were fixed for 30 minutes at room temperature using IC fixation buffer (Invitrogen, Cat. no. 00-8222-49), then cells were washed in permeabilization buffer (Invitrogen, Cat. no. 00-8333-56) and stained with IFNγ antibody (Invitrogen, Cat. no. 53-7311-82). Twenty million cells events were acquired on the Backman Coulter Gallions. Flow data were analyzed using Kaluza software (ver. 1.2). Populations were first gated on CD3$^+$ T cells, then gated on viable mononuclear cell using forward and side scatter. Subsequently, sub-gated on either CD4$^+$/IFNγ$^+$ double-positive cells or CD8$^+$/IFNγ$^+$ double-positive cells.

ELISpot

MabTech Mouse IFNγ ELISpot PLUS kit (3321-4HPW-2) and IL2 ELISpot PLUS kit (3441-4HPW-2) were used for evaluation of IFNγ and IL2 production. Cells were pre-plated overnight with capture antibody, as per the manufacturer's instructions. Splenocytes were isolated from vaccinated animals and subjected to red blood cell lysis. Cells were then resuspended at 2×10$^6$/mL and 100 μL of cells was combined with 100 μL of stimulation master mix. Master mixes included 10 μg/mL HPV16E7-pET32a, 2 μg/ml HPV16E7-peptide. Cells were incubated in ELISPOT plates for 24 h at 37° C., and the ELISpot assay was conducted as per the manufacturer's instructions. Plates were analyzed using the AID vSpot Spectrum. Values were calculated by averaging triplicate wells.

ELISA

PEK was plated in a 96 well plate (1 μg/well, Nunc Maxisorb) in 100 mM carbonate buffer overnight at 4° C. Plates were blocked with blocking buffer (5% Milk in PBS) for at least 1 h at 37° C., and then were washed with PBS+0.05% Tween 20. Serial 2-fold dilutions of serum samples were added to plates. After 1 h, plates were washed with PBS+0.05% Tween 20 and secondary antibody was added. Both peroxide labelled goat Anti-Mouse IgG1 (Southernbiotech, Cat. no. 1070-05) and goat anti-mouse IgG2b (Southernbiotech, Cat. no. 1090-05) diluted 1:4000 in 1% Milk-PBS were added separately for 1 h. The plates were washed with PBS+0.05% Tween 20 and were developed with TMB Chromogen Solution (Invitrogen, Cat. no. 00-2023) for 15 min, followed with stop solution (0.2 N H$_2$SO$_4$). The absorbance at 405 nm was recorded.recorded.

Splenocyte Sample Prepare and Flow Cytometric Analysis (Memory T Cell)

Spleen tissue was isolated from mice and processed into single cell suspensions using PP micro centrifuge sample pestle. Splenocytes were seeding on 6 well plate at 2×10$^7$/2 mL, cultivation for 2 h in a CO$_2$ incubator. After 2 h, stimulate with or without E7-peptide for 2 hours at 37° C., then treat cell with protein transport inhibitor Monensin (Invitrogen, Cat. no. 00-4505-51) and Brefeldin (Invitrogen, Cat. no. 00-4506-51) for 4 hours at 37° C. Afterward, cells were harvest then washed twice with PBS and then stained for surface CD3 (BioLegend, Cat. no. 100222), CD4 (BioLegend, Cat. no. 100540), CD8 (Invitrogen, Cat. no.

11-0081-86), CD44 (BioLegend, Cat. no. 103008), CD62L (BioLegend, Cat. no. 104412) for 30 minutes at 4° C. After washing, cells were fixed for 30 minutes at room temperature using IC fixation buffer (Invitrogen, Cat. no. 00-8222-49), then cells were washed in permeabilization buffer (Invitrogen, Cat. no. 00-8333-56) and stained with IFNγ antibody (Invitrogen, Cat. no. 48-7311-82), IL-2 antibody (Invitrogen, Cat. no. 25-7021-82) and TNFα antibody (Invitrogen, Cat. no. 48-7321-82). One point five million cells events were acquired on the Backman Coulter Gallions. Flow data were analyzed using Kaluza software (ver. 1.2). Populations were first gated on viable mononuclear cell using forward and side scatter, then gated on $CD3^+/CD4^+$ or $CD3^+/CD8^+$ T cells. Next, sub-gated $CD62L^-/CD44^+$ memory T cells. Subsequently, sub-gated on either $CD4^+/IFN\gamma^+$, $CD8^+/IFN\gamma^+$, $CD4^+/IL-2^+$, $CD8^+/IL-2^+$, $CD4/TNF\alpha^+$ and $CD8^+/TNF\alpha^+$ double-positive cells.

Results

A mouse-vaccination model was applied with an antigen PE-E7-K3 (PEK), a fusion protein consists of *pseudomonas* exotoxin, human papillomavirus protein E7 (HPV16 E7) and $KDEL_3$ peptide sequence. These were used to evaluate the adjuvants effect. Five mice per group were immunized three times at three weeks intervals with 50 µg of saponins and PEK (100 µg). The ability of our saponins and GPI-0100, as a positive control, to modulate the immunological response was then analyzed by flow cytometry, ELISpot and ELISA.

Specific T-Cell Activation

One weeks after the third dose, splenocytes from mice were harvested, and the effect of these saponins adjuvants with PEK antigen on the production of cytokines (IFNγ and IL-2) were measured by ELISpot (FIG. 1). Saponins adjuvants 56, 63, 79 greatly enhanced the secretion of cytokines IFNγ which was three to four times more than GPI0100, and also moderate in inducing IL-2 (FIG. 1).

T-Cell Activation

Antigen-specific T-cell activation was analyzed by flow cytometry. One weeks after the third dose, splenocytes from mice were harvested and twenty million cells events were acquired on the Backman Coulter Gallions. Populations were first gated on $CD3^+$ T cells, then gated on viable mononuclear cell using forward and side scatter. Subsequently, sub-gated on either $CD4^+/IFN\gamma^+$ (or TNFα) double-positive cells or $CD8^+/IFN\gamma^+$ (or TNFα) double-positive cells.

Figure 2:
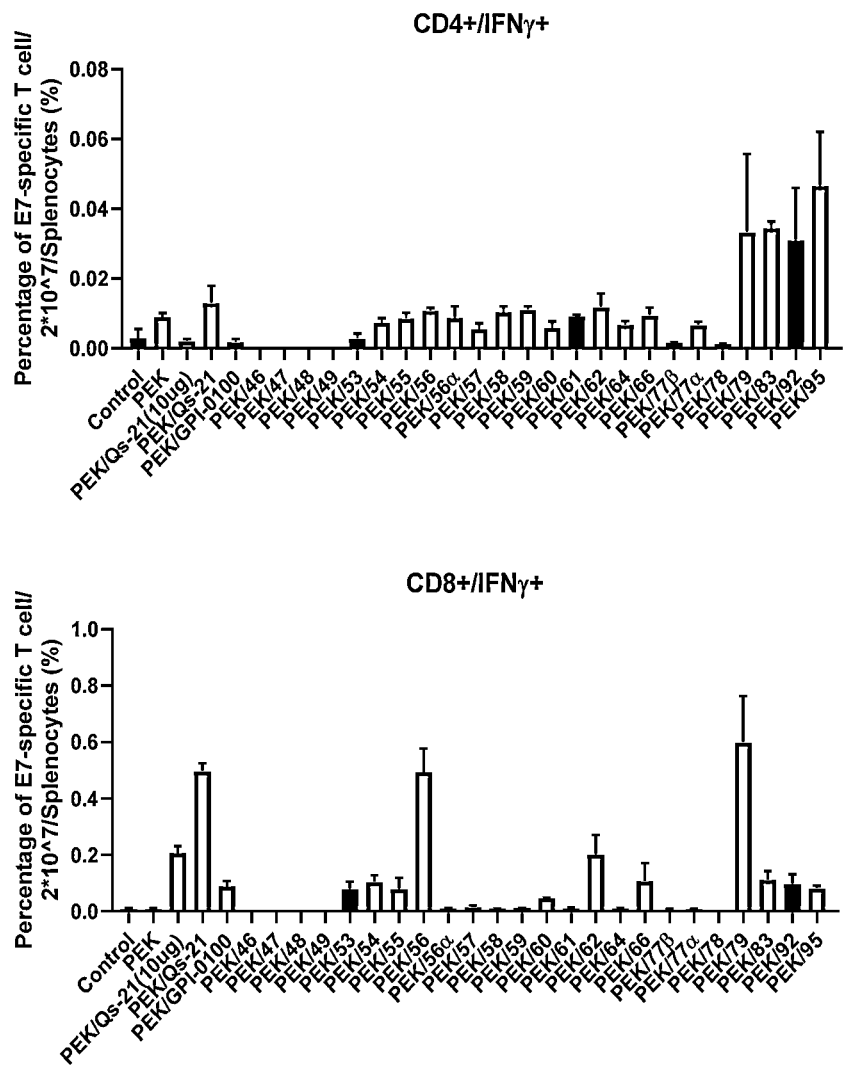
FIG. 2 Demonstrates a flow cytometric analysis of splenic IFNγ$^+$ (x-axis) CD4$^+$ or CD8$^+$ (y-axis) within the total CD3$^+$ T-cell population at 1 week post-third dose of saponins inventive herein.
Figure 3:
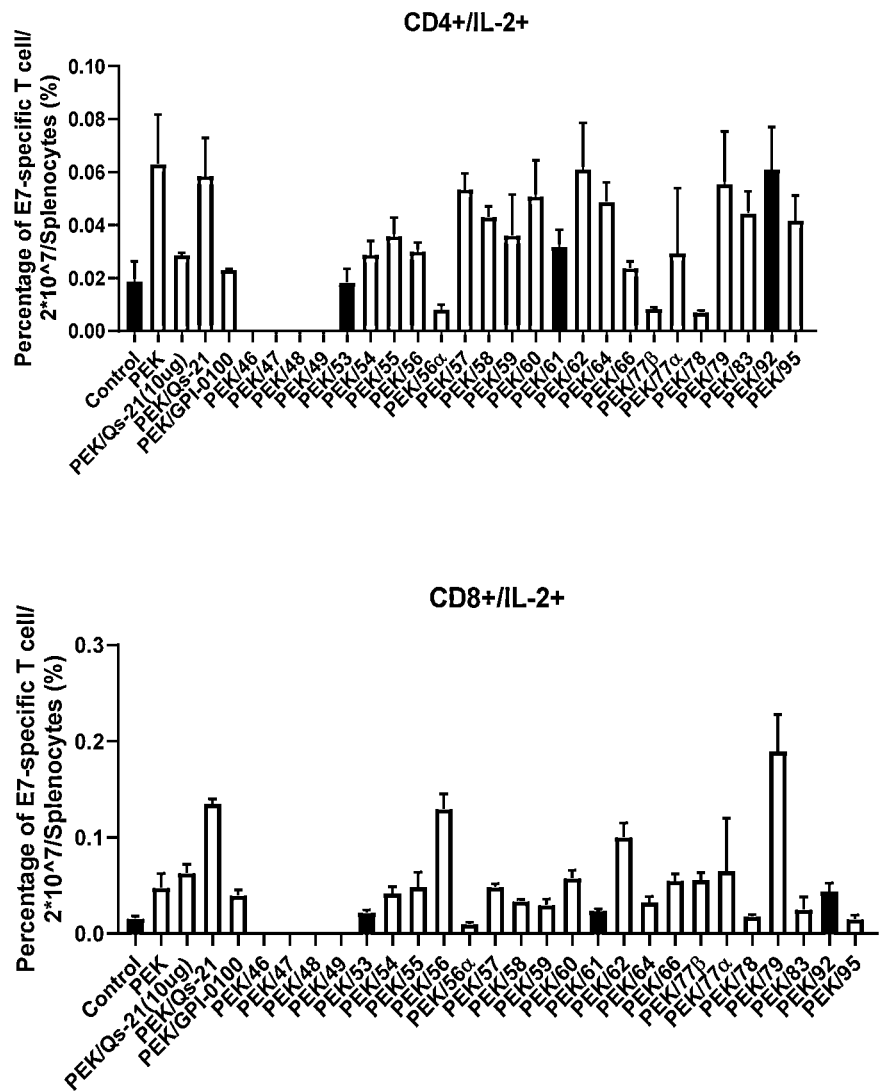
FIG. 3 Demonstrates a flow cytometric analysis of splenic IL-2$^+$ (x-axis) CD4$^+$ or CD8$^+$ (y-axis) within the total CD3$^+$ T-cell population at 1 week post-third dose of saponins inventive herein.
Figure 4:
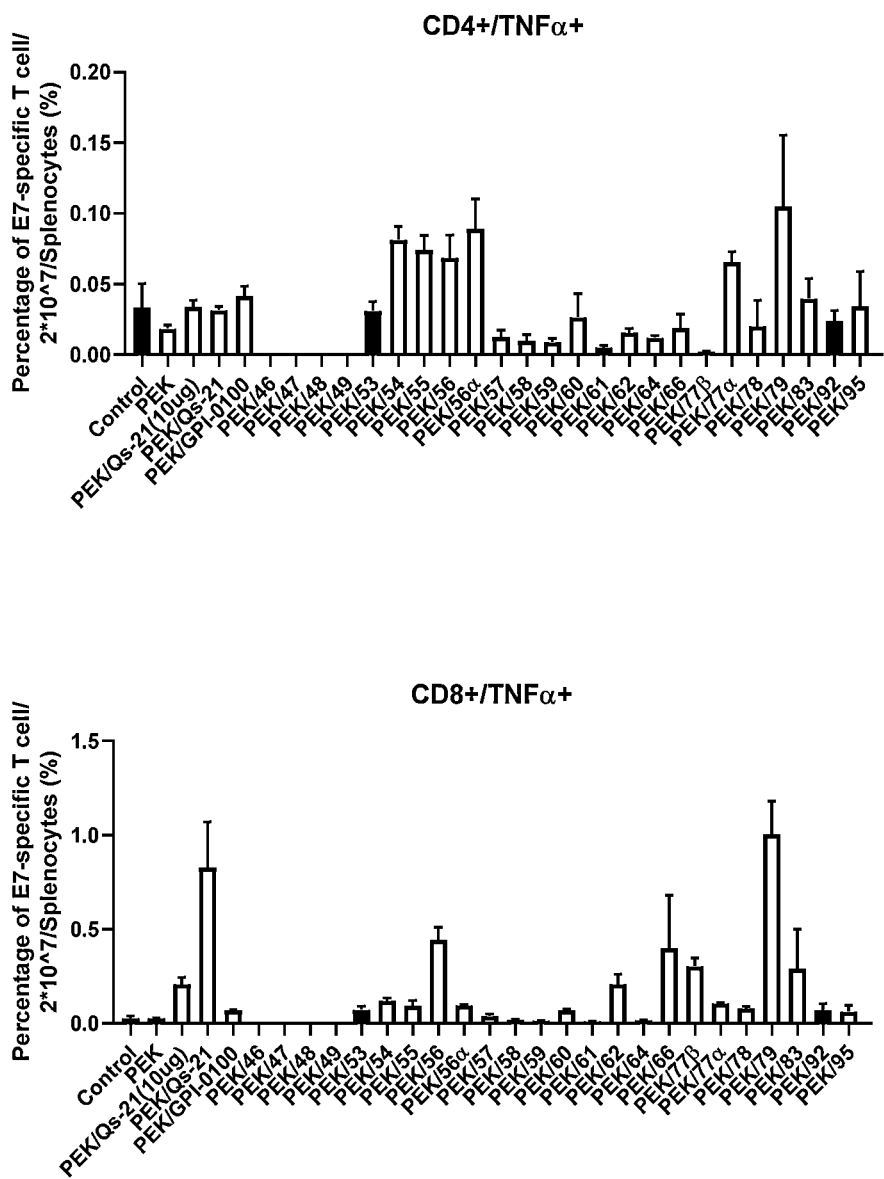
FIG. 4 Demonstrates a flow cytometric analysis of splenic TNFα$^+$ (x-axis) CD4$^+$ or CD8$^+$ (y-axis) within the total CD3$^+$ T-cell population at 1 week post-third dose of saponins inventive herein.

Based on the flow cytometry results (FIG. 2-4), the aliphatic chain modified saponins 志威 derived weaker activation of PEK specific $CD4^+$ and $CD8^+$ T-cell compare to GPI-0100. Terminal aryl-substituted saponins 56, 62, 79 induced 4- to 8-fold increases of PEK-specific IFN-γ secreting $CD8^+$ and TNF-α secreting $CD8^+$ T-cell proliferation than GPI-0100. However, the induction of $CD4^+$ T-cell by saponins were not significant. These results suggested that these saponins of this invention predominately mediated the $CD8^+$ T-cell immunity.

Memory T-Cell Stimulation

Figure 5:
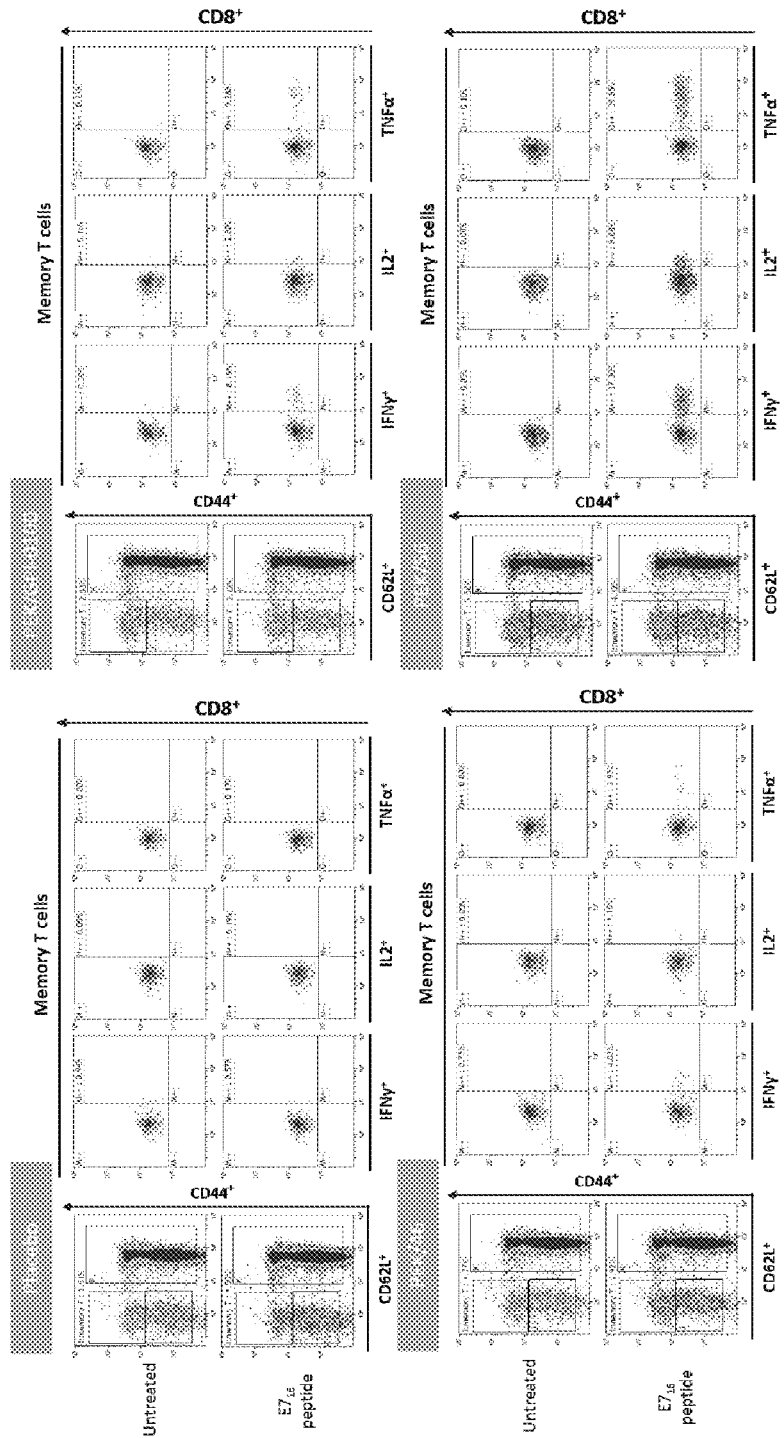
FIG. 5 demonstrates a flow cytometric analysis of T-cell population, representative scatter plots of splenic CD62L$^+$ (x-axis) CD44$^+$ (y-axis) within the total T-cell population after 1 week post-third dose of sponins inventive herein. CD62L low and CD44 high population were classified as memory T cells and the frequencies of viable CD8$^+$ splenocytes expressing IFN-γ, TNF-α, or IL-2 are shown. Cytokines positivity was determined when the frequency of positive events exceeded mean±S.E.M. of control group.
Figure 6:
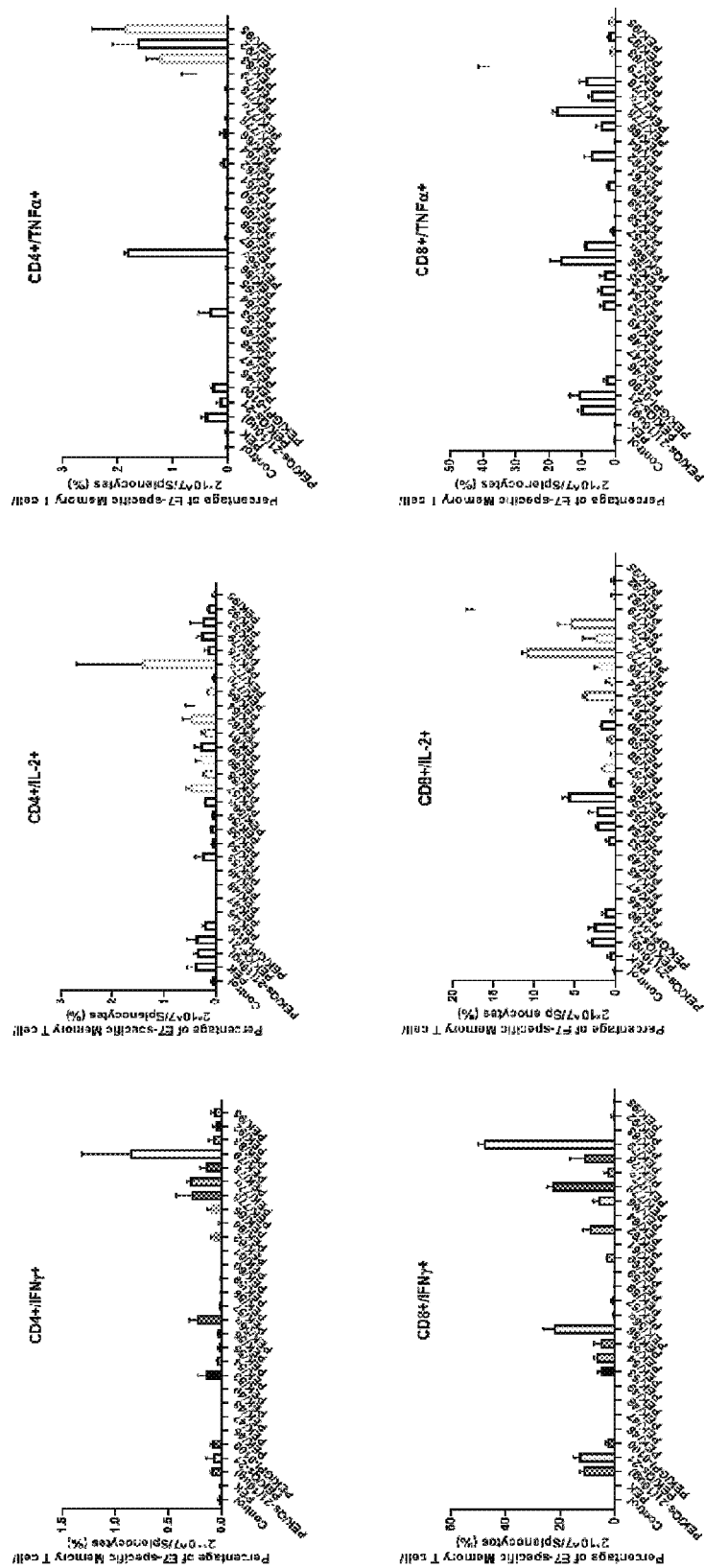
FIG. 6 demonstrates T-cell activation after 1 week post-third dose of sponins 46-49, 53-56, 56α, 57-62, 64, 66, 77α, 77β 78, 79, 83, 92, 95 where mean of spot forming PEK-specific IFNγ$^+$ or IL-2 or TNFα cells in quadruplicate wells from pooled splenocytes. Cytokines positivity was determined when the frequency of positive events exceeded mean±S.E.M. of control group FIG. 7 demonstrated the E7-specific IgG antibody. Sera were collected after each immunization of C57BL/6 mice immunized with PEK/saponins, and E7 protein-specific IgG antibodies in the sera were measured by an ELISA. OD$_{450}$ values of each sera being dilute 10000 times were recorded. The values are presented as means±S.E.M. (n=3).

Naive and activated T cells are known to express different adhesion molecules which are considered to exhibit different migratory patterns that result from their expression of discrete adhesion molecules. Two adhesion molecules associated with differentiating naive and activated/memory T cells are CD62L (L-selectin) and CD44 (H-CAM). It has been demonstrated that naive T cells express a high CD62L and low CD44 phenotype, whereas memory T cells exhibit a low CD62L and high CD44 phenotype. Flow-cytometric analysis (individual mice) of T-cells as frequency of viable $CD8^+$ or $CD4^+$ splenocytes expressing IFN-γ, TNF-α, or IL-2. Cytokine positivity was determined. Flow-cytometric analysis confirmed that the saponins 56, 62, 79 showed a higher frequency of $CD8^+$ T-cells that were positive for IFN-γ or TNF-α as compared to mice vaccinated with GPI-0100 (FIG. 5 and FIG. 6). Remarkably, no cytokine positive $CD4^+$ T-cells were detected. These results indicated that 56, 62, 79 can provide a long-lasting cellular immunity protection against the E7 antigen.

Antibody Production Assay

Figure 7:
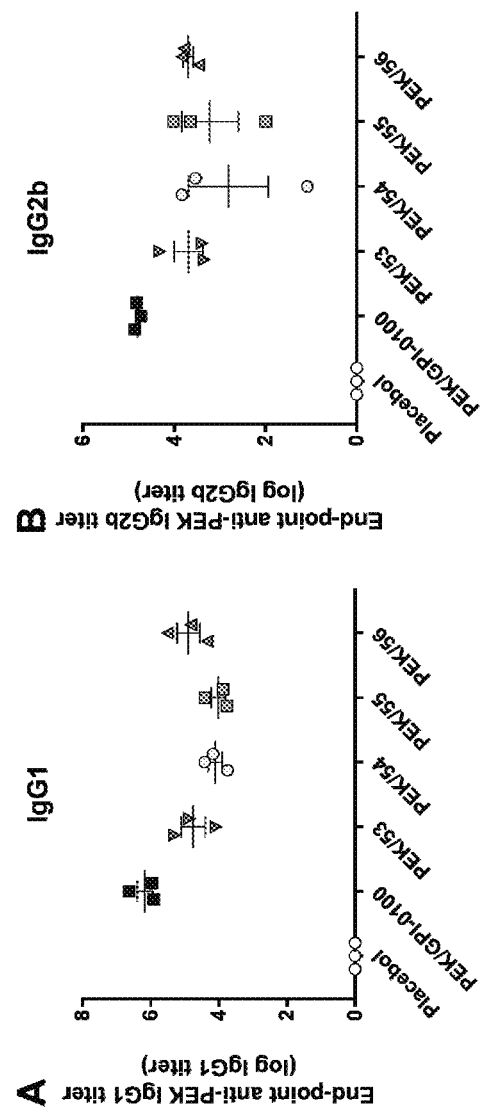

The serum PEK (coating with E7)-specific IgG antibody titers was determined using an ELISA after each dose. As shown in FIG. 7, PEK/GPI-0100 induced the highest level of antibody production in C57BL/6 mice. Amongst, compounds 53-56 were capable to induce moderate E7-specific antibody productions. Since cellular and humoral immunity are reciprocal inhibition, compounds induced higher cytotoxic T-cell immunity with lower antibody production were reasonable.

Vaccination after immunological analysis of our compounds suggested compound 46-62, 64, 66, 77-79, 83, 92, 95 are potent saponins-based adjuvant to develop cellular immunity to the host. Adjuvants with these properties are advantageous to combine with therapeutic vaccines, such as cancer, bacteria (tuberculosis), virus (HIV, herpes), protozoa (malarial) . . . etc.

Toxicity

Figure 8:
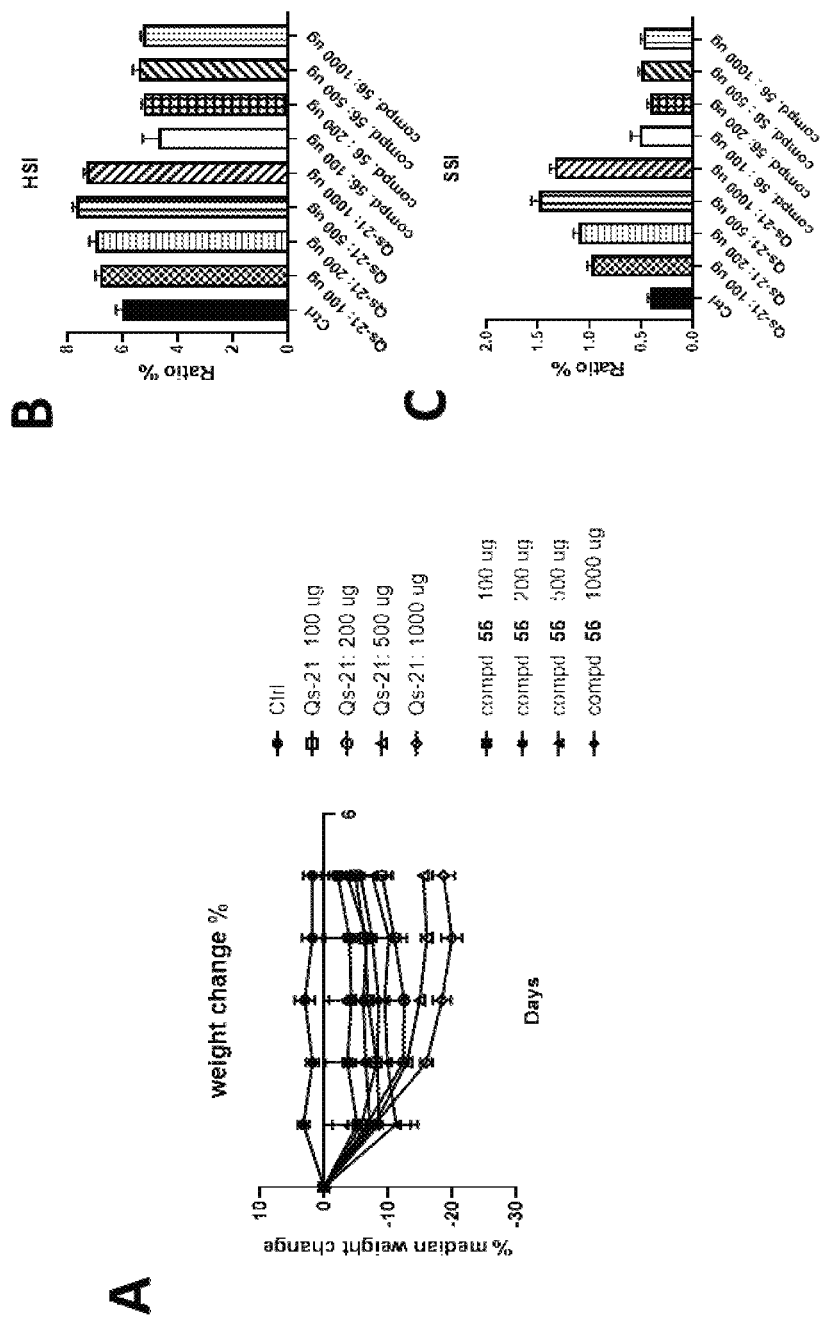
FIG. 8 (A) The percentage of median weight change of mice in 5 days. The values are presented as means±S.E.M. (n=5). (B) Hepato somatic index and (C) Spleen somatic index. The values are presented as means±S.E.M. (n=5). The percentage of median weight change of mice which was received increased dose of saponin adjuvant 56 was all less than 5%. The spleen somatic index and hepato somatic index in all experimental group were no change with compare to control group. These data suggested that saponin 56 is a potent and safer candidate as vaccine adjuvant.

Acute toxicity was examined with increased dose of saponin 56 form 100 µg to 1000 µg. The result was presented as the number of surviving animal per group of 5 mice (Female BALB/c mice, 9 weeks) in 7 days. After this test, all of the mice were survive and no obvious abnormality on their activity and diet behavior. (FIG. 8)

TABLE 1

| acute toxicity of saponin 56. | | |
|---|---|---|
| Dose (µg) | GPI-0100 | Saponin 56 |
| 0 | 5/5 | 5/5 |
| 100 | 5/5 | 5/5 |
| 200 | 5/5 | 5/5 |
| 500 | 5/5 | 5/5 |
| 1000 | 5/5 | 5/5 |

Results

The results represent in FIG. 8. It shows the percentage of median weight change of mice which was received increased dose of saponin adjuvant 56 was all less than 5%. The spleen somatic index and hepato somatic index in all experimental group were no change with compare to control group. These data suggested that saponin 56 is a potent and safer candidate as vaccine adjuvant.

Experimental Example II—Tumor Challenge by the OVA Peptide Vaccine

Material and Method

Adjuvant Stock

Dissolve sample powder in DMSO to 20 mg/mL.

Animal and Vaccinations

Female C57BL/6 mice 6-8 weeks of age obtained from NLAC Taiwan. Mice were injected s.c. with 200 µL of $1.5*10^6$ E. G7-OVA (OVA-expressing EL4 lymphoma) cells in PBS. Tumor volumes were measured at regular intervals using a caliper and calculated by the following formula:

tumor volume (mm³)=(long diameter)*(short diameter)²*0.52. When the average tumor volume reached ~100 mm³ (day 7), 100 μL of 100 μg OVA in PBS with or without 50 μg compound 56, alum, Qs-21 and GPI0100 was injected s.c. around the tumor. PBS (200 μL) was used as a control.

Results

A mouse-vaccination model was applied with an antigen OVA to evaluate anti-tumor efficacy. Five mice per group were immunized two times at three weeks intervals with 50 μg of saponins and 100 μg OVA. The evaluation of compound 56, and positive control groups (alum, Qs-21 and GPI-0100) anti-tumor efficacy were analyzed by caliper.

Antitumor Efficacy

Figure 9:
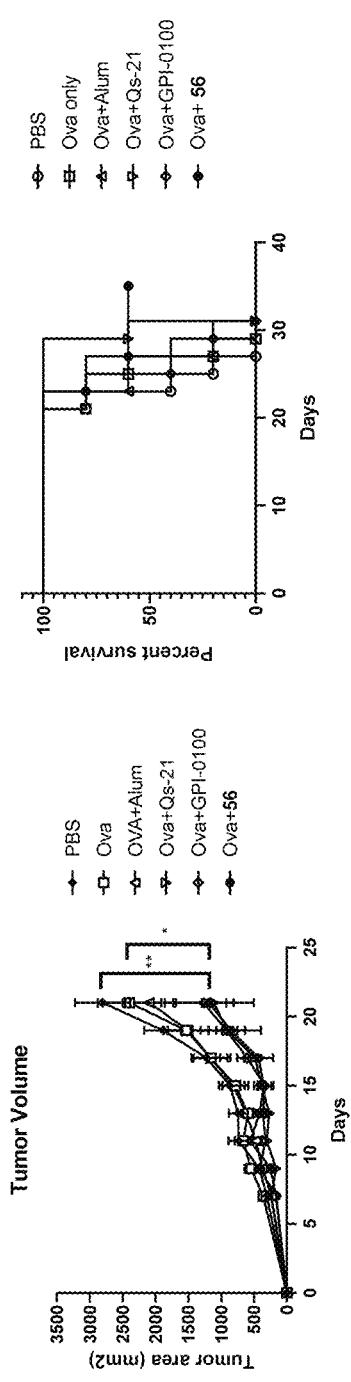
FIG. 9 demonstrates effect of signal dose of OVA vaccine with saponin conjugate 56 on the E.G7-OVA tumors in the Female C57BL/6 mice.

The E. G7-OVA tumor bearing mice were vaccinated with different formulations intradermally for two times on Days 7, 14 when compared with the control group (PBS), mice treated with OVA, OVA+Alum, groups exhibited slight tumor growth suppression at first, but the treatments were not effective enough, and rapid tumor growth resumed later. In contrast, for mice treated with OVA+ compound 56, OVA+Qs-21, and OVA+GPI0100 show significant tumor growth suppression effect. Further, OVA+ compound 56 had highest survival rate (FIG. 9).

Experimental Example III—Influenza Challenge by the OVA Peptide Vaccine

Material and Method

Adjuvant Stock

Dissolve sample powder in DMSO to 20 mg/mL.

Animal and Vaccinations

Female C57BL/6 mice 6-8 weeks of age were immunized through either s.c. injection with 100p of vaccines or the intranasal route with 30 μl of vaccines. All vaccine liquids were freshly prepared and diluted with 0.5% Tween 20 PBS. Vaccines used for the subcutaneous injection contained immunogens $NP_{366-374}/NP_{311-325}$ peptides, alone or combined with compound 56 (50 g). Vaccines used for the i.n. route contained immunogens alone or with compound 56 (30 μg). After two times vaccination, mice were infected with 110 plaque-forming units (PFU) of live PR8 virus by intronasal.

Results

Figure 10:
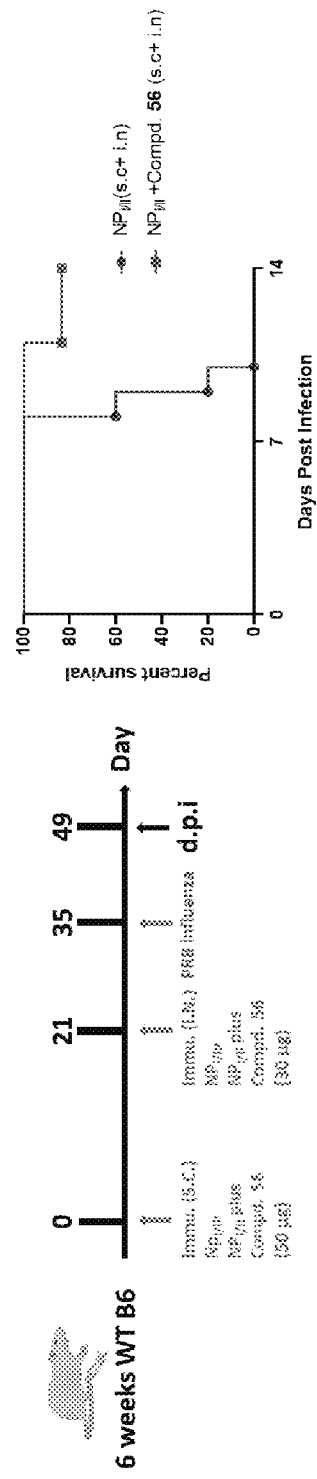
FIG. 10. The survival of mice administrated influenza vaccines combined with compound 56 through s.c. and intranasal administrated and then challenged with mice influenza (PR8).

A mouse-vaccination model was applied with an antigen OVA to evaluate anti-influenza efficacy. Five mice per group were immunized two times with compound 56 and $NP_{I/II}$. After two times vaccination, mice were infected with 110 plaque-forming units (PFU) of live PR8 virus by intronasal. Compared to mice immunized with NPI and NPII (NP I/II) peptides alone, the immunized with NPI/II plus compound 56 had a higher survival rate following PR8 infection (FIG. 10), Experimental Example IV—Immunological Evaluation of SARS-CoV-2 Antigen Combine with Compound 56 Immune Adjuvants Material and Method Adjuvant Stock Dissolve sample powder in DMSO to 20 mg/mL. Before administration, dilute stock with 0.5% (w/w) Tween-20 to 0.5 mg/mL and filtered through PTFE (0.1 m).

Animal and Vaccinations

Female C57BL/6 mice between 6 and 8 weeks of age were vaccinated with SARS-CoV-2 spike protein and w/o alum or compound 56 via the subcutaneous (S.C.) route and dose three times at six weeks intervals. For determination of the IgG levels, mice were bled by tail artery 10 days after each immunization.

ELISA

The levels of specific serum IgG against SARS-CoV-2 spike protein in each group were determined by ELISA using Maxisorp microtiter plates (NUNC International, Roskilde, Denmark) coated with Sars-CoV-2 spike RBD His protein (0.5 μg/well) in borate buffer saline (BBS; 100 mM NaCl, 50 mM boric acid, 1.2 mM $Na_2B_4O_7$, pH 8.2) at 4° C. overnight. Plates were blocked with blocking buffer (5% Milk in PBS) for at least 1 h at 37° C., and then were washed with PBS+0.05% Tween 20. Serial 5-fold dilutions of scrum samples were added to plates. After 1 h, plates were washed with PBS+0.05% Tween 20. Peroxide labelled goat Anti-Mouse IgG (Invitrogen, Cat. no. 81-6520) diluted 1:3000 in 1% BSA-PBS were added for 1 h. The plates were washed with PBS+0.05% Tween 20 and were developed with TMB Chromogen Solution (Invitrogen, Cat. no. 00-2023) for 15 min, followed with stop solution (0.2 N $H2_sO_4$). The absorbance at 450 nm was recorded.

Results

A mouse-vaccination model was applied with an antigen Sars-CoV-2 spike RBD His protein to evaluate anti-covid 19 efficacy. Mice were divided to three group: Compound 56 (50 μg), Sars-CoV-2 (2 μg)+Compound 56 (50 μg), Sars-CoV-2 (10 μg)+Alum (10 μg).

Antibody Production Assay

Figure 11:
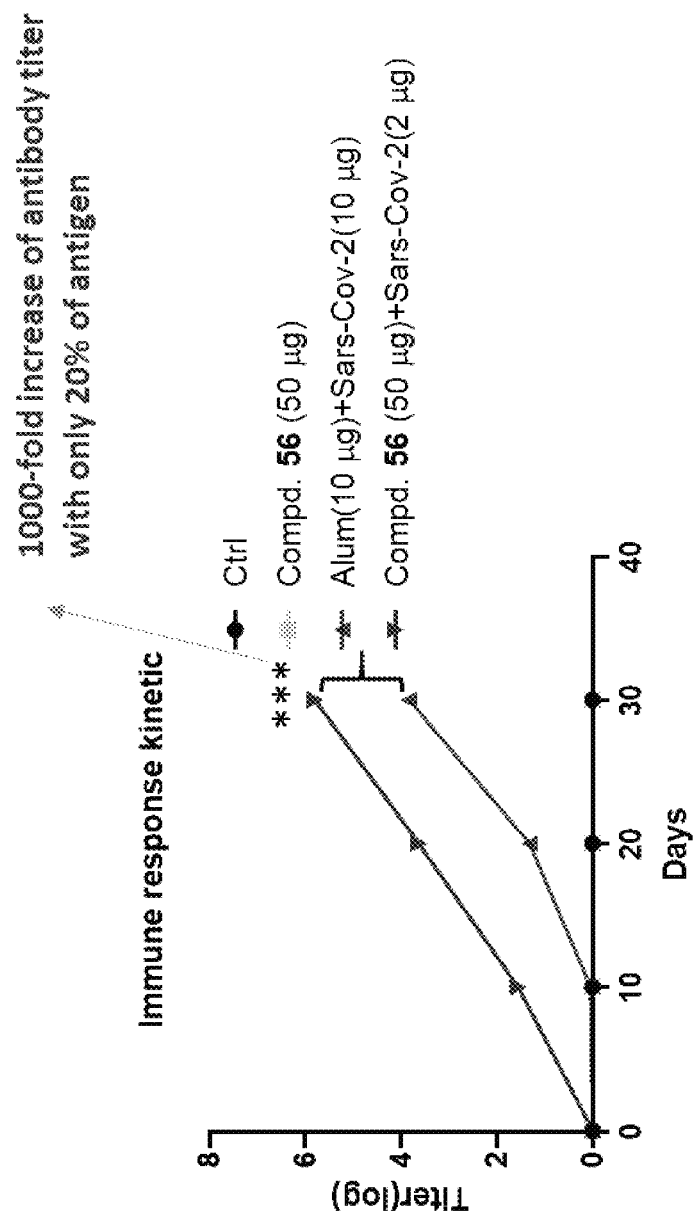
FIG. 11. The antibodies titers of mice s.c. administrated with SARS-CoV-2 (2 ug or 10 ug) and adjuvants (alum and compound 56).

The serum SARS-CoV-2-specific IgG antibody titers was determined using an ELISA after each dose. As shown in FIG. 11, SARS-CoV-2+ compound 56 group induced the highest level of antibody production in C57BL/6 mice. Amongst, SARS-CoV-2/compound 56 group show 1000-fold increase of antibody titer with only 20% of antigen.

What is claimed is:

1. A saponin conjugate of formula (I), or a pharmaceutically acceptable salt thereof,

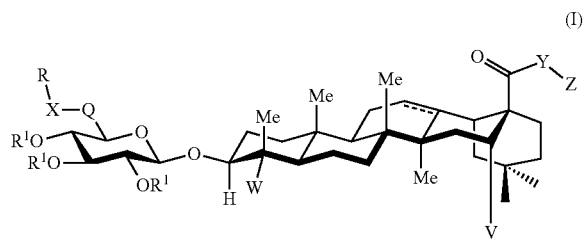

(I)

wherein: ═ is a single or double bond;
W is Me, —CHO,

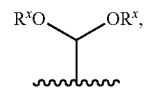

—$CH_2OR^x$, or —$C(O)R^x$, wherein $R^x$ is independently hydrogen or an oxygen protecting group selected from the group consisting of alkyl ethers, allyl ethers, benzyl ethers, silyl ethers, acetals, ketals, esters, carbamates, and carbonates;

V is H or OH;

Y is $CH_2$, —O—, —S—, —NR—, or —NH—;

R is (i) a moiety selected from the group consisting of acyl, aryl, an aryl-aliphatic group, a cyclo-aliphatic group, a heteroaryl-aliphatic group, an alkyloxy-aliphatic group, and an aryloxy-aliphatic group;

(ii) a moiety selected from the group consisting of an unsubstituted 5-10-membered arylaliphatic group, a 5-10-membered arylaliphatic group substituted with at least one group selected from the group consisting of a alkyl group, an alkoxy group, an aryloxy group, a halogen, a haloalkyl group, a hydroxyl group, a saturated heterocyclic group having 1-2 heteroatoms independently selected from the group consisting of nitrogen, oxygen, sulfur, and a combination thereof, and a 4-10-membered heteroaryl-aliphatic group having 1-4 heteroatoms independently selected from the group consisting of nitrogen, oxygen, sulfur, and a combination thereof, or (iii) one having the following structures:

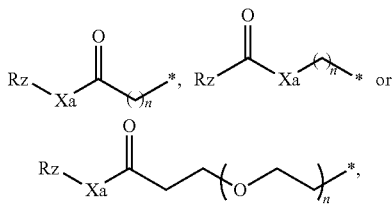

wherein Rz is alkyl, Xa is O, NH or S, n=1-20;

X is $CH_2$, —O—, —NH—, —NH—(C=O)—, —S—, or O—(C=O)—

Q is $CH_2$, C=O, C=N—OH, or C=N—OMe, $R^1$ is independently hydrogen, an oxygen protecting group selected from the group consisting of alkyl ethers, allyl ethers, benzyl ethers, silyl ethers, acetals, ketals, esters, carbamates, and carbonates, or a carbohydrate having the structure of monosaccharides; and Z is a linear or branched oligosaccharide or a group selected from the group consisting of amine, amide, acyl, arylalkyl, aryl, heteroaryl, an aliphatic group, a heteroaliphatic group, a cycloaliphatic group and heterocyclyl.

2. The saponin conjugate or the pharmaceutically acceptable salt thereof of claim 1, wherein R is an aryl-aliphatic group, a heteroaryl-aliphatic group, an alkyloxy-aliphatic group, or an aryloxy-aliphatic group.

3. The saponin conjugate or the pharmaceutically acceptable salt thereof of claim 1, wherein Z is a linear tetrasaccharide or a linear trisaccharide, wherein the first sugar residue is attached directly to Y.

4. The saponin conjugate or the pharmaceutically acceptable salt thereof of claim 1, wherein W is CHO and V is OH.

5. The saponin conjugate or the pharmaceutically acceptable salt thereof of claim 1, wherein Q is C=O and X is —NH—.

6. The saponin conjugate or the pharmaceutically acceptable salt thereof of claim 1, wherein Q is $CH_2$ and X is O—C(=O).

7. The saponin conjugate or the pharmaceutically acceptable salt thereof of claim 2, wherein R is:

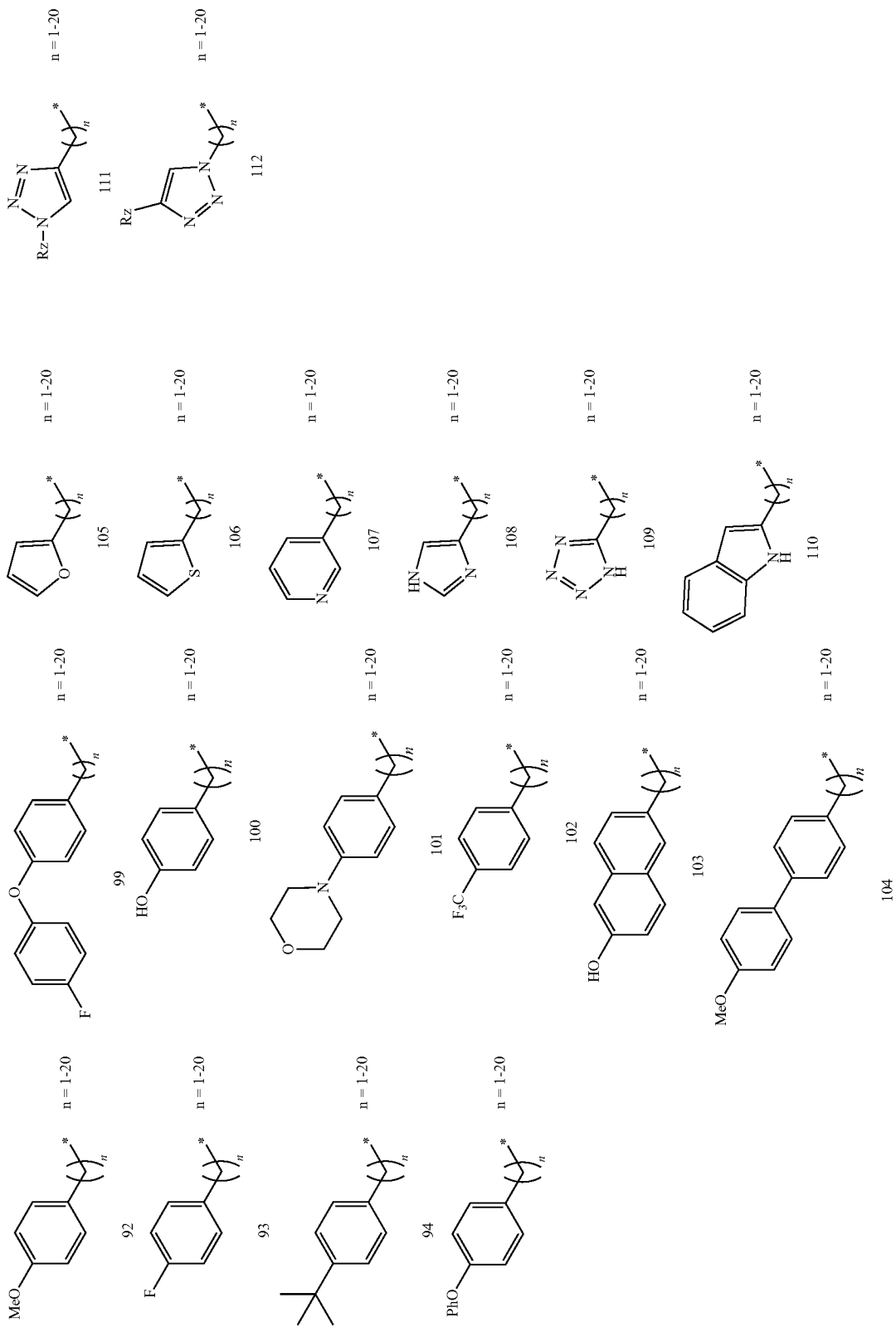

wherein Rz is alkyl.

8. The saponin conjugate or the pharmaceutically acceptable salt thereof of claim 1, which has the following structure:

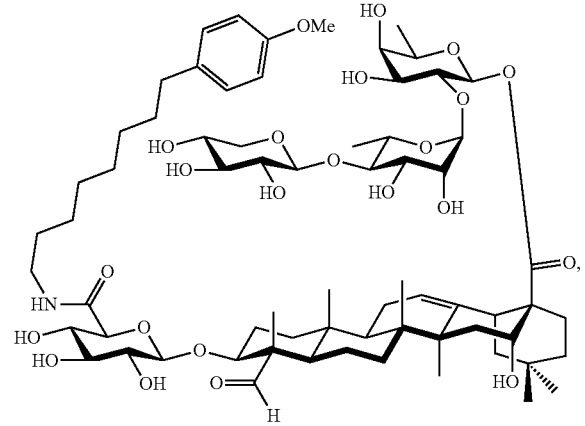

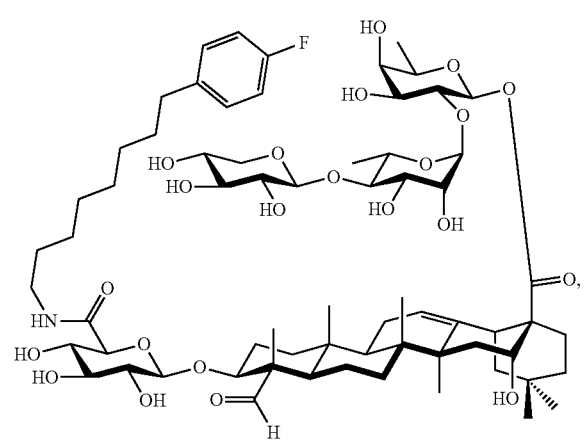

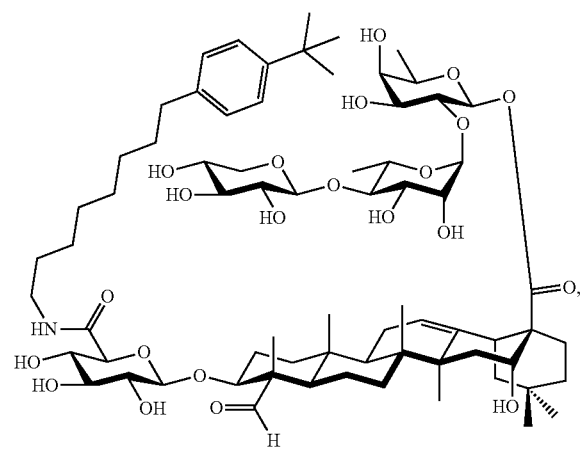

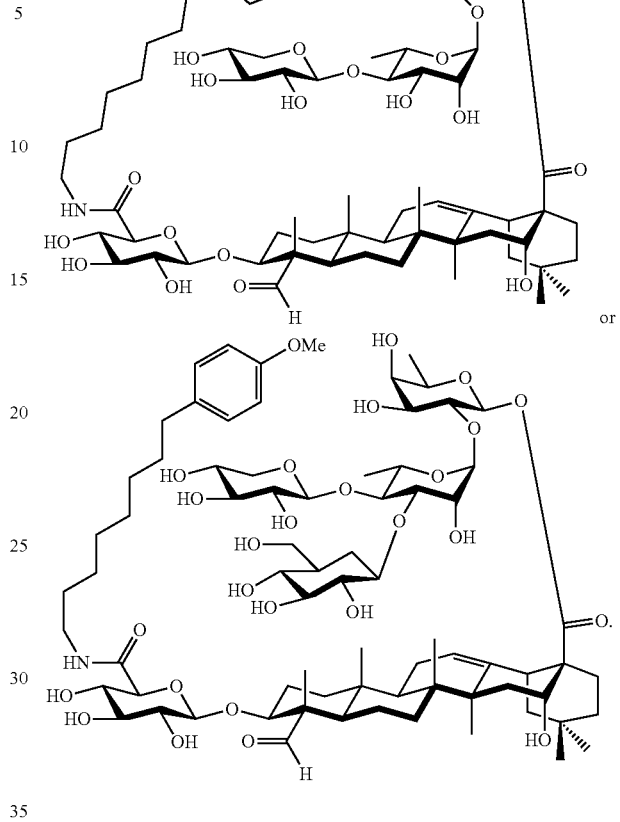

9. A vaccine composition, comprising an antigen and the saponin conjugate or the pharmaceutically acceptable salt thereof of claim 1.

10. The vaccine composition of claim 9, further comprising an additional adjuvant.

11. The vaccine composition of claim 9, further comprising a pharmaceutically acceptable carrier or diluents.

12. The vaccine composition of claim 9, wherein the antigen is selected from the group consisting of bacterial antigen, viral-associated antigen and tumor-associated antigen.

13. The vaccine composition of claim 12, wherein the bacterial antigens are antigens associated with a bacterium selected from the group consisting of *Bordetella pertussis, Bordetella parapertussis, Bordetella bronchiseptica, Borrelia burgdorferi, Borrelia* spp., *Chlamydia trachomatis, Helicobacter pylori, Chlamydia pneumoniae, Ureaplasma urealyticum, Mycoplasma pneumoniae, Staphylococcus* spp., *Staphylococcus aureus, Streptococcus pyogenes, Streptococcus* spp., *Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Campylobacter* spp., *Campylobacter jejuni, Clostridium* spp., *Clostridium difficile, Corynebacterium diphtheria, Mycobacterium* spp., *Mycobacterium tuberculosis, Pseudomonas aeruginosa, Treponema* spp., *Leptospria* spp., *Hemophilus ducreyi, hemophilus* influenza, *Escherichia coli, Shigella* spp., *Erlichia* spp., *Rickettsia* spp. and any combinations thereof.

14. The vaccine composition of claim 12, wherein the viral-associated antigens are antigens associated with a virus selected from the group consisting of influenza virus, parainfluenza virus, mumps virus, adenovirus, respiratory syncytial virus, Epstein-Barr virus, rhinovirus, poliovirus, coxsackievirus, echo virus, rubeola virus, rubella virus, varicell-zoster virus, herpes virus, herpes simplex virus, parvovirus, cytomegalovirus, hepatitis virus, human papillomavirus, alphavirus, flavivirus, bunyavirus, rabies virus, arenavirus, filovirus, HIV 1, HIV 2, HTLV-1, HTLV-II, FeLV, bovine LV, FeIV, canine distemper virus, canine contagious hepatitis virus, feline calicivirus, feline rhinotracheitis virus, TGE virus, foot and mouth disease virus, coronavirus, dengue virus, Favivirus and any combinations thereof.

15. The vaccine composition of claim 12, wherein the tumor-associated antigens are antigens selected from the group consisting of killed tumor cells and lysates thereof; MAGE-1, MAGE-3 and peptide fragments thereof; human chorionic gonadotropin and peptide fragments thereof; carcinoembryonic antigen and peptide fragments thereof; alpha fetoprotein and peptide fragments thereof; pancreatic oncofetal antigen and peptide fragments thereof; prostate-specific antigens and peptide fragments thereof; MUC-1 and peptide fragments thereof; CA 125, CA 15-3, CA 19-9, CA 549, CA 195 and peptide fragments thereof; prostate-specific membrane antigen and peptide fragments thereof; squamous cell carcinoma antigen and peptide fragments thereof; ovarian cancer antigen and peptide fragments thereof; pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein $p210^{BCR-ABL}$, STn, Tn, $Lewis^x$, $Lewis^y$, TF, GM1, GM2, GD2, GD3, Gb3, KH-1, Globo-H, SSEA-4; and any mixtures thereof.

16. A pharmaceutical composition, comprising one or more saponin conjugates or the pharmaceutically acceptable salt thereof of claim 1 and a pharmaceutically acceptable excipient.

17. A saponin conjugate intermediate of formula (II):

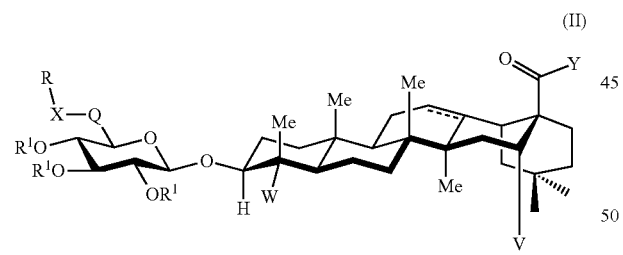

(II)

or a pharmaceutically acceptable salt thereof, wherein:
$\rightleftharpoons$ is a single or double bond;
W is Me, —CHO,

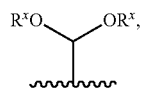

—C(O)$R^x$, or CH$_2$O$R^x$, wherein $R^x$ is independently hydrogen or an oxygen protecting group selected from the group consisting of alkyl ethers, allyl ethers, benzyl ethers, silyl ethers, acetals, ketals, esters, carbamates, and carbonates;

V is hydrogen or —OR$^x$;
Y is CH$_3$, —OH, —SH, —OR$^5$, —NH$_2$, wherein OR$^5$ is selected from the group consisting of alkyl ethers, allyl ethers, benzyl ethers, silyl ethers, acetals, ketals, esters, carbamates, and carbonates;
R is (i) a moiety selected from the group consisting of acyl, aryl, an aryl-aliphatic group, a cyclo-aliphatic group, a heteroaryl-aliphatic group, an alkyloxy-aliphatic group, and an aryloxy-aliphatic group or
(ii) a moiety selected from the group consisting of an unsubstituted 5-10-membered arylaliphatic group, a 5-10-membered arylaliphatic group substituted with at least one group selected from the group consisting of a alkyl group, an alkoxy group, an aryloxy group, a halogen, a haloalkyl group, a hydroxyl group, a saturated heterocyclic group having 1 2 heteroatoms independently selected from the group consisting of nitrogen, oxygen, sulfur, and a combination thereof, a 4-10-membered heteroaryl-aliphatic group having 1-4 heteroatoms independently selected from the group consisting of nitrogen, oxygen, sulfur, and a combination thereof, or does not exist, wherein when R does not exist, X is —N$_3$;
X is CH$_2$, —O—, —NH—, —NH—(C=O)—, —S—, O—(C=O)— or —N$_3$;
Q is CH$_2$, C=O, C=N—OH, or C=N—OMe,
$R^1$ is independently hydrogen or an oxygen protecting group selected from the group consisting of alkyl ethers, allyl ethers, benzyl ethers, silyl ethers, acetals, ketals, esters, carbamates, and carbonates, or a carbohydrate having the structure of

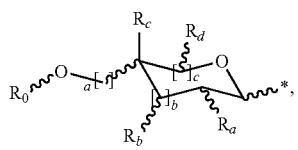

wherein:
each occurrence of a, b, and c is independently 0 or 1;
$R_0$ is independently hydrogen or an oxygen protecting group selected from the group consisting of alkyl ethers, allyl ethers, benzyl ethers, silyl ethers, acetals, ketals, esters, carbamates, and carbonates;
each occurrence of $R_a$, $R_b$, $R_c$, and $R_d$ is independently hydrogen, halogen, OH, OR, or OR$^x$; each occurrence of $R^x$ is independently hydrogen or an oxygen protecting group selected from the group consisting of alkyl ethers, allyl ethers, benzyl ethers, silyl ethers, acetals, ketals, esters, carbamates, and carbonates.

18. The saponin conjugate intermediate of formula (II) or a pharmaceutically acceptable salt thereof of claim 17, which is obtained by reacting a compound represented by the structure of formula III:

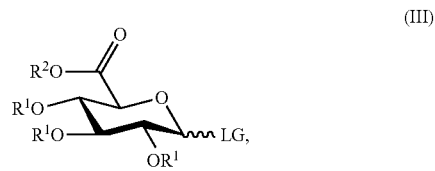

(III)

wherein:
R¹ is independently hydrogen, an oxygen protecting group selected from the group consisting of alkyl ethers, allyl ethers, benzyl ethers, silyl ethers, acetals, ketals, esters, carbamates, and carbonates, or a carbohydrate having the structure of

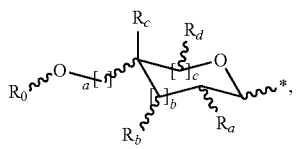

wherein:
each occurrence of a, b, and c is independently 0 or 1;
$R_0$ is independently hydrogen or an oxygen protecting group selected from the group consisting of alkyl ethers, allyl ethers, benzyl ethers, silyl ethers, acetals, ketals, esters, carbamates, and carbonates;
each occurrence of $R_a$, $R_b$, $R_c$, and $R_d$ is independently hydrogen, halogen, OH, OR, or $OR^x$; each occurrence of $R^x$ is independently hydrogen or an oxygen protecting group selected from the group consisting of alkyl ethers, allyl ethers, benzyl ethers, silyl ethers, acetals, ketals, esters, carbamates, and carbonates, and R is the same as defined in claim 17;
R² is hydrogen or an oxygen protecting group selected from the group consisting of alkyl ethers, allyl ethers, benzyl ethers, silyl ethers, acetals, ketals, esters, carbamates, and carbonates; and
LG is a leaving group;

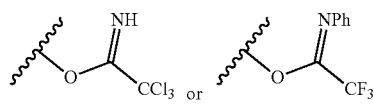

with a compound represented by the structure of formula IV:

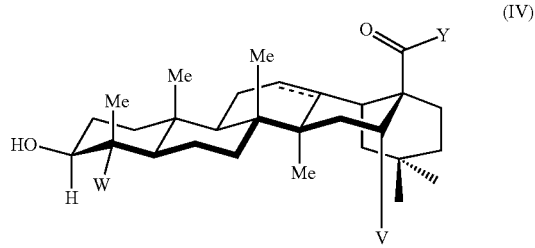

or a pharmaceutically acceptable salt thereof, wherein:
═ is a single or double bond;
W is Me, —CHO,

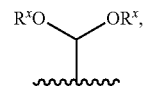

—CH₂OR$^x$, or —C(O)R$^x$;
V is hydrogen or —OR$^x$; and
Y is CH₃, —OH, —SH, —OR⁵, —NH₂, wherein OR⁵ is selected from the group consisting of alkyl ethers, allyl ethers, benzyl ethers, silyl ethers, acetals, ketals, esters, carbamates, and carbonates; and
R$^x$ is hydrogen or an oxygen protecting group selected from the group consisting of alkyl ethers, allyl ethers, benzyl ethers, silyl ethers, acetals, ketals, esters, carbamates, and carbonates.

* * * * *